US009895390B2

(12) United States Patent
Fillmore et al.

(10) Patent No.: US 9,895,390 B2
(45) Date of Patent: Feb. 20, 2018

(54) METHODS AND ASSAYS FOR COMBINATION TREATMENT OF CANCER

(71) Applicant: CHILDREN'S MEDICAL CENTER CORPORATION, Boston, MA (US)

(72) Inventors: Christine M. Fillmore, Waltham, MA (US); Carla F. Kim, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/650,473

(22) PCT Filed: Nov. 12, 2013

(86) PCT No.: PCT/US2013/069557
§ 371 (c)(1),
(2) Date: Jun. 8, 2015

(87) PCT Pub. No.: WO2014/092905
PCT Pub. Date: Jun. 19, 2014

(65) Prior Publication Data
US 2015/0320779 A1 Nov. 12, 2015

Related U.S. Application Data

(60) Provisional application No. 61/735,303, filed on Dec. 10, 2012.

(51) Int. Cl.
A61K 31/706 (2006.01)
A61K 31/7048 (2006.01)
C12Q 1/68 (2006.01)
A61K 45/06 (2006.01)

(52) U.S. Cl.
CPC ........ A61K 31/706 (2013.01); A61K 31/7048 (2013.01); A61K 45/06 (2013.01); C12Q 1/6886 (2013.01); C12Q 2600/106 (2013.01); C12Q 2600/156 (2013.01)

(58) Field of Classification Search
CPC .............. A61K 31/706; A61K 31/7048; C12Q 1/6886; C12Q 2600/106; C12Q 2600/156
USPC ................ 514/27; 435/6.11, 6.12; 506/16, 2
See application file for complete search history.

(56) References Cited

U.S. PATENT DOCUMENTS

2010/0286143 A1 11/2010 Dias-Santagata et al.

FOREIGN PATENT DOCUMENTS

WO 2011056688 A2 5/2011
WO 2012050532 A1 4/2012

OTHER PUBLICATIONS

He et al. EGFR Exon 19 Insertions: A New Family of Sensitizing EGFR Mutations in Lung Adenocarcinoma. Clin Cancer Res; 18(6); 1790-7. Published online Dec. 21, 2011.*
Medina et al. Frequent BRG1/SMARCA4—Inactivating Mutations in Human Lung Cancer Cell Lines. Human Mutation 0:1-6, 2008.*
Wu et al. Polycomb protein EZH2 regulates cancer cell fate decision in response to DNA damage. Cell Death and Differentiation (2011) 18, 1771-1779.*
Liu et al. The dynamic interplay in chromatin remodeling factors polycomb and trithorax proteins in response to DNA damage. Mol Biol Rep (2012) 39:6179-6185.*
Fillmore et al., "Targeting Polycomb Repressive Complexes to Modulate Chemotherapy Response in Non-Small Cell Lung Cancer", Keystone Symposium; Presentation & Abstract, Mar. 6-11, 2011.
Puppe et al., "BRCA1-deficient mammary tumor cells are dependent on EZH2 expression and sensitive to Polycomb Repressive Complex 2-inhibitor 3-deazaneplanocin A." Breast Cancer Res, 11(4): R63 (2009).
Tan et al., "Pharmacologic disruption of Polycomb-repressive complex 2-mediated gene repression selectively induces apoptosis in cancer cells." Genes and Development 21(9):1050-1063 (2007).
Dent et al., Molecular Interventions, 11(2):133-140 (2011). "CHK1 Inhibitors in Combination Chemotherapy. Thinking Beyond the Cell Cycle."
Romero et al., EMBO Mol Med, 4:603-616 (2012). "The tumour suppressor and chromatin-remodelling factor BRG1 antagonzies Myc activity and promotes cell differentiation in human cancer."
Chiba et al., "3-Deazaneplanocin A is a promising therapeutic agent for the eradication of tumor-initiating hepatocellular carcinoma cells." International Journal of Cancer 130(11):2557-2567 (2012).
Crea et al., "Pharmacologic disruption of Polycomb Repressive Complex 2 inhibits tumorigenicity and tumor progression in prostate cancer." Molecular Cancer 10(1):1-10 (2011).
Crea et al., "Polycomb genes and cancer: time for clinical application?." Critical Reviews in Oncology/Hematology 83 (2):184-193 (2012).
Fiskus et al., "Combined epigenetic therapy with the histone methyltransferase EZH2 inhibitor 3-deazaneplanocin A and the histone deacetylase inhibitor panobinostat against human AML cells." Blood 114(13):2733-2743 (2009).
Hayden et al., "S-adenosylhomocysteine hydrolase inhibition by 3-deazaneplanocin A analogues induces anti-cancer affects in breast cancer cell lines and synergy with both histone deacetylase and HER2 inhibition." Breast Cancer Res Treat 127(1):109-119 (2011).
Kemp et al., "Polycomb repressor complex-2 is a novel target for mesothelioma therapy." Clinical Cancer Research 18(1):77-90 (2012).
Miranda et al., "DZNep is a global histone methylation inhibitor that reactivates developmental genes not silenced by DNA methylation." Molecular Cancer Therapeutics 8(6):1579-1588 (2009).
Ougolkov et al., "Regulation of pancreatic tumor cell proliferation and chemoresistance by the histone methyltransferase enhancer of zeste homologue 2." Clinical cancer research 14(21):6790-6796 (2008).

(Continued)

Primary Examiner — Yih-Horng Shiao
(74) Attorney, Agent, or Firm — Nixon Peabody LLP; David S. Resnick; Nicole D. Kling

(57) ABSTRACT

The technology described herein is directed to the treatment of cancer, e.g. methods and assays relating to selecting and administering a chemotherapy with or without an EZH2 inhibitor.

12 Claims, 55 Drawing Sheets

(56) References Cited

OTHER PUBLICATIONS

Rao et al., "Inhibition of histone lysine methylation enhances cancer-testis antigen expression in lung cancer cells: Implications for adoptive immunotherapy of cancer." Cancer Research 71(12):4192-4204 (2011).
Suva et al., "EZH2 is essential for glioblastoma cancer stem cell maintenance." Cancer Research 69(24):9211-9218 (2009).
Tan et al., "Pharmacologic disruption of Polycomb-repressive complex 2-mediated gene repression selectively induces apoptosis in cancer cells." Genes & Development 21(9):1050-1063 (2007).
Xie et al., "Determinants of sensitivity to DZNep induced apoptosis in multiple myeloma cells." PloS One 6(6):e21583 (2011).
Zeidler et al., "The Polycomb group protein EZH2 impairs DNA repair in breast epithelial cells." Neoplasia 7 (11):1011-1019 (2005).

* cited by examiner

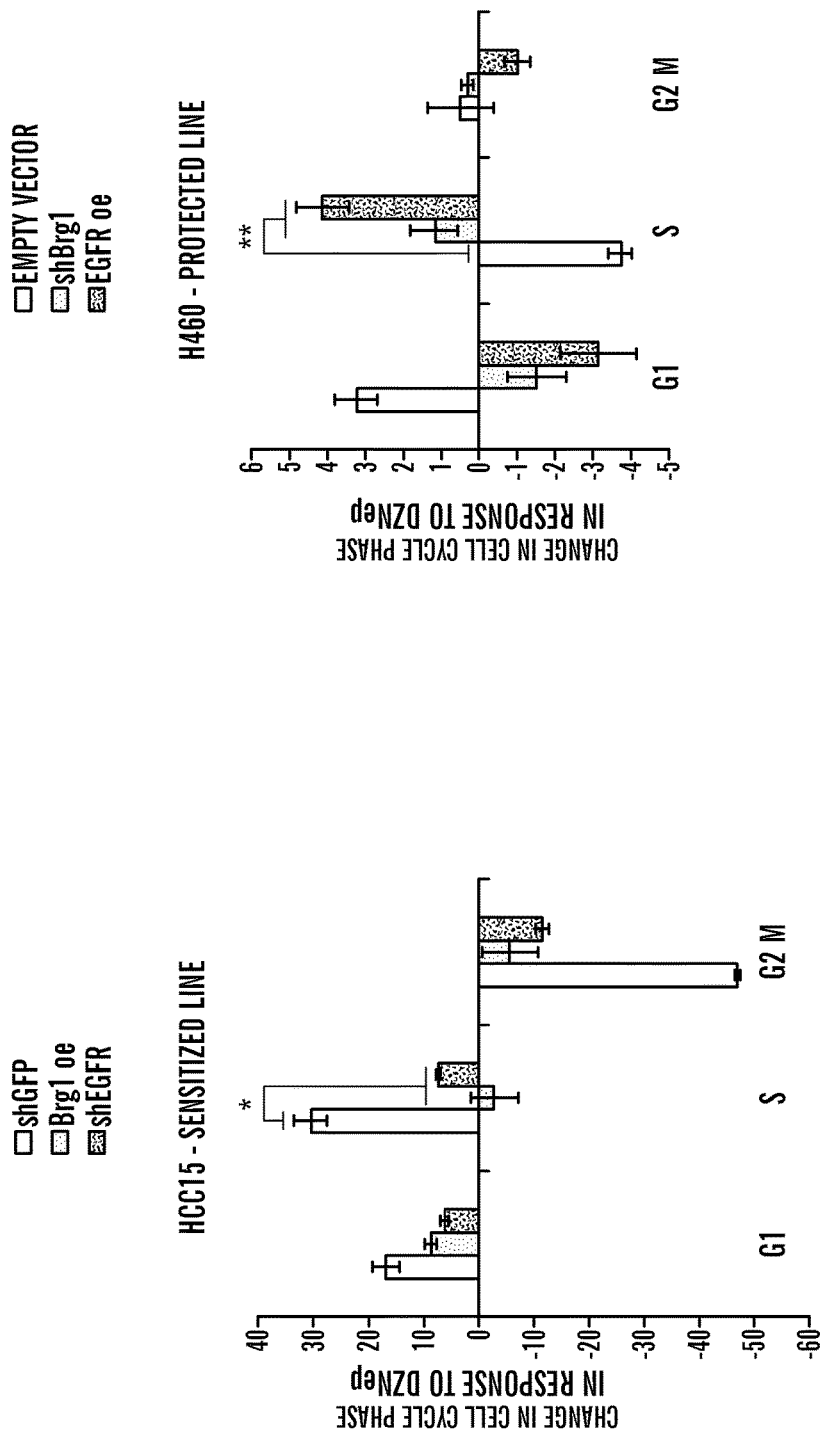

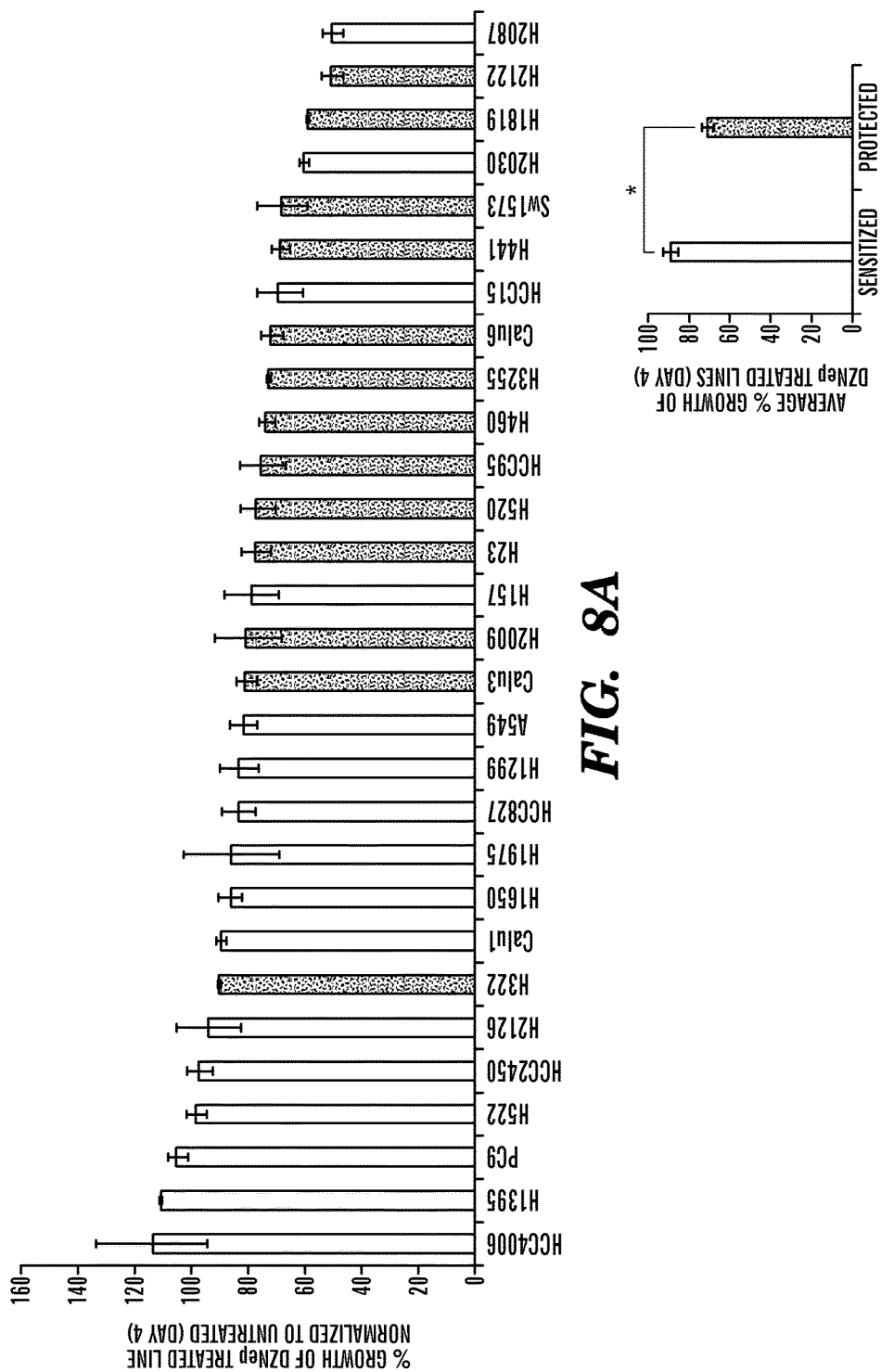
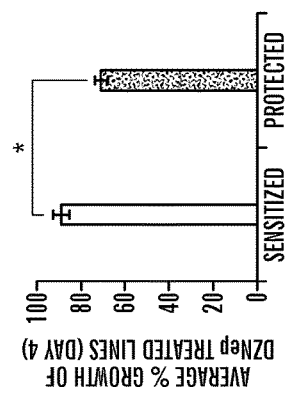
FIG. 8A
FIG. 8B

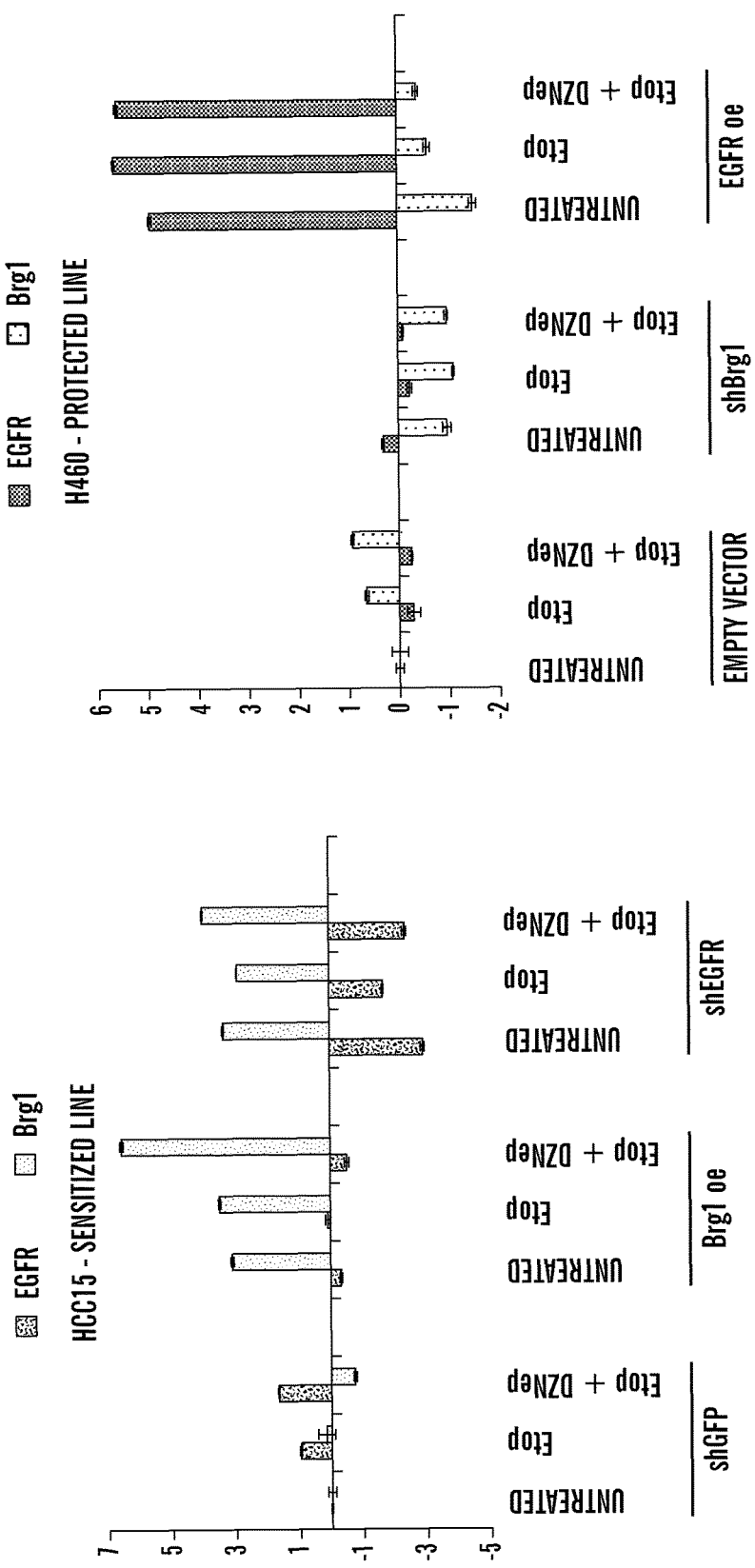

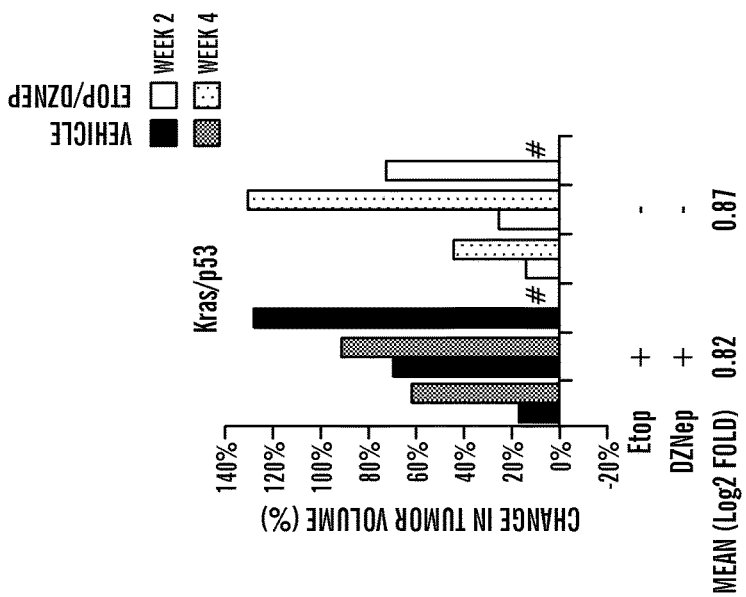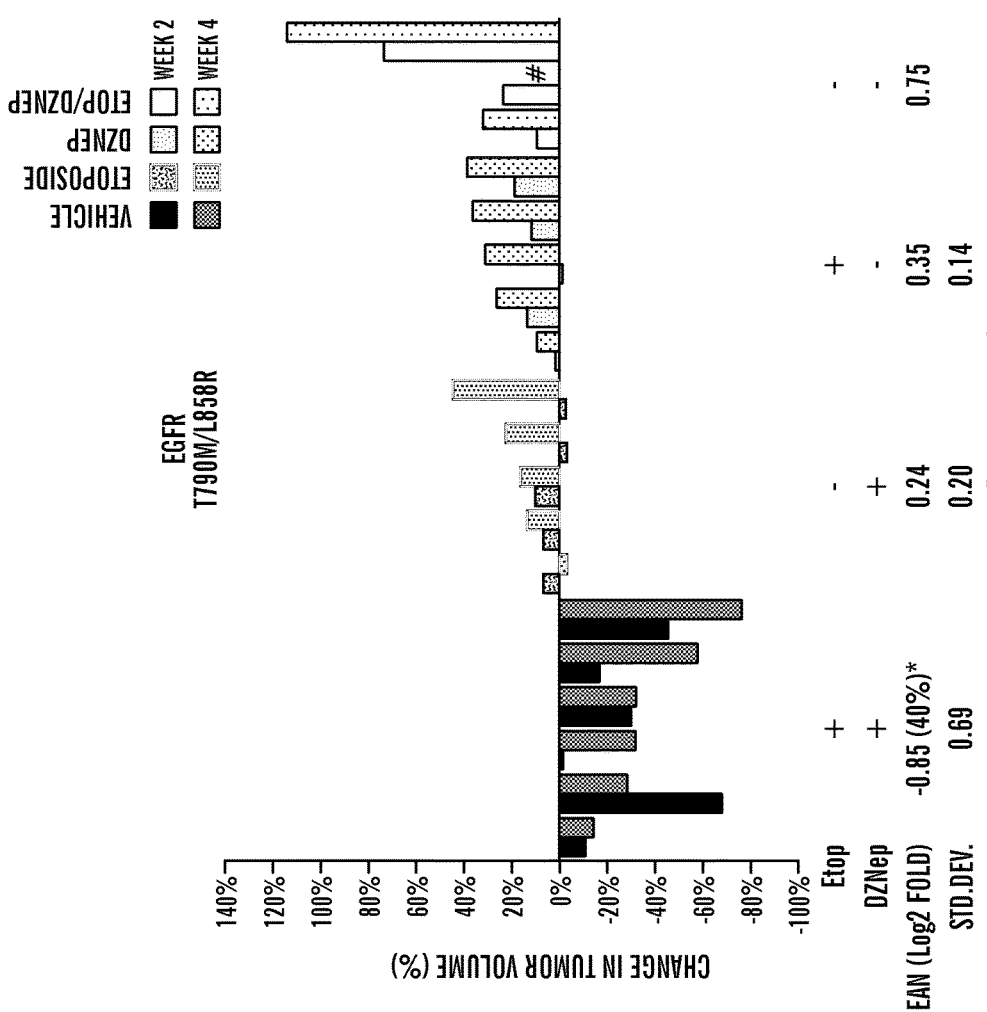
FIG. 20A
FIG. 20B

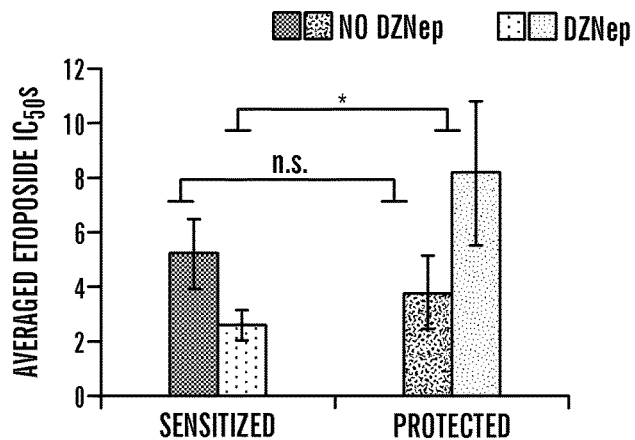
FIG. 25B
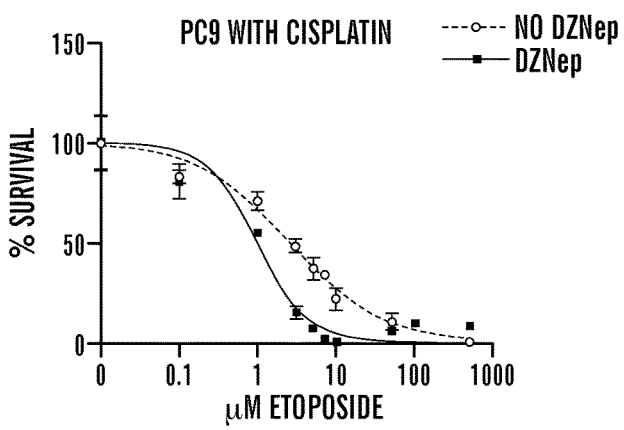
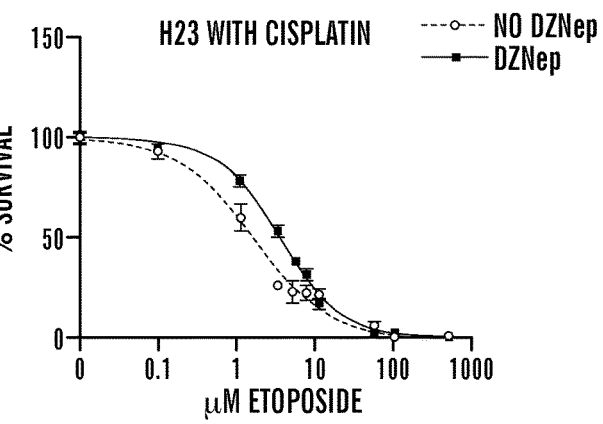
FIG. 25C

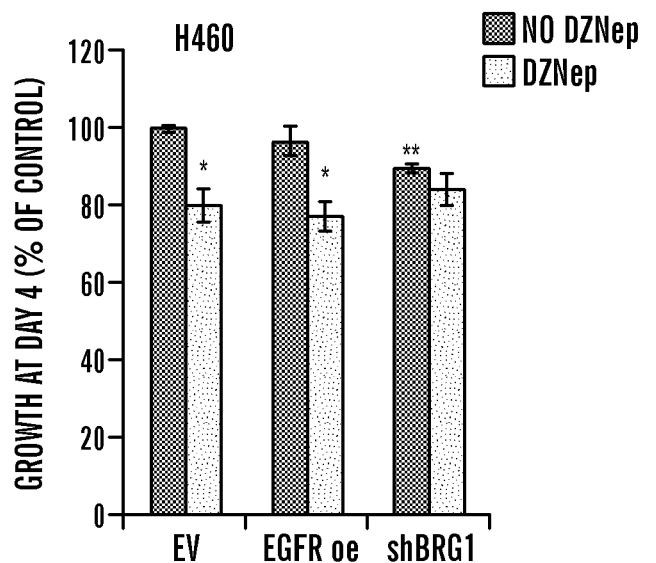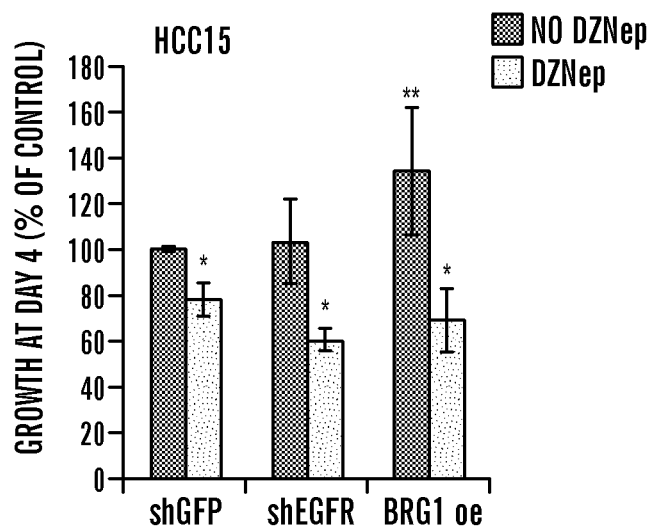
FIG. 28B

| Cell Line | Gender | Age | Ethnicity | Subtype | Stage | Smoke (pack/yr) | Biopsy | PIK3CA | Kras | Nras | p53 | SMARCA4 | EGFR | CDKN2A | LKB1 | B-Raf |
|---|---|---|---|---|---|---|---|---|---|---|---|---|---|---|---|---|
| HCC2450 | M | 52 | Caucasian | SCC | IIIB | unknown | primary | H1047R | N/A | N/A | deletion | N/A | N/A | N/A | N/A | WT |
| PC9 | M | 45 | East Asian | AdC | N/A | unknown | N/A | WT | WT | WT | N/A | N/A | E746_A750del | G67V | WT | WT |
| H522 | M | 60 | Caucasian | AdC | II | 60 | primary | WT | WT | WT | P191* | P270* | WT | WT | WT | WT |
| A549 | M | 58 | Caucasian | AdC | N/A | unknown | primary | WT | G12S | WT | WT | Q729* | WT | deletion | Q37* | WT |
| Calu1 | M | 47 | Caucasian | EpiC | III | unknown | pleura | N/A | G12C | WT | WT | WT | WT | WT | WT | WT |
| H2126 | M | 65 | Caucasian | LC | IIIB | non-smoker | pleura | WT | WT | WT | E62* | W764R | WT | deletion | deletion | WT |
| H157 | M | 59 | Caucasian | SCC | IIIB | 50 | metastasis | WT | G12R | WT | E298* | T58* | WT | E69* | deletion | WT |
| H1975 | F | N/A | N/A | AdC | N/A | non-smoker | primary | G118D | WT | WT | R273H | WT | T790M, L858R | E69* | Q37* het | WT |
| HCC15 | M | 47 | African-American | SCC | N/A | unknown | primary | WT | WT | mut | mut | M272* | WT | mut/hyperm | deletion | WT |
| H2030 | M | N/A | N/A | AdC | N/A | unknown | metastasis | WT | G12C | WT | G262V | deletion | WT | WT | E317* | WT |
| H1650 | M | 27 | Caucasian | AdC (BAC) | IIIB | 10 | pleura | WT | WT | WT | deletion | WT | E746X | deletion | WT | WT |
| HCC4006 | M | N/A | Caucasian | AdC | N/A | non-smoker | N/A | WT | WT | WT | N/A | N/A | L747_E749del | N/A | WT | WT |
| HCC827 | F | 39 | Caucasian | AdC | N/A | 4 | N/A | WT | WT | WT | N/A | WT | E746_A750del | N/A | WT | WT |
| H1299 | M | 43 | Caucasian | LC | IIIA | 50 | lymph node | WT | WT | Q61K | deletion | Y560* | WT | hypermeth | WT | WT |
| H322 | M | 52 | Caucasian | AdC (BAC) | IV | 60 | lymph node | WT | WT | WT | N/A | N/A | WT | deletion | WT | WT |
| HCC95 | M | 64 | Caucasian | SCC | IV | unknown | pleura | Amplified | WT | WT | WT | WT | WT | mut/hyperm | WT | WT |
| H2009 | F | 68 | Caucasian | AdC | IV | 30 | lymph node | E711D | G12A | WT | R273L | WT | WT | WT | WT | WT |
| Sw1573 | F | 44 | Caucasian | AdC | N/A | unknown | primary | K111E | G12C | WT | WT | WT | WT | deletion | WT | N/A |
| H2122 | F | 46 | Caucasian | AdC | IV | 30 | pleura | WT | G12C | WT | Q16L, C176F | WT | WT | deletion | P281* | WT |
| H520 | M | N/A | N/A | SCC | N/A | non-smoker | primary | WT | WT | WT | W146* | WT | WT | G45* | WT | WT |
| Calu6 | F | 61 | Caucasian | AdC (Ana) | N/A | unknown | primary | N/A | Q61K | WT | R196* | WT | WT | WT | WT | WT |
| Calu3 | M | 25 | Caucasian | AdC | N/A | unknown | pleura | Amplified | WT | WT | M237I | WT | WT | hypermeth | WT | WT |
| H460 | M | N/A | N/A | LC | N/A | non-smoker | primary | E545K | Q61H | WT | mut | WT | WT | deletion | Q37* | WT |
| H3255 | F | 47 | Caucasian | AdC | IIIB | non-smoker | N/A | Amplified | G12C | WT | N/A | N/A | L858R | N/A | N/A | WT |
| H23 | M | 51 | African-American | AdC | N/A | 40 | primary | WT | G12C | WT | M246I | K1533N | WT | hypermeth | W322* | WT |
| H441 | M | 33 | N/A | AdC (pap) | IIIA | non-smoker | pleura | WT | G12V | WT | R158L | WT | WT | hypermeth | WT | WT |

*FIG. 29*

METHODS AND ASSAYS FOR COMBINATION TREATMENT OF CANCER

CROSS-REFERENCE TO RELATED APPLICATION

This application is a 35 U.S.C. § 371 National Phase Entry Application of International Application No. PCT/US2013/069557 filed Nov. 12, 2013, which designates the U.S., and which claims benefit under 35 U.S.C. § 119(e) of U.S. Provisional Application No. 61/735,303 filed Dec. 10, 2012, the contents of which are incorporated herein by reference in its entirety.

GOVERNMENT SUPPORT

This invention was made with Government support under grants Nos. RO 1 HL090136 and U01 HL100402 awarded by the National Institutes of Health and the National Heart, Lung and Blood Institute. The government has certain rights in the invention.

SEQUENCE LISTING

The instant application contains a Sequence Listing which has been submitted electronically in ASCII format and is hereby incorporated by reference in its entirety. Said ASCII copy, created on Nov. 6, 2013, is named 701039-073361-PCT_SL.txt and is 77,118 bytes in size.

TECHNICAL FIELD

The technology described herein relates to the treatment of cancer.

BACKGROUND

The gene expression of a cell can be regulated by epigenetic mechanisms, i.e. by altering the physical state of the chromosomes themselves. One such epigenetic mechanism is based upon the modification of histones. Depending upon the modification, an area of the genome can be made more or less accessible to transcriptional machinery, essentially up or down regulating gene expression in that area, leading to changes in cell behavior and characteristics.

Such epigenetic mechanisms, such as histone modifications, are thought to be crucial for the survival of cancer cells, particularly metastatic cells and those which are resistant to standard therapies (Baylin, 2011, Crea et al., 2011a, Min et al., 2010, Iliopoulos et al., 2010). Therefore, combining epigenetic therapies with chemotherapy and radiation treatments may allow for more complete treatment responses.

Polycomb Repressive Complexes (PRCs) are key regulators of, e.g. histone modifications in cancer cells (Simon and Lange, 2008, Lee et al., 2006, Ben-Porath et al., 2008). PRC2 often contains EZH2, a methyltransferase that trimethylates histone H3 at lysine 27 (H3K27me3). Accordingly, EZH2 inhibition has been identified as a possible therapeutic strategy for the treatment of cancer.

SUMMARY

As described herein, the inventors have discovered that cancer cells can exhibit one of two phenotypes in response to EZH2 inhibition. In the first phenotype, the cell is rendered more sensitive to treatment with a chemotherapeutic agent (i.e. an agent other than the agent which inhibits EZH2), while in the second phenotype, the cell becomes more protected from treatment with the chemotherapeutic agent. Further, the inventors have identified methods and assays for determining which phenotype a cell will exhibit, permitting subjects who will benefit from the combination therapy to be identified and treated; and permitting practitioners to avoid administering a treatment that would be harmful to a subject with the resistant phenotype.

In some aspects, described herein is a method of treating cancer, the method comprising: administering or prescribing a chemotherapeutic agent and an EZH2 inhibitor to a subject determined to have a sensitizing mutation of BRG1, EGFR, or B-RAF in a tumor cell.

In some aspects, described herein, is a method of identifying a subject who is a candidate for treatment of cancer with a combination therapy comprising an EZH2 inhibitor and a chemotherapeutic agent, the method comprising: detecting a sensitizing mutation of BRG1, EGFR, or B-RAF in a tumor cell sample obtained from the subject; wherein if the sensitizing mutation is detected, the subject is identified as a candidate for cancer treatment with a combination therapy comprising a chemotherapeutic agent and an EZH2 inhibitor; and wherein if the sensitizing mutation is not detected, the subject is identified as a candidate for cancer treatment which does not comprise administering an EZH2 inhibitor.

In some aspects, described herein is a method of classifying a tumor cell as an EZH2 combination treatment responsive tumor, the method comprising: detecting a sensitizing mutation of BRG1, EGFR, or B-RAF in a sample comprising the tumor cell; wherein the presence of a sensitizing mutation of BRG1, EGFR, or B-RAF classifies the tumor as a EZH2 combination treatment responsive tumor and the absence of a sensitizing mutation of BRG1, EGFR, or B-RAF classifies the tumor as a EZH2 combination treatment non-responsive tumor.

In some embodiments of the foregoing aspects, the EZH2 inhibitor is selected from the group consisting of an inhibitory nucleic acid; DZNep; and S-adenosyl-L-homocysteine. In some embodiments of the foregoing aspects, the chemotherapeutic agent is selected from the group consisting of a topoisomerase inhibitor; a topoisomerase I inhibitor; and a topoisomerase II inhibitor. In some embodiments of the foregoing aspects, the chemotherapeutic agent is a topoisomerase I inhibitor selected from the group consisting of: camptothecins; topotecan; irinotecan; indenoisoquinolines; indotecan; and indimitecan; and lamellarin D. In some embodiments of the foregoing aspects, the chemotherapeutic agent is a topoisomerase II inhibitor selected from the group consisting of: doxorubicin; etoposide; amsacrine; teniposide; ICRF-193; genistein; daunorubicin; mitoxantrone; ellipticines; aurintricarboxylic acid; and HU-331. In some embodiments of the foregoing aspects, the chemotherapeutic agent is a PARP inhibitor. In some embodiments of the foregoing aspects, the chemotherapeutic agent is a CDK1 inhibitor. In some embodiments of the foregoing aspects, the chemotherapeutic agent is an EGFR inhibitor. In some embodiments of the foregoing aspects, the sensitizing mutation of BRG1 comprises a mutation selected from the group consisting of: a mutation which inactivates the ATPase activity of BRG1; a mutation which decreases the expression of BRG1; P270*; Q729*; W764R; T58*; and M272*. In some embodiments of the foregoing aspects, the sensitizing mutation of EGFR comprises a mutation selected from the group consisting of: a mutation which increased the expression level of EGFR; E746_A750del; E746_A749del;

T790M; and L858R. In some embodiments of the foregoing aspects, the sensitizing mutation of B-RAF comprises a mutation selected from the group consisting of: G496A and L597V. In some embodiments of the foregoing aspects, the presence of the mutation is determined using an assay selected from the group consisting of: hybridization; sequencing; exome capture; PCR; and high-throughput sequencing. In some embodiments of the foregoing aspects, the mutation is present in the genomic DNA of the tumor cell. In some embodiments of the foregoing aspects, the mutation is present in the mRNA transcripts of the tumor cell. In some embodiments of the foregoing aspects, the cancer is selected from the group consisting of: lung cancer; non-small cell lung cancer; ovarian cancer; EGFR-expressing ovarian cancer; B-Raf V600E melanomas; breast cancer; colon cancer; EGFR-mutated cancers; EGFR-mutated breast cancers; and EGFR-mutated colon cancers. In some embodiments of the foregoing aspects, the method further comprises the step of generating a report based on the detection of a sensitizing mutation in BRG1, EGFR, or B-RAF by a non-human machine.

In some aspects, described herein is an assay comprising: subjecting a tumor cell sample from a subject to at least one analysis to detect the presence of a sensitizing mutation of BRG1, EGFR, or B-RAF; wherein the presence of a sensitizing mutation of BRG1, EGFR, or B-RAF indicates the subject has a cancer which will respond to treatment with an EZH2 inhibitor and a chemotherapeutic agent. In some embodiments, the presence of the mutation is determined using an assay selected from the group consisting of: hybridization; sequencing; exome capture; PCR; and high-throughput sequencing.

In some aspects, described herein is an assay for selecting a treatment regimen for a subject with cancer, comprising: subjecting a nucleotide molecule derived from a biological sample of a subject, who is determined to suffer from or have a risk for cancer, to at least one genotyping analysis adapted to determine the the presence of a sensitizing mutation in one or more of B-RAF, EGFR, and BRG1: wherein if at least one sensitizing mutation is determined to be present, a treatment regimen comprising a combination of an EZH2 inhibitor and a chemotherapeutic agent is administered. In some embodiments, wherein if no sensitizing mutations are determined to be present, a treatment regimen comprising a combination of an EZH2 inhibitor and a chemotherapeutic agent is not administered. In some embodiments, the biological sample comprises a tumor cell.

In some aspects, described herein is an assay comprising: contacting a tumor cell sample obtained from a human subject having cancer with a nucleic acid probe to detect the presence of a sensitizing mutation in BRG1, EGFR, or B-RAF; and detecting the presence or intensity of a signal which indicates the presence of a sensitizing mutation in BRG1, EGFR, or B-RAF; wherein the presence of a sensitizing mutation of BRG1, EGFR, or B-RAF indicates the subject has a cancer which will respond to treatment with an EZH2 inhibitor and a chemotherapeutic agent.

In some embodiments of the foregoing aspects, a detectable signal is generated by the probe when a sensitizing mutation is present. In some embodiments of the foregoing aspects, the probe is detectably labeled. In some embodiments of the foregoing aspects, the sensitizing mutation of BRG1 comprises a mutation selected from the group consisting of: a mutation which inactivates the ATPase activity of BRG1; a mutation which decreases the expression of BRG1; P270*; Q729*; W764R; T58*; and M272*. In some embodiments of the foregoing aspects, the sensitizing mutation of EGFR comprises a mutation selected from the group consisting of: a mutation which increased the expression level of EGFR; E746_A750del; E746_A749del; T790M; and L858R. In some embodiments of the foregoing aspects, the sensitizing mutation of B-RAF comprises a mutation selected from the group consisting of: G496A and L597V. In some embodiments of the foregoing aspects, the mutation is present in the genomic DNA of the tumor cell. In some embodiments of the foregoing aspects, the mutation is present in the mRNA transcripts of the tumor cell. In some embodiments of the foregoing aspects, the assay further comprises the step of generating a report based on the detection of a sensitizing mutation in BRG1, EGFR, or B-RAF by a non-human machine.

In some aspects, described herein is a method of determining whether a subject is likely to respond to a combination treatment for cancer, the method comprising: detecting the presence of a sensitizing mutation in BRG1, EGFR, or B-RAF in a tumor cell sample obtained from the subject; wherein the presence of a sensitizing mutation in BRG1, EGFR, or B-RAF indicates the subject has an increased likelihood of responding to a treatment to cancer; wherein the treatment for cancer comprises administration of an EZH2 inhibitor and a chemotherapeutic agent.

In some embodiments of the foregoing aspects, the EZH2 inhibitor is selected from the group consisting of an inhibitory nucleic acid; DZNep; S-adenosyl-L-homocysteine. In some embodiments of the foregoing aspects, the chemotherapeutic agent is selected from the group consisting of: a topoisomerase inhibitor; a topoisomerase I inhibitor; a topoisomerase II inhibitor. In some embodiments of the foregoing aspects, the chemotherapeutic agent is a topoisomerase I inhibitor selected from the group consisting of camptothecins; topotecan; irinotecan; indenoisoquinolines; indotecan; and indimitecan; and lamellarin D. In some embodiments of the foregoing aspects, the chemotherapeutic agent is a topoisomerase II inhibitor selected from the group consisting of: doxorubicin; etoposide; amsacrine; teniposide; ICRF-193; genistein; daunorubicin; mitoxantrone; ellipticines; aurintricarboxylic acid; and HU-331. In some embodiments of the foregoing aspects, the chemotherapeutic agent is a PARP inhibitor. In some embodiments of the foregoing aspects, the chemotherapeutic agent is a CDK1 inhibitor. In some embodiments of the foregoing aspects, the chemotherapeutic agent is an EGFR inhibitor. In some embodiments of the foregoing aspects, the sensitizing mutation of BRG1 comprises a mutation selected from the group consisting of: a mutation which inactivates the ATPase activity of BRG1; a mutation which decreases the expression of BRG1; P270*; Q729*; W764R; T58*; and M272*. In some embodiments of the foregoing aspects, the sensitizing mutation of EGFR comprises a mutation selected from the group consisting of: a mutation which increased the expression level of EGFR; E746_A750del; E746_A749del; T790M; and L858R. In some embodiments of the foregoing aspects, the sensitizing mutation of B-RAF comprises a mutation selected from the group consisting of: G496A and L597V. In some embodiments of the foregoing aspects, the presence of the mutation is determined using an assay selected from the group consisting of: hybridization; sequencing; exome capture; PCR; and high-throughput sequencing. In some embodiments of the foregoing aspects, the mutation is present in the genomic DNA of the tumor cell. In some embodiments of the foregoing aspects, the mutation is present in the mRNA transcripts of the tumor cell. In some embodiments of the foregoing aspects, the cancer is selected from the group consisting of lung cancer;

non-small cell lung cancer; ovarian cancer; EGFR-expressing ovarian cancer; B-Raf V600E melanomas; breast cancer; colon cancer; EGFR-mutated cancers; EGFR-mutated breast cancers; and EGFR-mutated colon cancers.

In some aspects, described herein is a computer system for determining if a subject will be responsive to a cancer treatment, the system comprising: a determination module configured to detect the presence of a sensitizing mutation in BRG1, EGFR, or B-RAF in a tumor cell sample obtained from a subject; a storage module configured to store output data from the determination module; a comparison module adapted to compare the data stored on the storage module with a reference level, and to provide a retrieved content, and a display module for displaying whether a BRG1, EGFR, or B-RAF sensitizing mutation was detected in the tumor cell sample; wherein the cancer treatment comprises the administration of an EZH2 inhibitor and a chemotherapeutic agent. In some embodiments, the determining module measures the intensity of a detectable signal from a RT-PCR assay indicating the presence of a sensitizing mutation of BRG1, EGFR, or B-RAF tumor cell sample. In some embodiments, the determining module measures the intensity of a detectable signal from a sequencing assay indicating the presence of a sensitizing mutation of BRG1, EGFR, or B-RAF tumor cell sample. In some embodiments, the determining module measures the intensity of a detectable signal from a hybridization assay indicating the presence of a sensitizing mutation of BRG1, EGFR, or B-RAF tumor cell sample. In some embodiments, if the computing module determines that the a sensitizing mutation of BRG1, EGFR, or B-RAF is present in the sample obtained from the subject, the display module displays a signal indicating that a sensitizing mutation has been detected. In some embodiments, the signal indicates that the subject has an increased likelihood of responding to treatment with an EZH2 inhibitor and chemotherapeutic agent. In some embodiments, the EZH2 inhibitor is selected from the group consisting of: an inhibitory nucleic acid; DZNep; S-adenosyl-L-homocysteine. In some embodiments, the chemotherapeutic agent is selected from the group consisting of: a topoisomerase inhibitor; a topoisomerase I inhibitor; a topoisomerase II inhibitor. In some embodiments, the chemotherapeutic agent is a topoisomerase I inhibitor selected from the group consisting of: camptothecins; topotecan; irinotecan; indenoisoquinolines; indotecan; and indimitecan; and lamellarin D. In some embodiments, the chemotherapeutic agent is a topoisomerase II inhibitor selected from the group consisting of: doxorubicin; etoposide; amsacrine; teniposide; ICRF-193; genistein; daunorubicin; mitoxantrone; ellipticines; aurintricarboxylic acid; and HU-331. In some embodiments, the chemotherapeutic agent is a PARP inhibitor. In some embodiments, the chemotherapeutic agent is a CDK1 inhibitor. In some embodiments, the chemotherapeutic agent is an EGFR inhibitor. In some embodiments, the sensitizing mutation of BRG1 comprises a mutation selected from the group consisting of: a mutation which inactivates the ATPase activity of BRG1; a mutation which decreases the expression of BRG1; P270*; Q729*; W764R; T58*; and M272*. In some embodiments, the sensitizing mutation of EGFR comprises a mutation selected from the group consisting of: a mutation which increased the expression level of EGFR; E746_A750del; E746_A749del; T790M; and L858R. In some embodiments, the sensitizing mutation of B-RAF comprises a mutation selected from the group consisting of: G496A and L597V. In some embodiments, the presence of the mutation is determined using an assay selected from the group consisting of: hybridization; sequencing; exome capture; PCR; and high-throughput sequencing. In some embodiments, the mutation is present in the genomic DNA of the tumor cell. In some embodiments, the mutation is present in the mRNA transcripts of the tumor cell. In some embodiments, the cancer is selected from the group consisting of: lung cancer; non-small cell lung cancer; ovarian cancer; EGFR-expressing ovarian cancer; B-Raf V600E melanomas; breast cancer: colon cancer; EGFR-mutated cancers; EGFR-mutated breast cancers; and EGFR-mutated colon cancers.

In some aspects, described herein is a kit comprising: a nucleic acid probe which is specific for a sensitizing mutation of BRG1, EGFR, or B-RAF. In some embodiments, the probe is detectably labeled. In some aspects, described herein is a kit comprising: a nucleic acid probe which can amplify a nucleic acid sequence comprising a sensitizing mutation of BRG1, EGFR, or B-RAF. In some embodiments, the kit further comprises a reagent for producing a detectable signal.

In some aspects, described herein is the use of an EZH2 inhibitor in combination with a chemotherapeutic agent in treatment of a subject determined to have a sensitizing mutation of BRG1, EGFR, or B-RAF in a tumor cell obtained from the subject. In some embodiments, the EZH2 inhibitor is selected from the group consisting of: an inhibitory nucleic acid; DZNep; and S-adenosyl-L-homocysteine. In some embodiments, the chemotherapeutic agent is selected from the group consisting of: a topoisomerase inhibitor; a topoisomerase I inhibitor; and a topoisomerase II inhibitor. In some embodiments, the chemotherapeutic agent is a topoisomerase I inhibitor selected from the group consisting of: camptothecins; topotecan; irinotecan; indenoisoquinolines; indotecan; and indimitecan; and lamellarin D. In some embodiments, the chemotherapeutic agent is a topoisomerase II inhibitor selected from the group consisting of: doxorubicin; etoposide; amsacrine; teniposide; ICRF-193; genistein; daunorubicin; mitoxantrone; ellipticines; aurintricarboxylic acid; and HU-331. In some embodiments, the chemotherapeutic agent is a PARP inhibitor. In some embodiments, the chemotherapeutic agent is a CDK1 inhibitor. In some embodiments, the chemotherapeutic agent is an EGFR inhibitor. In some embodiments, the sensitizing mutation of BRG1 comprises a mutation selected from the group consisting of: a mutation which inactivates the ATPase activity of BRG1; a mutation which decreases the expression of BRG1; P270*; Q729*; W764R; T58*; and M272*. In some embodiments, the sensitizing mutation of EGFR comprises a mutation selected from the group consisting of: a mutation which increased the expression level of EGFR; E746_A750del; E746_A749del; T790M; and L858R. In some embodiments, the sensitizing mutation of B-RAF comprises a mutation selected from the group consisting of: G496A and L597V. In some embodiments, the presence of the mutation is determined using an assay selected from the group consisting of: hybridization; sequencing; exome capture; PCR; and high-throughput sequencing. In some embodiments, the mutation is present in the genomic DNA of the tumor cell. In some embodiments, the mutation is present in the mRNA transcripts of the tumor cell. In some embodiments, the cancer is selected from the group consisting of: lung cancer; non-small cell lung cancer; ovarian cancer; EGFR-expressing ovarian cancer; B-Raf V600E melanomas; breast cancer; colon cancer; EGFR-mutated cancers; EGFR-mutated breast cancers; and EGFR-mutated colon cancers. In some embodiments, the use further comprises the step of generating a report based on the detection of a sensitizing mutation in BRG1, EGFR, or B-RAF by a non-human machine.

BRIEF DESCRIPTION OF THE DRAWINGS

FIG. 1A depicts images of film. Cell lines were infected with pLK0.1 lentivirus encoding either shGFP or shEZH2 and selected with puromycin for 1 week. Western Blot for EZH2 and H3K27me3 was performed on whole cell extracts from indicated lines for EZH2 and its catalytic mark H3K27me3, β-actin is shown as loading control. FIG. 1B depicts a graph of growth rates of matched shGFP and shEZH2 cell lines assayed by Cell Titer Glo at days 3, 5, 7, and 10 post plating at equal densities. Average luminescence ±s.e.m, for 3 replicate wells is shown based on when each shGFP cell line reached logarithmic growth, * indicates p<0.03. FIG. 1C depicts a graph of cell survival of shGFP and shEZH2 cell lines plated and treated with etoposide for 4 days. Average change ±s.e.m. in % survival between shGFP and shEZH2 lines is graphed for 1 μM and 10 μM etoposide, n=3 technical replicates, ** indicates p<0.0001.

FIG. 2A depicts a Western Blot for EZH2 and H3K27me3 performed on whole cell extracts 4 days after indicated treatments, β-actin shown as a loading control. FIG. 2B depicts a graph of the growth rates of matched shGFP and shGFP cells treated with 1 μM DZNep and assayed by Cell Titer Glo at days 3, 5, 7, and 10 post plating at equal densities. Average luminescence ±s.e.m. for 3 replicate wells is shown based on when each shGFP cell line reached logarithmic growth, * indicates p<0.03. FIG. 2C depicts a graph of the response to Etoposide. Cell lines were plated at equal densities and treated a range of etoposide doses with or without 1 μM DZNep. On the 4th day, cell viability was measured using Cell Titer Glo and the percent survival at each dose of etoposide was calculated. Dose response curves were generated for the no DZNep and DZNep treated cells using the GraphPad prism software and IC50s were extrapolated. The fold change±s.e.m. of etoposide IC50 in response to DZNep is plotted, n=4 biological replicates, * indicates p<0.05. Cell lines with mutations in Brg1, EGFR and B-Raf are indicated.

FIG. 4A depicts a graph of Gene Ontology term enrichment for the EZH2 co-expressed gene signature, of 64 enriched GO terms with p<0.001, 12 selected gene sets are graphed. All 64 GO terms are described in Table 3. FIG. 4B depicts a graph of survival of patients whose tumor samples had either high expression or low expression of the EZH2 co-expression gene signature. FIG. 4C depicts a graph of 7-AAD cell cycle flow cytometry performed on cell lines were plated cultured with or without 10 μM etoposide or 1 uM DZNep for 4 deays. The average change in % of each cell cycle stage in response to DZNep is plotted, * indicates p=0.0001. FIG. 4D depicts a graph of the same analysis in (FIG. 4C) performed with shGFP and shEZH2 cells, ** indicates P=0.0006. For all these studies the average of 3 biological replicates ±s.e.m. is shown. FIG. 4E depicsts a graph of quantitative RT-PCR for change in expression of p57, Brg1 and EGFR in response to etoposide and etoposide/DZNep treatment. Results from two biological replicates of HCC2450, H157, H522 and HCC15 (sensitized) and H441, H460, H23, and Calu6 (protected) lines were averaged and graphed ±s.e.m, * indicates p=0.03 for Brg1,  indicates p=0.005 for EGFR, and * indicates p=0.01 for p57.

FIG. 5A depicts a graph of EGFR and BRG1 expression in tumors. Tumors from the Director's Challenge with a normalized expression of more than 1400 for either EGFR or Brg1 were plotted and correlation was assessed, Spearman's correlation coefficient –0.619, p=0.0002. FIG. 5B depicts a graph of average probe intensity of EGFR probe (201983_s_at) on the U133A Affymetrix array in primary squamous cell carcinoma samples from TCGA with various EGFR and Brg1 mutational statuses, * indicates p=0.003,  indicates p<0.0001. FIG. 5C depicts a graph of average probe intensity of EGFR probe (201983_s_at) on the U133A Affymetrix array for cell lines with various EGFR and Brg1 mutational statuses, * indicates p=0.02.

FIGS. 6A-6D demonstrate that Brg1 and EGFR genetically interact to control the sensitized phenotype. FIGS. 6A and 6B depict graphs of HCC15 (FIG. 6A) and H460 (FIG. 6B) cells as analyzed by 7AAD flow cytometry to assess changes in cell cycle status in response to DZNep, n=2 technical replicates, * indicates p=0.002, ** indicates p=0.02. FIGS. 6C and 6D depict graphs of quantitative RT-PCR for p57, Brg1 and EGFR expression in the various indicated treated transduced cell lines * indicates p=x,  indicates p=y, * indicates p=z.

FIG. 7A depicts images of western blots of shGFP and shEZH2 cell line lysates for H3K27me3, β-actin is shown as loading control. FIG. 7B depicts a graph of primary tumorsphere formation, visible spheres per 5,000 cells plated were counted at day 10. FIG. 7C depicts a graph of secondary non-adherent tumorsphere formation quantified 10 days after plating single dissociated cells from primary tumorspheres on super-low attachment plates. Average sphere number from 3 replicate wells is plotted.

FIGS. 8A-8D depict the effects of EZH2 combination treatment. FIG. 8A depicts a waterfall plot of cell line growth in 1 μM DZNep for 4 days compared to untreated cells. FIG. 8B depicts a graph of the average growth of all sensitized and all protected lines grown in DZNep for 4 days compared to untreated cells. FIG. 8C depicts a graph of fold change in doxorubicin IC50 in response to DZNep, n=2 biological replicates. FIG. 8D depicts a graph of fold change in cis-platinum IC50 in response to DZNep, n=3 biological replicates.

FIG. 9A depicts H157 xenografts with dosing scheme B, * indicates p=0.21 DZNep vs untreated and ** indicates p=0.009 DZNep vs dual. FIG. 9B depicts H23 xenografts with dosing scheme A, * indicates p=0.18 DZNep vs dual, ** indicates p=0.011 DZNep vs untreated.

FIGS. 10A-10B depict representative 7AAD flow cytometry histograms analyzed with ModFit LT software. Both the 'sensitized' H157 line (FIG. 10A) and the 'protected' H460 lines (FIG. 10B) are shown. FIG. 10C depicts a graph of RT qPCR for EZH2 expression in indicated cell lines after 4 days of indicated treatments. FIG. 10D depicts a graph of RT qPCR for p27 and p21 expression. FIG. 10E depicts a graph of the results of quantitative RT-PCR for p27 and p21 in H522, H157, HCC15 (sensitized) and H460, H23, H441 (protected) lines in indicated treatments. FIG. 10F depicts a graph of the results of quantitative RT-PCR for p57 in H522, H157, HCC15, HCC2450, A549 (sensitized) and H460, H23, H441, Sw1573, and Calu6 (protected) lines. Average changes relative to untreated for the groups of lines are plotted.

FIG. 11A depicts a Venn diagram of differential gene expression over-lap between cell lines of various genotypes. FIG. 11B depicts a graph of averaged EZH2 probe (203358_s_at) intensity within each cell line genotype indicated. FIG. 11C depicts a graph of RT-qPCR of EZH2 and Suz12 gene expression in the indicated cell lines graphed relative to the average expression among the lines. A trend line for EZH2 expression was added to show no significant difference between sensitized (left side) and protected (right side) cell lines. FIG. 11D depicts graphs of additional Brg1 and EGFR modulation cell line RT-qPCR, the protected cell line H2122 and the sensitized cell line H1299 are shown.

FIG. 12A depicts etoposide dose response curves for HCC15 cells corresponding to data graphed in FIG. 6A. FIG. 12B depicts etoposide dose response curves for H460 cells corresponding to data graphed in FIG. 6B.

FIGS. 17A-17B depict graphs of the results of quantitative RT-PCR for Brg1 and EGFR expression in the various indicated treated transduced cell lines.

FIG. 18A depicts graphs of survival of lung adenocarcinoma patients in the Director's Challenge dataset. Samples were hierarchically clustered using the primary tumor generated EZH2 co-expression signature (Table 2) into two risk groups. The Kaplan-Meier curves for the groups are shown for all patients (n=416), only Stage 1 patients (n=142) or only patients with moderately differentiated tumors (n=74). FIG. 18B depicts a graph of expression of EZH2 mRNA in human NSCLC cell lines compared to lung cells isolated from 4 normal patient samples (see methods). FIG. 18C depicts western blot results. Cell lines were infected with pLKO.1 lentivirus encoding either shGFP or shEZH2 and selected with puromycin. Western Blot for EZH2 and H3K27me3 was performed on whole cell extracts from indicated lines for EZH2 and its catalytic mark H3K27me3, total Histone H3 is shown as loading control. CR indicates a coding region targeting hairpin. FIG. 18D depicts graphs of shGFP and shEZH2 cell lines plated and treated with etoposide for 4 days. Cell growth was measured using CellTiter-Glo and dose response curves were constructed using GraphPad Prism software. Representative H157 and H460 curves are shown. FIG. 18E depicts a graph of average fold change in etoposide $IC_{50}$±s.e.m. is graphed, n=3-4 biological replicates, * indicates p<0.04, ** p<0.002. FIG. 18F depicts a graph of rescue of 3'UTR hairpin by overexpression of EZH2 cDNA. Also see FIG. 24A.

FIG. 19A depicts the results of a Western Blot. Western Blot for EZH2 and H3K27me3 was performed on whole cell extracts 4 days after administration of 1 μM DZNep or vehicle, total Histone H3 is shown as a loading control. FIG. 19B depicts graphs of cell viability. Cell lines were plated at equal densities and treated a range of etoposide doses with or without 1 μM DZNep. On the 4$^{th}$ day, cell viability was measured using CellTiter-Glo and the percent survival at each dose of etoposide was calculated. Dose response curves were generated for the vehicle- and DZNep-treated cells using the GraphPad prism software and $IC_{50}$s were extrapolated. The fold change ±s.e.m. of etoposide $IC_{50}$ in response to DZNep is plotted, n=4 biological replicates, * indicates p<0.01. Cell lines with mutations in BRG1 or EGFR are indicated. FIG. 19C depicts a Western Blot for EZH2 and H3K27me3 performed on whole cell extracts from cultures treated with 10 μM GSK126 or vehicle, total Histone H3 is shown as a loading control. FIG. 19D depicts a graph of dose response curves generated as described in FIG. 19B using 10 μM GSK126 in the place of 1 μM DZNcp, * indicates p<0.03, ** p<0.01. Also see FIGS. 25A-25C.

FIGS. 20A-20B demonstrate that in vitro sensitivities to DZNep/etoposide predict in vivo responses. FIG. 20A depicts a waterfall plot depicting tumor growth of EGFR-driven tumors after 2 weeks and 4 weeks of treatment with vehicle, etoposide, DZNep, and etoposide/DZNep. The y-axis indicates % tumor growth vs. day 0. Each bar represents an individual mouse. Statistical analyses were performed on the 4 week log 2 transformed data, p=0.008 dual vs. DZNep and p=0.004 dual vs. etoposide. FIG. 20B depicts a waterfall plot depicting tumor growth of Kras/p53 tumors after 2 weeks and 4 weeks of treatment with vehicle and etoposide/DZNep.

FIG. 21A depicts graphs of the % S phase of the indicated cells. 7-AAD cell cycle flow cytometry was performed on cell lines cultured with or without 5 μM etoposide or 1 μM DZNep for 4 days. The average % S phase+/-s.e.m. of each culture is plotted, n=3-4 biological replicates, * indicates p<0.05 ** p<0.009. FIG. 21B depicts graphs of Annexin V+/7AAD- cells quantified by flow cytometry from cultures 4 days after indicated treatments. n=3-4 biological replicates, * indicates p<0.03 dual vs.

etoposide, ** p=0.001 DZNep vs. vehicle. FIG. 21C depicts representative images of nuclei undergoing a normal anaphase and of nuclei that scored positively for the presence of anaphase bridges. FIG. 21D depicts a graph of the quantification of the percentage of anaphase cells that showed bridges in untreated or DZNep treated cell lines. n=4 biological replicates of 18-25 anaphase nuclei, * indicates p<0.05, ** p<0.03. FIG. 21E depicts a graph of real time RT-PCR for BRG1 levels in indicated cell lines in response to 4 days of 1 μM DZNep, * indicates p<0.02, ** p<0.0005.

FIGS. 23A and 23B depict graphs of etoposide dose response curves performed in the presence or absence of DZNep in the indicated HCC15 and H460 stably transduced cell lines. The fold change ±range of etoposide $IC_{50}$ in response to DZNep is plotted, n=3 biological replicates, * indicates p<0.04, ** p<0.0001. FIGS. 23C and 23D depict graphs for the indicated HCC15 and H460 stably transduced etoposide treated cell lines, where 7AAD flow cytometry was used to assess changes in S phase percentage in response to DZNep, n=3 biological replicates, * indicates p=0.02, ** p<0.001. FIGS. 23E and 23F depict graphs of the quantification of the percentage of anaphase cells that showed bridges in untreated or DZNep treated cell lines, n=3 biological replicates of 11-25 anaphase nuclei, * indicates p<0.04, ** p<0.02. FIG. 23G depicts a model of the interaction of EZH2 with BRG1 and EGFR.

FIG. 24A depicts the results of a Western blot. Western Blot was performed on whole cell extracts from indicated lines for EZH2 and its catalytic mark H3K27me3, total Histone H3 is shown as loading control. CR indicates a coding region targeting hairpin. FIG. 24B depicts a graph of growth. The indicated stably transduced cell lines were plated at equal density. On the $4^{th}$ day of culture, cell viability was measured using CellTiter-Glo and the percent survival relative to the shGFP line was calculated, n=3-4 biological replicates, * indicates p<0.03, ** p<0.002; y-axis begins at 60% to more clearly show the differences between cell lines. FIG. 24C depicts a graph of Real time RT-PCR for EZH2 mRNA in the indicated cell lines after plating at equal density and treating for 4 days with indicated treatments. Each cell line is normalized to its shGFP control.

FIGS. 25A-25C demonstrate the effect of combination treatment using DZNep. FIG. 25A is a Waterfall plot of cell line growth in 1 μM DZNep for 4 days compared to untreated cells, n=3-5 biological replicates, * indicates p<0.04, ** p<0.007. FIG. 25B is a graph of average etoposide $IC_{50}$ for two classes of cell lines, sensitized to etoposide by EZH2 inhibition, and protected from etoposide by EZH2 inhibition, in the presence or absence of DZNep, * indicates p=0.032. FIG. 25C is a pair of representative etoposide dose response curves performed in the presence of 5 μM cisplatin, the sensitized line PC9 (4.2-fold decrease, p<0.0001) and the protected line H23 (3.4-fold increase, p<0.0001) are shown.

FIG. 26A depicts a graph of average change in % of S phase between DZNep treated cultures and vehicle treated is plotted, * indicates p=0.0001. FIG. 26B depicts a graph of the average change in % of S phase in shEZH2 cultures and shGFP cultures is plotted, * indicates p=0.0006. FIG. 26C depicts graphs of 7-AAD cell cycle flow cytometry on cultures corresponding to the matched controls for each experiment shown in FIG. 3A. The average % S phase+/−s.e.m. of each culture is plotted, n=3-4 biological replicates.

FIG. 28A-28C demonstrates the interaction of EZH2 and BRG1 and EGFR FIG. 28A depicts graphs of real time RT-PCR for BRG1 and EGFR expression in the various indicated treated transduced cell lines. FIG. 28B depicts graphs of cell survival of the indicated stably transduced cell lines were plated at equal density. On the $4^{th}$ day of culture, cell viability was measured using CellTiter-Glo and the percent survival relative to the shGFP line was calculated, n=3 biological replicates, * indicates p<0.05, ** p<0.008. FIG. 28C depicts graphs of sub-G1 fractions of the indicated 4-day cultures as assessed during 7AAD cell cycle flow cytometry analysis. Critically, for these assays the supernatant of each culture was retained and combined with the trypsinized adherent cells to accurately reflect the total amount of apoptosis/necrosis in each culture, n=3 biological replicates, * indicates p=0.03.

FIG. 29 depicts a table of the mutational status of the cell lines used in the Examples.

DETAILED DESCRIPTION

Figure 1A:
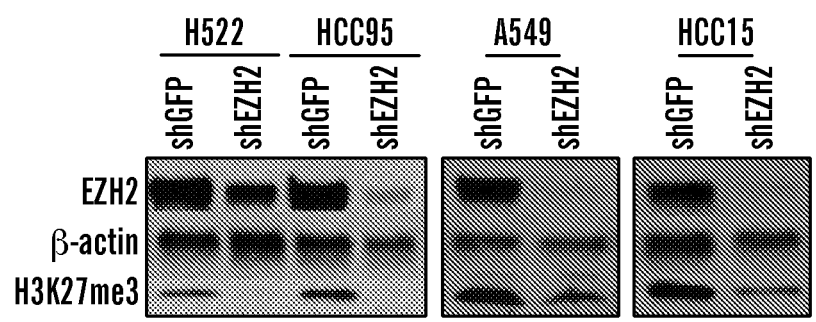
FIGS. 1A-1C demonstrate that EZH2 knock-down has differential effects on chemotherapy sensitivities.

One route of improving cancer treatment is to seek to combine therapeutics, which target different molecules or pathways within a cancerous cell. Occassionally, such combination therapies can produce additive or even synergistic effects. As described in the Examples herein, the inventors were examining combination therapies involving EZH2 inhibition and found that while in some cases a combination therapy performs better than administration of the chemotherapeutic alone, in other cases, the combination of an inhibitor of EZH2 and a chemotherapeutic actually increased the cancer's resistance to the chemotherapeutic, worsening the outcome. As further described herein, the inventors have determined the molecular and genetic basis for these divergent resistant/susceptible phenotypes.

The inventors' discoveries regarding the effect of EZH2 inhibition on different populations of cancer cells as regards their responsiveness to chemotherapy permits the identification and treatment of subjects who can benefit from the described EZH2 inhibition combination therapies. Conversely, patients who should not receive such combination therapies can also be identified, permitting practitioners to avoid administering therapies that would be ineffective or actually worsen a cancer. Described herein are methods of treatment, assays, and systems related to these discoveries.

As described in the Examples herein, the inventors have determined that sensitizing mutations in BRG1, EGFR, or B-RAF result in an "EZH2 inhibitor sensitizing" phenotype, i.e. inhibiting EZH2 in such cells will sensitize them to the action of a chemotherapeutic. When cells that do not comprise such sensitizing mutations are contacted with an EZH2 inhibitor, they will either experience no change in their response to a chemotherapeutic or become protected from the chemotherapeutic. Accordingly, in one aspect, the technology described herein relates to a method of treating cancer, the method comprising: administering a chemotherapeutic agent and an EZH2 inhibitor to a subject determined to have a sensitizing mutation of BRG1, EGFR, or B-RAF in a tumor cell. In some embodiments, the subject can be determined to have more than one sensitizing mutation, e.g. a sensitizing mutation in BRG1 and a sensitizing mutation in EGFR, or two sensitizing mutations in BRG1. In some embodiments, the technology described herein relates to a method of treating cancer, the method comprising: administering a chemotherapeutic agent to a subject determined not to have a sensitizing mutation of BRG1, EGFR, or B-RAF in a tumor cell, and wherein the subject is not administered an EZH2 inhibitor.

As used herein, "brahma-related gene 1" or "BRG1" (e.g. NCBI Gene ID: 6597) refers to a member of the SWI/SNF family of proteins which is similar to the brahma protein of *Drosophila*. Members of this family have helicase and ATPase activities and are thought to regulate transcription of certain genes by altering the chromatin structure around those genes. The encoded protein is part of the large ATP-dependent chromatin remodeling complex SNF/SWI, which is required for transcriptional activation of genes normally repressed by chromatin. In addition, this protein can bind BRCA1, as well as regulate the expression of the tumorigenic protein CD44. Multiple isoforms of BRG1 are known. The sequences of BRG1 isoforms, genes, and transcripts are known in a variety of species, e.g. human BRG1 isoform 1 mRNA (e.g. SEQ ID NO: 004; NCBI Ref Seq: NM_001128844) and amino acid (e.g. SEQ ID NO: 003; NCBI Ref Seq: NP_001122316) sequences.

As used herein, "epidermal growth factor receptor" or "EGFR" (e.g. NCBI Gene ID: 1956) refers to a transmembrane glycoprotein that is a member of the protein kinase superfamily. This protein is a receptor for members of the epidermal growth factor family. Binding of the protein to a ligand induces receptor dimerization and tyrosine autophosphorylation and leads to cell proliferation. Multiple isoforms of EGFR are known. The sequences of EGFR isoforms, genes, and transcripts are known in a variety of species, e.g. human EGFR isoform 1 mRNA (e.g. SEQ ID NO: 006; NCBI Ref Seq: NM_005228) and amino acid (e.g. SEQ ID NO: 005; NCBI Ref Seq: NP_005219) sequences.

As used herein, "v-raf murine sarcoma viral oncogene homolog B1" or "B-RAF" (e.g. NCBI Gene ID: 6635) refers to a member of the Raf kinase family of serine/threonine-specific protein kinases. This protein plays a role in regulating the MAP kinase/ERKs signaling pathway. The sequences of B-RAF genes, transcripts, and polypeptides are known in a variety of species, e.g. human B-RAF mRNA (e.g. SEQ ID NO: 008; NCBI Ref Seq: NM_004333) and polypeptide (e.g. SEQ ID NO: 009; NCBI Ref Seq: NP_004324) sequences.

As referred to herein, a "sensitizing mutation" is a mutation which causes, at least in part, or is found associated with, a phenotype in which a cell carrying the mutation, when contacted with an agent that causes EZH2 inhibition will thereafter be more sensitive to the action of a chemotherapeutic agent, i.e. the growth of the cell will be reduced after being contacted with a chemotherapeutic agent or be more likely to die after being contacted with a chemotherapeutic agent. Described herein are sensitizing mutations in BRG1, EGFR, and B-RAF. Exemplary sensitizing mutations of BRG1 include, but are not limited to a mutation which inactivates the ATPase activity of BRG1; a mutation which decreases the expression of BRG1; and/or mutations corresponding to P270*; Q729*; W764R; T58*; and/or M272* relative to SEQ ID NO: 003. In some embodiments, the sensitizing mutation of BRG1 can be a mutation corresponding to P270*; Q729*; W764R; T58*; and/or M272* relative to SEQ ID NO: 003.

Exemplary sensitizing mutations of EGFR include, but are not limited to, a mutation which increases the expression level of EGFR; and/or a mutation corresponding to E746_A750del; E746_A749del; T790M; and/or L858R relative to SEQ ID NO: 005. In some embodiments, the sensitizing mutation of EGFR can be E746_A750del. In some embodiments, the sensitizing mutation of EGFR can be a mutation which increases the expression level of EGFR; and/or a mutation corresponding to E746_A750del; E746_A749del; T790M relative to SEQ ID NO: 005; and/or L858R. In some embodiments, the sensitizing mutation of EGFR can be a mutation corresponding to E746_A750del; E746_A749del; and/or T790M relative to SEQ ID NO: 005. In some embodiments, the sensitizing mutation of EGFR can be a mutation which deletes exon 19 of EGFR, e.g. a deletion of any or all of the nucleotides corresponding to nucleotides 2530-2715 of SEQ ID NO: 6.

Exemplary sensitizing mutations of B-RAF include, but are not limited to mutations corresponding to G496A and/or L597V relative to SEQ ID NO: 007.

In some embodiments, a cell can comprise a single sensitizing mutation. In some embodiments, a cell can comprise two or more sensitizing mutations e.g. two sensitizing mutations, three sensitizing mutations, four sensitizing mutations, or more sensitizing mutations. Multiple sensitizing mutations can be present in the same gene, e.g. two sensitizing mutations in EGFR or present in two or more genes, e.g. sensitizing mutations in B-RAF and EGFR. Exemplary examples of combinations of sensitizing mutations are shown in Table 6.

TABLE 6

Exemplary combinations of sensitizing mutations

| | | Additional possible mutations (not mutually exclusive) | | | | | | | | | | |
|---|---|---|---|---|---|---|---|---|---|---|---|---|
| First sensitizing | | EGFR | | | | B-RAF | | BRG1 | | | | |
| | mutation | E746_A750del | E746_A749del | T790M | L858R | G496A | L597V | P270* | Q729* | W764R | T58* | M272* |
| EGFR | E746_A750del | X | X | X | X | X | X | X | X | X | X | X |
| | E746_A749del | X | X | X | X | X | X | X | X | X | X | X |
| | T790M | X | X | X | X | X | X | X | X | X | X | X |
| | L858R | X | X | X | X | X | X | X | X | X | X | X |
| B-RAF | G496A | X | X | X | X | X | X | X | X | X | X | X |
| | L597V | X | X | X | X | X | X | X | X | X | X | X |
| BRG1 | P270* | X | X | X | X | X | X | X | X | X | X | X |

TABLE 6-continued

Exemplary combinations of sensitizing mutations

| First sensitizing mutation | Additional possible mutations (not mutually exclusive) | | | | | | | | | | |
|---|---|---|---|---|---|---|---|---|---|---|---|
| | EGFR | | | | B-RAF | | BRG1 | | | | |
| | E746_A750del | E746_A749del | T790M | L858R | G496A | L597V | P270* | Q729* | W764R | T58* | M272* |
| Q729* | X | X | X | X | X | X | X | X | X | X | X |
| W764R | X | X | X | X | X | X | X | X | X | X | X |
| T58* | X | X | X | X | X | X | X | X | X | X | X |
| M272* | X | X | X | X | X | X | X | X | X | X | X |

As used herein, "enhancer of zeste homolog 2" or "EZH2" (e.g. NCBI Gene ID: 2146) refers to Polycomb-group enzyme which acts as a transcriptional silencer by adding 3 methyl groups to Lysine 27 of histone 3. This methylation leads to condensation of chromosomes. Multiple isoforms of EZH2 are known to exist, e.g. five different isoforms are known in humans. The sequences of EZH2 isoforms, genes, and transcripts are known in a variety of species, e.g. human (NCBI Gene ID NO: 2146: isoform c (protein: SEQ ID NO: 10 (NCBI Ref Seq: NP_001190176); mRNA: SEQ ID NO: 9 (NCBI Ref Seq: NM_001203247); or isoform a (protein: SEQ ID NO: 1 (NCBI Ref Seq: NP_004447); mRNA: SEQ ID NO: 2 (NCBI Ref Seq: NM_004456)). In humans, five isoforms of EZH2, isoforms, namely EZH2a; EZH2b; EZH2c; EZH2d; EZH2e, are known to exist, with isoform c being the form most prevalently expressed. In some aspects of all the embodiments of the invention, the term "EZH2" refers to any of the five isoforms of EZH2. In some aspects of all the embodiments of the invention the EZH2 is EZH2a. In some aspects of all the embodiments of the invention the EZH2 is EZH2b. In some aspects of all the embodiments of the invention the EZH2 is EZH2c. In some aspects of all the embodiments of the invention the EZH2 is EZH2d. In some aspects of all the embodiments of the invention the EZH2 is EZH2e.

The inhibition in the methods of the invention can relate to one specific isoform or a combination thereof. Table A sets forth the different combinations of the isoforms that are contemplated to be inhibited in the methods of the invention. For example, in some aspects one can inhibit all or any combination of the EZH2 isoforms.

TABLE A

| | EZH2a | EZH2b | EZH2c | EZH2d | EZH2e |
|---|---|---|---|---|---|
| EZH2a | X | X | X | X | X |
| EZH2b | X | X | X | X | X |
| EZH2c | X | X | X | X | X |
| EZH2d | X | X | X | X | X |
| EZH2e | X | X | X | X | X |

In some embodiments, the methods described herein relate to the treatment of cancer, wherein the treatment comprises administering to the human subject an EZH2 inhibitor if the human subject has been determined to be sensitive to EZH2 inhibitors. As used herein, the term "inhibitor of EZH2" or "EZH2 inhibitor" refers to an agent, which reduces the expression and/or activity of EZH2. The reuction in expression and/or activity can be, for example, by at least about 10%, e.g. by 10% or more, 20% or more, 30% or more, 50% or more, 75% or more, 90% or more, 95% or more, 98% or more, or 99% or more. The reduction of the expression and/or activity of EZH2 is not intended to encompass complete inhibition or total reduction of EZH2 expression and/or activity.

In some aspects of all the embodiments, the reduction of EZH2 expression and/or activity can be a "complete reduction" or "complete inhibition", i.e. a 100% reduction of the expression and/or activity of EZH2. In some aspects of all the EZH2 inhibitor can be an agent that inhibits the expression level, e.g. mRNA and/or polypeptide expression product level of EZH2. In some aspects of all the embodiments, an EZH2 inhibitor can be an agent that inhibits the activity of EZH2.

EZH2 is known to interact with SUZ12, ATRX, HDAC1, Histone deactylase 2, VAV1, EED (4 possible isoforms), RBBP4, RBBP7, PHF1, MTF2, PHF19, JARID1A, JARID1B, DNMT1, DNMT3A, DNMT3B, HDAC1, HDAC2. EZH2 polypeptide can be located within a multiple polypeptide complex, e.g. PRC2, PRC3, and/or PRC4 (for further discussion of the PRC complexes, see, e.g. Kuzmichev et al. Molecular Cell 2004 14:183-193; Simon and Lange. Mutation Research 2008 647:21-9; Simon and Kingston. Mol Cell Biol 2009 10:697-708; and Sauvageau and Sauvageau. Cell Stem Cell 2010 7:299-313; each of which is incorporated by reference herein in its entirety). An inhibitor of EZH2 can inhibit the EZH2 function or reduce the EZH2 amount which is present in any of these complexes.

In some instances, the function of EZH2 can be replicated by EZH1 (see, e.g. Ho and Crabtree. Cell Stem Cell 2008 3:577-8; which is incorporated by reference herein in its entirety). Accordingly, in some aspects of all the embodiments, an EZH2 inhibitor inhibits the EZH2-like activity of EZH1.

The term "agent" refers generally to any entity which is normally not present or not present at the levels being administered to a cell, tissue or subject. An agent can be selected from a group comprising: polynucleotides; polypeptides; small molecules; antibodies; or functional fragments thereof. Exemplary, but non-limiting examples of EZH2 inhibitors can an inhibitory nucleic acid; DZNep (CAS 102052-95-9); S-adenosyl-L-homocysteine. EZH2 inhibitors are commercially available, e.g. DZNep (Cat No: 13828, Cayman Chemical; Ann Arbor, Mich.) Additional examples of EZH2 inhibitors and methods of producing them are described in in U.S. Patent Publications 2012/0071418 (see, e.g. compound 75), which is incorporated by reference herein in its entirety; 2011/0251216 which is incorporated by reference herein in its entirety; 2009/0012031 which is incorporated by reference herein in its entirety; isoliquiritigenin; inhibitors as described in International Patent Publications WO/05/034845 which is incorporated by reference herein in its entirety; WO/12/068589 (see, e.g. paragraphs [0037]-[105], particularly Table 1), which is incorporated by reference herein in its entirety; WO/12/075080 (see, e.g. page 2, line 20—page 4 line 33) which is incorporated by reference herein in its entirety; WO/11/140324 (see, e.g. page 2, line 20—page 4, line 29; pages 37-79) which is incorporated by reference herein in its entirety; WO/12/005805 (see, e.g. page 2, line 20-page 3, line 21; the structures shown in Examples 1-125), which is incorporated by reference herein in its entirety; WO/11/140325 (see, e.g. page 3, line 1-page 5, line 6; the structures shown in Examples 1-131), which is incorporated by reference herein in its entirety; and including nucleic acid inhibitors as described in US Patent Publications 2005/0159382, which is incorporated by reference herein in its entirety; and 2011/0286990 which is incorporated by reference herein in its entirety. EZH2 inhibitors and methods of screening for EZH2 inhibitors are also described, e.g. in Diaz et al. J Biomol Screen 2012; which is incorporated by reference herein in its entirety. In some embodiments, an EZH2 inhibitor can be GSK126, e.g. an agent with the structure of formula I.

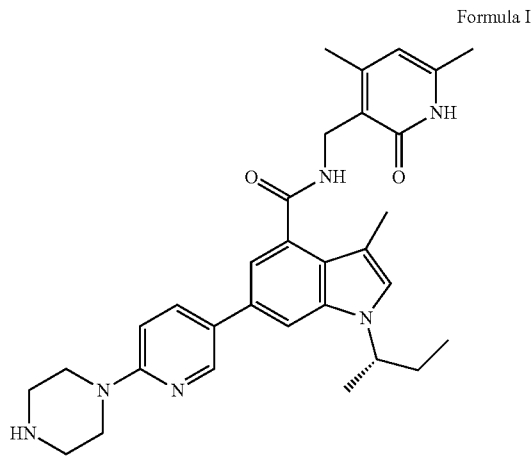 [SMILES: CC[C@H](C)n1cc(C)c2c(C(=O)NCc3c(C)cc(C)[nH]c3=O)cc(-c3ccc(N4CCNCC4)nc3)cc21]

Formula I

In some embodiments, the technology described herein relates to the treatment of cancer, comprising at least in part, administering a drug that inhibits EZH2 in combination with one or more chemotherapeutic agent. As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof. Exemplary chemotherapeutic agents can include, but are not limited to, a topoisomerase inhibitor; a topoisomerase I inhibitor; a topoisomerase II inhibitor; a PARP inhibitor; a CDK1 inhibitor; and an EGFR inhibitor.

As used herein, a "topoisomerase inhibitor" refers to an agent that can reduce the level and/or activity of a topoisomerase, e.g. topoisomerase I and/or topoisomerase II. A topoisomerase inhibitor can be specific for either topoisomerase I or topoisomerase II; or inhibit both topoisomerase I and II. Topoisomerase I inhibitors are known in the art and include, by way of non-limiting example, camptothecins; topotecan; irinotecan; indenoisoquinolines; indotecan; and indimitecan; and lamellarin D. Topoisomerase II inhibitors are known in the art and include, by way of non-limiting example, doxorubicin (e.g. ADRIAMYCIN™); etoposide; amsacrine; teniposide; ICRF-193; genistein; daunorubicin; mitoxantrone; ellipticines; aurintricarboxylic acid; and HU-331.

In some embodiments, a chemotherapeutic agent can be a targeted therapeutic, i.e. an agent that prevents proliferation of only a subset of cells, e.g. cells that have high levels of EGFR signaling. Exemplary examples of targeted therapies include, but are not limited to, a PARP inhibitor; a CDK1 inhibitor; and an EGFR inhibitor As used herein, a "PARP inhibitor" refers to an agent that can reduce the level and/or activity of poly ADP ribose polymerase (PARP). PARP inhibitors are known in the art and include, by way of non-limiting example, olaparib, veliparib, iniparib, rucaparib, AG14361, INO-1001, A-966492, BMN-673; CEP 9722; 3-aminobenzamide; and MK-4827. PARP inhibitors are commercially available, e.g. olaparib (Cat No. S1060 SelleckBio; Houston, Tex.).

As used herein, a "CDK1 inhibitor" refers to an agent that can reduce the level and/or activity of cyclin-dependent kinase 1 (CDK1). CDK1 inhibitors are known in the art and include, by way of non-limiting example, PD 0332991, flavopiridol, roscovitine, SNS-032, AT7519, JNJ-7706621, PHA-793887, dinaciclib, BMS-265246, PHA-848125, PHA-767491, SCH 900776, 8547, A-674563, AZD5438, BS-181 HCl, RO-3306, CGP754514A, and NU6102. CDK1 inhibitors are commercially available, e.g. flavopiridol (Cat No. S1230 SelleckBio; Houston, Tex.).

As used herein, an "EGFR inhibitor" refers to an agent that can reduce the level and/or activity of epidermal growth factor receptor (EGFR). EGFR inhibitors are known in the art and include, by way of non-limiting example, erlotinib, gefitinib, lapatinib, afatinib, CI-1033, neratinib, CP-724714, TAK-285, AST-1306, ARRY334543, Any-380, AG-1478, dacomitinib, desmethyl erlotinib, OSI-420, AZD8931, AEE788, pelitinib, CUDC-101, WS8040, WZ4002, WZ3146, AG-490, XL647, PD153035 HCl, BMS-599626, AG 825, AG 494, AG 555, BIBU 1361, BIBX 1382, DAPH, JNJ 28871063, lavendustin A, hypericin, etc. EGFR inhibitors are commercially available, e.g. erlotinib (Cat No. S1023 SelleckBio; Houston, Tex.).

In some embodiments, the technology described herein relates to the treatment of cancer, at least in part, by adminsitering an EZH2 inhibitor in combination with one or more chemotherapeutic agents. In some embodiments, an EZH2 inhibitor and a second chemotherapeutic agent can be administered. In some embodiments, an EZH2 inhibitor and two or more chemotherapeutic agents can be administered, e.g. two chemotherapeutic agents can be administered, three chemotherapeutic agents can be administered, or four chemotherapeutic agents can be administered in addition to an EZH2 inhibitor. In some embodiments, multiple agents belonging to the same class of agents can be administered, e.g. two EGFR inhibitors, two EZH2 inhibitors, or two CDK1 inhibitors can be administered. In some embodiments, multiple agents belonging to different classes of agents can be administered, e.g. an EZH2 inhibitor, a CDK1 inhibitor, and a topoisomerase inhibitor can be administered. In some embodiments of any of the aspects described herein, a subject can be administered an EZH2 inhibitor, a CDK1 inhibitor, and a further chemotherapeutic agent. In some embodiments, the further chemotherapeutic agent can include, but is not limited to, a topoisomerase inhibitor; a topoisomerase I inhibitor; a topoisomerase II inhibitor; a PARP inhibitor; and an EGFR inhibitor.

In one aspect, provided herein is a method of identifying a subject who is a candidate for treatment of cancer, the method comprising: detecting a sensitizing mutation of BRG1, EGFR, or B-RAF in a tumor cell sample obtained from the subject; wherein the treatment comprises the administration of a chemotherapeutic agent and an EZH2 inhibitor. In one aspect, provided herein is a method of identifying a subject who is a candidate for treatment of cancer, the method comprising: detecting the absence of a sensitizing mutation of BRG1, EGFR, or B-RAF in a tumor cell sample obtained from the subject; wherein the treatment comprises the administration of a chemotherapeutic agent and does not comprise the administration of an EZH2 inhibitor. In one aspect, provided herein is a method of determining whether a subject is likely to respond to a treatment for cancer, the method comprising: detecting the presence of a sensitizing mutation in BRG1, EGFR, or B-RAF in a tumor cell sample obtained from the subject; wherein the presence of a sensitizing mutation in BRG1, EGFR, or B-RAF indicates the subject has an increased likelihood of responding to a treatment to cancer; wherein the treatment for cancer comprises administration of an EZH2 inhibitor and a chemotherapeutic agent. In one aspect, provided herein is a method of determining whether a subject is likely to respond to a treatment for cancer, the method comprising: detecting the absence of a sensitizing mutation in BRG1, EGFR, or B-RAF in a tumor cell sample obtained from the subject; wherein the absence of a sensitizing mutation in BRG1, EGFR, or B-RAF indicates the subject has an increased likelihood of responding to a treatment to cancer; wherein the treatment for cancer comprises administration of a chemotherapeutic agent and does not comprise the administration of an EZH2 inhibitor.

In one aspect, provided herein is an assay comprising: subjecting a tumor cell sample from a subject to at least one analysis to detect the presence of a sensitizing mutation of BRG1, EGFR, or B-RAF; wherein the presence of a sensitizing mutation of BRG1, EGFR, or B-RAF indicates the subject has a cancer which will respond to treatment with an EZH2 inhibitor and a chemotherapeutic agent. In some embodiments, the presence of the mutation can be determined using an assay selected from the group consisting of: hybridization; sequencing; exome capture; PCR; high-throughput sequencing; allele-specific probe hybridization; allele-specific primer extension, allele-specific amplification; 5' nuclease digestion; molecular beacon assay; oligonucleotide ligation assay; size analysis; single-stranded conformation polymorphism; real-time quantitative PCR, and any combinations thereof. In some embodiments, the absence of a sensitizing mutation of BRG1, EGFR, or B-RAF indicates the subject has a cancer which will respond to treatment with a chemotherapeutic agent in the absence of an EZH2 inhibitor.

In some embodiments, the presence and/or absence of a sensitizing mutation, e.g. in BRG1, EGFR, and/or B-RAF can be detected by determining the sequence of a genomic locus and/or an mRNA transcript. Such molecules can be isolated, derived, or amplified from a biological sample, such as a tumor sample. Nucleic acid (e.g. DNA) and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; and proteinase K extraction can be used to obtain nucleic acid from blood (Roiff, A et al. PCR: Clinical Diagnostics and Research, Springer (1994)).

In some embodiments, the nucleic acid sequence of a target gene (e.g. BRG1, EGFR, and/or B-RAF) in a sample obtained from a subject can be determined and compared to a reference sequence to determine if a sensitizing mutation is present in the subject. In some embodiments, the sequence of the target gene can be determined by sequence the target gene (e.g. the genomic sequence and/or the mRNA transcript thereof). Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (3 ed.), Cold Spring Harbor Laboratory Press, Cold Spring Harbor, N.Y., USA (2001); which are incorporated by reference herein in their entireties.

In some embodiments, sequencing can comprise exome sequencing (i.e. targeted exome capture). Exome sequencing comprises enriching for an exome(s) of interest and then sequencing the nucleic acids comprised by the enriched sample. Sequencing can be according to any method known in the art, e.g. those described above herein. Methods of enrichment can include, e.g. PCR, molecular inversion probes, hybrid capture, and in solution capture. Exome capture methodologies are well known in the art, see, e.g. Sulonen et la. Genome Biology 2011 12:R94; and Teer and Mullikin. Hum Mol Genet 2010 19:R2; which are incorporated by reference herein in their entireties. Kits for performing exome capture are available commercially, e.g. the TRUSEQ™ Exome Enrichment Kit (Cat. No. FC-121-1008; Illumnia, San Diego, Calif.). Exome capture methods can also readily be adapted by one of skill in the art to enrich specific exomes of interest.

In some embodiments, the presence of a sensitizing mutation can be determined using a probe that is specific for the sensitizing mutation. In some embodiments, the probe can be detectably labeled. In some embodiments, a detectable signal can be generated by the probe when a sensitizing mutation is present.

In some embodiments, the probe specific for the sensitizing mutation can be a probe in a hybridization assay, i.e. the probe can specifically hybridize to a nucleic acid comprising a sensitizing mutation (as opposed to a wild-type nucleic acid sequence) and the hybridization can be detected, e.g. by having the probe and or the target nucleic acid be detectably labeled. Hybridization assays are well known in the art and include, e.g. northern blots and Southern blots.

In some embodiments, the probe specific for the sensitizing mutation can be a probe in a PCR assay, i.e. a primer. In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a thermostable DNA polymerase, and optionally, (iii) screening the PCR products for a band or product of the correct size. The primers used are oligonucleotides of sufficient length and appropriate sequence to provide initiation of polymerization, i.e. each primer is specifically designed to be complementary to a strand of the genomic locus to be amplified. In an alternative embodiment, the presence of a sensitizing mutation in an mRNA transcript can be determined by reverse-transcription (RT) PCR and by quantitative RT-PCR (QRT-PCR) or real-time PCR methods. Methods of RT-PCR and QRT-PCR are well known in the art. In some embodiments, the PCR product can be labeled, e.g. the primers can comprise a detectable label, or a label can be incorporated and/or bound to the PCR product, e.g. EtBr detection methods. Other non-limiting detection methods can include the detection of a product by mass spectroscopy or MALDI-TOF.

The term "label" refers to a composition capable of producing a detectable signal indicative of the presence of an antibody reagent (e.g. a bound antibody reagent). Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The nucleic acid sequences of BRG1, B-RAF, and EGFR have been assigned NCBI accession numbers for different species such as human, mouse and rat. In particular, the NCBI accession numbers for the nucleic acid sequences of the human expression products are included herein (SEQ ID NOs: 004, 006, and 008). Accordingly, a skilled artisan can design appropriate primers based on the known sequence for determining the mRNA level of the respective gene.

A sensitizing mutation will typically be present in the genomic DNA of a tumor (e.g. cancerous) cell. Accordingly, the mutation can be detected in either or both of the genomic DNA or the mRNA transcripts of a tumor cell. In some embodiments, the sensitizing mutation can occur within a DNA and/or RNA sequence that is translated. Accordingly, in some embodiments, the sensitizing mutation can be detected in the polypeptide of a tumor cell.

Detection of polypeptides comprising a sensitizing mutation can be according to any method known in the art (e.g. mass spectroscopy, flow cytometry, and/or immunological-based methods). Immunological methods to detect polypeptides comprising a sensitizing mutation in accordance with the present technology include, but are not limited to antibody techniques such as immunohistochemistry, immunocytochemistry, flow cytometry, fluorescent-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g. the antigen or in the embodiments described herein, a polypeptide or fragment thereof comprising a sensitizing mutation). In some embodiments, an antibody reagent for determining the presence of a sensitizing mutation in a sample can be an antibody reagent specific for a polypeptide comprising a sensitizing mutation, e.g. a sensitizing mutant of BRG1, EGFR, and/or B-RAF as described herein.

In some embodiments, the assays, methods, and/or systems described herein can comprise: an anti-sensitizing mutation antibody reagent, i.e. an antibody reagent specific for a polypeptide comprising a sensitizing mutation. In some embodiments, the antibody reagent can be detectably labeled. In some embodiments, the antibody reagent can be attached to a solid support (e.g. bound to a solid support). In some embodiments, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g. a polypeptide comprising a sensitizing mutation). The solid support can then be contacted with a second labeled antibody reagent (e.g. a detection antibody reagent). The detection antibody reagent can, e.g. comprise a detectable signal, be covalently linked to an enzyme, or can itself be detected by a secondary antibody, which is linked to an enzyme through bio-conjugation. The presence of a signal indicates that both the first antibody reagent immobilized on the support and the second "detection" antibody reagent have bound to an antigen, i.e. the presence of a signal indicated the presence of polypeptide comprising a sensitizing mutation. Between each step the plate is typically washed with a mild detergent solution to remove any proteins or antibodies that are not specifically bound. After the final wash step the plate is developed by adding an enzymatic substrate to produce a visible signal, which indicates the presence of a sensitizing mutation in the sample. Older ELISAs utilize chromogenic substrates, though newer assays employ fluorogenic substrates with much higher sensitivity. There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem. 22:895-904. These references are hereby incorporated by reference in their entirety.

In one embodiment, the assays, systems, and methods described herein can comprise a lateral flow immunoassay test (LFIA), also known as the immunochromatographic assay, or strip test to measure or determine the presence of a polypeptide comprising a sensitizing mutation. LFIAs are a simple device intended to detect the presence (or absence) of a target in a sample. There are currently many LFIA tests are used for medical diagnostics either for home testing, point of care testing, or laboratory use. LFIA tests are a form of immunoassay in which the test sample flows along a solid substrate via capillary action. After the sample is applied to the test it encounters a colored antibody reagent, which mixes with the sample, and if bound to a portion of the sample, transits the substrate encountering lines or zones which have been pretreated with a second antibody reagent. Depending upon the presence or absence of the target in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, tumor cell lysates etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles, which are labeled with antibody reagents specific for a target. The test line will also contain antibody reagents. The test line will show as a colored band in positive samples. In some embodiments, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i. e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line, which contains an antibody that picks up free latex/gold in order to confirm the test has operated correctly.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technology for the detection of a sensitizing mutation.

Immunochemistry is a family of techniques based on the use of a specific antibody, wherein antibodies are used to specifically target molecules inside or on the surface of cells. In some embodiments, immunohistochemistry ("IHC") and immunocytochemistry ("ICC") techniques can be used to detect the presence of a sensitizing mutation. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for a polypeptide comprising a sensitizing mutation. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments, immunocytochemistry may be utilized where, in general, tissue or cells are obtained from a subject are fixed by a suitable fixing agent such as alcohol, acetone, and paraformaldehyde, to which is reacted an antibody. Methods of immunocytological staining of human samples is known to those of skill in the art and described, for example, in Burry. "Immunocytochemistry: A Practical Guide for Biomedical Research" Springer (2009); which is incorporated by reference herein in its entirety.

In some embodiments, one or more of the antibody reagents described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments, detectable labels can include labels that can be detected by spectroscopic, photochemical, biochemical, immunochemical, electromagnetic, radiochemical, or chemical means, such as fluorescence, chemifluorescence. or chemiluminescence, or any other appropriate means the detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or noncovalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is label with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allopycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TR1TC)). biotin, phycoerythrin, MCA, CyDyes™, 6-carboxyfhiorescein (commonly known by the abbreviations FAM and F), 6-carboxy-2',4',7',4,7-hexachlorofluorescein (HEX), 6-carboxy-4',5'-dichloro-2', 7'-dimethoxyfluorescein (JOE or J), N,N,N',N'-tetramethyl-6carboxhyrdodamine (TAMRA or TI, 6-carboxy-X-rhodamine (ROX or R), 5-carboxyrhodamine-6G (R6G5 or G5), 6-carboxyrhodamine-6G (R6G6 or G6), and rhodamine 110: cyanine dyes. e.g. Cy3, Cy5 and Cy7 dyes; coumarins, e.g umbelliferone; benzimide dyes, e.g. Hoechst 33258: phenanthridine dyes. e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline; dyes. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

In some embodiments of any of the aspects described herein, the sequence, expression level, and/or mutational status of more than one gene can be determined simultaneously (e.g. a multiplex assay) or in parallel. In some embodiments, the sequence, expression level, and/or mutational status of no more than 20 other genes is determined. In some embodiments, the sequence, expression level, and/or mutational status of no more than 10 other genes is determined.

In some embodiments, the sequence and/or mutational status of BRG1, EGFR, and B-RAF can be determined simulataneously (e.g. a multiplex assay). Where the sequences of sensitizing mutations and wildtype sequences are known as described herein (both in nucleic acid and polypeptide sequences), methods of creating multiplex assays for both nucleic acid or polypeptide targets are known in the art (e.g. multiplex assays can include, but are not limited to multiplexed RTPCR assays, multiplex nucleic acid hybridization assays, and multiplex immunochemical assays). By way of non-limiting example, primers for detecting the level of, e.g. BRG1 and EGFR expression in a quantitative RTPCR assay can be used to detect the presence of 1) a sensitizing mutation which increases the expression level of EGFR and 2) a sensitizing mutation which decreases the expression of BRG1 in one reaction. Non-limiting examples of such primers include those described in the Examples herein, i.e. BRG1 F AGCGATGACGTCTCT-GAGGT (SEQ ID NO: 11); BRG1 R GTACAGGGACAC-CAGCCACT (SEQ ID NO: 12); EGFR F TAACAAGCT-CACGCAGTTGG (SEQ ID NO: 13); and EGFR R GTTGAGGGCAATGAGGACAT (SEQ ID NO: 14).

By way of non-limiting example, probes for detecting the level of, e.g. BRG1 and EGFR expression in a microarray assay can be used to detect the presence of 1) a sensitizing mutation which increases the expression level of EGFR and 2) a sensitizing mutation which decreases the expression of BRG1 in one reaction. As but one example, the Human Genome U133A 2.0 Array (Cat No. 900471, Affymetrix, Cleveland, Ohio), or the probes comprised therein can be used to detect the level of, e.g. BRG1 and EGFR expression in a single assay, as described in the Examples herein.

By way of further non-limiting example, antibodies specific for polypeptides comprising a sensitizing mutation as described herein can be produced and used to detect the presence or absence of multiple sensitizing mutations in a single assay.

The term "sample" or "test sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, a test sample can be a tumor cell test sample, e.g. the sample can comprise cancerous cells, cells from a tumor, and/or a tumor biopsy.

The test sample can be obtained by removing a sample of cells from a subject, but can also be accomplished by using previously isolated cells (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the presence of a sensitizing mutation as described herein.

In some embodiments, the methods, assays, and systems described herein can further comprise a step of obtaining a test sample from a subject. In some embodiments, the subject can be a human subject.

In one aspect, provided herein is an assay comprising: contacting a tumor cell sample obtained from a subject having cancer with a nucleic acid probe to detect the presence of a sensitizing mutation in BRG1, EGFR, or B-RAF; and detecting the presence or intensity of a signal which indicates the presence of a sensitizing mutation in BRG1, EGFR, or B-RAF; wherein the presence of a sensitizing mutation of BRG1, EGFR, or B-RAF indicates the subject has a cancer which will respond to treatment with an EZH2 inhibitor and a chemotherapeutic agent. In some embodiments, the absence of a sensitizing mutation of BRG1, EGFR, or B-RAF indicates the subject has a cancer which will respond to treatment with a chemotherapeutic agent, wherein the treatment does not comprise, or in otherwirds, specifically excludes administering an EZH2 inhibitor to the subject if the subject has been determined to be unresponsive to EZH2 inhibitors using the assays or methods of the invention.

In any of the aspects and embodiments described herein, the subject can be human. In some embodiments, the subject can be a subject having, at risk of having, or in need of treatment for cancer. In some embodiments, the cancer can be selected from the group consisting of lung cancer; non-small cell lung cancer; ovarian cancer; EGFR-expressing ovarian cancer; B-Raf V600E melanomas; breast cancer; colon cancer; EGFR-mutated cancers; EGFR-mutated breast cancers; and EGFR-mutated colon cancers. In some embodiments, the cancer can be lung cancer. In some embodiments, the cancer can be non-small cell lung cancer. In some embodiments, the cancer is not lymphoma.

In one aspect, provided herein is a method of classifying a tumor as an EZH2 combination treatment responsive tumor, the method comprising: detecting a sensitizing mutation of BRG1, EGFR, or B-RAF in a tumor cell sample; wherein the presence of a sensitizing mutation of BRG1, EGFR, or B-RAF indicates the tumor is a EZH2 combination treatment responsive tumor. As used herein, the term "EZH2 combination treatment responsive tumor" refers to a tumor comprising cells that, after being contacted with an effective dose of an EZH2 inhibitor will be more sensitive to at least one chemotherapeutic agent than the same cell would be in the absence of being contacted with the EZH2 inhibitor.

In any embodiment of the methods and assays described herein, the method or assay can further comprise the step of generating a report based on the detection of a sensitizing mutation in BRG1, EGFR, or B-RAF. In some embodiments, the report can be generated by a non-human machine, e.g. a computer system as described elsewhere herein.

In some embodiments of various aspects described herein, the combination of an EZH2 inhibitor and a chemotherapeutic agent is indicated for the treatment of cancer (e.g. lung cancer) in patients with one or more of the following genetic variants as determined by an FDA approved diagnostic test: a variant corresponding to P270*; Q729*; W764R; T58*; and/or M272* of SEQ ID NO: 003; a variant corresponding to E746_A750del; E746_A749del; T790M; and/or L858R of SEQ ID NO: 003; and/or a variant corresponding to G496A and/or L597V of SEQ ID NO: 003 or any combination of the foregoing variants.

In some embodiments, the methods described herein relate to treating a subject having or diagnosed as having cancer with an EZH2 inhibitor and a chemotherapeutic agent. Subjects having cancer can be identified by a physician using current methods of diagnosing cancer. Symptoms and/or complications of cancer which characterize these conditions and aid in diagnosis are well known in the art and include but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer, or exposure to risk factors for cancer (e.g. tobacco products, radiation, etc.) can also aid in determining if a subject is likely to have cancer or in making a diagnosis of cancer.

The compositions and methods described herein can be administered to a subject having or diagnosed as having cancer. In some embodiments, the methods described herein comprise administering an effective amount of compositions described herein, e.g. an EZH2 inhibitor and chemotherapeutic agent to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of an EZH2 inhibitor and/or chemotherapeutic agent needed to alleviate at least one or more symptom of the disease or disorder, and relates to a sufficient amount of pharmacological composition to provide the desired effect. The term "therapeutically effective amount" therefore refers to an amount of an EZH2 inhibitor and/or chemotherapeutic agent that is sufficient to effect a particular anti-cancer effect when administered to a typical subject. An effective amount, as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an EZH2 inhibitor and/or chemotherapeutic agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for cell death, among others. The dosage can be determined by a physician and adjusted, as necessary, to suit observed effects of the treatment.

In some embodiments, the technology described herein relates to a pharmaceutical composition comprising an EZH2 inhibitor and/or chemotherapeutic agent as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as scrum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an EZH2 inhibitor and/or chemotherapeutic agent as described herein.

In some embodiments, the pharmaceutical composition comprising an EZH2 inhibitor and/or chemotherapeutic agent as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of an EZH2 inhibitor and/or chemotherapeutic agent as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an EZH2 inhibitor and/or chemotherapeutic agent as disclosed herein can also be incorporated into the parenteral dosage forms of the disclosure, including conventional and controlled-release parenteral dosage forms.

Pharmaceutical compositions comprising an EZH2 inhibitor and/or chemotherapeutic agent can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the an EZH2 inhibitor and/or chemotherapeutic agent can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation or radiation therapy. In some embodiments, cisplatin can be administered in combination with a topoisomerase inhibitor as described above herein, e.g. cisplatin can be administered in combination with etoposide. Further, the methods of treatment can further include the use of surgical treatments.

In some embodiments, an EZH2 inhibitor can be administered in any combination with, e.g. concurrently or sequentially, with a chemotherapeutic agent. In some embodiments, an EZH2 inhibitor and a chemotherapeutic agent can be administered in a single composition. In some embodiments, an EZH2 inhibitor and a chemotherapeutic agent can be administered in separate compositions. In embodiments where multiple compositions are administered (e.g. one composition comprising an EZH2 inhibitor and a second composition comprising a chemotherapeutic agent), the compositions can be administered at varying times and/or for varying durations.

In certain embodiments, an effective dose of a composition comprising an EZH2 inhibitor and/or chemotherapeutic agent as described herein can be administered to a patient once. In certain embodiments, an effective dose of a composition comprising an EZH2 inhibitor and/or chemotherapeutic agent can be administered to a patient repeatedly. For systemic administration, subjects can be administered a therapeutic amount of a composition comprising an EZH2 inhibitor and/or chemotherapeutic agent, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising an EZH2 inhibitor and/or chemotherapeutic agent can be administered over a period of time, such as over a 5 minute, 10 minute, 15 minute, 20 minute, or 25 minute period. The administration can be repeated, for example, on a regular basis, such as hourly for 3 hours, 6 hours, 12 hours or longer or such as biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. tumor size by at least 10%, at least 15%, at least 20%, at least 25%, at least 30%, at least 40%, at least 50%, at least 60%, at least 70%, at least 80% or at least 90% or more.

In some embodiments, the EZH2 inhibitor and chemotherapeutic agent can be administered daily. In some embodiments, the EZH2 inhibitor and chemotherapeutic agent can be administered daily for at least 3 days, e.g. 3 days, 4 days, 5 days, 6 days, 7 days, or longer. In some embodiments, the EZH2 inhibitor and chemotherapeutic agent can be administered daily for 2 weeks or less, e.g. 14 days, 13 days, 12 days, 11 days, 10 days, 9 days, 8 days, or 7 days or less. In some embodiments, the EZH2 inhibitor and chemotherapeutic agent can be administered daily for between 1 days and 14 days. In some embodiments, the EZH2 inhibitor and chemotherapeutic agent can be administered daily for between 3 days and 10 days. In some embodiments, the EZH2 inhibitor and chemotherapeutic agent can be administered daily for between 3 days and 10 days. In some embodiments, the EZH2 inhibitor, e.g. DZNep can be administered at a dose of about 0.1 mg/kg/day to 20 mg/kg/day. In some embodiments, the EZH2 inhibitor, e.g. DZNep can be administered at a dose of about 1 mg/kg/day to 10 mg/kg/day. In some embodiments, the EZH2 inhibitor, e.g. DZNep, can be administered at a dose of about 2 mg/kg/day.

In some embodiments, the EZH2 inhibitor and chemotherapeutic agent can be administered weekly. In some embodiments, the EZH2 inhibitor and chemotherapeutic agent can be administered twice per week or more frequently, e.g. twice per week, three times per week, four times per week, five times per week, six times per week, or daily.

In some embodiments, the EZH2 inhibitor and chemotherapeutic agent can be administered for at least 3 days, e.g. 3 days, 4 days, 5 days, 6 days, 7 days, or longer. In some embodiments, the EZH2 inhibitor and chemotherapeutic agent can be administered for 2 weeks or less, e.g. 14 days, 13 days, 12 days, 11 days, 10 days, 9 days, 8 days, or 7 days or less. In some embodiments, the EZH2 inhibitor and chemotherapeutic agent can be administered for between 1 days and 14 days. In some embodiments, the EZH2 inhibitor and chemotherapeutic agent can be administered for between 3 days and 10 days. In some embodiments, the EZH2 inhibitor and chemotherapeutic agent can be administered for between 3 days and 10 days.

In some embodiments, the EZH2 inhibitor, e.g. DZNep can be administered at a dose of about 0.1 mg/kg/day to 20 mg/kg/day. In some embodiments, the EZH2 inhibitor, e.g. DZNep can be administered at a dose of about 1 mg/kg/day to 10 mg/kg/day. In some embodiments, the EZH2 inhibitor, e.g. DZNep, can be administered at a dose of about 2 mg/kg/day.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subjects sensitivity to an EZH2 inhibitor and/or chemotherapeutic agent. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of an EZH2 inhibitor and/or chemotherapeutic agent, according to the methods described herein depend upon, for example, the form of an EZH2 inhibitor and/or chemotherapeutic agent, its potency, and the extent to which symptoms, markers, or indicators of a condition described herein are desired to be reduced, for example the percentage reduction desired for tumor size and/or growth. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an EZH2 inhibitor and/or chemotherapeutic agent in, e.g. the treatment of a condition described herein, or to induce a response as described herein (e.g. a decrease in tumor size and/or growth rate) can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor growth rate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or impaired organ function); or (2) relieving the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size, metastasis, and/or mortality). It is well within the ability of one skilled in the art to monitor efficacy of administration and/or treatment by measuring any one of such parameters, or any combination of parameters. Efficacy can be assessed in animal models of a condition described herein, for example treatment of a mouse model of cancer. When using an experimental animal model, efficacy of treatment is evidenced when a statistically significant change in a marker is observed, e.g. tumor size and/or mortality.

In vitro and animal model assays are provided herein which allow the assessment of a given dose of an EZH2 inhibitor and/or chemotherapeutic agent. By way of non-limiting example, the effects of a dose of an EZH2 inhibitor and/or chemotherapeutic agent can be assessed by a cytotoxicity assay. A non-limiting example of a protocol for such an assay is as follows: Cell lines are dissociated, counted and plated at 5000 cells per well in flat bottom opaque tissue culture treated 96 well plates (CytoOne). The following day, an EZH2 inhibitor and one or more chemotherapeutic agents can be added to each well. After 4 days, Cell Titer Glo™ (Promega) can be added and luminescence read on a BioTec plate reader to determine relative cell number in each well.

The efficacy of a given dosage combination can also be assessed in an animal model, e.g. a mouse model of xeno-transplated lung cancer cells. For example, lung cancer cell lines can be injected subcutaneously with 1×106 cells in four spots on flanks of 8- to 16-week-old Foxn1nu (nude) mice (Harlan). An EZH2 inhibitor and one or more chemotherapeutic agents can be administered from day 12 to day 25 post injections. Tumor growth can be measured every other day by caliper.

In some embodiments of the assays and/or methods described herein, the assay/method comprises or consists essentially of a system for determining (e.g. transforming and measuring) the presence of a sensitizing mutation in BRG1, EGFR, and/or B-RAF as described herein. If the comparison system, which can be a computer implemented system, indicates that one or more sensitizing mutations are present, the subject from which the sample is collected can be identified as, e.g. having an increased likelihood of responding to a treatment comprising the administration of an EZH2 inhibitor and a chemotherapeutic agent. In some embodiments, the sequence of BRG1, EGFR, and/or B-RAF or an expression product thereof can be compared to a reference sequence, e.g. SEQ ID NOs: 003-008. In some embodiments, the absence of a sensitizing mutation in BRG1, EGFR, and/or B-RAF indicates the subject as, e.g. having an increased likelihood of responding to a treatment that does not comprise the administration of an EZH2 inhibitor.

Figure 14:
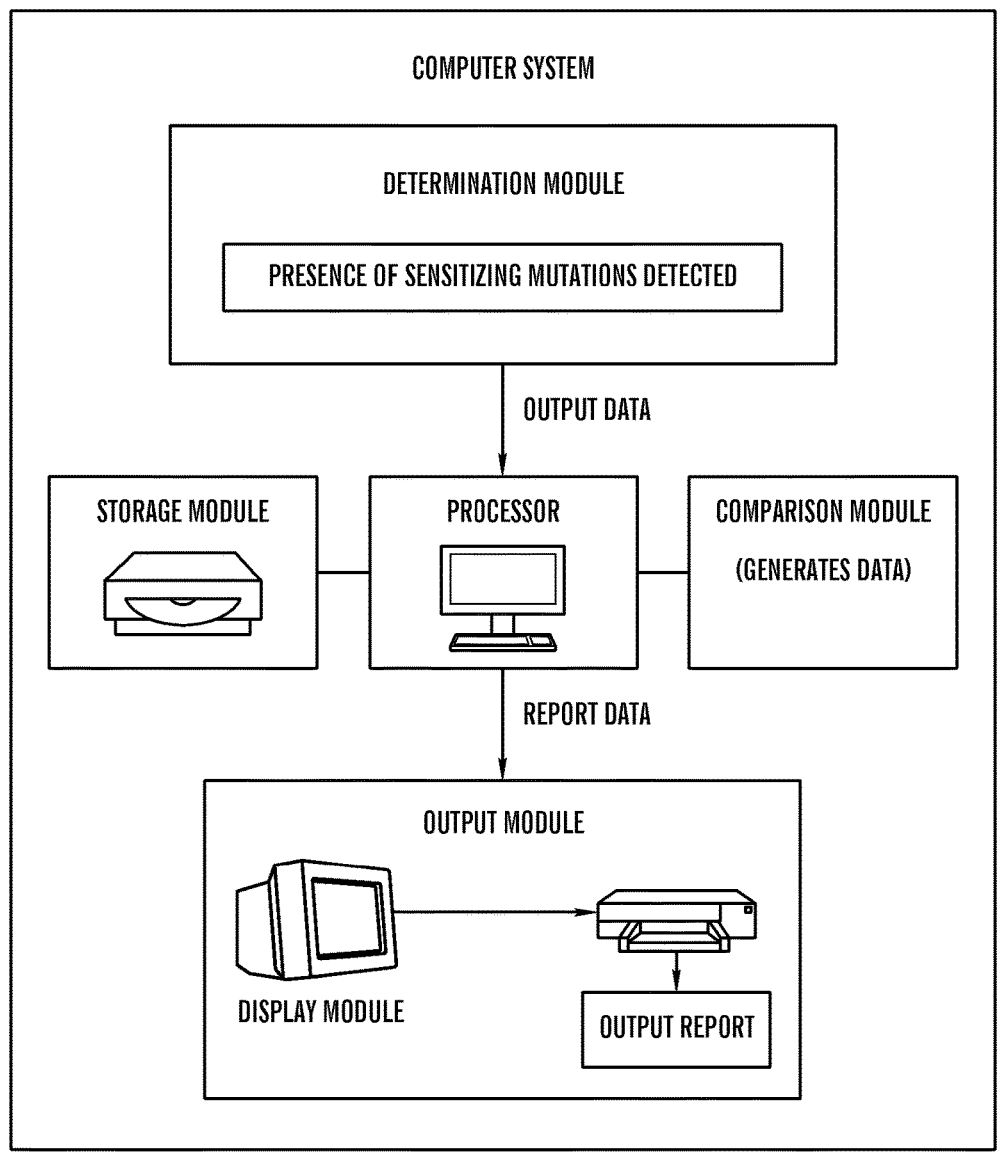
FIG. 14 is a diagram of an exemplary embodiment of a system for performing an assay for determining the presence of a sensitizing mutation in sample obtained from a subject.

In one embodiment, provided herein is a system comprising: (a) at least one memory containing at least one computer program adapted to control the operation of the computer system to implement a method that includes (i) a determination module configured to identify and detect the presence of a sensitizing mutation in BRG1, EGFR, and/or B-RAF in a test sample obtained from a subject; (ii) a storage module configured to store output data from the determination module; (iii) a computing module adapted to identify from the output data whether a sensitizing mutation in BRG1, EGFR, and/or B-RAF is present in the test sample obtained from the subject, and (iv) a display module for displaying whether a sensitizing mutation in BRG1, EGFR, and/or B-RAF is present in the test sample, optionally, as compared to a reference sequence (see FIG. 14).

Embodiments can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing. Computer-readable storage medium do not include a signal.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the technology discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the technology described herein. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments can include at minimum a determination module, a storage module, a computing module, and a display module. The functional modules can be executed on one, or multiple, computers, or by using one, or multiple, computer networks. The determination module has computer executable instructions to provide e.g., levels of expression products etc in computer readable form.

The determination module can comprise any system for detecting a signal elicited from the genomic sequence and/or expression products of BRG1, EGFR, and/or B-RAF in a biological sample. In some embodiments, such systems can include an instrument, e.g., the HiSeq 2500 (Illumina; San Diego, Calif.) for sequencing, e.g. nucleic acids isolated by exome capture (e.g. with the TruSeq Exome Enrichment Kit (Illumina; San Diego, Calif.). In another embodiment, the determination module can comprise multiple units for different functions, such as amplification and hybridization. In some embodiments, the determination module can be further configured to identify and detect the presence of at least one additional gene, allele, and/or gene expression product.

The information determined in the determination system can be read by the storage module. As used herein the "storage module" is intended to include any suitable computing or processing apparatus or other device configured or adapted for storing data or information. Examples of electronic apparatus suitable for use with the technology described herein include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, alleleic variants (e.g. sensitizing mutations or wild-type sequences), and frequency of each alleleic variant. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising sequence information.

In one embodiment of any of the systems described herein, the storage module stores the output data from the determination module. In additional embodiments, the storage module stores the reference information such as the sequence of BRG1, EGFR, and/or B-RAF in cells which are not EZH2 combination treatment responsive, wild-type sequences, and/or sequences comprising sensitizing mutations.

Figure 15:
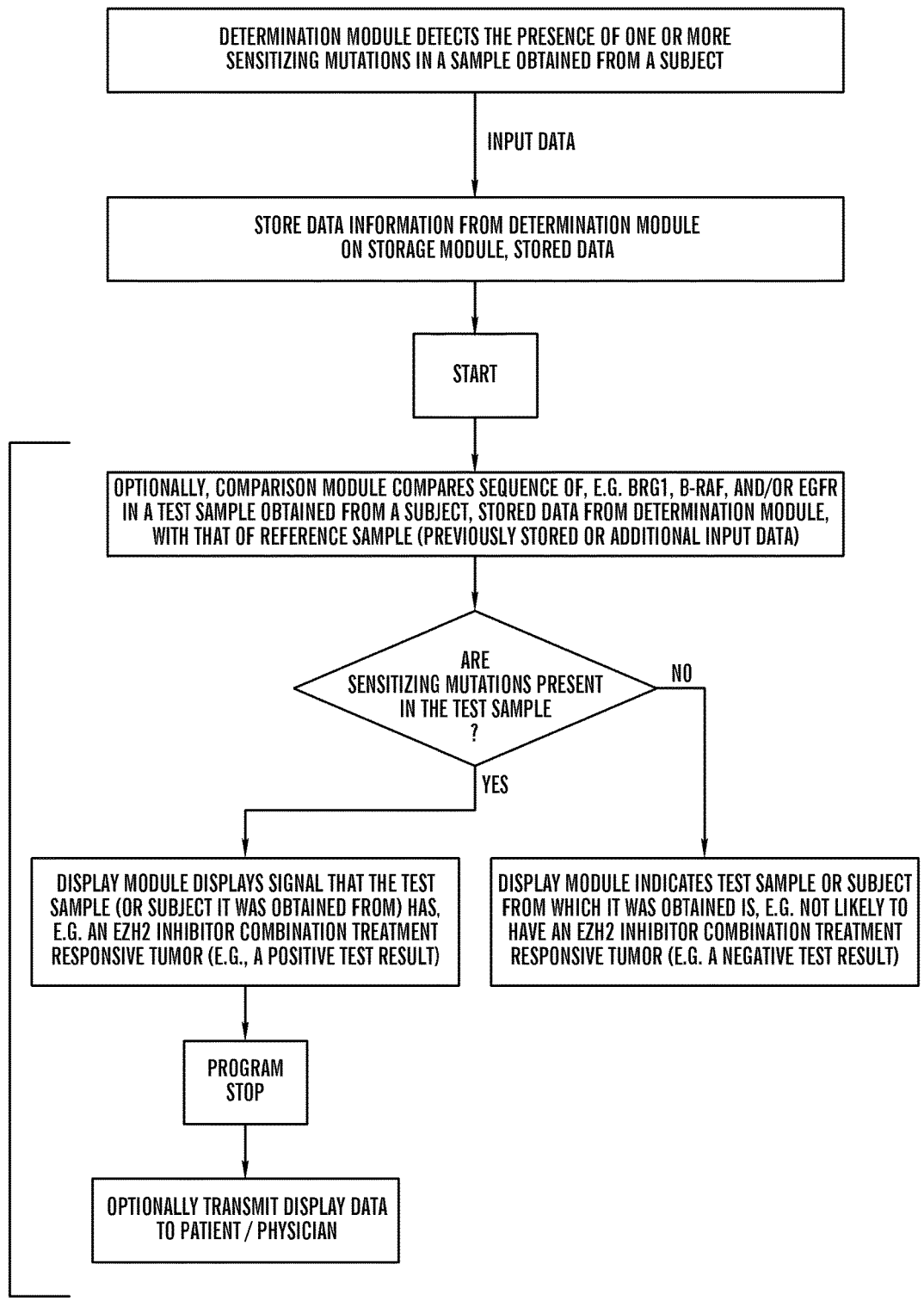
FIG. 15 is a diagram of an embodiment of a comparison module as described herein.

The "computing module" can use a variety of available software programs and formats for computing the presence and/or absence of a sensitizing mutation in BRG1, EGFR, and/or B-RAF, e.g. aligning two or more sequences and determining if a sensitizing mutation is present in a test sequence as compared to a reference and/or wild-type sequence. Such algorithms are well established in the art. A skilled artisan is readily able to determine the appropriate algorithms based on the size and quality of the sample and type of data. The data analysis can be implemented in the computing module. In one embodiment, the computing module further comprises a comparison module, which compares the sequence of BRG1, EGFR, and/or B-RAF in the test sample obtained from a subject as described herein with the reference sequence of those genes and/or their expression products (FIG. 15). By way of example, when the sequence of BRG1 in the test sample obtained from a subject is measured, a comparison module can compare or match the output data, e.g. with the reference sequence of BRG1 in a reference sample. In certain embodiments, the reference sequence can have been pre-stored in the storage module. During the comparison or matching process, the comparison module can determine whether the sequence in the test sample obtained from a subject differs from the reference sequence in such a way as to indicate a sensitizing mutation. Alternatively, the comparison module can determine whether the sequence in the test sample obtained from a subject matches a sequence known to comprise a sensitizing mutation. In various embodiments, the comparison module can be configured using existing commercially-available or freely-available software for comparison purpose, and may be optimized for particular data comparisons that are conducted.

Figure 16:
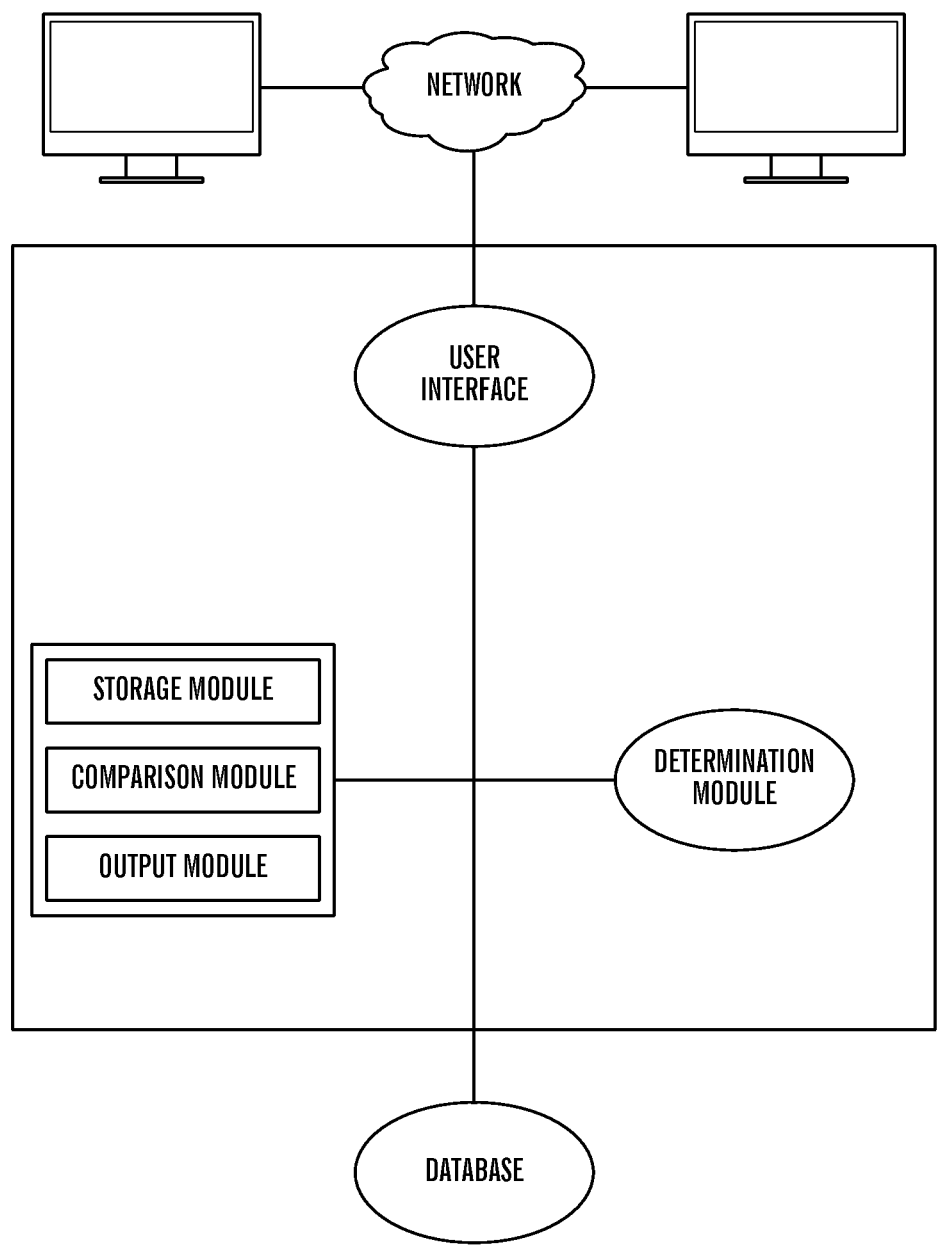
FIG. 16 is a diagram of an exemplary embodiment of an operating system and instructions for a computing system as described herein.

The computing and/or comparison module, or any other module, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file, which contains pointers and addresses to the various software entities that comprise the server as well as the various external and internal databases which must be accessed to service user requests. The Configuration file also directs requests for server resources to the appropriate hardware as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment, users can directly access data (via Hypertext links for example) residing on Internet databases using a HTML interface provided by Web browsers and Web servers (FIG. 16).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, described herein is a computer system for determining if a subject will be responsive to a cancer treatment, the system comprising: a determination module configured to detect the presence of a sensitizing mutation in BRG1, EGFR, or B-RAF in a tumor cell sample obtained from a subject; a storage module configured to store output data from the determination module; a comparison module adapted to compare the data stored on the storage module with a reference level, and to provide a retrieved content, and a display module for displaying whether a BRG1, EGFR, or B-RAF sensitizing mutation was detected in the tumor cell sample; wherein the cancer treatment comprises the administration of an EZH2 inhibitor and a chemotherapeutic agent. In some embodiments, the determining module can measure the intensity of a detectable signal from a RT-PCR assay indicating the presence of a sensitizing mutation of BRG1, EGFR, or B-RAF tumor cell sample. In some embodiments, the determining module can measure the intensity of a detectable signal from a sequencing assay indicating the presence of a sensitizing mutation of BRG1, EGFR, or B-RAF tumor cell sample. In some embodiments, the determining module can measure the intensity of a detectable signal from a hybridization assay indicating the presence of a sensitizing mutation of BRG1, EGFR, or B-RAF tumor cell sample.

In some embodiments, if the computing module determines that a sensitizing mutation of BRG1, EGFR, or B-RAF is present in the sample obtained from the subject, the display module can display a signal indicating that a sensitizing mutation has been detected. In some embodiments, the signal can indicate that the subject has an increased likelihood of responding to treatment with an EZH2 inhibitor and chemotherapeutic agent. In some embodiments, the content displayed on the display module can be a numerical value indicating one of these risks or probabilities. In such embodiments, the probability can be expressed in percentages or a fraction. For example, higher percentage or a fraction closer to 1 indicates a higher likelihood of a subject being responsive. In some embodiments, the content displayed on the display module can be single word or phrases to qualitatively indicate a risk or probability. For example, a word "unlikely" can be used to indicate a lower likelihood for being responsive to an EZH2 inhibitor combination therapy as described herein, while "likely" can be used to indicate a high likelihood for being responsive to an EZH2 inhibitor combination therapy as described herein.

In one embodiment, the content based on the computing and/or comparison result is displayed on a computer monitor. In one embodiment, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the technology relating to determining the presence of a sensitizing mutation, and therefore are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

Provided herein are kits and devices for practicing the assays and methods described herein. In some embodiments, described herein is a device for determining the presence of a sensitizing mutation in BRG1, EGFR, and/or B-RAF in a test sample from a subject comprising a nucleic acid probe which is specific for a sensitizing mutation of BRG1, EGFR, or B-RAF. In some embodiments, described herein is a device for the presence of a sensitizing mutation in BRG1, EGFR, and/or B-RAF in a test sample from a subject comprising a nucleic acid probe which can amplify a nucleic acid sequence comprising a sensitizing mutation of BRG1, EGFR, or B-RAF. In some embodiments, the probe can be detectably labeled. In some embodiments, the kit can further comprise a reagent for producing a detectable signal.

In some embodiments, the kit can comprise further reagents, e.g. a restriction enzyme, a universal adaptor to be conjugated to a nucleotide molecule, a primer complementary to the universal adaptor, a wash agent, free nucleotide bases, a polymerase, or any combinations thereof.

In some embodiments, the kit can comprise at least one protein-binding moiety (e.g. an antibody reagent) specific for a protein comprising a sensitizing mutation of BRG1, EGFR, or B-RAF. In some embodiments, the kit can further comprise a solid substrate support affixed with the at least one protein-based binding moiety. In some embodiments, the solid substrate support is a microtiter plate for ELISA. In some embodiments, the solid substrate support is a dipstick. In some embodiments, the solid substrate support comprises a magnetic bead. In some embodiments, the kit comprises at least one further reagent, e.g. a reagent for detecting a detectable label.

In some embodiments, the kit or device can comprise a reference, e.g. a reference sample or reference signal. In some embodiments, the reference can comprise a wild-type sequence and/or wild-type expression product of one or more of BRG1, EGFR, and/or B-RAF.

In some embodiments, the kit or device can comprise a multiplex assay or the reagents for performing a multiplex assay, e.g. multiple sets of probes and/or primers or multiple antibody reagents such that the presence or absence of multiple sensitizing mutations can be detected in a single reaction mixture. In some embodiments, the kit or device can comprise a an assay or the reagents for performing a assay for multiple sensitizing mutations in parallel, e.g. multiple sets of probes and/or primers or multiple antibody reagents such that the presence or absence of multiple sensitizing mutations can be detected in parallel.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or more or any decrease of at least 10% as compared to a reference level. These terms are not intended to cover complete reduction or inhibition.

In some aspects of all the embodiments, inhibition or reduction can be complete inhibition or complete reduction, i.e., a 100% decrease, i.e. absent or non-detectable level as compared to a reference level. In the context of a marker or symptom, a "decrease" is a statistically significant decrease in such level. The decrease can be, for example, at least 10%, at least 20%, at least 30%, at least 40% or more, and is preferably down to a level accepted as within the range of normal for an individual without such disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. In some embodiments, a cancer cell can be a cell obtained from a tumor. By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The terms "compound" and "agent" refer to any entity which is normally not present or not present at the levels being administered and/or provided to a cell, tissue or subject. An agent can be selected from a group comprising: chemicals; small organic or inorganic molecules; signaling molecules; nucleic acid sequences; nucleic acid analogues; proteins; peptides; enzymes; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the agent is any chemical, entity or moiety, including without limitation synthetic and naturally-occurring non-proteinaceous entities. In certain embodiments the agent is a small molecule having a chemical moiety. For example, chemical moieties include unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, "specific" when used in the context of an oligonucleotide primer or specific for a target nucleic acid refers to a level of complementarity between the primer and the target such that there exists an annealing temperature at which the primer will anneal to and mediate amplification of the target nucleic acid and will not anneal to or mediate amplification of non-target sequences present in a sample.

As used herein, the terms "treat," "treatment," "treating," or "amelioration" refer to therapeutic treatments, wherein the object is to alleviate, ameliorate, inhibit, slow down or stop the progression or severity of a condition associated with a disease or disorder, e.g. cancer. The terms are not intended to encompass a complete cure. The term "treating" includes reducing or alleviating at least one adverse effect or symptom of a condition, disease or disorder associated with cancer.

In some aspects, a complete cure can be achieved, and in those situations, the method is considered a method for curing cancer.

Treatment is generally "effective" if one or more symptoms or clinical markers associated with the disease are objectively or subjectively reduced. Alternatively, treatment is "effective" if the progression of a disease is reduced or halted. That is, "treatment" includes not just the improvement of symptoms or markers, but also a cessation of some symptoms, or at least slowing of, progress or worsening of symptoms compared to what would be expected in the absence of treatment. Beneficial or desired clinical results include, but are not limited to, alleviation of one or more symptom(s), diminishment of extent of disease, stabilized e., not worsening) state of disease, delay or slowing of disease progression, amelioration or palliation of the disease state, and/or decreased mortality. The term "treatment" of a disease also includes providing at least some relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating cancer, the method comprising:
   administering or prescribing a chemotherapeutic agent and an EZH2 inhibitor to a subject determined to have a sensitizing mutation of BRG1, EGFR, or B-RAF in a tumor cell.
2. A method of identifying a subject who is a candidate for treatment of cancer with a combination therapy comprising an EZH2 inhibitor and a chemotherapeutic agent, the method comprising:
   detecting a sensitizing mutation of BRG1, EGFR, or B-RAF in a tumor cell sample obtained from the subject;
   wherein if the sensitizing mutation is detected, the subject is identified as a candidate for cancer treatment with a combination therapy comprising a chemotherapeutic agent and an EZH2 inhibitor; and
   wherein if the sensitizing mutation is not detected, the subject is identified as a candidate for cancer treatment which does not comprise administering an EZH2 inhibitor.
3. A method of classifying a tumor cell as an EZH2 combination treatment responsive tumor, the method comprising:
   detecting a sensitizing mutation of BRG1, EGFR, or B-RAF in a sample comprising the tumor cell;
   wherein the presence of a sensitizing mutation of BRG1, EGFR, or B-RAF classifies the tumor as a EZH2 combination treatment responsive tumor and the absence of a sensitizing mutation of BRG1, EGFR, or B-RAF classifies the tumor as a EZH2 combination treatment non-responsive tumor.
4. The method of any of paragraphs 1-3, wherein the EZH2 inhibitor is selected from the group consisting of:
   an inhibitory nucleic acid; DZNep; and S-adenosyl-L-homocysteine; and GSK126.
5. The method of any of paragraphs 1-4, wherein the chemotherapeutic agent is selected from the group consisting of:
   a topoisomerase inhibitor; a topoisomerase I inhibitor; and a topoisomerase II inhibitor.
6. The method of paragraph 5, wherein the chemotherapeutic agent is a topoisomerase I inhibitor selected from the group consisting of:
   camptothecins; topotecan; irinotecan; indenoisoquinolines; indotecan; and indimitecan; and lamellarin D.
7. The method of paragraph 5, wherein the chemotherapeutic agent is a topoisomerase II inhibitor selected from the group consisting of:
   doxorubicin; etoposide; amsacrine; teniposide; ICRF-193; genistein; daunorubicin; mitoxantrone; ellipticines; aurintricarboxylic acid; and HU-331.
8. The method of any of paragraphs 5-7, wherein the subject is further administered cisplatin.
9. The method of any of paragraphs 1-4, wherein the chemotherapeutic agent is a PARP inhibitor.
10. The method of any of paragraphs 1-4, wherein the chemotherapeutic agent is a CDK1 inhibitor.
11. The method of any of paragraphs 1-4, wherein the chemotherapeutic agent is an EGFR inhibitor.
12. The method of any of paragraphs 1-11, wherein the sensitizing mutation of BRG1 comprises a mutation selected from the group consisting of
    a mutation which inactivates the ATPase activity of BRG1; a mutation which decreases the expression of BRG1; P270*; Q729*; W764R; T58*; and M272*.
13. The method of any of paragraphs 1-12, wherein the sensitizing mutation of EGFR comprises a mutation selected from the group consisting of:
    a mutation which increased the expression level of EGFR; an exon 19 deletion of EGFR; E746_A750del; E746_A749del; T790M; and L858R.
14. The method of any of paragraphs 1-13, wherein the sensitizing mutation of B-RAF comprises a mutation selected from the group consisting of:
    G496A and L597V.
15. The method of any of paragraphs 1-14, wherein the presence of the mutation is determined using an assay selected from the group consisting of:
    hybridization; sequencing; exome capture; PCR; and high-throughput sequencing.
16. The method of any of paragraphs 1-15, wherein the mutation is present in the genomic DNA of the tumor cell.
17. The method of any of paragraphs 1-15, wherein the mutation is present in the mRNA transcripts of the tumor cell.
18. The method of any of paragraphs 1-17, wherein the cancer is selected from the group consisting of:
    lung cancer; non-small cell lung cancer; ovarian cancer; EGFR-expressing ovarian cancer; B-Raf V600E melanomas; breast cancer; colon cancer; EGFR-mutated cancers; EGFR-mutated breast cancers; and EGFR-mutated colon cancers.

19. The method of any of paragraphs 1-18, further comprising the step of generating a report based on the detection of a sensitizing mutation in BRG1, EGFR, or B-RAF by a non-human machine.

20. An assay comprising:
   subjecting a tumor cell sample from a subject to at least one analysis to detect the presence of a sensitizing mutation of BRG1, EGFR, or B-RAF;
   wherein the presence of a sensitizing mutation of BRG1, EGFR, or B-RAF indicates the subject has a cancer which will respond to treatment with an EZH2 inhibitor and a chemotherapeutic agent.

21. The assay of paragraph 20, wherein the presence of the mutation is determined using an assay selected from the group consisting of:
   hybridization; sequencing; exome capture; PCR; and high-throughput sequencing.

22. An assay for selecting a treatment regimen for a subject with cancer, comprising:
   subjecting a nucleotide molecule derived from a biological sample of a subject, who is determined to suffer from or have a risk for cancer, to at least one genotyping analysis adapted to determine the the presence of a sensitizing mutation in one or more of B-RAF, EGFR, and BRG1:
   wherein if at least one sensitizing mutation is determined to be present, a treatment regimen comprising a combination of an EZH2 inhibitor and a chemotherapeutic agent is administered.

23. The assay of paragraph 22, wherein if no sensitizing mutations are determined to be present, a treatment regimen comprising a combination of an EZH2 inhibitor and a chemotherapeutic agent is not administered.

24. The assay of any of paragraphs 20-23, wherein the biological sample comprises a tumor cell.

25. An assay comprising:
   contacting a tumor cell sample obtained from a human subject having cancer with a nucleic acid probe to detect the presence of a sensitizing mutation in BRG1, EGFR, or B-RAF; and
   detecting the presence or intensity of a signal which indicates the presence of a sensitizing mutation in BRG1, EGFR, or B-RAF;
   wherein the presence of a sensitizing mutation of BRG1, EGFR, or B-RAF indicates the subject has a cancer which will respond to treatment with an EZH2 inhibitor and a chemotherapeutic agent.

26. The assay of any of paragraphs 20-25, wherein a detectable signal is generated by the probe when a sensitizing mutation is present.

27. The assay of any of paragraphs 20-26, wherein the probe is detectably labeled.

28. The assay of any of paragraphs 20-27, wherein the sensitizing mutation of BRG1 comprises a mutation selected from the group consisting of:
   a mutation which inactivates the ATPase activity of BRG1; a mutation which decreases the expression of BRG1; P270*; Q729*; W764R; T58*; and M272*.

29. The assay of any of paragraphs 20-28, wherein the sensitizing mutation of EGFR comprises a mutation selected from the group consisting of:
   a mutation which increased the expression level of EGFR; an exon 19 deletion of EGFR; E746_A750del; E746_A749del; T790M; and L858R.

30. The assay of any of paragraphs 20-29, wherein the sensitizing mutation of B-RAF comprises a mutation selected from the group consisting of:
   G496A and L597V.

31. The assay of any of paragraphs 20-30, wherein the mutation is present in the genomic DNA of the tumor cell.

32. The assay of any of paragraphs 20-31, wherein the mutation is present in the mRNA transcripts of the tumor cell.

33. The assay of any of paragraphs 20-32, further comprising the step of generating a report based on the detection of a sensitizing mutation in BRG1, EGFR, or B-RAF by a non-human machine.

34. A method of determining whether a subject is likely to respond to a combination treatment for cancer, the method comprising:
   detecting the presence of a sensitizing mutation in BRG1, EGFR, or B-RAF in a tumor cell sample obtained from the subject;
   wherein the presence of a sensitizing mutation in BRG1, EGFR, or B-RAF indicates the subject has an increased likelihood of responding to a treatment to cancer;
   wherein the treatment for cancer comprises administration of an EZH2 inhibitor and a chemotherapeutic agent.

35. The method of paragraph 34, wherein the EZH2 inhibitor is selected from the group consisting of:
   an inhibitory nucleic acid; DZNep; S-adenosyl-L-homocysteine; and GSK126.

36. The method of any of paragraphs 34-35, wherein the chemotherapeutic agent is selected from the group consisting of:
   a topoisomerase inhibitor; a topoisomerase I inhibitor; a topoisomerase II inhibitor 37. The method of paragraph 36, wherein the chemotherapeutic agent is a topoisomerase I inhibitor selected from the group consisting of:
   camptothecins; topotecan; irinotecan; indenoisoquinolines; indotecan; and indimitecan; and lamellarin D.

38. The method of paragraph 36, wherein the chemotherapeutic agent is a topoisomerase II inhibitor selected from the group consisting of:
   doxorubicin; etoposide; amsacrine; teniposide; ICRF-193; genistein; daunorubicin; mitoxantrone; ellipticines; aurintricarboxylic acid; and HU-331.

39. The method of any of paragraphs 36-38, wherein the subject is further administered cisplatin.

40. The method of any of paragraphs 34-35, wherein the chemotherapeutic agent is a PARP inhibitor.

41. The method of any of paragraphs 34-35, wherein the chemotherapeutic agent is a CDK1 inhibitor.

42. The method of any of paragraphs 34-35, wherein the chemotherapeutic agent is an EGFR inhibitor.

43. The method of any of paragraphs 34-42, wherein the sensitizing mutation of BRG1 comprises a mutation selected from the group consisting of:
   a mutation which inactivates the ATPase activity of BRG1; a mutation which decreases the expression of BRG1; P270*; Q729*; W764R; T58*; and M272*.

44. The method of any of paragraphs 34-43, wherein the sensitizing mutation of EGFR comprises a mutation selected from the group consisting of:
   a mutation which increased the expression level of EGFR; an exon 19 deletion of EGFR; E746_A750del; E746_A749del; T790M; and L858R.

45. The method of any of paragraphs 34-44, wherein the sensitizing mutation of B-RAF comprises a mutation selected from the group consisting of:
   G496A and L597V.

46. The method of any of paragraphs 34-45, wherein the presence of the mutation is determined using an assay selected from the group consisting of:
   hybridization; sequencing; exome capture; PCR; and high-throughput sequencing.

47. The method of any of paragraphs 34-46, wherein the mutation is present in the genomic DNA of the tumor cell.

48. The method of any of paragraphs 34-47, wherein the mutation is present in the mRNA transcripts of the tumor cell.

49. The method of any of paragraphs 34-48, wherein the cancer is selected from the group consisting of:
   lung cancer; non-small cell lung cancer; ovarian cancer; EGFR-expressing ovarian cancer; B-Raf V600E melanomas; breast cancer; colon cancer; EGFR-mutated cancers; EGFR-mutated breast cancers; and EGFR-mutated colon cancers.

50. A computer system for determining if a subject will be responsive to a cancer treatment, the system comprising:
   a determination module configured to detect the presence of a sensitizing mutation in BRG1, EGFR, or B-RAF in a tumor cell sample obtained from a subject;
   a storage module configured to store output data from the determination module;
   a comparison module adapted to compare the data stored on the storage module with a reference level, and to provide a retrieved content, and
   a display module for displaying whether a BRG1, EGFR, or B-RAF sensitizing mutation was detected in the tumor cell sample;
   wherein the cancer treatment comprises the administration of an EZH2 inhibitor and a chemotherapeutic agent.

51. The system of paragraph 50, wherein the determining module measures the intensity of a detectable signal from a RT-PCR assay indicating the presence of a sensitizing mutation of BRG1, EGFR, or B-RAF tumor cell sample.

52. The system of paragraph 50, wherein the determining module measures the intensity of a detectable signal from a sequencing assay indicating the presence of a sensitizing mutation of BRG1, EGFR, or B-RAF tumor cell sample.

53. The system of paragraph 50, wherein the determining module measures the intensity of a detectable signal from a hybridization assay indicating the presence of a sensitizing mutation of BRG1, EGFR, or B-RAF tumor cell sample.

54. The system of any of paragraphs 50-53, wherein if the computing module determines that the a sensitizing mutation of BRG1, EGFR, or B-RAF is present in the sample obtained from the subject, the display module displays a signal indicating that a sensitizing mutation has been detected.

55. The system of any of paragraphs 50-54, wherein the signal indicates that the subject has an increased likelihood of responding to treatment with an EZH2 inhibitor and chemotherapeutic agent.

56. The system of any of paragraphs 50-55, wherein the EZH2 inhibitor is selected from the group consisting of:
   an inhibitory nucleic acid; DZNep; S-adenosyl-L-homocysteine; and GSK126.

57. The system of any of paragraphs 50-56, wherein the chemotherapeutic agent is selected from the group consisting of:
   a topoisomerase inhibitor; a topoisomerase I inhibitor; a topoisomerase II inhibitor 58. The system of paragraph 55, wherein the chemotherapeutic agent is a topoisomerase I inhibitor selected from the group consisting of:
   camptothecins; topotecan; irinotecan; indenoisoquinolines; indotecan; and indimitecan; and lamellarin D.

59. The system of paragraph 55, wherein the chemotherapeutic agent is a topoisomerase II inhibitor selected from the group consisting of:
   doxorubicin; etoposide; amsacrine; teniposide; ICRF-193; genistein; daunorubicin; mitoxantrone; ellipticines; aurintricarboxylic acid; and HU-331.

60. The system of any of paragraphs 57-59, wherein the subject is further administered cisplatin.

61. The system of any of paragraphs 50-54, wherein the chemotherapeutic agent is a PARP inhibitor.

62. The system of any of paragraphs 50-54, wherein the chemotherapeutic agent is a CDK1 inhibitor.

63. The system of any of paragraphs 50-54, wherein the chemotherapeutic agent is an EGFR inhibitor.

64. The system of any of paragraphs 50-63, wherein the sensitizing mutation of BRG1 comprises a mutation selected from the group consisting of:
   a mutation which inactivates the ATPase activity of BRG1; a mutation which decreases the expression of BRG1; P270*; Q729*; W764R; T58*; and M272*.

65. The system of any of paragraphs 50-64, wherein the sensitizing mutation of EGFR comprises a mutation selected from the group consisting of:
   a mutation which increased the expression level of EGFR; an exon 19 deletion of EGFR; E746_A750del; E746_A749del; T790M; and L858R.

66. The system of any of paragraphs 50-65, wherein the sensitizing mutation of B-RAF comprises a mutation selected from the group consisting of:
   G496A and L597V.

67. The system of any of paragraphs 50-66, wherein the presence of the mutation is determined using an assay selected from the group consisting of:
   hybridization; sequencing; exome capture; PCR; and high-throughput sequencing.

68. The system of any of paragraphs 50-67, wherein the mutation is present in the genomic DNA of the tumor cell.

69. The system of any of paragraphs 50-68, wherein the mutation is present in the mRNA transcripts of the tumor cell.

70. The system of any of paragraphs 50-69, wherein the cancer is selected from the group consisting of:

lung cancer; non-small cell lung cancer; ovarian cancer; EGFR-expressing ovarian cancer; B-Raf V600E melanomas; breast cancer; colon cancer; EGFR-mutated cancers; EGFR-mutated breast cancers; and EGFR-mutated colon cancers.

71. A kit comprising:
   a nucleic acid probe which is specific for a sensitizing mutation of BRG1, EGFR, or B-RAF.

72. The kit of paragraph 71, wherein the probe is detectably labeled.

73. A kit comprising:
   a nucleic acid probe which can amplify a nucleic acid sequence comprising a sensitizing mutation of BRG1, EGFR, or B-RAF.

74. The kit of any of paragraphs 71-73, further comprising a reagent for producing a detectable signal.

75. The use of an EZH2 inhibitor in combination with a chemotherapeutic agent in treatment of a subject determined to have a sensitizing mutation of BRG1, EGFR, or B-RAF in a tumor cell obtained from the subject.

76. The use of paragraph 75, wherein the EZH2 inhibitor is selected from the group consisting of:
   an inhibitory nucleic acid; DZNep; and S-adenosyl-L-homocysteine; and GSK126.

77. The use of any of paragraphs 75-76, wherein the chemotherapeutic agent is selected from the group consisting of:
   a topoisomerase inhibitor; a topoisomerase I inhibitor; and a topoisomerase II inhibitor.

78. The use of paragraph 77, wherein the chemotherapeutic agent is a topoisomerase I inhibitor selected from the group consisting of:
   camptothecins; topotecan; irinotecan; indenoisoquinolines; indotecan; and indimitecan; and lamellarin D.

79. The use of paragraph 77, wherein the chemotherapeutic agent is a topoisomerase II inhibitor selected from the group consisting of:
   doxorubicin; etoposide; amsacrine; teniposide; ICRF-193; genistein; daunorubicin;
   mitoxantrone; ellipticines; aurintricarboxylic acid; and HU-331.

80. The use of any of paragraphs 77-79, wherein the subject is further administered cisplatin.

81. The use of any of paragraphs 75-76, wherein the chemotherapeutic agent is a PARP inhibitor.

82. The use of any of paragraphs 75-76, wherein the chemotherapeutic agent is a CDK1 inhibitor.

83. The use of any of paragraphs 75-76, wherein the chemotherapeutic agent is an EGFR inhibitor.

84. The use of any of paragraphs 75-83, wherein the sensitizing mutation of BRG1 comprises a mutation selected from the group consisting of
   a mutation which inactivates the ATPase activity of BRG1; a mutation which decreases the expression of BRG1; P270*; Q729*; W764R; T58*; and M272*.

85. The use of any of paragraphs 75-84, wherein the sensitizing mutation of EGFR comprises a mutation selected from the group consisting of:
   a mutation which increased the expression level of EGFR; E746_A750del; E746_A749del; T790M; and L858R.

86. The use of any of paragraphs 75-85, wherein the sensitizing mutation of B-RAF comprises a mutation selected from the group consisting of
   G496A and L597V.

87. The use of any of paragraphs 75-86, wherein the presence of the mutation is determined using an assay selected from the group consisting of:
   hybridization; sequencing; exome capture; PCR; and high-throughput sequencing.

88. The use of any of paragraphs 75-87, wherein the mutation is present in the genomic DNA of the tumor cell.

89. The use of any of paragraphs 75-88, wherein the mutation is present in the mRNA transcripts of the tumor cell.

90. The use of any of paragraphs 75-89, wherein the cancer is selected from the group consisting of:
   lung cancer; non-small cell lung cancer; ovarian cancer; EGFR-expressing ovarian cancer; B-Raf V600E melanomas; breast cancer; colon cancer; EGFR-mutated cancers; EGFR-mutated breast cancers; and EGFR-mutated colon cancers.

91. The use of any of paragraphs 75-90, further comprising the step of generating a report based on the detection of a sensitizing mutation in BRG1, EGFR, or B-RAF by a non-human machine.

EXAMPLES

Example 1

Drugs targeting epigenetic enzymes such as EZH2 may help to combat many cancers, including non-small cell lung cancer (NSCLC). As described herein, the effects of EZH2 inhibition on lung cancer growth and chemotherapy response both were examined both in vitro and in vivo. EZH2 inhibition via small hairpin or drug DZNep slowed growth of the majority of cell lines, and sensitized half of the lines to the chemotherapy etoposide. Unexpectedly, the remaining lines (termed "protected lines") showed an increase in etoposide IC50 in response to EZH2 inhibition. Cell lines sensitized to etoposide entered S phase in response to EZH2 inhibition, while protected lines showed cell cycle arrest and up-regulation of the cell cycle inhibitor p57. Sensitized lines were highly enriched for Brg1 and EGFR mutations, and modulation of Brg1 or EGFR levels changed the sensitized and protected phenotypes. Genes co-expressed with EZH2 in primary human lung cancer samples were highly enriched for cell cycle regulators and strongly predicted poor survival. These data further knowledge of the effects of EZH2 inhibition on cancer cells, and permit methods, assays, and systems to predict whether patients will benefit from dual chemotherapy and EZH2 inhibitor therapies.

Understanding which tumors will respond to epigenetic therapies will be essential for this new class of drugs to benefit patients. It is demonstrated herein, for the first time, that EZH2 inhibition changes chemotherapy sensitivities of lung cancer cells dependent on genetic interactions of the Brg1-containing SWI/SNF complex and EGFR signaling. These findings suggest that patients with lung tumors bearing, e.g., EGFR or Brg1 mutations will benefit from EZH2 inhibition treatment combined with chemotherapy, while patients with wild-type EGFR and Brg1 will respond well to EZH2 inhibition as a single therapy. EZH2 inhibition differentially affects lung cancer chemotherapy sensitivities; Brg1 and EGFR mutations are negatively correlated and predict sensitization; Brg1 and EGFR interact genetically to control EZH2 inhibition response; and an EZH2 expression gene signature significantly predicts patient survival.

Lung cancer is the leading cause of cancer related deaths worldwide, and its poor prognosis is attributable to metastasis and therapy resistance (Herbst et al., 2008). Epigenetic mechanisms, such as histone modifications, are thought to be crucial for the survival of metastatic and therapy resistant cells (Baylin, 2011, Crea et al., 2011a, Min et al., 2010, Iliopoulos et al., 2010). Therefore, combining epigenetic therapies with chemotherapy and radiation treatments may allow for more complete treatment responses. Polycomb Repressive Complexes (PRCs) are key regulators of chromatin states in stem cells and cancer (Simon and Lange, 2008, Lee et al., 2006, Ben-Porath et al., 2008). Binding of PRCs to regions of chromatin, and histone modifications mediated by these PRCs, can affect higher order chromatin structure, rendering areas in the genome inaccessible to transcriptional machinery (Simon and Kingston, 2009).

PRC2 often contains EZH2, a methyltransferase that tri-methylates histone H3 at lysine 27 (H3K27me3). H3K27me3 moieties are known to be docking sites for the Bmi1 containing complex PRC1, which can subsequently ubiquitylate histone H2A (Spamann and van Lohuizen, 2006, Bracken et al., 2009).

Many lines of evidence suggest that EZH2 inhibition may help to eradicate aggressive lung tumor cells, including, by way of non-limiting example, non-small cell lung cancer cells. Previous work by the inventors demonstrated that in the absence of Bmi1, progression of lung adenocarcinomas driven by oncogenic Kras was impaired (Dovey et al., 2007). Further, expression of EZH2 is highly correlated with poor prognosis in all stages of both adenocarcinoma and squamous cell carcinoma, the two major subtypes of NSCLC (Kikuchi et al., 2010, Takawa et al., 2011, Huqun et al., 2011). Of note, studies also found that Bmi1 expression has no predictive value (Kikuchi et al. 2010, Breuer et al., 2004), suggesting that EZH2 is more important for human lung cancers than is Bmi1. Because EZH2 is an enzyme, it is a particularly attractive target for development of small molecule inhibitors (Simon and Lange, 2008). Furthermore, EZH2 and other PRC components home to sites of DNA damage after ionizing radiation (Chou et al., 2010). Therefore, without wishing to be bound by theory, incorporation of PRC complex inhibitors may lead to more complete responses of tumors to standard therapies by preventing proper DNA repair (Crea et al., 2011, Iliopoulos et al., 2010). In support of this concept, EZH2 inhibition was shown to increase apoptosis of one lung cancer cell line when combined with chemotherapy in vitro (Wu et al., 2011).

Lung cancer is one of the most genetically complex diseases in humans. The most common genetic lesions in lung cancer include inactivating mutations in p53 (50-70% of NSCLC), deletion and mutation of LKB1 (20-35% of NSCLC), and activating mutations in K-ras (10-30% of NSCLC, Herbst et al., 2008, TCGA, 2012, Imielinski et al., 2012). Also frequently observed are activating mutations and amplifications in EGFR (10-40% of NSCLC), which cause increased Raf-MEK-MAPK signaling (Herbst et al., 2008, Rodriguez-Nieto et al., 2011, TCGA, 2012, Imielinski et al., 2012). The Raf-MEK-MAPK pathway can also be activated in lung tumors through activating mutations in B-Raf (3% of NSCLC, Herbst et al., 2008, Ji et al, 2007, TCGA, 2012, Imielinski et al., 2012). Recently, Brg1, the ATPase in the SWI/SNF chromatin-remodeling complex, was identified as a gene commonly deleted or truncated in lung tumors (2-10% of NSCLC, Rodriguez-Nieto et al., 2011, TCGA, 2012, Imielinski et al., 2012). Because of this genetic complexity, testing EZH2 inhibitors must be performed by carefully considering the mutations driving each tumor tested. As the inventors have previously demonstrated, laboratories studies found that consideration of lung tumor genotype is essential to understanding the complex biological processes which allow tumor cells to survive and propagate (Curtis et al., 2010).

In order to validate the use of EZH2 inhibition to treat NSCLC, the effects of EZH2 inhibition on lung tumor progression and chemotherapy responses were examined, using a large panel of human lung cancer cell lines grown both in vivo and in vitro. It was found that mutations in EGFR, B-Raf and Brg1 significantly predict whether a cell line will be sensitized or protected from chemotherapy by EZH2 inhibition. These data link, for the first time, EZH2 inhibition phenotypes to common mutations in NSCLC.

Results

EZH2 Knock-Down has Differential Effects on Chemotherapy Sensitivities.

Figure 1B:
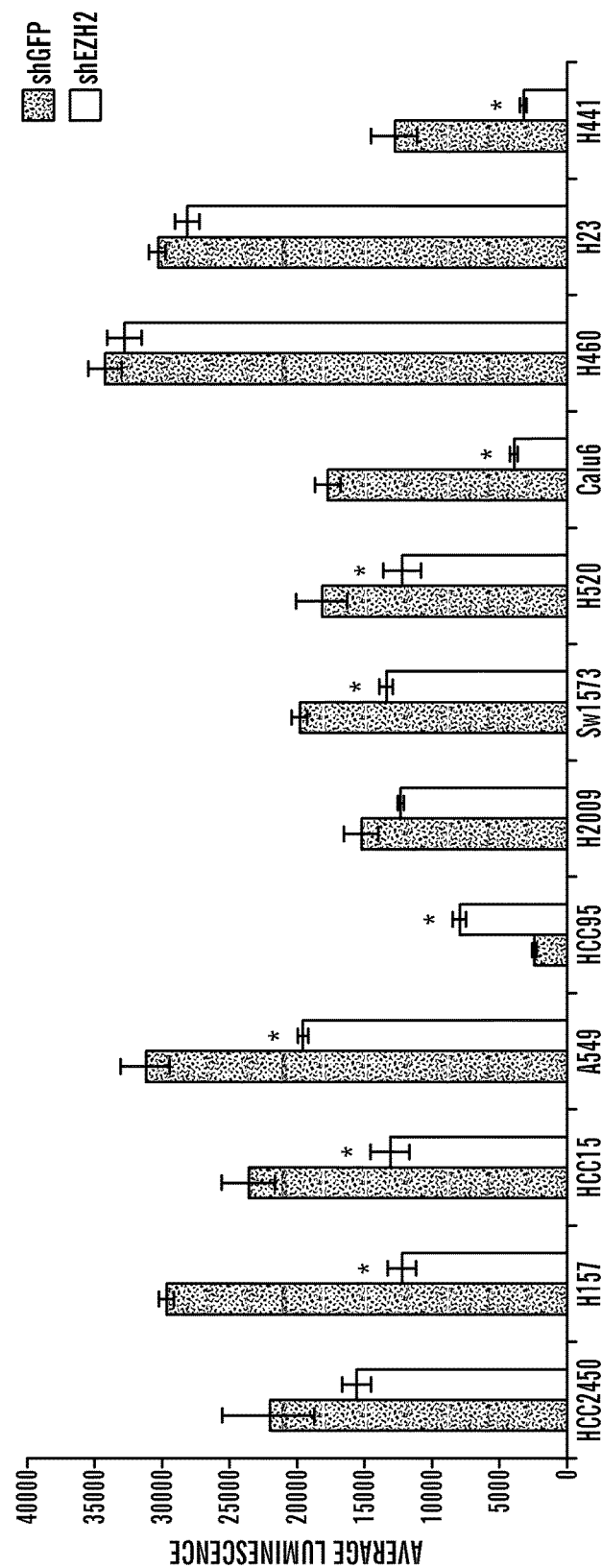
Figure 7A:
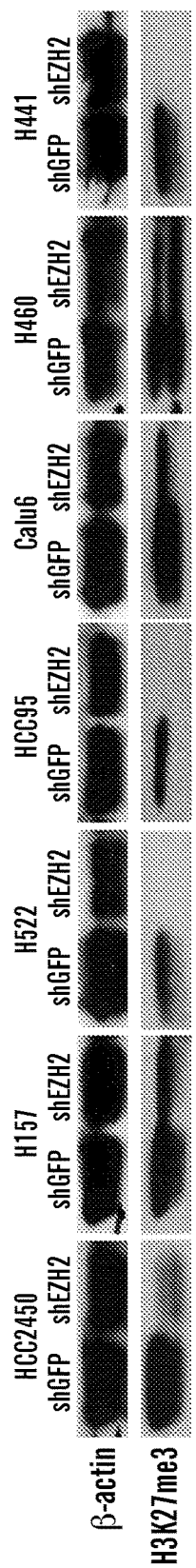
FIGS. 7A-7C depict the formation of tumorspheres.
Figure 7B:
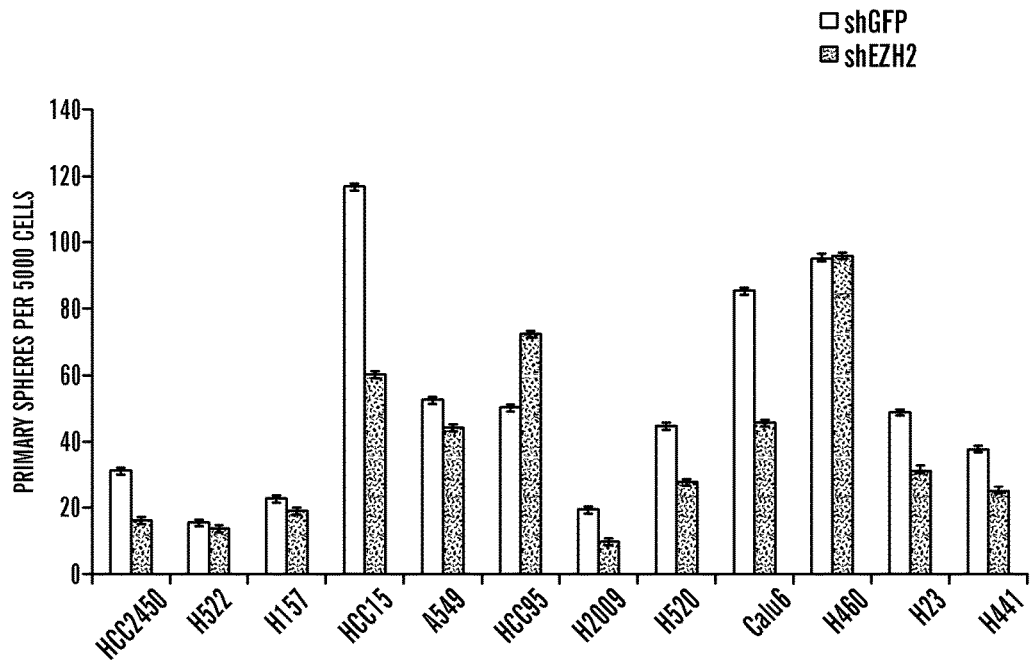
Figure 7C:
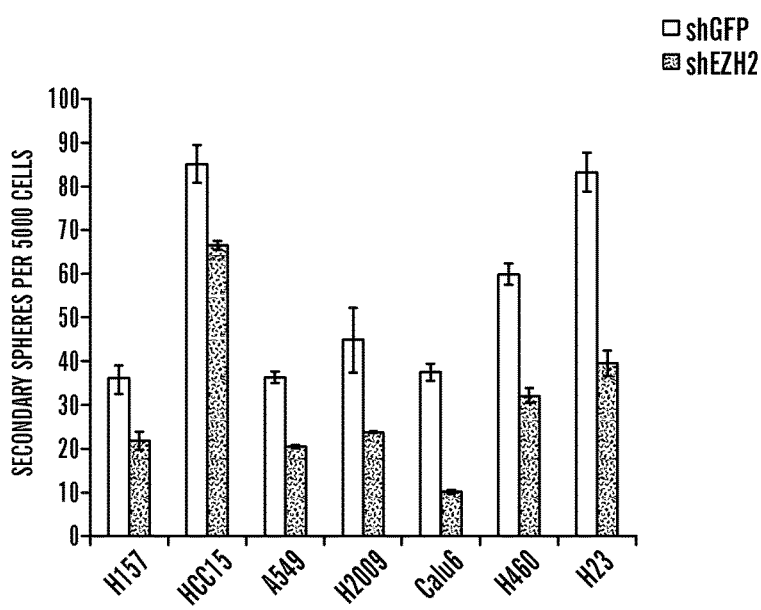

In order to test EZH2 inhibition as a therapy for NSCLC, we obtained ~30 human NSCLC lines that vary in genotype, stage and subtype (Table SI) and used a lentiviral small hairpin targeting EZH2 to stably knock-down EZH2 expression. By Western Blot, EZH2 protein and the PRC2 catalytic mark, H3K27me3, was diminished in every cell line transduced with this hairpin when compared to matched shGFP transduced cells (FIG. 1A, FIG. 7A). Growth rates in standard 2D adherent cultures were attenuated in 9 out of 12 cell lines in response to small-hairpin mediated EZH2 ablation over a period of 10 days (FIG. 1B). The shEZH2 Calu6, H441 and H157 lines were the most affected cell lines with 4.5-fold, 3.9-fold and 2.1-fold decreases in proliferation respectively when compared to their shGFP control lines. HCC95 shEZH2 was the outlier, which proliferated 3.2-fold more than the matched shGFP control line. To assess self-renewal capacity of the shEZH2 lines, efficiency of primary and secondary 3D sphere colonies was quantified (FIGS. 7B-7C). All of the shEZH2 cell lines had diminished secondary sphere forming capacity relative to their shGFP controls.

Figure 1C:
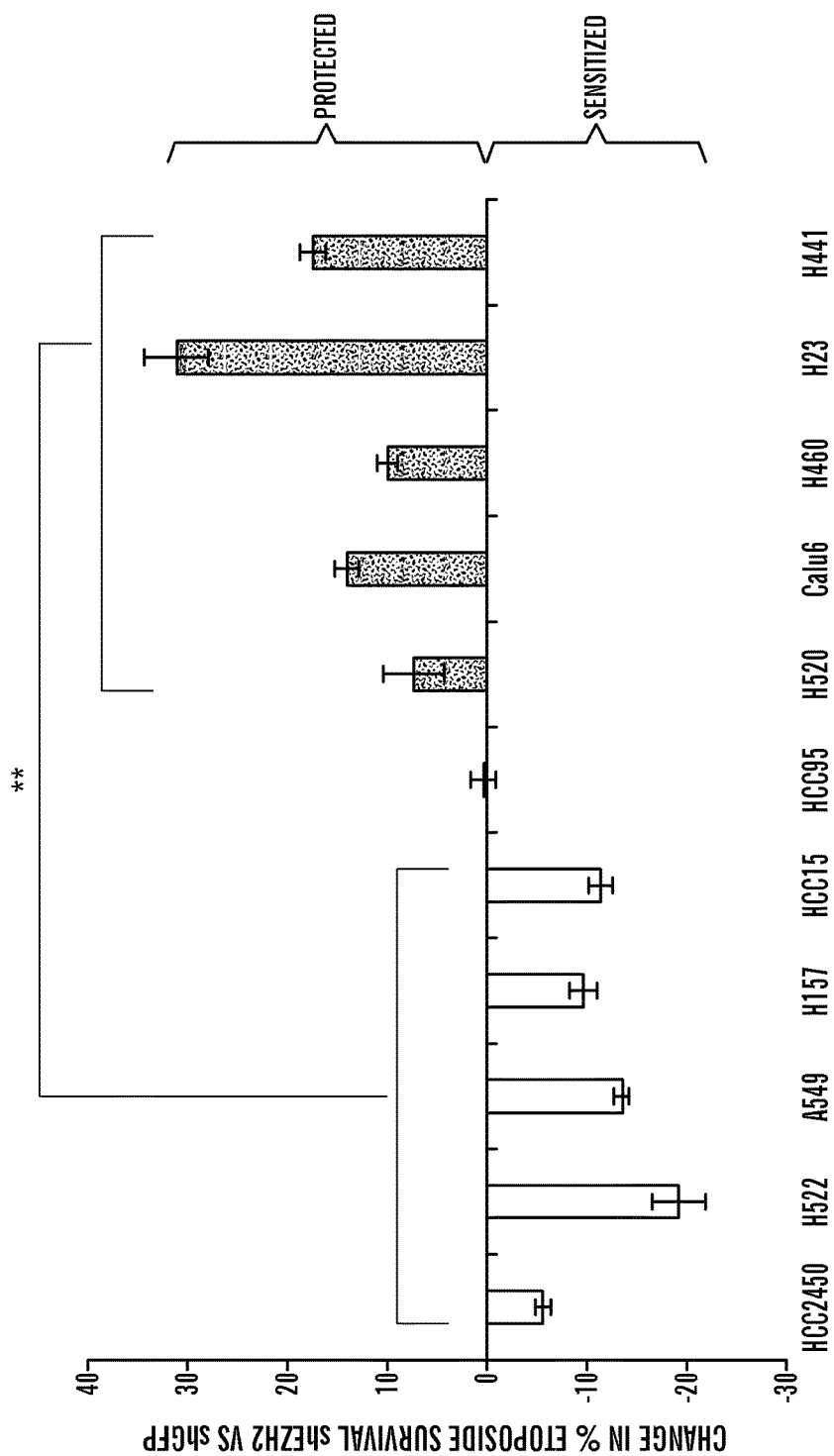

To test if EZH2 depleted cells are more sensitive to standard therapeutics such as chemotherapy, cell viability assays were performed with the commonly used chemotherapy etoposide. Both shGFP or shEZH2 cell lines were treated for 4 days with several doses of etoposide, and cell viability was measured. Each cell line was normalized to the untreated control thereby accounting for the decrease in proliferation of the shEZH2 lines, and change in percent survival between the shGFP and shEZH2 lines for both 1 μM and 10 μM etoposide was determined (FIG. 1C). Unexpectedly, though some cell lines were more sensitive to etoposide when EZH2 was knocked down, others were more viable. For example the H522 shEZH2 was an average of 19% less viable in 1 μM and 10 μM etoposide than H522 shGFP, while the H23 shEZH2 was an average of 31% more viable than its shGFP control line. These two classes of cell lines are referred to herein as those that are sensitized to etoposide by EZH2 inhibition (i.e. EZH2 inhibitor combination treatment responsive) and those that are protected.

EZH2 Inhibition by DZNep has Differential Effects on Chemotherapy Sensitivities.

Figure 2A:
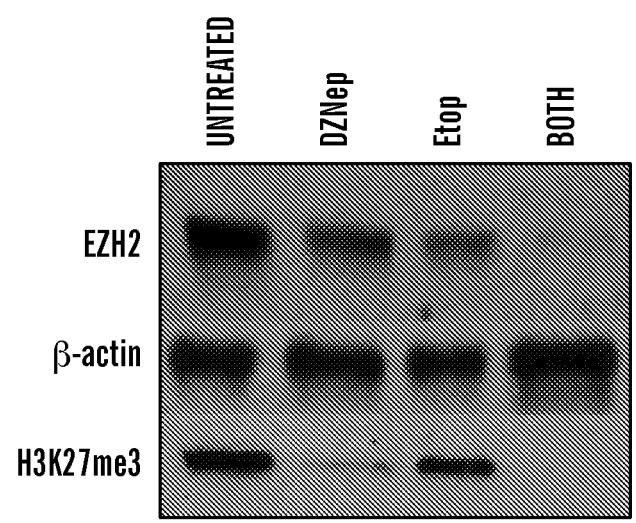
FIGS. 2A-2C demonstrate that EZH2 inhibition by DZNep has differential effects on chemotherapy sensitivities.
Figure 2B:

Next, to learn if these results could be reproduced by chemical inhibition of EZH2, a small molecule known to target EZH2 termed DZNep was obtained (Tan et al., 2007, Puppe et al., 2009, Crea et al., 2011a, Crea et al., 2011b, Wu et al., 2011, Kikuchi et al., 2012). Western Blot confirmed that a 1 µM dose of DZNep during a 4-day treatment effectively reduced EZH2 protein abundance and the H3K27me3 catalytic mark (FIG. 2A). At the 4-day time point, 1 µM DZNep caused an average of 20% reduction in growth of the cell lines (FIG. 8A). This dose of DZNep also lead to reduced growth rates of 11 out of 12 cell lines assessed over a 10 day time-course (FIG. 2B). Similarly to the results with shEZH2, Calu6, H441 and H157 all showed 2.1-fold decreases in proliferation in response to DZNep. HCC15 was the most affected cell line with a 3.2-fold decrease in response to DZNep, while HCC95 was again the outlier that increased proliferation in response to the EZH2 inhibitor. Together these data indicate that an EZH2 inhibitor may be a viable therapeutic strategy to slow the growth of the majority of NSCLCs.

Figure 2C:
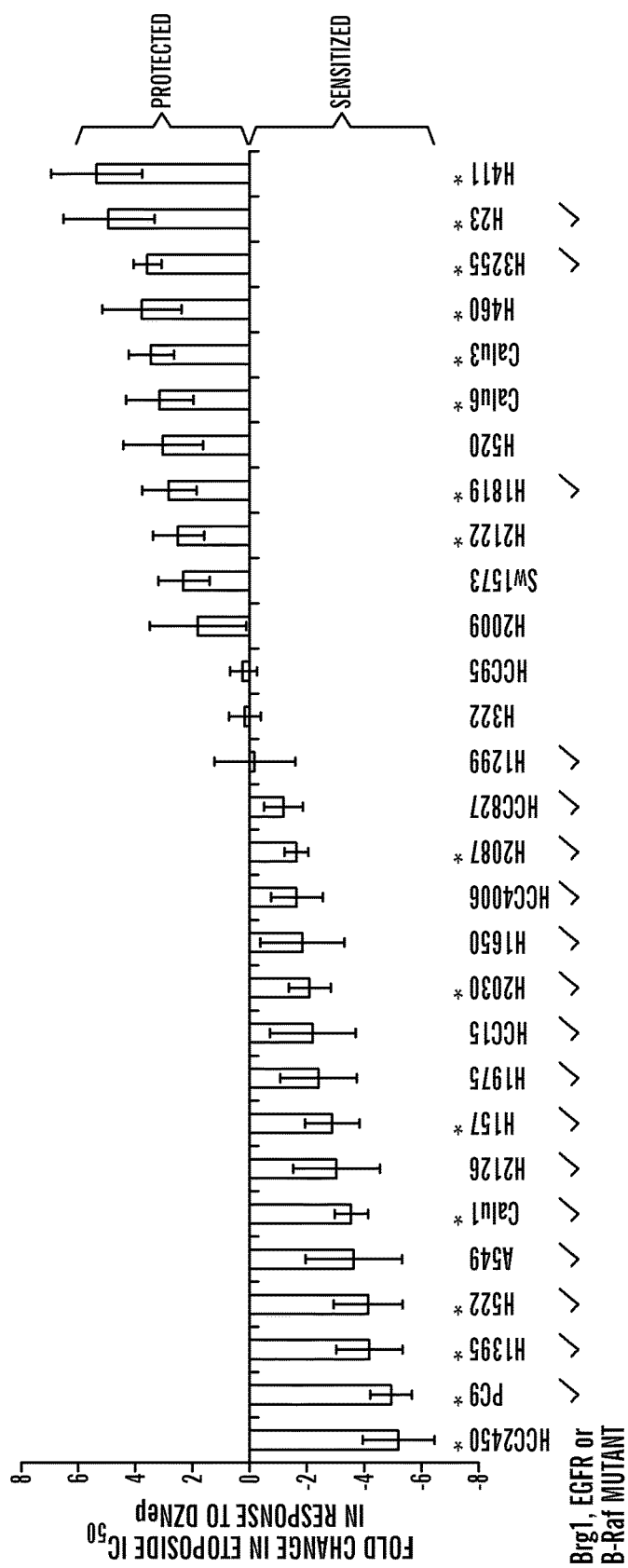

The synergy of DZNep with etoposide was assessed by performing etoposide dose response curves in the presence and absence of DZNep. After 4 days, cell viability was measured and the etoposide IC50s for each cell line with and without DZNep were compared. 16 of the 29 cell lines, including H157, HCC15 and PC9, were more sensitive to etoposide, while the other lines, such as H23, H460 and H441, were less sensitive to the chemotherapy in the presence of DZNep (FIG. 2C). Importantly, when the etoposide IC50 values were averaged for the two classes, no significant difference between the sensitized and protected cell lines was observed, suggesting that sensitization was not unique to chemo-resistant cell lines as seen in previous studies (FIG. 25B, Ougolkov et al., 2008).

Figure 8C:
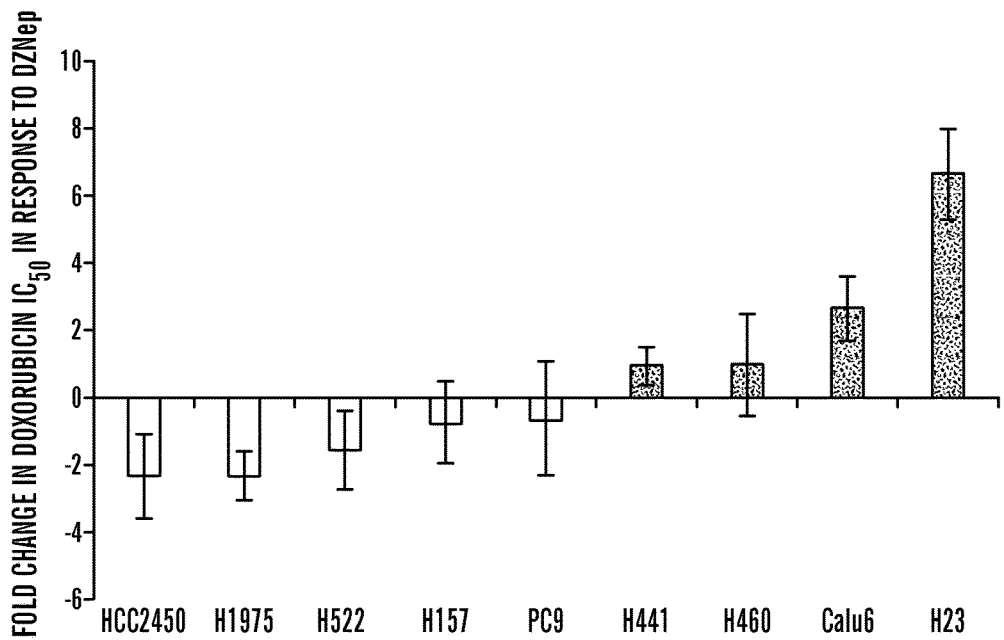
Figure 8D:
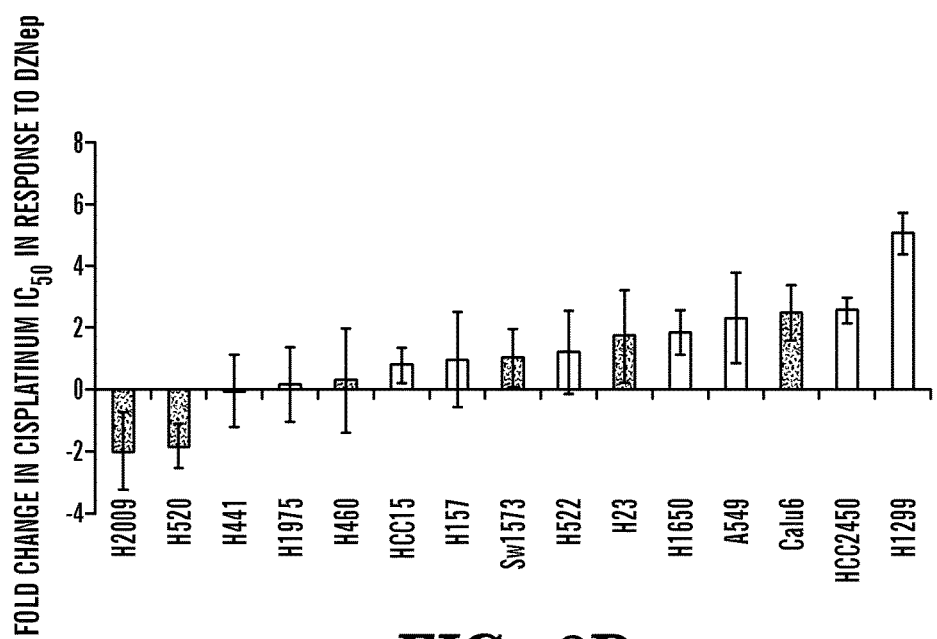

Etoposide acts by binding within the Topoisomerase II (TopoII) complex and preventing re-ligation of the double strand break required to unwind DNA during S phase (Baldwin and Osheroff, 2005). To learn if the described results were specific to TopoII inhibition, two other common chemotherapies were used: doxorubicin, which also targets the TopoII complex, and cis-platinum, which causes double strand breaks through pyrimidine dimers. Cell lines segregated into the same protected and sensitized classes with doxorubicin combined with DZNep, but the pattern was not observed when cis-platinum and DZNcp were combined (FIGS. 8C, 8D).

In Vitro Sensitivities to DZNep/Etoposide Predict In Vivo Responses.

To determine if the protected and sensitized phenotypes could be observed in vivo, cells were transplanted subcutaneously, tumors allowed to initiate, and mice treated with etoposide and DZNep. 12 days after cell injection, tumor bearing mice were randomized into groups that received either etoposide (20 mg/kg/day) or placebo (corn oil) daily for five days. The cohorts were further subdivided into groups that also received DZNep, either 2 mg/kg/day twice during the first week (dosing scheme A), or 1 mg/kg/day twice during the first two weeks (dosing scheme B).

Figure 3A:
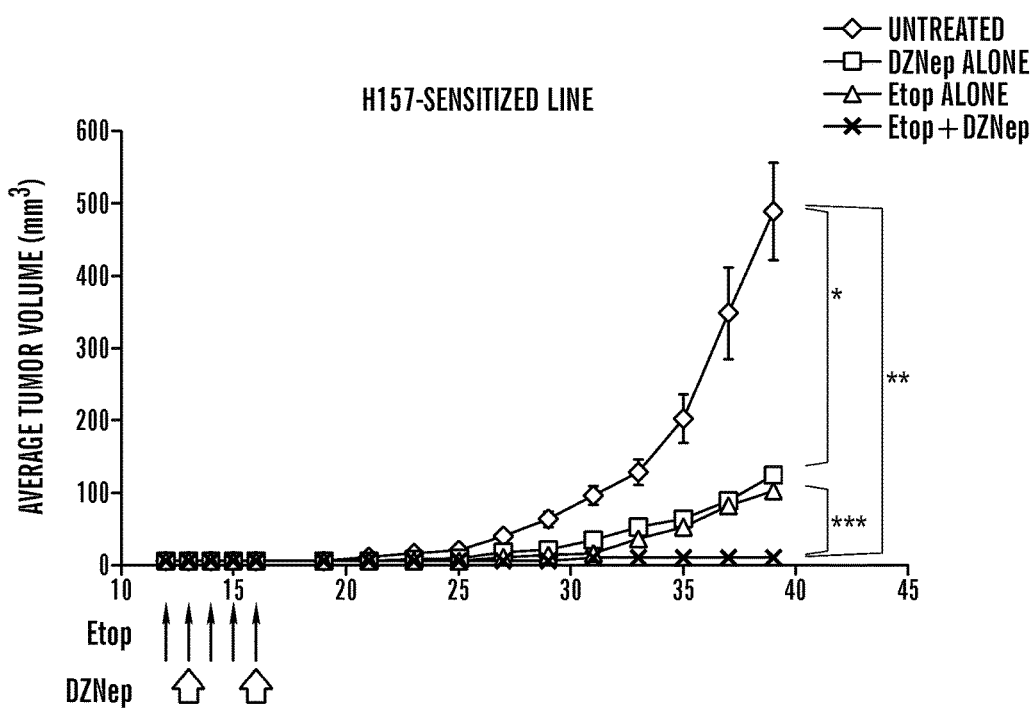
FIGS. 3A-3B demonstrate that in vitro sensitivities to DZNep/etoposide predict in vivo responses. Either the H157 (FIG. 3A) or H23 (FIG. 3B) cell lines were injected into the flanks of Nude mice and tumors were allowed to form. On day 12, mice were randomly segregated into cohorts that received either placebo or etoposide for five consecutive days. For H157 mice, a subset of the placebo and etoposide cohorts also received 2 mg/kg/day DZNcp twice in the first week (dosing scheme A), * indicates p=0.03 untreated vs. DZNep,  indicates p=0.0002 untreated vs. dual, and * indicates p=0.015 for etoposide vs. dual. For the H23 mice, the DZNep dose administered was 1 mg/kg/day twice per week for two weeks (dosing scheme B), * indicates p=0.001 untreated vs. DZNep,  indicates p=0.01 dual vs. etoposide, and * indicates p<0.0001 for dual vs. DZNep. Tumor growth was measured by caliper every other day until the tumor burden for the control mice was the maximum allowed by CHB IACUC. Results for at least 8 xenografts per condition were averaged and graphed ±s.c.m. Each cell line with the alternative dosing strategy is shown in FIGS. 9A-9B.
Figure 9A:
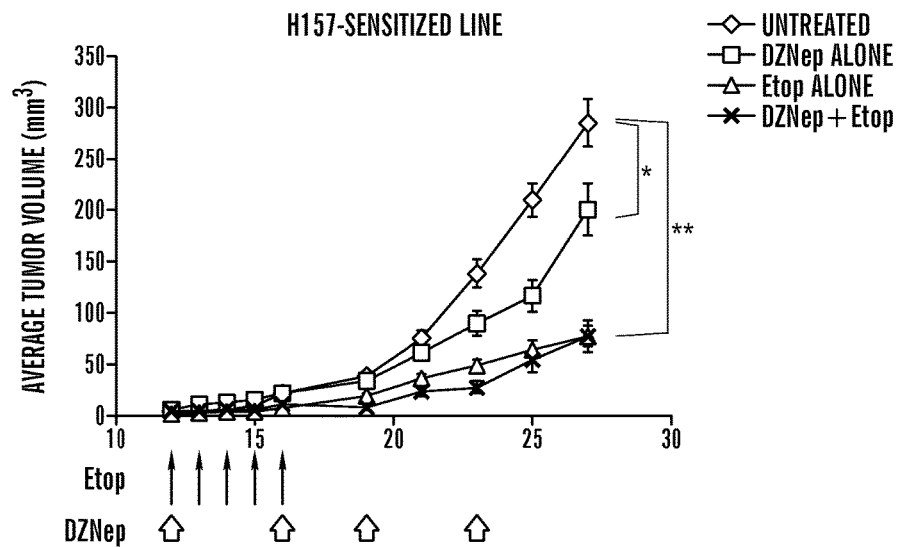
FIGS. 9A-9B depict alternative Dosing Strategies for DZNep and etoposide for H157 and H23 xenografts.

For the sensitized cell line H157, dosing scheme A yielded the most significant results. DZNep alone was effective at reducing tumor burden (FIG. 3A, p=0.03 untreated vs. DZNep), and dual therapy prevented tumors from forming in 7/8 xenografts, proving more efficacious than etoposide alone (p=0.0002 untreated vs. dual, p=0.015 etoposide vs. dual). Dosing scheme B was not as effective for the H157 line. In particular, treatment with DZNep during the second week appeared to have the unwanted effect of causing tumors to grow larger (FIG. 9A, p=0.21 untreated vs. DZNep, p=0.49 etoposide vs. dual). This result indicates that for sensitized lines, higher doses of DZNep earlier in tumor development are more effective that lower doses administered over a longer time period.

Figure 3B:
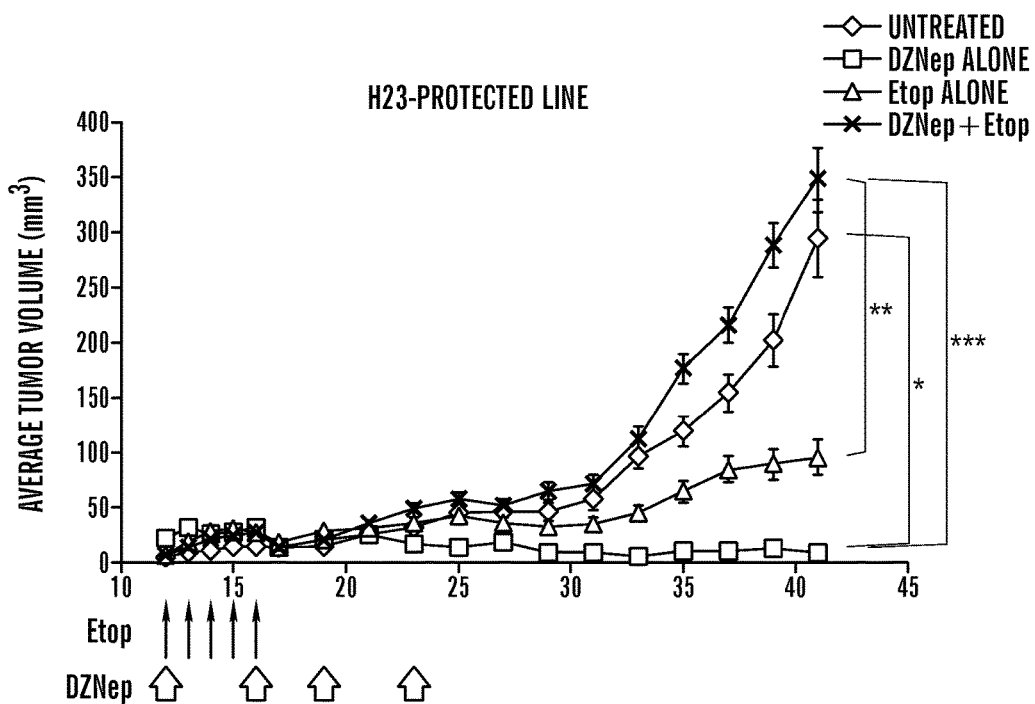
Figure 9B:
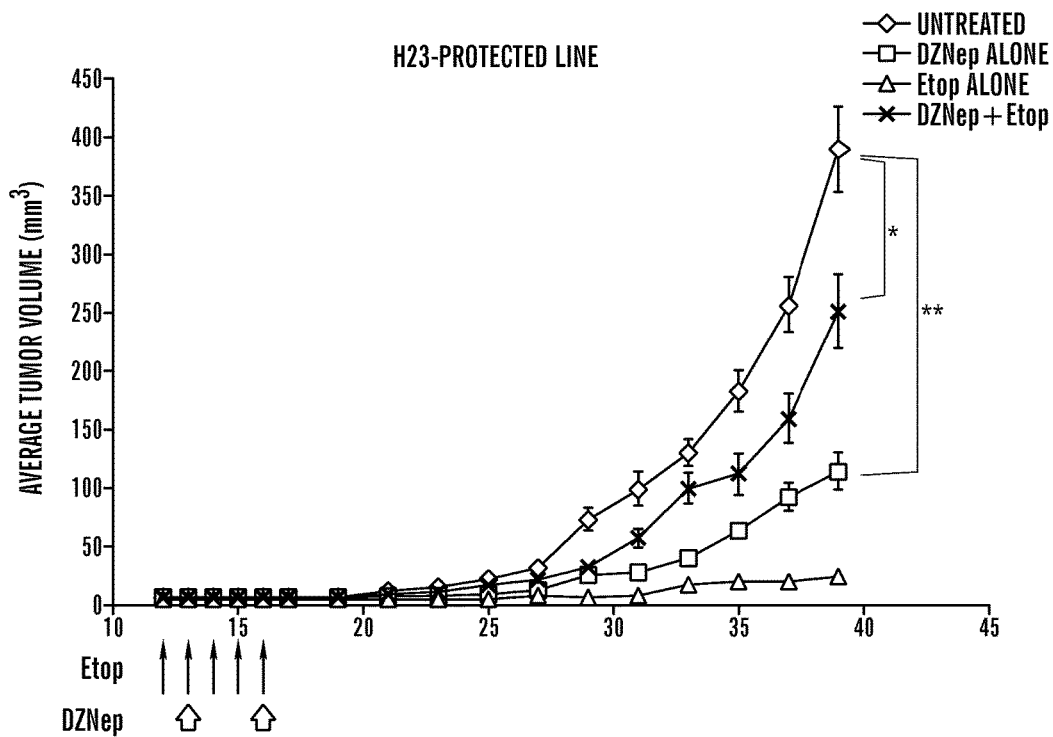

In contrast, for the protected cell line H23, dosing scheme B was most effective. H23 xenografts were very sensitive to DZNep as a single therapy (FIG. 3B, p=0.001 untreated vs. DZNep), but those that received dual therapy grew significantly larger than those treated with either DZNep or etoposide alone (p<0.0001 dual vs. DZNep, p=0.01 dual vs. etoposide). For this line, treatment with DZNep during the second week was required for the long-term cytostatic effect of DZNep alone. Using dosing scheme A, the difference between untreated xenografts and those that received only DZNep was less significant (FIG. 9B, p=0.01 untreated vs. DZNep). Together these data demonstrate that sensitized and protected phenotypes can be observed in xenografts, and that dosing schemes for both types of tumors can effectively reduce tumor burden.

EZH2 Inhibition in Presence of Chemotherapy Differentially Affects Cell Cycle.

Figure 4A:
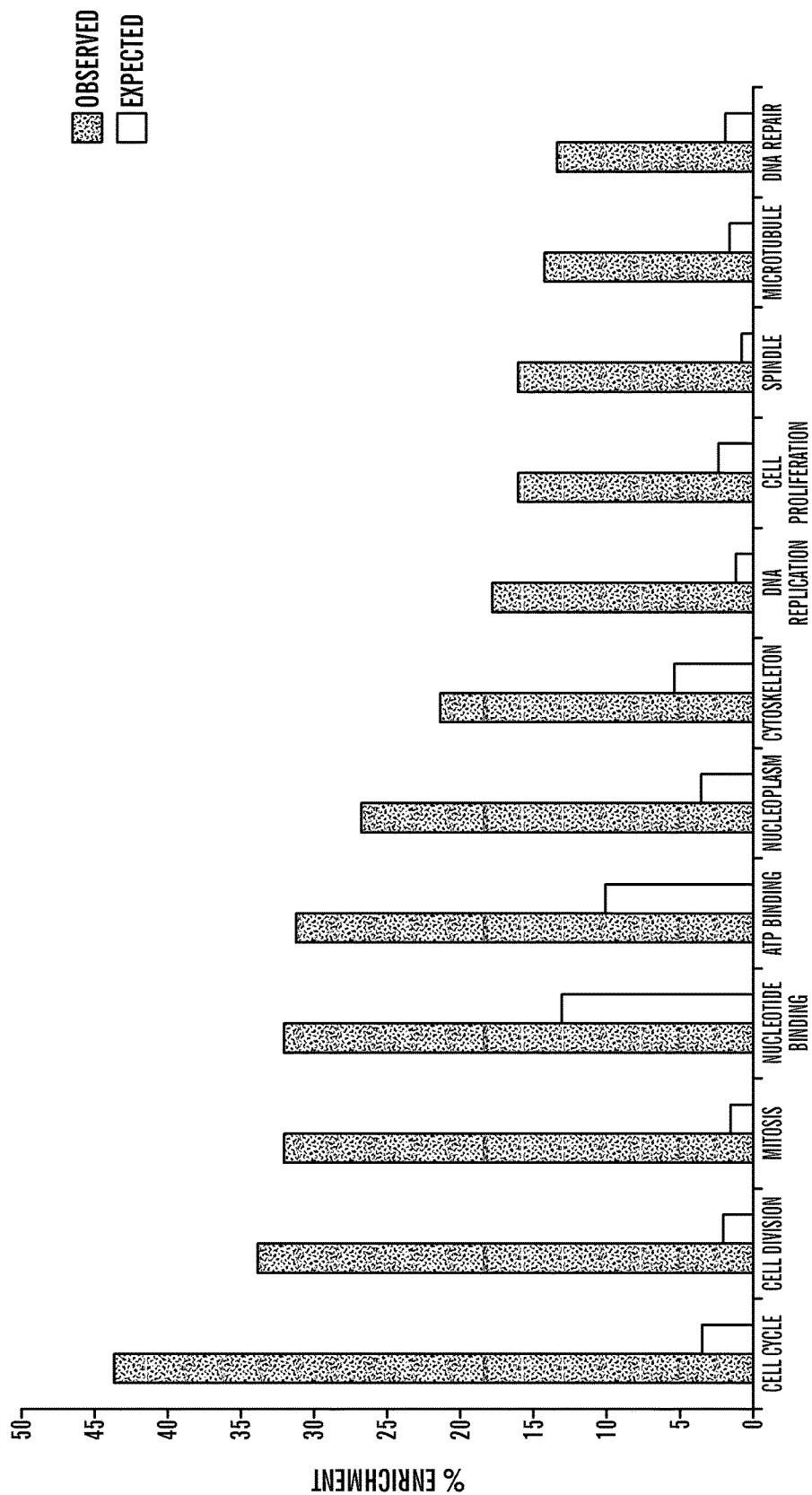
FIGS. 4A-4E demonstrate that EZH2 inhibition in presence of chemotherapy differentially affects cell cycle.
Figure 4B:
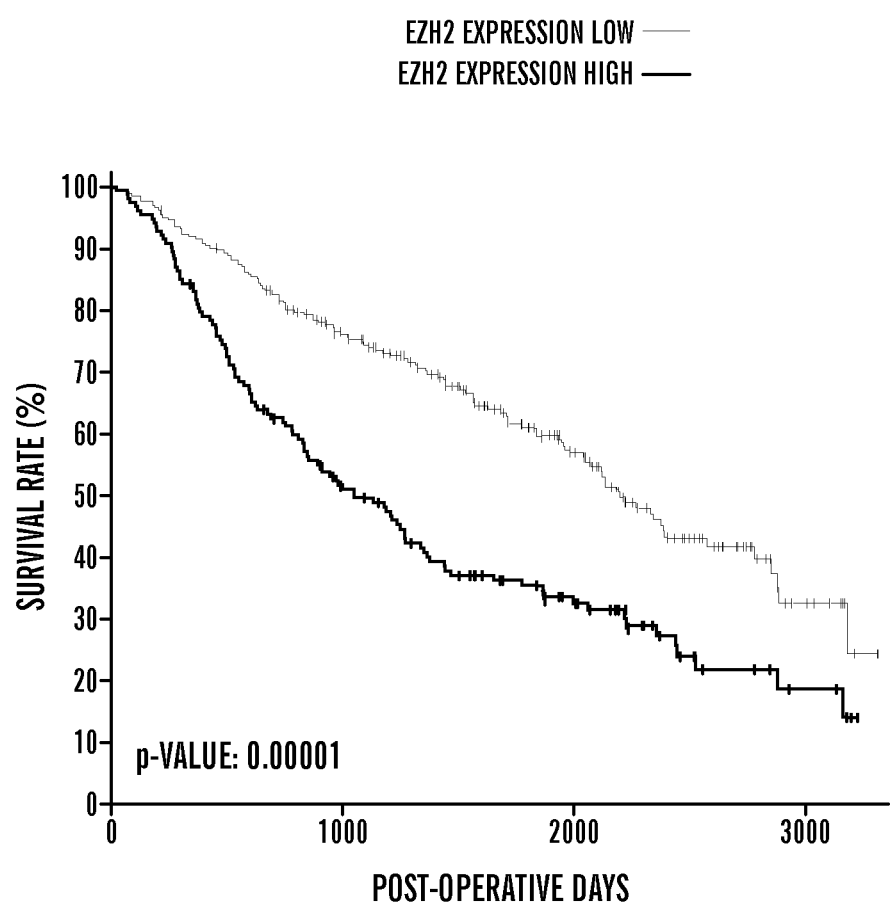

It was next sought to learn the mechanism through which the protected cells were surviving chemotherapy in the presence of EZH2 inhibition. Using Oncomine, an EZH2 expression gene signature was generated by annotating the top 20 genes co-expressed with EZH2 in 9 studies consisting of over 1,000 primary non-small cell lung cancer samples. Of the 180 probes, 64 were redundant, leading to a list of 116 genes highly co-expressed with EZH2 (Table 2). By gene ontology, these 116 genes are highly enriched for cell cycle, DNA synthesis and DNA repair (Table 3, FIG. 4A, p<0.001). Whether this EZH2 expression signature had predictive power for cancer progression was queried using the Director's Challenge dataset of 410 human lung adenocarcinomas (Director's Challenge, 2008). When patients were clustered into 2 groups, those whose tumors had high expression of the EZH2 expression signature, and those whose tumors had low expression, a significant difference was observed in survival between the two groups (FIG. 4B, p<0.00001). Patients with EZH2 expression high tumors survived a median of 3 years post tumor biopsy, while patients with EZH2 expression low tumors survived a median of 6 years.

Figure 4C:
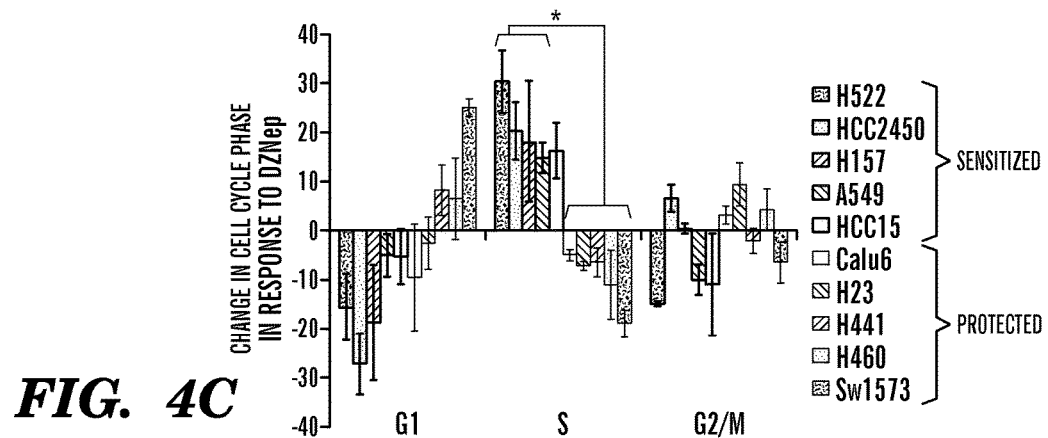
Figure 4D:
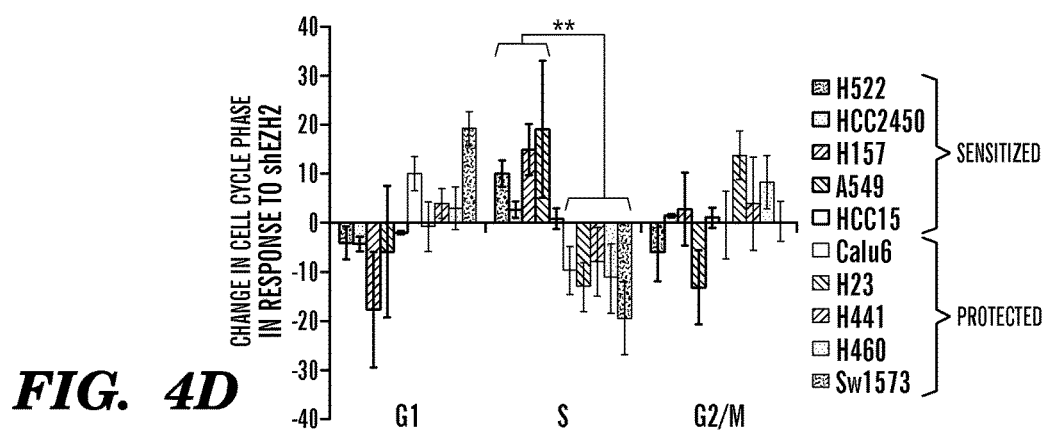
Figures 10A, 10B:
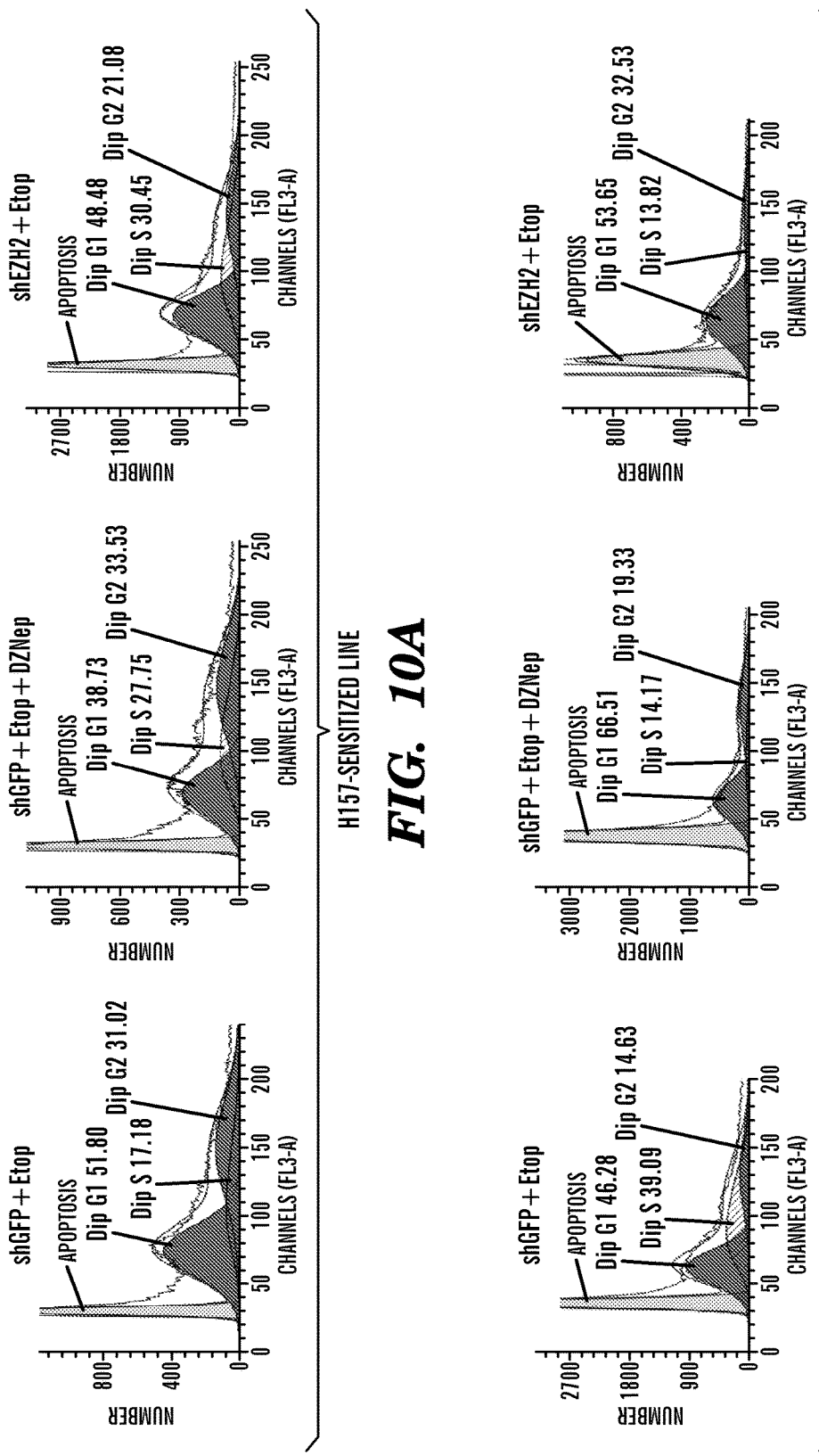
FIGS. 10A-10F depict the effects of EZH2 inhibition and chemotherapy combination treatment.
Figure 10C:
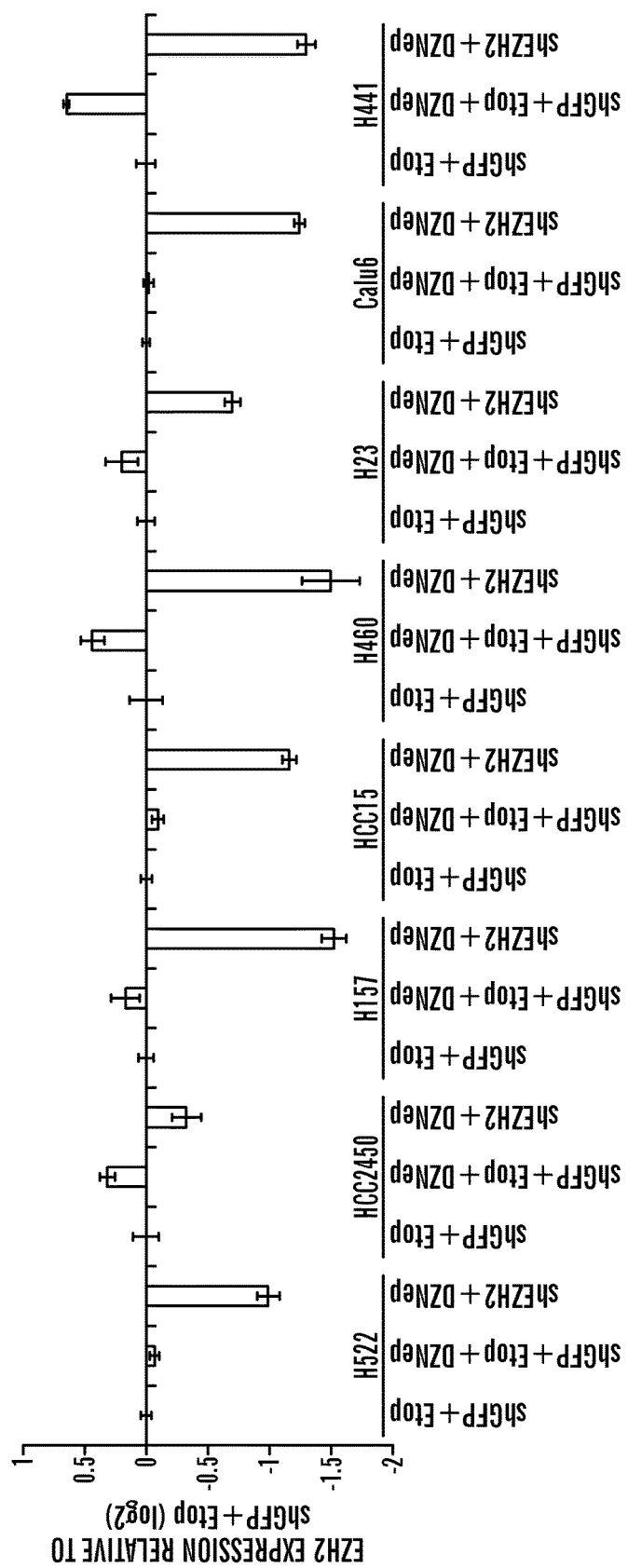

Due to the significant enrichment of cell cycle regulatory genes in the EZH2 expression signature, it was hypothesized that EZH2 inhibition caused changes in cell cycle status that rendered cells more or less sensitive to chemotherapy. It was further hypothesized that protected lines undergo a cell cycle arrest in response to EZH2 inhibition, thus sparing them from etoposide-induced DNA damage, while sensitized lines are unable to arrest and instead continue to cycle in the presence of etoposide. To test this hypothesis, various cell lines were treated with 10 µM etoposide (~IC50), 1 µM DZNep, or both for 4 days, and cells were fixed and stained with 7AAD to visualize ploidy by flow cytometry. The protected cell lines had an average of 10% fewer cells in S phase when treated with etoposide and DZNep compared to treatment with etoposide alone (FIG. 4C, FIG. 10A-10B S phase p=0.0001). These protected cell lines also appeared to be collecting in the GI and G2/M phases of the cell cycle, consistent with cell cycle arrest. In contrast, etoposide-treated sensitized cell lines had an average of 20% more cells in S phase in response to DZNep. Similar results were seen when comparing shGFP to shEZH2 lines treated with etoposide, and it was confirmed that EZH2 remains knocked down during the 4 day drug treatment (FIG. 4D, FIG. 10A-10C, S phase p=0.0006). These data indicate that EZH2 inhibition has differential effects on cell cycle regulation, which in turn mediates differential survival in the presence of TopoII inhibitors.

Figure 4E:
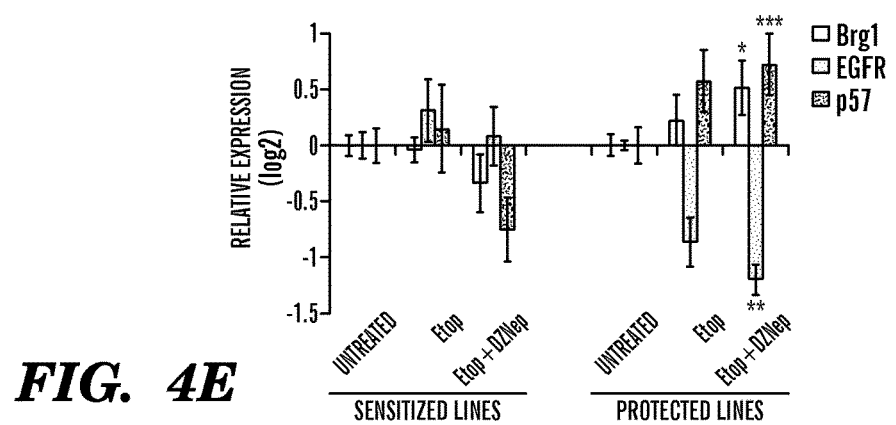
Figure 10D:
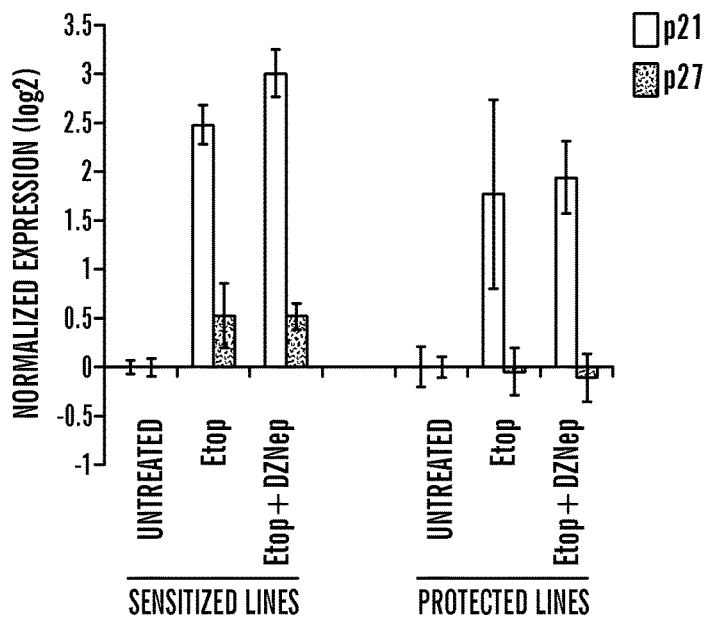
Figure 10E:
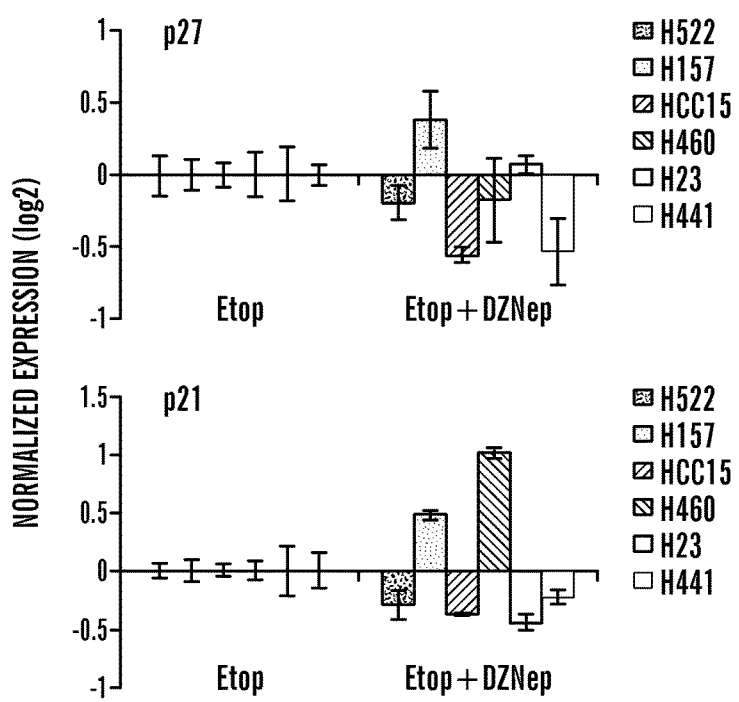
Figure 10F:
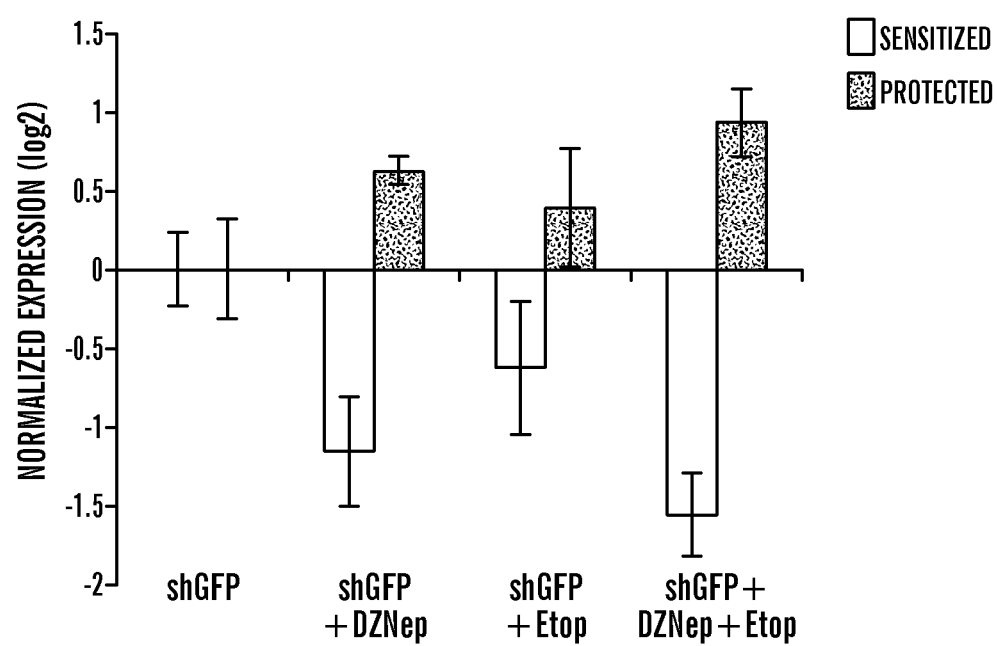

To learn how cell cycle arrest is mediated in protected cell lines, RNA was isolated from the treated cell lines (4 sensitized lines: H522, HCC2450, H157 and HCC15, 4 protected lines: H460, H441, H23 and Calu6) and quantitative RT-PCR performed for cell cycle inhibitors. Several non-mutated cell cycle regulators are up-regulated in response to dual EZH2 inhibition and etoposide treatment, including p21, while others, such as p27, were unchanged (FIG. 10D). Of note, p57 is down-regulated in sensitized lines in response to etop/DZNep, and up-regulated in protected lines, following the pattern predicted by the cell cycle data (FIG. 4E, p=0.01).

Figure 18A:
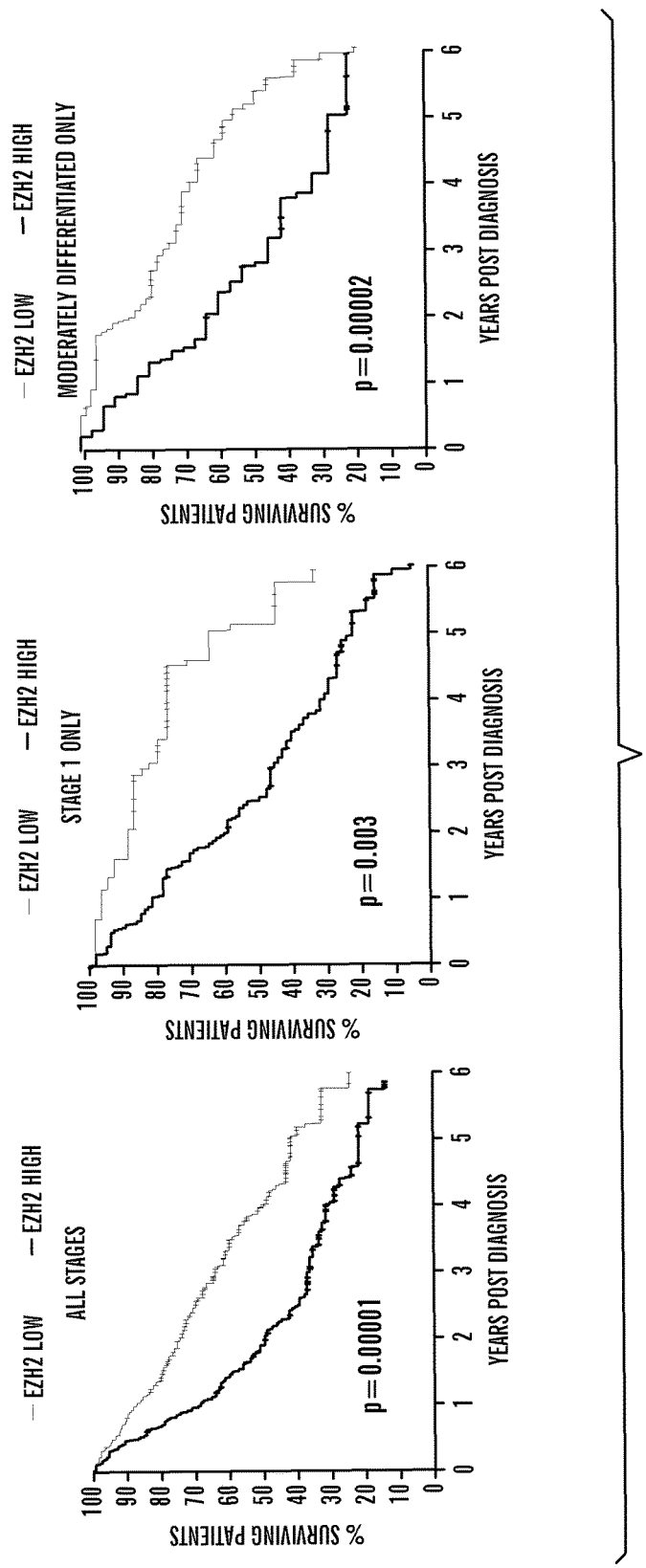
FIGS. 18A-18F demonstrate that EZH2 expression is clinically relevant and influences etoposide sensitivities.

Brg1 and EGFR Mutations are Negatively Correlated and Predict Sensitized Phenotypes. By using mutation annotation available for the NSCLC lines, it was discovered that 14 of the 16 sensitized cell lines harbored mutations in Brg1 (also known as SMARCA4), B-Raf or EGFR, while 10 of the 13 protected cell lines were WT for the three genes (Table 1, Fisher's exact test p=0.001). Of note, H23 and H1819 lines are protected from etoposide by DZNep, yet have Brg1 mutations. However, these mutations are both late in the coding region and are predicted to produce a protein with an intact ATPase (Medina et al., 2008). Expression changes were assessed in EGFR and Brg1 in response to therapy using the RNA isolated for cell cycle inhibitor analysis. In protected cell lines, Brg1 expression is significantly up-regulated and EGFR expression is significantly down-regulated in response to etoposide/DZNep, while remaining unchanged in sensitized lines (FIG. 18A, p=0.03 Brg1, p=0.005 EGFR).

In addition to correlating with etoposide/DZNep sensitivities, Brg1 and EGFR/B-Raf mutations appeared to be negatively correlated. In our panel of 29 cell lines, 31% have a Brg1 mutation and 27.5% have an EGFR or B-Raf mutation. With these mutation frequencies, 8.5% of cell lines are expected to have both Brg1 and EGFR/B-Raf mutations. However, no NSCLC cell line in this panel or elsewhere was observed that harbored both mutations (Table 1, Table 4, Fisher's exact test p=0.001). To examine the pattern of Brg1 and EGFR mutations in primary human lung cancers, lung adenocarcinoma whole exome sequencing from The Cancer Genome Atlas (TCGA) and a recent publication were queried (Imielinski et al., 2012). Of the 424 adenocarcinoma samples, 86 (20.3%) had exon 19 deletion or missense mutation in EGFR or missense mutations in B-Raf, while 46 (10.8%) had missense, nonsense, deletion or insertion mutations in Brg1. With these allele frequencies, one would expect 2% of the tumor samples to have both Brg1 and EGFR/B-Raf mutations, though only 3 (0.7%) were observed (Fisher's exact test, p=0.006, B-Raf_G466E/SMARCA4_G594A, EGFR_R574L/SMARCA4_A1249S, EGFR_H1129Y/SMARCA4homozygous focal deletion, all from Imielinski dataset). If the cell lines are included with the primary tumor data, the anti-correlation of EGFR/B-Raf mutations and SMARCA4 mutations becomes very significant (Fisher's exact test, p<0.0001). In squamous cell carcinoma (TCGA, 2012), a similar trend was observed.

Figure 5C:
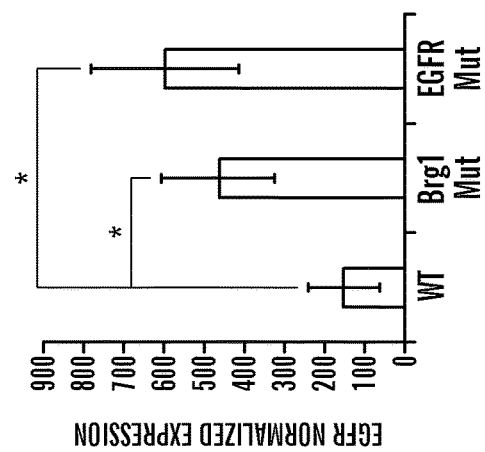
FIGS. 5A-5C demonstrate that Brg1 and EGFR mutations are negatively correlated and predict sensitized phenotypes.
Figure 5B:
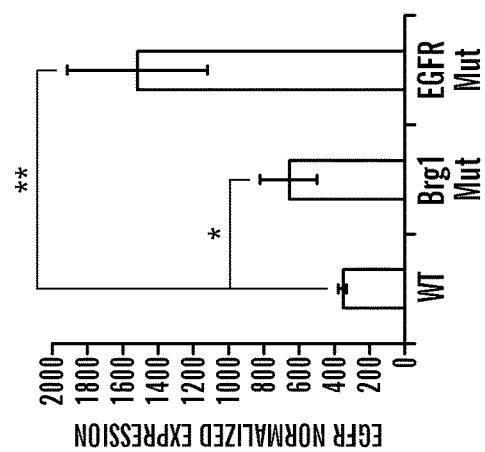
Figure 5A:
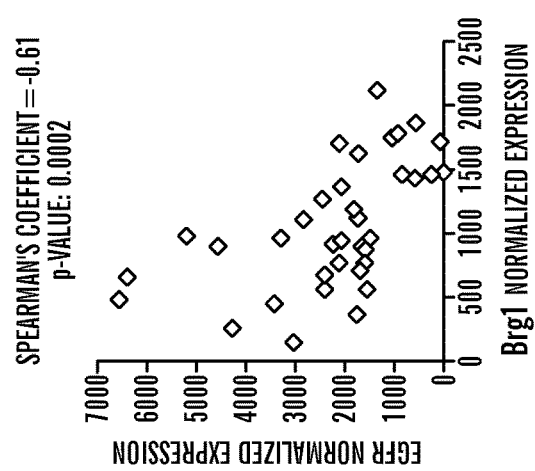
Figure 11A:
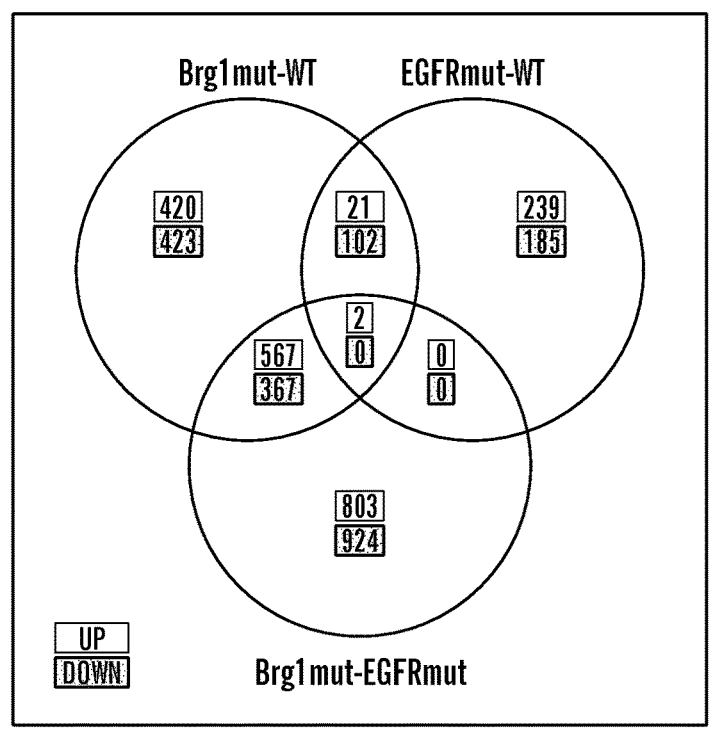
FIGS. 11A-11D demonstrate gene expression in different cell lines/genotypes.
Figure 11B:
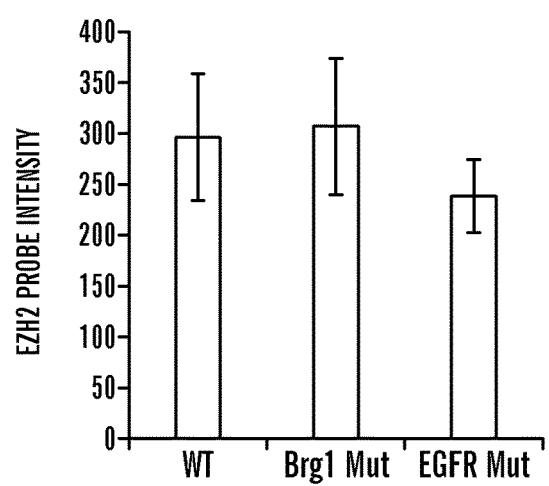
Figure 11C:
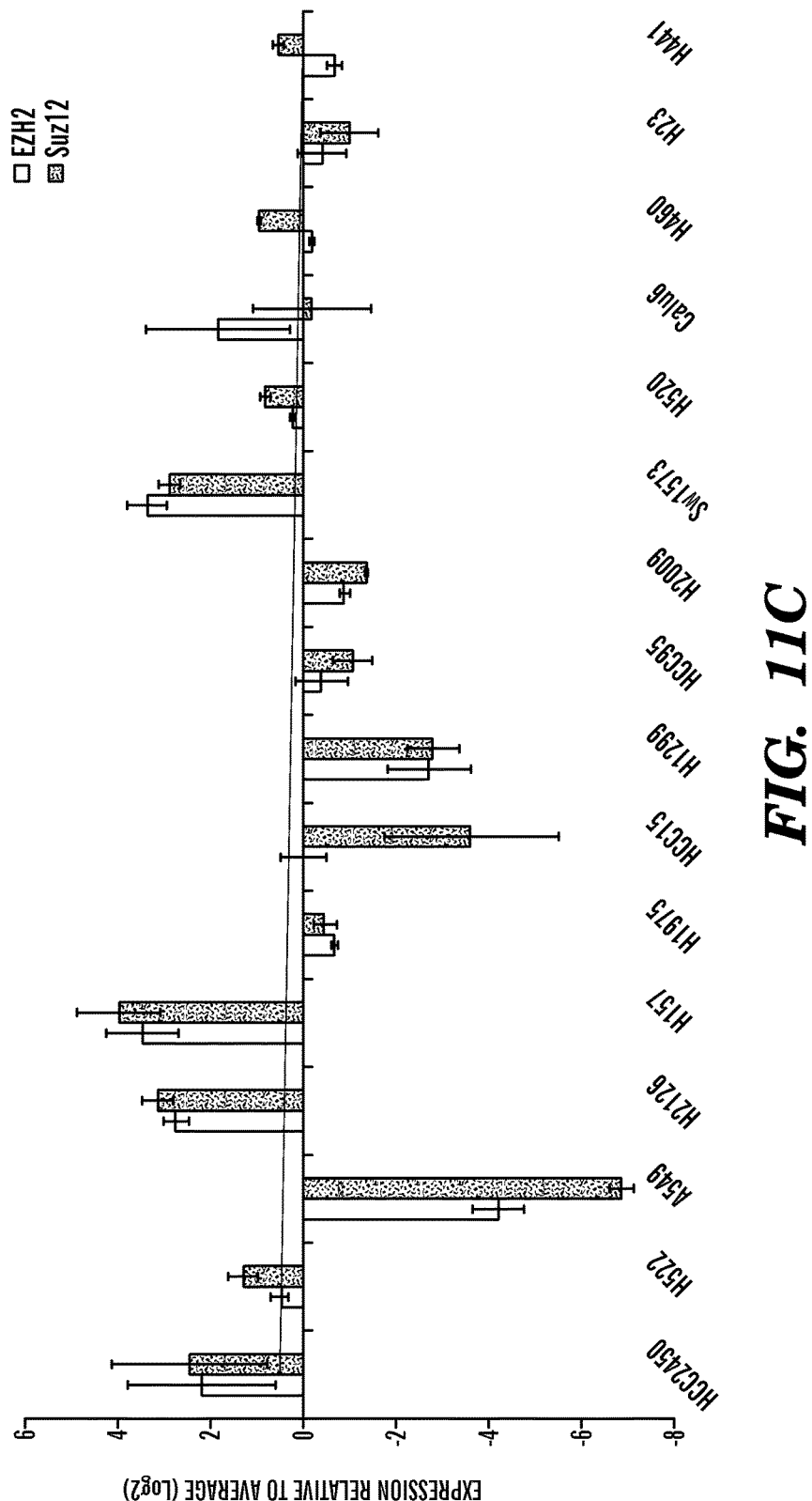

The negative correlation of Brg1 and EGFR mutations suggests that these pathways interact genetically and that these mutations may be functionally redundant. In the Director's Challenge dataset of primary human lung adenocarcinomas, samples that showed high expression of EGFR and/or Brg1 were analyzed for a correlation between these two genes. A strong negative correlation was found, which supports the theory that loss of Brg1 may be permissive for high expression of EGFR (Spearman's correlation=−0.619, p=0.0002, FIG. 5A). Likewise in the primary squamous cell carcinoma data-set (TCGA, 2012), tumors with mutations in Brg1 had significantly higher expression of EGFR than Brg1 WT/EGFR WT tumors (FIG. 5B, p=0.003). To explore the relationship between these mutations in the cell lines used in the experiments described above, Affymetrix arrays were used to compare gene expression signatures in the various genotypes. Overlap between differentially expressed genes in EGFR mutant lines vs. EGFR/Brg1 WT lines, and Brg1 mutant lines vs. EGFR/Brg1 WT lines was queried (FIG. 11A). Interestingly, it was found that EGFR was the first shared up-regulated gene, over-expressed in 4.5-fold in Brg1 mutant cell lines compared to EGFR/Brg1 WT lines and 4.7-fold in EGFR mutant cell lines compared to EGFR/Brg1 WT lines (FIG. 5C, Table 5, p=0.014). Immuno-fluorescence for EGFR confirmed that Brg1 mutant cell lines have high expression of cell surface bound EGFR compared to Brg1 WT cell lines, which have very little detectable EGFR staining (data not shown). Importantly, it was also confirmed that EZH2 levels are not different in the various genotypes (FIG. 11B). This observation was in agreement with RT PCR analysis for EZH2 and Suz12 in the cell lines showing that PRC2 gene levels were not different between sensitized and protected lines (FIG. 11C).

Figure 18C:
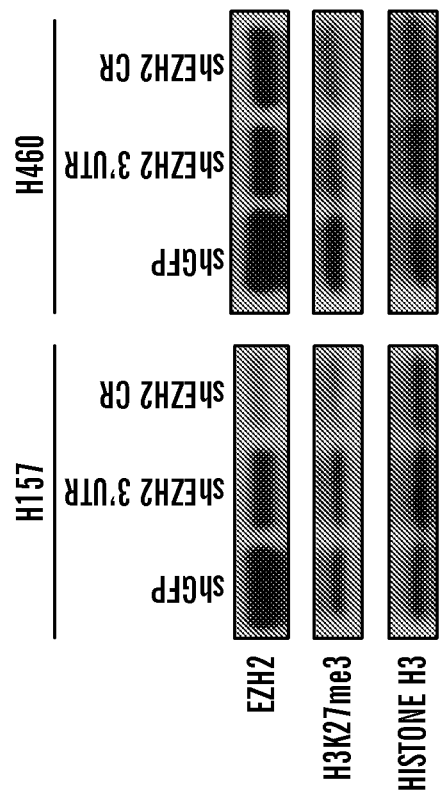
Figure 18B:
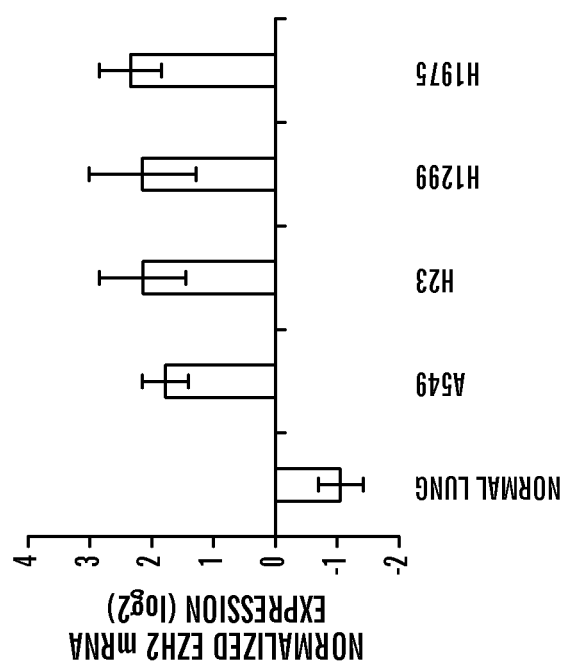

To further explore the genetic relationship between these two pathways, EGFR and Brg1 expression were manipulated via knock-down and over-expression viruses in protected and sensitized cell lines. In the Brg1 mutant cell line HCC15, which expressed high levels of WT EGFR, EGFR knock-down or re-introduction of Brg1 both decreased the amount of EGFR transcript (FIG. 18A, making bioreps for p values currently). In contrast, in the H460 line, which is WT for Brg1 and has little detectable EGFR expression, knock-down of Brg1 led to up-regulation of EGFR (p=0.009) and over-expression of WT EGFR led to a decrease in Brg1 transcript (FIG. 18B, p=0.002). Similar results were observed in several cell lines (FIG. 11D, making bioreps for p values currently).

Brg1 and EGFR Genetically Interact to Control the Sensitized Phenotype.

Figure 12A:
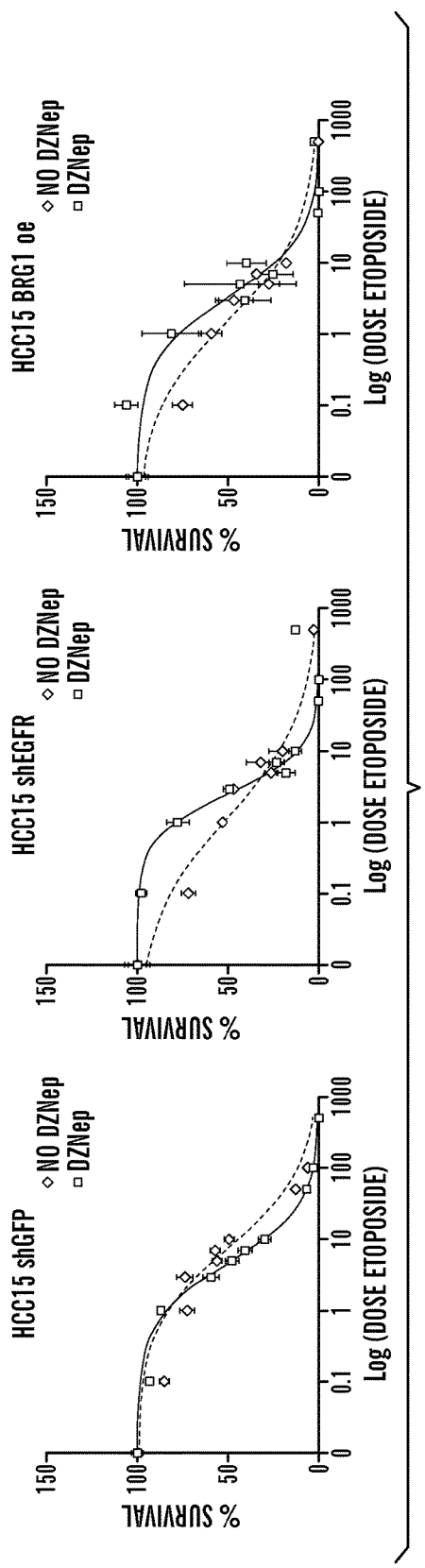
FIGS. 12A-12B depict etoposide dose response curves.
Figure 12B:
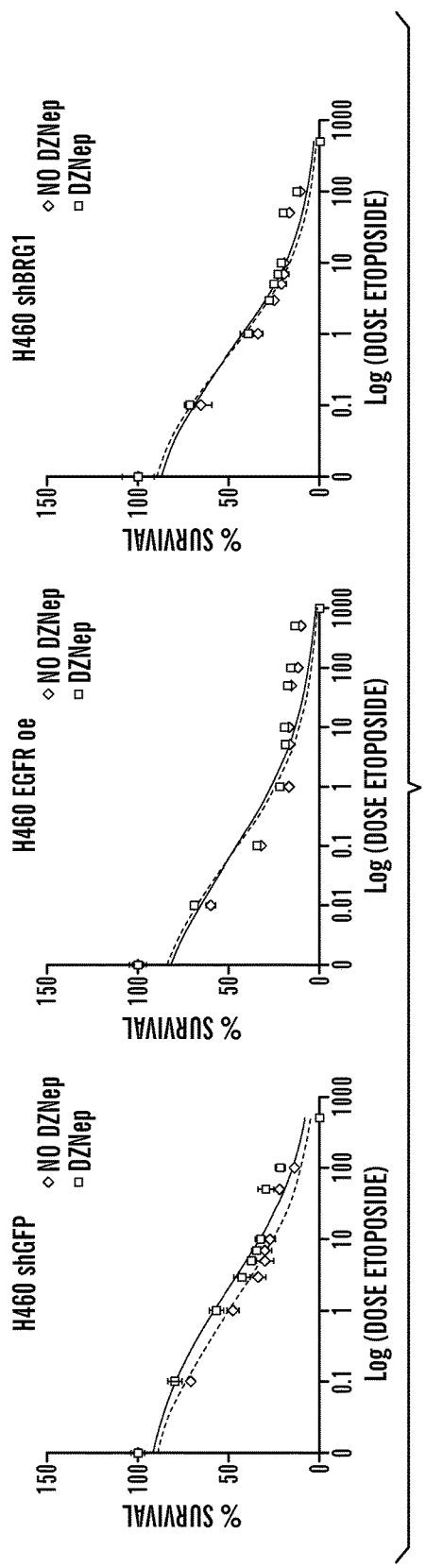
Figure 13:
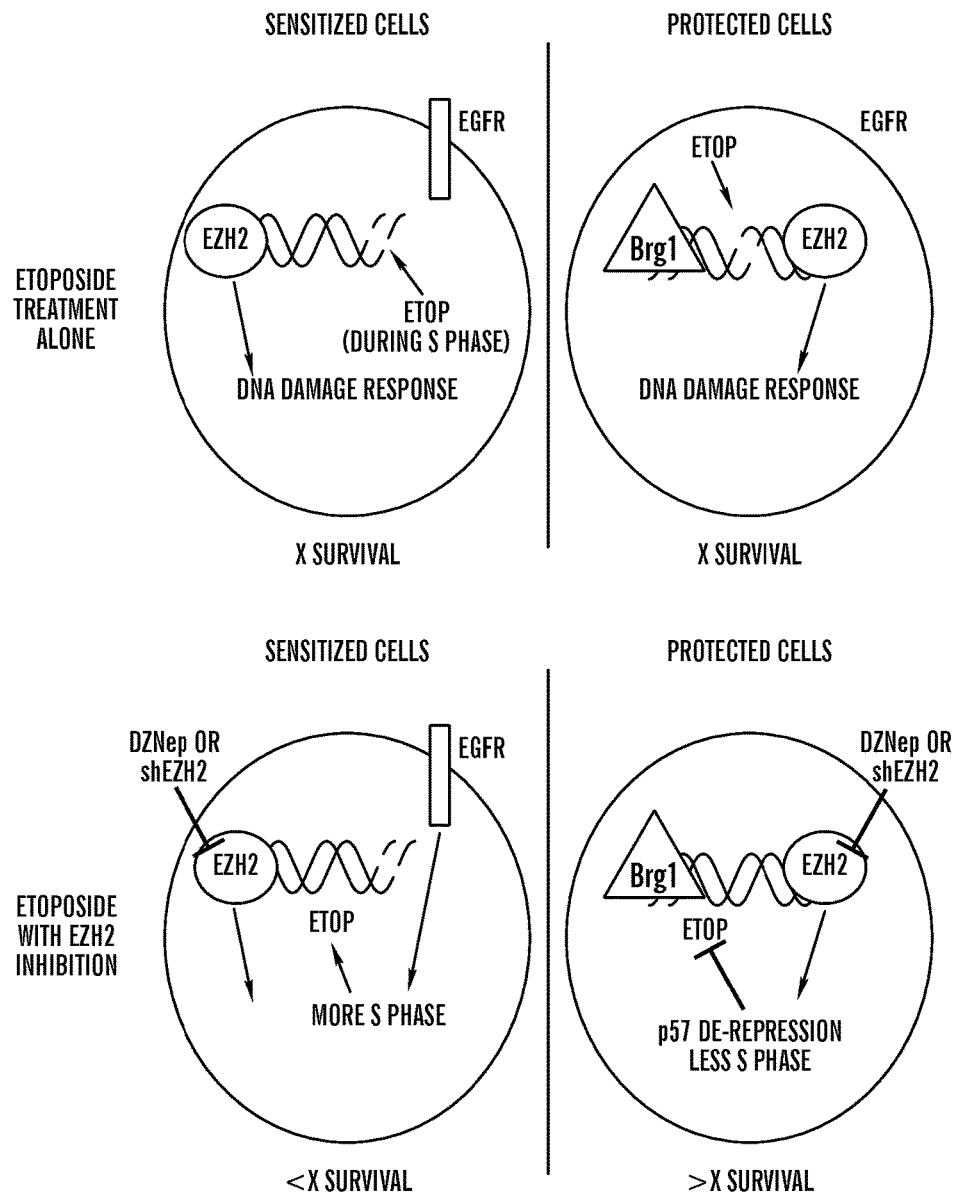
FIG. 13 depicts a graphical representation of the effect of EZH2 inhibition combination treatment on responsive (sensistized) and nonresponsive cells (protected).
Figure 23A:
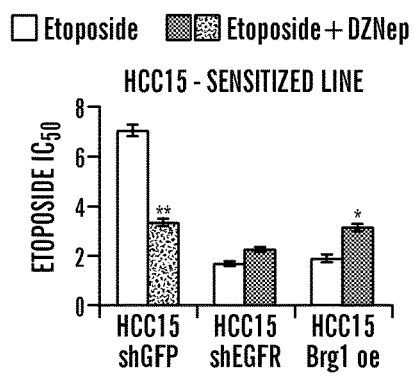
FIGS. 23A-23G demonstrate that BRG1 and EGFR control the sensitized phenotype.
Figure 23B:
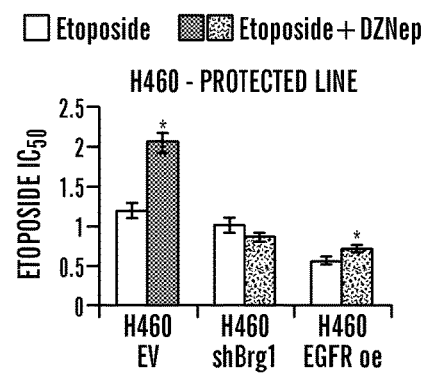

To learn if Brg1 and EGFR mutations are functional mediators, or merely predictors, of DZNep/etoposide response, we performed etoposide dose response curves on the Brg1 and EGFR knock-down and over-expression cell lines. For the HCC15 control cells, DZNep decreased the etoposide IC50 2-fold consistent with its sensitized phenotype (p<0.0001). However, both the EGFR knock-down and the Brg1 over-expressing HCC15 lines showed an increase in etoposide IC50, suggesting that the phenotype of the line was converted from sensitized to protected through loss of EGFR or re-introduction of Brg1 (p=0.004 and p<0.0001 respectively) (FIG. 23A, FIG. 12A). For the protected cell line H460, DZNep raised the etoposide IC50 2-fold in the control cells (p=0.0005), yet had no effect on etoposide IC50 when EGFR was over-expressed (p=0.78) or Brg1 was knocked-down (p=0.2) (FIG. 6B, FIG. 12B). These data demonstrate that the sensitized and protected phenotypes are partially reliant upon the levels of Brg1 and EGFR within the cells.

Figure 6C:
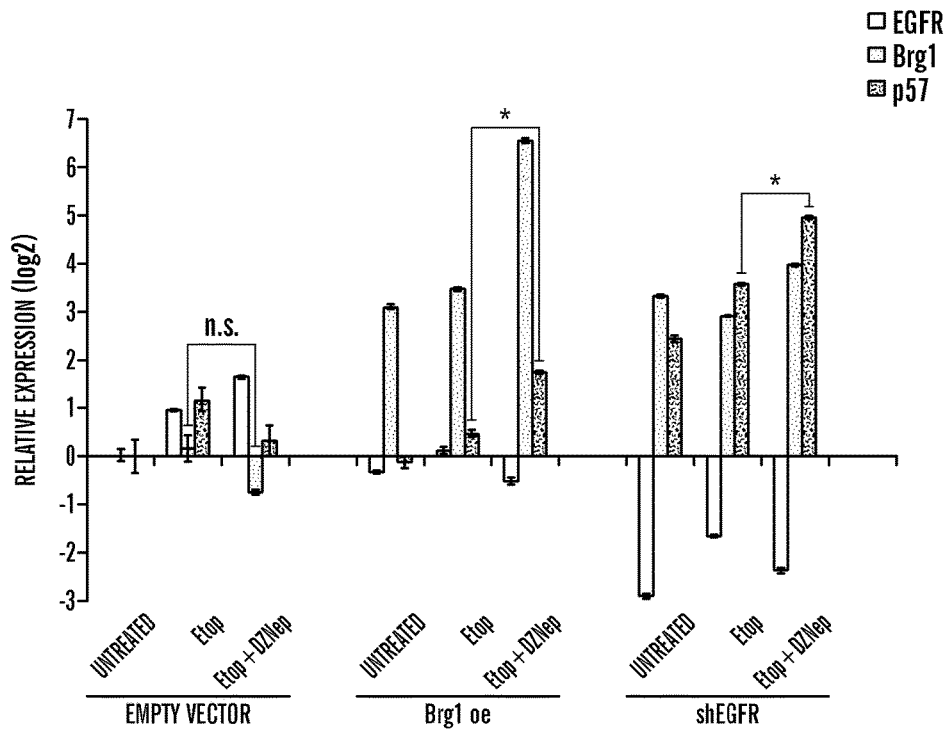
Figure 6D:
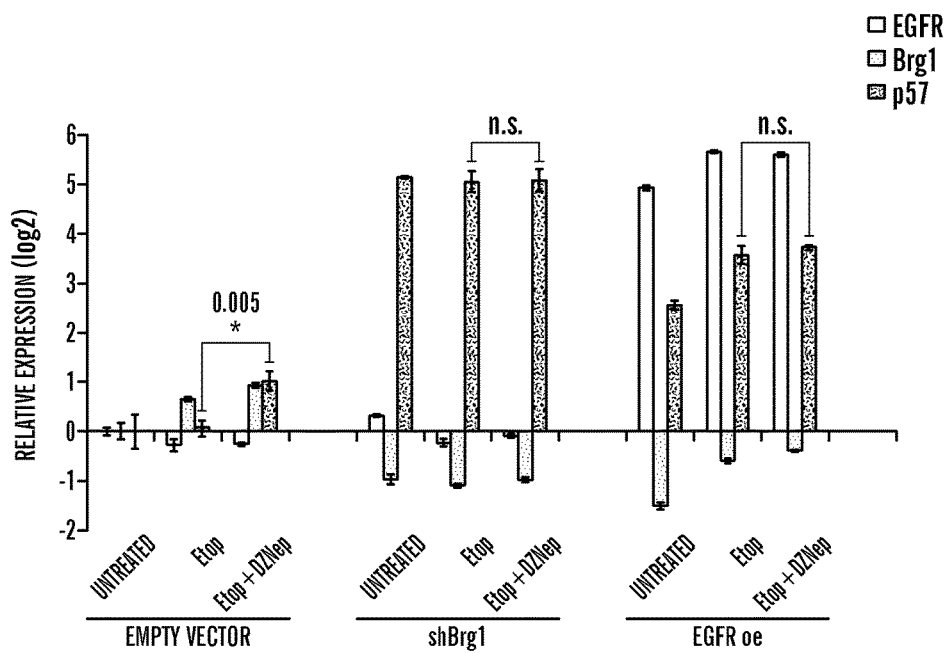

To learn if the changes in etoposide sensitivity of the Brg1- and EGFR-modulated DZNep-treated cell lines were attributable to cell cycle changes, 7AAD cell cycle analysis was performed. Etoposide treated HCC15 Brg1 over-expression cell lines showed a dramatically smaller accumulation in S phase in response to DZNep than the control shGFP cells (FIG. 6A). The HCC15 shEGFR line, which was significantly less sensitive to etoposide in the presence of DZNep, showed a decrease in S phase instead of the increase normally observed with this cell line. Add p57 qPCR data for HCC15 treated lines here (FIG. 6B). Consistent with the increase in etoposide sensitivity, the etoposide treated H460 shBrg1 and EGFR over-expression cell lines were enriched for S phase (FIG. 6C). This was in contrast to the control H460 cell line, which again showed accumulation in G1 and G2/M phases and a loss of S phase in response to the dual therapy. Consistent with previous results, shGFP H460 cells showed a significant increase in p57 levels when treated with etoposide and DZNep (FIG. 6D). However, the levels of p57 were much higher in untreated H460 shBrg1 and EGFR oe cells, and the addition of etoposide and DZNep had no effect on p57 levels. Together these data demonstrate that EZH2 inhibition in the presence of etoposide altered cell cycle dynamics, and that this effect was dependent on the level of Brg1 and EGFR expression in the cells.

DISCUSSION

Understanding the molecular determinants of epigenetic therapy responses will be essential for this new class of drugs to benefit cancer patients. It is demonstrated herein that EZH2 inhibition had differential effects on lung cancer chemotherapy sensitivities both in vitro and in vivo. Nearly half of the cell lines tested were sensitized to etoposide by EZH2 inhibition, while the other half were protected from the chemotherapy by the epigenetic therapy. These sensitized and protected phenotypes were mediated by differential cell cycle regulation and correlated with regulation of p57 expression. Within the panel of lung cancer cell lines, Brg1 and EGFR mutations were mutually exclusive and significantly predicted chemotherapy sensitization by EZH2 inhibition. Using primary tumor data and genetic manipulation of Brg1 and EGFR, it was demonstrated that these pathways genetically interact, and control response to chemotherapy and EZH2 inhibition. Changing the level of EGFR or Brg1 in a cell line can switch a line from sensitized to protected. These data link, for the first time, common mutations found in non-small cell lung cancer to responses to epigenetic therapy, and provide a strategy to predict which patients will benefit from dual EZH2 inhibitor and chemotherapy treatments or epigenetic therapy alone.

The differential effects of EZH2 inhibition on chemotherapy in vitro predicted response of the cell lines to therapies in vivo. Using two dosing schemes for DZNep, growth of xenografts of both sensitized and protected lines could be effectively prevented. For protected lines, a two week time course of DZNep alone was most effective, while for sensitized line, a one week time-course of DZNep and etoposide together significantly reduced tumor growth. Without wishing to be bound by theory, the observation that a second week of DZNep treatment increased H157 tumor burden suggests that in vivo, DZNep may cause etoposide challenged H157 cells to enter S phase just as they do in vitro. Of important clinical note, the combination of chemotherapy and DZNep for the protected line caused tumors to grow faster than tumors treated with either drug alone. These data reveal that planning dosing schemes to maximize cell cycle entry when chemotherapy is present is likely essential for this phenomenon to benefit patients. Furthermore, these data suggest that while EGFR and Brg1 mutation carriers may benefit from dual chemotherapy/EZH2 inhibitor strategies, the combination may be ineffective, or even dangerous, for patients with EGFR/Brg1 WT tumors, who can benefit from treatment with an EZH2 inhibitor alone.

In addition to EGFR and Brg1 mutations predicting chemo-sensitization by EZH2 inhibition, Brg1 inactivating mutations and EGFR activating mutations were significantly anti-correlated. By knocking down and over-expressing Brg1 and EGFR, a genetic interaction between the two pathways became evident. Genetic antagonism between the Brg1 containing SWI/SNF complex and EZH2 has been demonstrated for lymphomas (Wilson et al., 2010), and genetic interaction between Brg1 and EGFR has been shown in Drosophila (Herr et al., 2010). However, to the inventors' knowledge, this is the first reported data to implicate cooperation of these three pathways in lung cancer. Together these data suggest that one main effect of Brg1 inactivation is de-repression of EGFR signaling. Because B-Raf mutations also predicted chemo-sensitization via EZH2 inhibition, it is likely that activated MAPK signaling is involved in the sensitized phenotype. However, more than half of the protected cell lines harbor mutations in K-Ras, suggesting that expression of mutant K-Ras causes effects unique to activation of the EGFR-Raf-MAPK pathway in respect to the chemo-sensitization phenotype. Cells with high levels of EGFR react to EZH2 inhibition differently than cells that have lower levels of EGFR. The data described herein indicate that the cell cycle inhibitor p57 is a mediator in the lung cancer cell therapy protection phenotype. Whereas p57 mutations have not been reported in lung cancer, previous reports have characterized p57 as a target of PRC-mediated repression (Yang et al., 2009, Guo et al., 2011, Zacharek et al., 2011). Thus, de-repression of direct targets of Polycomb, such as p57, can be critical in regulating lung cancer response to targeted therapies.

These data indicate several possible combination therapies that may also be useful to combat lung cancers. In Brg1 and EGFR mutant cell lines, EZH2 inhibition caused sensitization to the TopoII inhibitors etoposide and doxorubicin. Double strand breaks (DSBs) caused by these agents cause formation of BRCA1 foci and can be repaired by homologous recombination if the sister chromatid can be found, or non-homologous end-joining if the homologous template is not available. BRCA1 mutant breast cancers express more EZH2, and are therefore intrinsically more sensitive to EZH2 inhibition (Puppe et al., 2009). PARP inhibitors, which lead to double strand breaks by preventing single strand break repair, are synthetically lethal with CDK1 inhibition, in part because BRCA1 requires CDK1 phosphorylation to function (Johnson et al., 2011). Because another substrate for CDK1 is EZH2 (Wei et al., 2010, Chen et al., 2010), the data indicate that inhibition of EZH2 can also contribute to the synthetic lethality of PARP and CDK1 inhibitors. Furthermore, because of the reliance of BRCA1 mutant tumors on EZH2, tumors treated with CDK1 inhibitors may be exquisitely sensitive to drugs such as DZNep. Therefore, a combination of all three therapies (DSB initiation, CDK1 inhibition and EZH2 inhibition) can be effective.

Therapeutic strategies targeting epigenetic factors have risen as promising new candidates for lung cancer and other difficult to treat cancers. Whereas many studies suggest that epigenetic therapy may offer a treatment avenue for broader patient groups than drugs targeting specific oncogenic changes, the work described herein indicates that selection of patient subsets will be critical in designing clinical trials and treatment strategies for drugs inspired by epigenetics. The initial cell culture approach examining dual treatment responses has revealed important, predictable in vivo drug sensitivities driven by lung cancer oncogenotype. Interestingly, the histological subtype of NSCLC was not a major factor in determining response to EZH2 inhibition.

Experimental Procedures

Cell Lines and Small Hairpins.

Cell lines used are listed in Table 1, Table 4, and FIG. 29. All cell lines were maintained in RPMI 1640 media with 10% fetal bovine serum, 4 mM L-glutamine and penicillin/streptomycin at 37° C., 5% CO2. The pLKO.1 EZH2 shRNA construct clone TRCN0000040076 was purchased from SIGMA and the shGFP plasmid 12273 is available on Addgene. Both shBrg1 and the matched empty vector were provided by the Smale lab (Ramirez et al., 2006), the Brg1 over-expression plasmid 19148 was purchased through Addgene, and the shEGFR and EGFR WT overexpression contracts were provided by the Jänne lab (Engelman et al., 2006). Small hairpin sequences:

```
GFP:
                                        (SEQ ID NO: 15)
GCCC(GCAAGCTGACCCTGAAGTTCAT)TCAAGAG(ATGAACTTCAGGGT
CAGCTTGC)TTTT

EZH2:
                                        (SEQ ID NO: 16)
CCGG(CGGAAATCTTAAACCAAGAAT)CTCGAG(ATTCTTGGTTTAAGAT
TTCCG)TTTTT

EGFR:
                                        (SEQ ID NO: 17)
CCGG(GCTGAGAATGTGGAATACCTA)CTCGAG(TAGGTATTCCACATTC
TCAGC)TTTTT

BRG1:
                                        (SEQ ID NO: 18)
TTTG(TGGATAAGCAGCACAAGATT)TCAAGAG(AATCTTCTGCTGCTTC
TCCA)TTTTT.
```

Drugs.

Etoposide, cis-platinum, and doxorubicin (SIGMA) were diluted to a stock of 100 mM in DMSO for all cell culture experiments. DZNep was diluted in DMSO to a stock of 10 mM. All stocks were diluted in DMSO to 1000× concentration prior to addition into media at 2×concentration and final dilution onto plated cells 1:1.

Cytotox Assays.

Cell lines were dissociated, counted and plated at 5000 cells per well in flat bottom opaque tissue culture treated 96 well plates (CytoOne). Edge wells were filled with PBS. The following day, 2× drug diluted in media was added to each well such that the well then contained 100 ul media with 1× drug concentration. After 4 days, Cell Titer Glo™ (Promega) was added and luminescence was read on a BioTec plate reader to determine relative cell number in each well. Data were averaged for triplicate or quadruplicate technical replicates, normalized to the untreated wells and input into GraphPad Prism software to extrapolate IC50.

Cell Cycle Flow Cytometry.

Cell lines were plated at $1.5 \times 10^6$ cells per 10 cm plate and treated with drug for 4 days. Cells were then dissociated, fixed with 100% ice cold Ethanol for at least 2 hours, incubated for 30 minutes with 1 mg/mL RNase A and resuspended in 20 µg/mL 7AAD. 30,000 events were collected on the BD Facscalibur™ and analyzed with the ModFit LT™ software. In cases where etoposide treated cells had such abnormal ploidy that ModFit LT™ was unable to correctly model the cell cycle, the data was analyzed manually on FlowJo™ software by setting the gates on the etoposide sample and copying them to the etoposide+DZNep and etoposide shEZH2 samples.

Quantitative RT PCR.

RNA from treated cell lines was extracted from using Trizol. Equal amounts of RNA were incubated with DNAse I before cDNA was made using the SuperScript III™ kit (Invitrogen). Relative gene expression was assayed with Sybr green on the StepOnePlus™ Real-Time PCR System (Applied Biosystems). Relative expression was calculated by Gene of Interest (Ctreference-Ctexprimental)-CYPA (Ctreference-Ctexperimental) and graphed on the log 2 scale. For all experiments, the reference sample was a matched untreated or control transduced cell line. Primer sequences:

| | | | |
|---|---|---|---|
| CYPA | F | TCATCTGCACTGCCAAGACTG | (SEQ ID NO: 19) |
| CYPA | R | CATGCCTTCTTTCACTTTGCC | (SEQ ID NO: 20) |
| EZH2 | F | AGGAGTTTGCTGCTGCTCTC | (SEQ ID NO: 21) |
| EZH2 | R | CCGAGAATTTGCTTCAGAGG | (SEQ ID NO: 22) |
| BRG1 | F | AGCGATGACGTCTCTGAGGT | (SEQ ID NO: 11) |
| BRG1 | R | GTACAGGGACACCAGCCACT | (SEQ ID NO: 12) |
| EGFR | F | TAACAAGCTCACGCAGTTGG | (SEQ ID NO: 13) |
| EGFR | R | GTTGAGGGCAATGAGGACAT | (SEQ ID NO: 14) |
| SUZ12 | F | TACGGCTCCTATTGCCAAAC | (SEQ ID NO: 23) |
| SUZ12 | R | TGCTTCAGTTTGTTGCCTTG | (SEQ ID NO: 24) |
| P57 | F | GGCCTCTGATCTCCGATTTC | (SEQ ID NO: 25) |
| P57 | R | TGGGCTCTAAATTGGCTCAC | (SEQ ID NO: 26) |
| P21 | F | ATGAAATTCACCCCCTTTCC | (SEQ ID NO: 27) |
| P21 | R | CCCTAGGCTGTGCTCACTTC | (SEQ ID NO: 28) |
| P27 | F | CCGGCTAACTCTGAGGACAC | (SEQ ID NO: 29) |
| P27 | R | CGAGCTGTTTACGTTTGACG | (SEQ ID NO: 30) |

Mice.

Cell lines were dissociated into single cells, counted and resuspended at $1 \times 10^6$ cells per 250 µL of 1:1 media/matrigel (BD). 8- to 16-week-old Foxn1nu (nude) mice (Harlan) were injected subcutaneously with $1 \times 10^6$ cells in four spots on flanks. Chemo and DZNep were administered from day 12 to day 17 post injections, Etoposide: 20 mg/kg/day i.p. in corn oil once per day for 5 consecutive days, and DZNep 2 mg/kg/day i.p. in corn oil twice per week for 1 week (dosing scheme A) OR 1 mg/kg/day i.p. in corn oil twice per week for 2 weeks (dosing scheme B). Tumor growth was measured every other day by caliper.

Generation of the EZH2 Co-Expressed Gene Signature.

Oncomine was used to query the top 20 genes co-expressed with EZH2 in all datasets containing human non-small cell lung cancer samples and co-expression data. The 9 datasets correspond to Beer et al., 2008, Director's Challenge, 2008, Garber et al., 2001, Gordon et al., 2002, Landi et al., 2008, Rohrbeck et al., 2008, Su et al., 2001, Yu et al., 2008, and Kim Lung unpublished. Of the 180 probes, 64 were redundant, leading to a list of 116 genes highly co-expressed with EZH2. Because data sets on Oncomine were from various microarray platforms, the gene list was then used to generate a probe list for the 116 genes corresponding to probes on the U133A Affymetrix array using the batch query function on the NetAffx website (available on the world wide web at www(dot)Affymetrix(dot)com(backslash)analysis(backslash)index(dot)affx).

Kaplan Meier Analysis.

Raw gene expression data from human lung adenocarcinoma samples were obtained (Director's Challenge). Probe intensities from the Affymetrix U133A platform used in these studies were normalized and modeled using dChip software (Li C and Wong W H. PNAS 2001 Vol. 98, 31-36; which is incorporated by reference herein in its entirety). Kaplan-Meier survival analyses were implemented after the samples were hierarchically clustered using centroid linkage into two risk groups using the EZH2 co-expressed gene signature. Differences of the survival risk between the two risk groups were assessed using the Mantel-Haenszel log rank test. The larger area between the two risk groups and its associated smaller p value from the Mantel-Haenszel log rank test implicate a better classification model.

Cell Line Micro-Array.

Array quality was assessed using the R/Bioconductor package (see, e.g. Gentleman R. C. et al. Genome Biol. 2004 5(10): R80; which is incorporated by reference herein in its entirety). Raw CEL files from U133A Affymetrix arrays were processed using the robust multiarray average (RMA) algorithm (Irizarry et al., 2003). To identify genes correlating with the phenotypic groups, limma (Smyth, 2004) was used to fit a statistical linear model to the data and then tested for differential gene expression in the three groups, WT: H460, H441, H2122, H2009, Calu6, HCC95, EGFR mutant: H1650, HCC827, HCC4006, H1975, H3255, PC9, Brg1 mutant: A549, H1299, H157, H2126, H522, HCC15. Results were adjusted for multiple testing using the Benjamini and Hochberg (BH) method (Benjamini and Hochberg, 1995), and significance was determined using a False-Discovery-Rate cutoff of less than 5%.

Statistical Analysis.

Except where indicated, Student's t-test was used to compare measurements between 2 conditions. Unless noted otherwise, pooled data is represented by the mean and standard error. p-values less than 0.05 were considered significant.

Western Blot.

For Western blotting, 25 µg of protein extract per sample was denatured with heat and reducing agents, separated on a 4-12% acrylimide gel and transferred to nitrocellulose. Antibodies used for Western blotting were: EZH2 (Cell Signalling), β-actin (AbCAM) and H3K27me3 (Upstate).

References

Each of the following references is incorporated by reference herein in its entirety.
1. Avan, A., Crea, F, Paolicchi, E, Funel, N., Galvani, E. Marquez, V. E., Honeywell, R. J., Danesi, R., Peters, G. J., and Giovannetti, E. (2012). Molecular mechanisms involved in the synergistic interaction of the EZH2 inhibitor 3-deazaneploanocin A (DZNep) with gemcitabine in pancreatic cancer cells. Mol. Cancer Ther. Epub.
2. Baldwin, E. L. and Osheroff, N. (2005). Etoposide, topoisomerase II and cancer. Curr. Med. Chem. Anticancer Agents 5, 363-372.
3. Baylin, S. B. (2011). Resistance, epigenetics and the cancer ecosystem. Nat. Med. 17, 288-289.
4. Beer, D. G., S. L. Kardia, S. L., C. C. Huang, C. C., T. J. Giordano, T. J., A. M. Levin, A. M., D. E Misek, D. E., L. Lin, L., G. Chen, G., T. G. Gharib, T. G., D. G. Thomas, D. G. et al. (2002). Gene-expression profiles predict survival of patients with lung adenocarcinoma. Nat. Med. 8, 816-824.
5. Ben-Porath, I., Thomson, M. W., Carey, V. J., Ge, R., Bell, G. W., Regev, A., and Weinberg, R. A. (2008). An embryonic stem cell-like gene expression signature in poorly differentiated aggressive human tumors. Nat. Gen. 40, 499-507.
6. Bracken, A. P. and Refill, K. 2009. Polycomb group proteins: navigators of lineage pathways led astray in cancer. Nat. Rev. Cancer 9, 7730-784.
7. Breuer, R. H. J., Snijders, P. J. F., Smit, E. F., Sutedja, T. G., Sewalt, R. G. A. B., Otte, A. P., van Kemenade, F. J., Postmus, P. E., Meijer, C. J. L. M., and Raaphorst, F. M. (2004). Increased expression of the Ezh2 polycomb group gene in Bmi1-positive neoplastic cells during bronchial carcinogenesis. Neoplasia 6, 736-743.
8. Chen, S., Bohrer, L. R., Rai, A. N., Pan, Y., Gan, L., Zhou, X., Bagchi, A., Simon, J. A. and Huang, H. (2010). Cyclin-dependent kinases regulate epigenetic gene silencing through phosphorylation of EZH2. Nat. Cell Biol. 12, 1108-1114.
9. Chou, D. M., Adamson, B., Dephoure, N. E., Tan, X., Nottke, A. C., Hurov, K. E., Gygi, S. P., Colaiacovo, M. P, and Elledge, S. J. (2010). A chromatin localization screen reveals poly (ADP ribose)-regulated recruitment of the repressive Polycomb and NuRD complexes to sites of DNA damage. Proc. Natl. Acad. Sci. USA 107, 18475-18480.
10. Crea, F., Paolicchi, E., Marquez, V. E. and Danesi, R. (2011a). Polycomb genes and cancer: Time for clinical application? Crit. Rev. Oncol./Hematol. Epub.
11. Crea, F., Hurt, E. M., Mathews, L. A., Cabarcas, S. M., Sun, L., Marquez, V. E., Danesi, R., and Farrar, W. L. (2011b). Pharmacologic disruption of Polycomb Repressive Complex 2 inhibits tumorigenicity and tumor progression in prostate cancer. Mol. Cancer 10, Epub.
12. Curtis, S. J., Sinkevicius, K. W., Li, D., Lau, A. N., Roach, R. R., Zamponi, R., Woolfenden, A. E., Kirsch, D. G., Wong, K. K., and Kim, C. F. (2010). Primary tumor genotype is an important determinant in identification of lung cancer propagating cells. Cell Stem Cell 7, 127-133.
13. Director's Challenge Consortium for the Molecular Classification of Lung Adenocarcinoma: Shedden, K., Taylor, J. M. G., Enkemann, S. A., Tsao, M., Yeatman, T. J., Gerald, W. L., Eschrich, S., Jurisica, I., Giordano, T. J., Misek, D. E. et al. (2008). Gene expression-based survival prediction in lung adenocarcinoma: a multi-site, blinded validation study. Nat. Med. 14, 822-827.
14. Dovey, J. S., Zacharek, S. J., Kim, C. F., and Lees, J. A. (2008). Bmi1 is critical for lung tumorigenesis and bronchioalveolar stem cell expansion. Proc. Natl. Acad. Sci. USA 105, 11857-11862.
15. Engelman, J. A., Mukohara, T., Zejnullahu, K., Lifshits, E., Borrás, A. M., Gale, C. M., Naumov, G. N., Ycap, B. Y., Jarrell, E., Sun, J. et al. (2006). Allelic dilution obscures detection of a biologically significant resistance mutation in EGFR-amplified lung cancer. J. Clin. Invest. 116, 2695-26706.
16. Garber, M. E., Troyanskaya, O. G., Schluens, K., Petersen, S., Thaesler, Z., Pacyna-Gengelbach, M., van de Rijn, M., Rosen, G. D., Perou, C. M., Whyte, R. I. et al. (2001). Diversity of gene expression in adenocarcinoma of the lung. Proc. Natl. Acad. Sci. USA 98, 13784-13789.
17. Gordon G. J., Jensen, R. V., Hsiao, L. L., Gullans, S. R., Blumenstock, J. E., Ramaswamy, S., Richard, W. D., Sugarbaker, D. J. and Bueno, R. (2002). Translation of 17. microarray data into clinically relevant cancer diagnostic tests using gene expression ratios in lung cancer and mesothelioma. Cancer Res. 62, 4963-4967.

18. Hassan, K. A., Chen, G., Kalemkerian, G. P., Wicha, M. S., and Beer, D. G. (2009). An embryonic stem cell-like signature identifies poorly differentiated lung adenocarcinoma but not squamous cell carcinoma. Clin. Cancer Res. 15, 6386-6390.

19. Herbst, R. S., and Heymach J. V. (2008). Lung cancer. N. Engl. J. Med. 359, 1367-1380.

20. Herr, A., Mckenzie, L., Suryadinata, R., Sadowski, M., Parsons, L. M., Sarcevic, B., and Richardson, H. E. (2010). Geminin and Brahma act antagonistically to regulate EGFR-Ras-MAPK signaling in Drosophila. Dev. Biol. 344, 36-51.

21. Huqun, Ishikawa, R., Zhang, J., Miyazawa, H., Goto, Y., Shimizu, Y., Hagiwara, K., and Koyama, N. (2012). Enhancer of Zeste Homolog 2 is a novel prognostic biomarker in nonsmall cell lung cancer. Cancer 118, 1599-1606.

22. Iliopoulos, D., Lindahl-Allen, M., Polytarchou, C., Hirsch, H. A., Tsichlis, P. N., and Struhl, K. (2010). Loss of miR-200 inhibition of Suz12 leads to Polycomb-mediated repression required for the formation and maintenance of cancer stem cells. Mol. Cell 39, 761-772.

23. Imielinksi, M., Berger, A. H., Hammerman, P. S., Hernandez, B., Pugh, T. J., Hodis, E., Cho, J., Suh, J., Capelletti, M., Sivachenko, A., et al. (2012). Mapping the hallmarks of lung adenocarcinoma with massively parallel sequencing. Cell 150, 1107-1120.

24. Ji, H., Wang, Z., Perera, S. A., Li, D., Liang, M. C., Zaghlul, S., McNamara, K., Chen, L., Albert, M., Sun, Y. et al. (2007). Mutations in BRAF and KRAS converge on activation of the mitogen-activated protein kinase pathway in lung cancer mouse models. Cancer Res. 67, 4933-4939.

25. Johnson, N., Li, Y., Walton, Z. E., Cheng, K. A., Li, D., Rodig, S., Moreau, L. A., Unitt, C., Bronson, R. T., Thomas, H. D., Newell, D. R. et al. (2011). Compromised CDK1 activity sensitizes BRCA-proficient cancers to PARP inhibition. Nat. Med. 17, 875-883.

26. Kikuchi, J., Kinoshita, I., Shimizu, Y., Kikuchi, E., Konishi, J., Oizumi, S., Kaga, K., Matsuno, Y., Nishimura, M., and Dosaka-Akita, H. (2010). Distinctive expression of the Polycomb group proteins Bmi1 polycomb ring finger oncogene and enhancer of zeste homolog 2 in nonsmall cell lung cancers and their clinical and clinicophatologic significance. Cancer 116, 3015-3024.

27. Kikuchi, J., Takashina, T., Kinoshita, I., Kikuchi, E., Shimizu, Y., Sakakibara-Konishi, J., Oizumi, S., Marquez, V. E., Nishimura, M., and Dosaka-Akita, H. (2012). Epigenetic therapy with 3-deazaneplanocin A, an inhibitor of the histone mehtylatrasferase EZH2, inhibits growth of non-small cell lung cancer cells. Lung Cancer Epub.

28. Landi, M. T., Dracheva, T., Rotunno, M., Figueroa, J. D., Liu, H., Dasgupta, A., Mann, F. E., Fukuoka, J., Hames, M., Bergen, A. W. et al. (2008). Gene expression signature of cigarette smoking and its role in lung adenocarcinoma development and survival. PLoS One 3, e1651.

29. Lee, T. I., Jenner, R. G., Boyer, L. A., Guenther, M. G., Levine, S. S., Kumar, R. M., Chevalier, B., Johnstone, S. E., Cole, M. F., Isono, K. et al. (2006). Control of developmental regulators by polycomb in human embryonic stem cells. Cell 125, 301-313.

30. Medina, P. P., Romero, O. A., Kohno, T., Montuenga, L. M., Pio, R., Yokota, J., and Sanchez-Cespedes, M. (2008). Frequent BRG1/SMARCA4-inactivating mutations in human lung cancer cell lines. Hum. Mutat. 29, 617-622.

31. Min, J., Zaslaysky, A., Fedele, G., McLaughlin, S. K., Reczek, E. E., De Raedt, T., Guney, I., Strochlic, D. E., Macconaill, L. E., Beroukhim, R. et al. (2010). An oncogene-tumor suppressor cascade drives metastatic prostate cancer by coordinately activating Ras and nuclear factor-kappaB. Nat. Mcd. 16, 286-294.

32. Ougolkov, A. V., Bilim, V. N., and Billadeau, D. D. (2008). Regulation of pancreatic tumor cell proliferation and chemoresistance by the histone methyltransferase Enhancer of Zeste Homologue 2. Ciln. Cancer Res. 14, 6790-6796.

33. Puppe, J., Drost, R., Liu, X., Joosse, S. A., Evers, B., Cornelissen-Steijger, P., Nederlof, P., Qiang, Y., Jonkers, J., van Lohuizen, M., and Pietersen, A. M. (2009). BRCA1-deficient mammary tumor cells are dependent on EZH2 expression and sensitive to Polycomb Repressive Complex 2-inhibitor 3-deazaneplanocin A. Breast Cancer Res. 11, R36.

34. Ramirez-Carrozzi, V. R., Nazarian, A. A., Li, C. C., Gore, S. L., Sridharan, R., Imbalzano, A. N. and Smale, S. T. (2006). Selective and antagonistic functions of SWI/SNF and Mi-2beta nucleosome remodeling complexes during an inflammatory response. Genes Dev. 20, 282-296

35. Rodriguez-Nieto, S. A., Cañada, A., Pros, E., Pinto, A. I., Torres-Lanzas, J., Lopez-Rios, F., Sanchez-Verde, L., Pisano, D. G. and Sanchez-Cespedes, M. (2011). Massive parallel DNA pyrosequencing analysis of the tumor suppressor BRG1/SMARCA4 in lung primary tumors. Hum. Mutat. 32, E1999-2017.

36. Rohrbeck, A., Neukirchen, J., Rosskopf, M., Pardillos, G. G., Geddert, H., Schwalen, A., Gabbert, H. E., von Haeseler, A., Pitschke, G., Schott, M. et al. (2008). Gene expression profiling for molecular distinction and characterization of laser captured primary lung cancers. J. Transl. Med. 6, e69.

37. Sauvageau, M. and Sauvageau, G. (2010). Polycomb group proteins: Multi-faceted regulators of somatic stem cells and cancer. Cell Stem Cell 7, 299-313.

38. Simon, J. A., and Lange, C. A. (2008). Roles of EZH2 histone methyltransferase in cancer epigenetics. Mutat. Res. 647, 21-29.

39. Simon, J. A. and Kingston, R. E. (2009). Mechanisms of Polycomb gene silencing: knowns and unknowns. Nat. Rev. Mol. Cell Biol. 10, 697-708.

40. Smyth, G. K. (2004). Linear models and empirical Bayes methods for assessing differential expression in microarray experiments. Stat. Appl. Genet. Mol. Biol., 3.

41. Spamann, A., and van Lohuizen, M. (2006). Polycomb silencers control cell fate, development and cancer. Nat. Rev. Genet. 6, 846-856.

42. Su, A. I., Welsh, J. B., Sapinoso, L. M., Kern, S. G., Dimitrov, P., Lapp, H., Schultz, P. G., Powell, S. M., Moskaluk, C. A., Frierson, H. F., and Hampton, G. M. (2001). Molecular classification of human carcinomas by use of gene expression signatures. Cancer Res. 61, 7388-7393.

43. Takawa, M., Masuda, K., Kunizaki, M., Daigo, Y., Takagi, K., Iwai, Y., Cho, H., Toyokawa, G., Yamne, Y., Maejima, K. et al. (2011). Validation of the histone methyltransferase EZH2 as a therapeutic target for various types of human cancer and as a prognostic marker. Cancer Sci. 102, 1298-1305.

44. Tan, J., Yang, X., Zhuang, L., Jiang, X., Chen, W., Lee, P. L., Karuturi, R. K., Tan, P. B., Liu, E. T. and Yu, Q. (2007). Pharmacologic disruption of Polycomb-repressive complex 2-mediated gene repression selectively induces apoptosis in cancer cells. Genes Dev. 21, 1050-1063.
45. The Cancer Genome Atlas Research Network. (2012). Comprehensive genomic characterization of squamous cell lung cancers. Nature Epub.
46. Wei, Y., Chen, Y. H., Li, L. Y., Lang, J., Yeh, S. P., Shi, B., Yang, C. C., Yang, J. Y., Lin, C. Y., Lai, C. C., and Hung, M. C. (2010). CDK1-dependent phosphorylation of EZH2 suppresses methylation of H3K27 and promotes osteogenic differentiation of human mesenchymal stem cells. Nat. Cell Biol. 13, 87-94.
47. Wilson, B. G., Wang, X., Shen, X., McKenna, E. S., Lemieux, M. E., Cho, Y. J., Koellhoffer, E. C., Pomeroy, S. L., Orkin, S. H., and Roberts, C. W. (2010). Epigenetic antagonism between polycomb and SWI/SNF complexes during oncogenic transformation. Cancer Cell. 18, 316-328.
48. Wu, Z., Lee, S. T., Qiao, Y., Li, Z., Lee, P. L., Lee, Y. J., Jiang, X., Tan, J., Aau, M., Lim, C. Z., and Yu, Q. (2011). Polycomb protein EZH2 regulates cancer cell fate decision in response to DNA damage repair. Cell Death Differ. 18, 1771-1779.
49, Yamamoto, H., Shigematsu, H., Nomura, M., Lockwood, W. W., Sato, M., Okumura, N., Soh, J., Suzuki, M., and Wistuba, L I., Fong, K. M. et al. (2008). PIK3C A mutations and copy number gains in human lung cancers. Cancer Res. 68, 6913-6921.
50. Yu K., Ganesan, K., Tan, L. K., Laban, M., Wu, J., Zhao, X. D., Li, H., Leung, C. H., Zhu, Y., Wei, C. L. et al. (2008), A precisely regulated gene expression cassette potently modulates metastasis and survival in multiple solid cancers. PLoS Genet. 4, e1000129.

TABLE 1

B-Raf, EGFR, and BRG1 Annotation

| Cell Line | B-Raf | EGFR | BRG1 |
|---|---|---|---|
| HCC2450 | WT | WT | n/a |
| PC9 | WT | E746_A750del | n/a |
| H1395 | G469A | WT | WT |
| H522 | WT | WT | P270* |
| A549 | WT | WT | Q729* |
| Calu1 | WT | WT | WT |
| H2126 | WT | WT | W764R |
| H157 | WT | WT | T58* |
| H1975 | WT | T290M, L858R | WT |
| HCC15 | WT | WT | M272* |
| H2030 | WT | WT | Null |
| H1650 | WT | E746X | WT |
| HCC4006 | WT | L747_A749del | WT |
| H2087 | L597V | WT | WT |
| HCC827 | WT | E746_A750del | WT |
| H1299 | WT | WT | Y560* |
| H322 | WT | WT | WT |
| HCC95 | WT | WT | WT |
| H2009 | WT | WT | WT |
| Sw1573 | WT | WT | WT |
| H2122 | WT | WT | WT |
| H1819 | WT | WT | L1085* |
| H520 | WT | WT | WT |
| Calu6 | WT | WT | WT |
| Calu3 | WT | WT | WT |
| H460 | WT | WT | WT |
| H3255 | WT | L858R | WT |
| H23 | WT | WT | K1533N |
| H441 | WT | WT | WT |

TABLE 2

EZH2 Co-Expression Gene Signature.

| Gene Symbol | Description |
|---|---|
| ALS2CR4 | amyotrophic lateral sclerosis 2 (juvenile) chromosome region, candidate 4 |
| ATIC | 5-aminoimidazole-4-carboxamide ribonucleotide formyltransferase/IMP cyclohydrolase |
| ATP2A2 | ATPase, Ca++ transporting, cardiac muscle, slow twitch 2 |
| AURKA | aurora kinase A |
| BIRC5 | baculoviral IAP repeat-containing 5 |
| BOP1 | block of proliferation 1 |
| BUB1 | budding uninhibited by benzimidazoles 1 homolog (yeast) |
| BUB1B | budding uninhibited by benzimidazoles 1 homolog beta (yeast) |
| C13orf34 | chromosome 13 open reading frame 34 |
| C1orf112 | chromosome 1 open reading frame 112 |
| CCNA2 | cyclin A2 |
| CCNB1 | cyclin B1 |
| CCNB2 | cyclin B2 |
| CDC20 | cell division cycle 20 homolog (S. cerevisiae) |
| CDC25A | cell division cycle 25 homolog A (S. pombe) |
| CDC6 | cell division cycle 6 homolog (S. cerevisiae) |
| CDC7 | cell division cycle 7 homolog (S. cerevisiae) |
| CDCA3 | cell division cycle associated 3 |
| CDCA8 | cell division cycle associated 8 |
| CDK1 | cyclin-dependent kinase 1 |
| CDKN3 | cyclin-dependent kinase inhibitor 3 |
| CENPE | centromere protein E, 312 kDa |
| CENPF | centromere protein F, 350/400 kDa (mitosin) |
| CENPM | centromere protein M |
| CENPW | centromere protein W |
| CHEK1 | CHK1 checkpoint homolog (S. pombe) |
| CKAP2 | cytoskeleton associated protein 2 |
| CKS1B | CDC28 protein kinase regulatory subunit 1B |
| CKS2 | CDC28 protein kinase regulatory subunit 2 |
| CSE1L | CSE1 chromosome segregation 1-like (yeast) |
| CSTF1 | cleavage stimulation factor, 3' pre-RNA, subunit 1, 50 kDa |
| CTPS | CTP synthase |
| DBF4 | DBF4 homolog (S. cerevisiae) |
| DBN1 | drebrin 1 |
| DEPDC1 | DEP domain containing 1 |
| DLGAP5 | discs, large (Drosophila) homolog-associated protein 5 |
| DTL | denticleless homolog (Drosophila) |
| ECT2 | Epithelial cell transforming sequence 2 oncogene |
| ESCO2 | establishment of cohesion 1 homolog 2 (S. cerevisiae) |
| ESPL1 | extra spindle pole bodies homolog 1 (S. cerevisiae) |
| EXO1 | exonuclease 1 |
| EZH2 | enhancer of zeste homolog 2 (Drosophila) |
| FANCI | Fanconi anemia, complementation group I |
| FBXO5 | F-box protein 5 |
| FEN1 | flap structure-specific endonuclease 1 |
| FOXM1 | forkhead box M1 |
| GINS1 | GINS complex subunit 1 (Psf1 homolog) |
| GINS2 | GINS complex subunit 2 (Psf2 homolog) |
| GMNN | geminin, DNA replication inhibitor |
| GOT1 | glutamic-oxaloacetic transaminase 1, soluble (aspartate aminotransferase 1) |
| GPD2 | glycerol-3-phosphate dehydrogenase 2 (mitochondrial) |
| H2AFX | H2A histone family, member X |
| H2AFZ | H2A histone family, member Z |
| HMGA1 | high mobility group AT-hook 1 |
| HMGB2 | high-mobility group box 2 |
| HMMR | hyaluronan-mediated motility receptor (RHAMM) |
| HN1 | hematological and neurological expressed 1 |
| KIAA0101 | KIAA0101 |
| KIF11 | kinesin family member 11 |
| KIF14 | kinesin family member 14 |
| KIF15 | kinesin family member 15 |
| KIF18A | kinesin family member 18A |
| KIF18B | kinesin family member 18B |
| KIF20A | kinesin family member 20A |
| KIF20B | kinesin family member 20B |
| KIF23 | kinesin family member 23 |
| KIF2C | kinesin family member 2C |
| KIFC1 | kinesin family member C1 |
| KNTC1 | kinetochore associated 1 |
| KPNA2 | karyopherin alpha 2 (RAG cohort 1, importin alpha 1) |

TABLE 2-continued

EZH2 Co-Expression Gene Signature.

| Gene Symbol | Description |
|---|---|
| LMNB1 | lamin B1 |
| LMNB2 | lamin B2 |
| MAD2L1 | MAD2 mitotic arrest deficient-like 1 (yeast) |
| MCM10 | minichromosome maintenance complex component 10 |
| MCM7 | minichromosome maintenance complex component 7 |
| MKI67 | antigen identified by monoclonal antibody Ki-67 |
| MLF1IP | MLF1 interacting protein |
| MTHFD2 | methylenetetrahydrofolate dehydrogenase (NADP+ dependent) 2, |
| NCAPG | non-SMC condensin I complex, subunit G |
| NCAPG2 | non-SMC condensin II complex, subunit G2 |
| NCAPH | non-SMC condensin I complex, subunit H |
| NDC80 | NDC80 homolog, kinetochore complex component (S. cerevisiae) |
| NUP205 | nucleoporin 205 kDa |
| OLA1 | Obg-like ATPase 1 |
| PAICS | phosphoribosylaminoimidazole carboxylase |
| PBK | PDZ binding kinase |
| PCNA | proliferating cell nuclear antigen |
| PFN2 | profilin 2 |
| PLK4 | polo-like kinase 4 |
| POLA1 | polymerase (DNA directed), alpha 1, catalytic subunit |
| POLE2 | polymerase (DNA directed), epsilon 2 (p59 subunit) |
| PPAT | Phosphoribosyl pyrophosphate amidotransferase |
| PRIM1 | primase, DNA, polypeptide 1 (49 kDa) |
| PSMD14 | proteasome (prosome, macropain) 26S subunit, non-ATPase, 14 |
| PTTG1 | pituitary tumor-transforming 1 |
| RFC4 | replication factor C (activator 1) 4, 37 kDa |
| SLC7A5 | solute carrier family 7 (cationic amino acid transporter, y+ system), member 5 |
| SMC2 | structural maintenance of chromosomes 2 |
| SMC4 | structural maintenance of chromosomes 4 |
| SPAG5 | sperm associated antigen 5 |
| SRM | spermidine synthase |
| STIL | SCL/TAL1 interrupting locus |
| STMN1 | stathmin 1 |
| TACC3 | transforming, acidic coiled-coil containing protein 3 |
| TFRC | Transferrin receptor (p90, CD71) |
| TMEM106C | transmembrane protein 106C |
| TOP2A | Topoisomerase (DNA) II alpha 170 kDa |
| TOPBP1 | topoisomerase (DNA) II binding protein 1 |
| TPX2 | TPX2, microtubule-associated, homolog (Xenopus laevis) |
| TRIP13 | thyroid hormone receptor interactor 13 |
| TROAP | trophinin associated protein (tastin) |
| TYMS | thymidylate synthetase |
| UBE2C | ubiquitin-conjugating enzyme E2C |
| UBE2S | ubiquitin-conjugating enzyme E2S |
| UNG | uracil-DNA glycosylase |
| WDR12 | WD repeat domain 12 |

Top 116 genes co-expressed with EZH2 across 9 Oncomine studies (Beer et al., 2008, Director's Challenge, 2008, Garber et al., 2001, Gordon et al., 2002, Landi et al., 2008, Rohrbeck et al., 2008, Su et al., 2001, Vu et al., 2008, and Kim Lung unpublished)

TABLE 3

Gene Function enrichment analysis of EZH2 expressed gene signature

| *Gene Ontology | | | | P-value | Term Name |
|---|---|---|---|---|---|
| C1 | C2 | C3 | C4 | | |
| 81 | 112 | 5956 | 12364 | 0 | protein binding |
| 73 | 112 | 3967 | 12364 | 0 | nucleus |
| 58 | 112 | 3873 | 12364 | 0.000005 | cytoplasm |
| 49 | 112 | 439 | 12364 | 0 | cell cycle |
| 38 | 112 | 243 | 12364 | 0 | cell division |
| 36 | 112 | 186 | 12364 | 0 | mitosis |
| 36 | 112 | 1621 | 12364 | 0 | nucleotide binding |
| 35 | 112 | 1250 | 12364 | 0 | ATP binding |
| 30 | 112 | 436 | 12364 | 0 | nucleoplasm |
| 24 | 112 | 667 | 12364 | 0 | cytoskeleton |
| 20 | 112 | 144 | 12364 | 0 | DNA replication |
| 18 | 112 | 294 | 12364 | 0 | cell proliferation |
| 18 | 112 | 103 | 12364 | 0 | spindle |
| 16 | 112 | 203 | 12364 | 0 | microtubule |
| 15 | 112 | 224 | 12364 | 0 | DNA repair |
| 14 | 112 | 155 | 12364 | 0 | chromosome |
| 12 | 112 | 46 | 12364 | 0 | phosphoinositide-mediated signaling |
| 11 | 112 | 53 | 12364 | 0 | condensed chromosome kinetochore |
| 11 | 112 | 71 | 12364 | 0 | kinetochore |
| 11 | 112 | 54 | 12364 | 0 | microtubule motor activity |
| 11 | 112 | 65 | 12364 | 0 | microtubule-based movement |
| 11 | 112 | 109 | 12364 | 0 | motor activity |
| 10 | 112 | 236 | 12364 | 0.000062 | response to DNA damage stimulus |
| 10 | 112 | 47 | 12364 | 0 | spindle pole |
| 8 | 112 | 59 | 12364 | 0 | anaphase-promoting complex-dependent proteasomal |
| 8 | 112 | 41 | 12364 | 0 | chromosome segregation |
| 7 | 112 | 47 | 12364 | 0 | chromosome, centromeric region |
| 7 | 112 | 135 | 12364 | 0.000247 | microtubule organizing center |
| 7 | 112 | 14 | 12364 | 0 | spindle organization |
| 6 | 112 | 12 | 12364 | 0 | chromosome condensation |
| 6 | 112 | 58 | 12364 | 0.000017 | negative regulation of mitotic ubiquitin-protein ligase |
| 6 | 112 | 61 | 12364 | 0.000022 | positive regulation of mitotic ubiquitin-protein ligase |
| 6 | 112 | 38 | 12364 | 0.000002 | regulation of cyclin-dependent protein kinase activity |
| 5 | 112 | 49 | 12364 | 0.000092 | microtubule cytoskeleton |
| 5 | 112 | 14 | 12364 | 0 | mitotic sister chromatid segregation |
| 5 | 112 | 25 | 12364 | 0.000004 | spindle microtubule |
| 4 | 112 | 19 | 12364 | 0.00003 | chromosome organization |
| 4 | 112 | 23 | 12364 | 0.000063 | condensed chromosome |
| 4 | 112 | 5 | 12364 | 0 | condensin complex |
| 4 | 112 | 36 | 12364 | 0.000347 | DNA metabolic process |
| 4 | 112 | 44 | 12364 | 0.000734 | G1/S transition of mitotic cell cycle |
| 4 | 112 | 8 | 12364 | 0.000001 | M phase of mitotic cell cycle |
| 4 | 112 | 19 | 12364 | 0.00003 | midbody |
| 4 | 112 | 12 | 12364 | 0.000005 | mitotic cell cycle checkpoint |
| 4 | 112 | 11 | 12364 | 0.000004 | mitotic cell cycle spindle assembly checkpoint |
| 4 | 112 | 12 | 12364 | 0.000005 | mitotic chromosome condensation |
| 4 | 112 | 26 | 12364 | 0.000101 | nuclear chromosome |
| 3 | 112 | 6 | 12364 | 0.000025 | 'de novo' IMP biosynthetic process |
| 3 | 112 | 20 | 12364 | 0.000846 | anaphase-promoting complex |
| 3 | 112 | 14 | 12364 | 0.000302 | DNA unwinding involved in replication |
| 3 | 112 | 20 | 12364 | 0.000846 | G2/M transition of mitotic cell cycle |
| 3 | 112 | 13 | 12364 | 0.000243 | kinesin complex |
| 3 | 112 | 15 | 12364 | 0.000369 | male germ cell nucleus |
| 3 | 112 | 10 | 12364 | 0.000113 | mitotic cell cycle |
| 3 | 112 | 15 | 12364 | 0.000369 | mitotic spindle organization |
| 3 | 112 | 17 | 12364 | 0.00053 | nucleotide-excision repair, DNA gap filling |

TABLE 3-continued

Gene Function enrichment analysis
of EZH2 expressed gene signature

| *Gene Ontology | | | | P- | |
|---|---|---|---|---|---|
| C1 | C2 | C3 | C4 | value | Term Name |
| 3 | 112 | 13 | 12364 | 0.000243 | oocyte maturation |
| 3 | 112 | 8 | 12364 | 0.000059 | outer kinetochore of condensed chromosome |
| 3 | 112 | 15 | 12364 | 0.000369 | purine nucleotide biosynthetic process |
| 3 | 112 | 15 | 12364 | 0.000369 | regulation of mitosis |
| 3 | 112 | 11 | 12364 | 0.000149 | replication fork |
| 2 | 112 | 5 | 12364 | 0.000987 | lamin filament |
| 2 | 112 | 5 | 12364 | 0.000987 | purine base biosynthetic process |

TABLE 4

B-RAF, EGFR, and BRG1 mutations
in additional NSCLC cell lines.

| Cell Line | EGFR | BRG1 |
|---|---|---|
| HCC2279 | E746_A750del | WT |
| HCC2935 | E746_A750del | WT |
| PC14 | E746_A750del | WT |
| A427 | WT | Null |
| H661 | WT | L1161fs*3 |
| H1703 | WT | E668_Q758del |
| DMS-114 | WT | E1310* |
| RERF-LC-MS | WT | A1245fs*13 |
| H1573 | WT | E1399* |
| H1581 | WT | E1310* |
| H1693 | WT | L1085fs*32 |
| H838 | WT | Null |
| H1819 | WT | L1085fs*6 |
| H596 | WT | WT |
| H1648 | WT | WT |
| H1437 | WT | WT |
| H1755 | WT | WT |
| H2087 | WT | WT |
| H1395 | WT | WT |

TABLE 5

Shared differentially expressed genes in EGFR and BRG1 mutants ("DEAD
(Asp-Glu-Ala-Asp) box" disclosed as SEQ ID NO: 31)

| Probe | Symbol | Description | p-value | log2 fold change for Brg1mut − WT | log2 fold change for EGFRmut − WT |
|---|---|---|---|---|---|
| 201983_s_at | EGFR | epidermal growth factor receptor | 0.014 | 2.178 | 2.232 |
| 210986_s_at | TPM1 | tropomyosin 1 (alpha) | 0.007 | 1.525 | 1.743 |
| 218368_s_at | TNFRSF12A | tumor necrosis factor receptor, 12A | 0.004 | 1.172 | 1.173 |
| 205130_at | MOK | MOK protein kinase | 0.013 | 0.928 | 0.891 |
| 217785_s_at | YKT6 | YKT6 v-SNARE homolog (S. cerevisiae) | 0.01 | 0.913 | 1.196 |
| 219088_s_at | ZNF576 | zinc finger protein 576 | 7E−04 | 0.907 | 1.008 |
| 202408_s_at | PRPF31 | PRP31 pre-mRNA processing factor 31 | 0.001 | 0.755 | 0.974 |
| 218261_at | AP1M2 | adaptor-related protein complex 1, mu | 0.013 | 0.748 | 0.937 |
| 202578_s_at | DDX19A | DEAD (Asp-Glu-Ala-Asp) box 19A | 0.002 | 0.716 | 0.531 |
| 201144_s_at | EIF2S1 | eukaryotic translation initiation factor 2 | 0.012 | 0.69 | 0.79 |
| 216299_s_at | XRCC3 | X-ray repair complementing defective | 0.003 | 0.574 | 0.572 |
| 217784_at | YKT6 | YKT6 v-SNARE homolog (S. cerevisiae) | 0.002 | 0.531 | 0.81 |
| 1773_at | FNTB | farnesyltransferase, CAAX box, beta | 0.003 | 0.514 | 0.408 |
| 218408_at | TIMM10 | membrane 10 homolog (yeast) | 0.004 | 0.475 | 0.727 |
| 221769_at | SPSB3 | SOCS box containing 3 | 0.008 | 0.471 | 0.614 |
| 202927_at | PIN1 | peptidylprolyl cis/NIMA-interacting 1 | 0.007 | 0.456 | 0.451 |
| 211289_x_at | CDK11 | cyclin dependent kinase 11 | 0.006 | 0.438 | 0.373 |
| 218206_x_at | SCAND1 | SCAN domain containing 1 | 0.005 | 0.396 | 0.543 |
| 214244_s_at | ATP6V0E1 | ATPase V0 subunit e1 | 0.005 | 0.384 | 0.481 |
| 221907_at | TRMT61A | tRNA methyltransferase | 0.006 | 0.378 | 0.522 |
| 221650_s_at | MED18 | mediator complex subunit 18 | 0.008 | 0.251 | 0.29 |

TABLE 3-continued

Gene Function enrichment analysis
of EZH2 expressed gene signature

| *Gene Ontology | | | | P- | |
|---|---|---|---|---|---|
| C1 | C2 | C3 | C4 | value | Term Name |
| 2 | 112 | 3 | 12364 | 0.00036 | regulation of chromosome segregation |

C1: number of genes in a cluster or list that have this annotation term
C2: number of annotated genes in this cluster or list
C3: number of all genes on array that have this annotation term
C4: number of all annotated genes on array
P-value: binomial approximated p-value for hypergeometric distribution
64 reported significant, 0 expected false positive
(209 terms assessed for enrichment at p-value threshold 0.001)

Example 2: EZH2 Inhibition Sensitizes BRG1 and EGFR Mutant Lung Tumors to TopoII Inhibitors Lung cancer is a complex disease for which epigenetic therapies may improve outcomes. It is demonstrated herein that EZH2 inhibition had differential effects on topoisomerase II (TopoII) inhibitor response of non-small cell lung cancers in vitro and in vivo. EGFR and BRG1 mutations could be used as genetic biomarkers to predict enhanced sensitivity to TopoII inhibitors in response to EZH2 inhibition. BRG1 loss-of-function lung cancer cell lines responded to EZH2 inhibition with increased S phase, anaphase bridging, apoptosis, and TopoII inhibitor sensitivity. EGFR mutant lung cancer cells were also sensitive to EZH2/TopoII inhibition, due to genetic antagonism between EGFR and BRG1. In stark contrast, EGFR/BRG1 wild-type tumors upregulated BRG1 in response to EZH2 inhibition and ultimately became more resistant to TopoII inhibition. These findings suggest a genetic network involving EZH2, BRG1, EGFR and TopoII that, under proper circumstances, can be exploited to cause lung cancer cell death.

Non-small cell lung cancer (NSCLC) is the leading cause of cancer-related death worldwide[1]. This year, NSCLC will claim the lives of approximately 160,000 individuals in the United States alone[2]. The current standard of care for NSCLC is combined modality therapy consisting of radiation treatment and chemotherapy[3,4]. A combination of cisplatin and etoposide (VP-16) are often used to treat NSCLC[5-7]. Cisplatin induces apoptosis through formation of DNA adducts, while etoposide acts by binding within the Topoisomerase II (TopoII) complex and preventing re-ligation of the double strand break required to decatenate DNA; during mitosis, TopoII dysfunction can be visualized by anaphase bridges[8-10]. Despite some advances in timing and dosing strategies, combination chemotherapies effectively control disease in only ~15% of NSCLC patients[3,4].

In order to achieve more durable treatment response, alternative drug targets, including epigenetic enzymes, are under consideration for therapeutic intervention[11]. Among potential epigenetic targets is the methyltransferase EZH2, which in the context of the Polycomb Repressive Complex 2 (PRC2), is well known to tri-methylate Histone H3 at lysine 27 (H3K27me3) to elicit gene silencing[12]. EZH2 also has non-histone substrates, including STATS and GATA4, and acts a transcriptional co-activator in concert with androgen receptor[13-15]. Furthermore, EZH2 has been implicated in both gene transcription control and also DNA replication and repair, and appears to be a critical regulator of both stem cell and cancer phenotypes[12,16,17]. The chemical 3-Deazaneplanocin A (DZNep) is a prototypical drug that decreases EZH2 levels and causes growth suppression in a variety of tumor cell lines, including lung cancer cell lines[18-23]; however, DZNep may also target other methyltransferases[24]. More recently, several small molecule inhibitors that specifically target EZH2 methyltransferase activity including GSK126 were described[25-27].

Despite the genetic complexity of lung cancer, epigenetic therapy, and specifically EZH2 inhibition, has not been tested with regard to the predominant onco-genotypes identified in patient populations. The most common genetic lesions in NSCLCs include inactivating mutations in TP53 (50-70%), deletion and mutation of LKB1 (20-35%), and activating mutations in KRAS (10-30%)[28-30]. Activating mutations and amplifications in EGFR (10-40%), which cause increased RAF-MEK-MAPK signaling, are also frequently observed. Recently, BRG1 (aka SMARCA4), an ATPase in the SW1/SNF chromatin-remodeling complex, was identified as a gene commonly deleted or truncated in NSCLCs (2-12%)[29-31]. Several of these common mutations in lung cancer define patient subsets that respond to therapeutics targeting the oncogenic changes, such as EGFR inhibitors for tumors harboring activating EGFR mutations[32-34].

To explore the potential of EZH2 inhibition as a treatment for lung cancer, EZH2 was targeted, as described herein, via small hairpin RNA, DZNep, or GSK126 in combination with chemotherapy. EZH2-inhibited lung cancer cells segregated into 2 distinct classes when challenged with chemotherapy: those with BRG1-inactivating mutations or EGFR-activating mutations were sensitized to the TopoII inhibitor etoposide, while EZH2 inhibition conferred less sensitivity ("protection") to the same chemotherapy for cells that were wild-type for BRG1/EGFR. Protected lines showed cell cycle arrest, up-regulation of BRG1 and a decrease in incidence of anaphase bridging. In contrast, sensitized lines showed increases in S phase, apoptosis and anaphase bridging in response to EZH2 inhibition and etoposide dual therapy. The sensitized phenotypes were observed in response to dual DZNep and etoposide treatment in mice bearing BRG1-mutant xenografts and mice harboring EGFR-driven endogenous lung tumors, while the protected phenotype was observed in mice bearing BRG1/EGFR wild-type xenografts or BRG1/EGFR wild-type endogenous lung tumors. EGFR and BRG1 mutations were mutually exclusive in lung cancer, and BRG1 directly binds to the EGFR promoter region to down-regulate EGFR expression. These studies define a method to predict which lung cancer patients may benefit from epigenetic therapy alone or combined with chemotherapeutics.

Results

EZH2 Expression is Clinically Relevant and Influences Etoposide Sensitivities.

It was first sought to determine whether expression of EZH2 in primary tumors supported the hypothesis that EZH2 is an important target for NSCLC. Using Oncomine[35], an EZH2 co-expression gene signature was generated by annotating the top 20 genes co-expressed with EZH2 in 9 studies consisting of over 1,000 primary NSCLC samples[36-43]. Of 180 probes (top 20 probes from each of the 9 studies), 64 were redundant, leading to a list of 116 genes highly co-expressed with EZH2 (Table 2). It was determined whether this EZH2 co-expression signature had predictive power for cancer progression using the Director's Challenge dataset of 410 human lung adenocarcinomas[41]. When patients were clustered into 2 groups, those whose tumors had high expression of the EZH2 co-expression signature, and those whose tumors had low expression, a significant difference in survival was observed between the two groups (FIG. 18A, p<0.00001). This survival difference was significant even when only the Stage 1 lung cancer patients or only tumors of moderate differentiation were considered (p=0.003 and p=0.00002, respectively), suggesting that this EZH2 co-expression signature is an independent, robust method to further stratify patients into risk groups. Gene ontology analysis revealed that the 116 gene EZH2 co-expression signature was highly enriched for cell cycle, DNA synthesis and DNA repair (Table 3), p<0.001). One of the genes highly co-expressed with EZH2 in primary tumors was Topoisomerase 2A (TOP2A), a subunit of the TopoII complex targeted by etoposide[9].

Figure 24A:
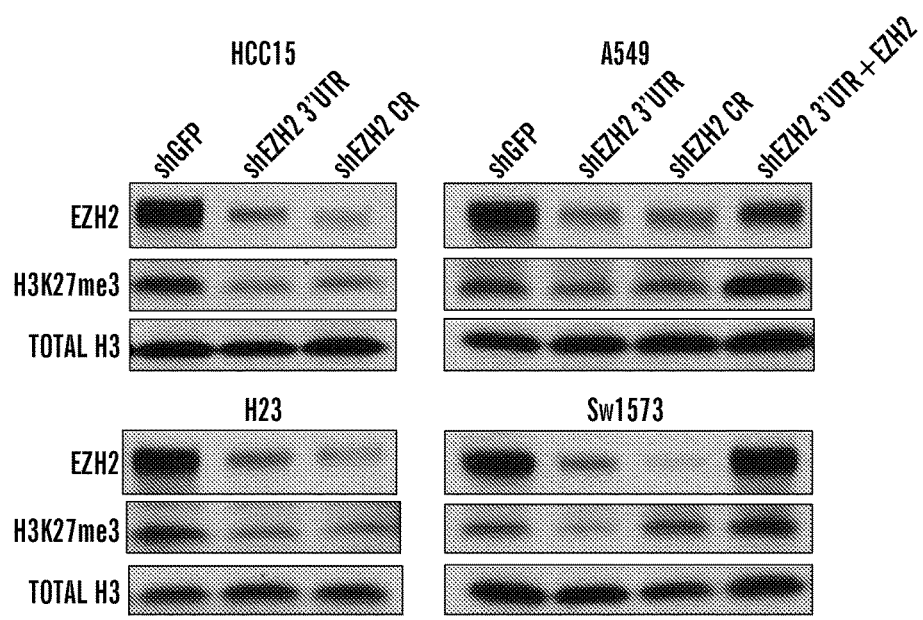
FIGS. 24A-24C demonstrate the effects of EZH2 inhibition.
Figure 24B:
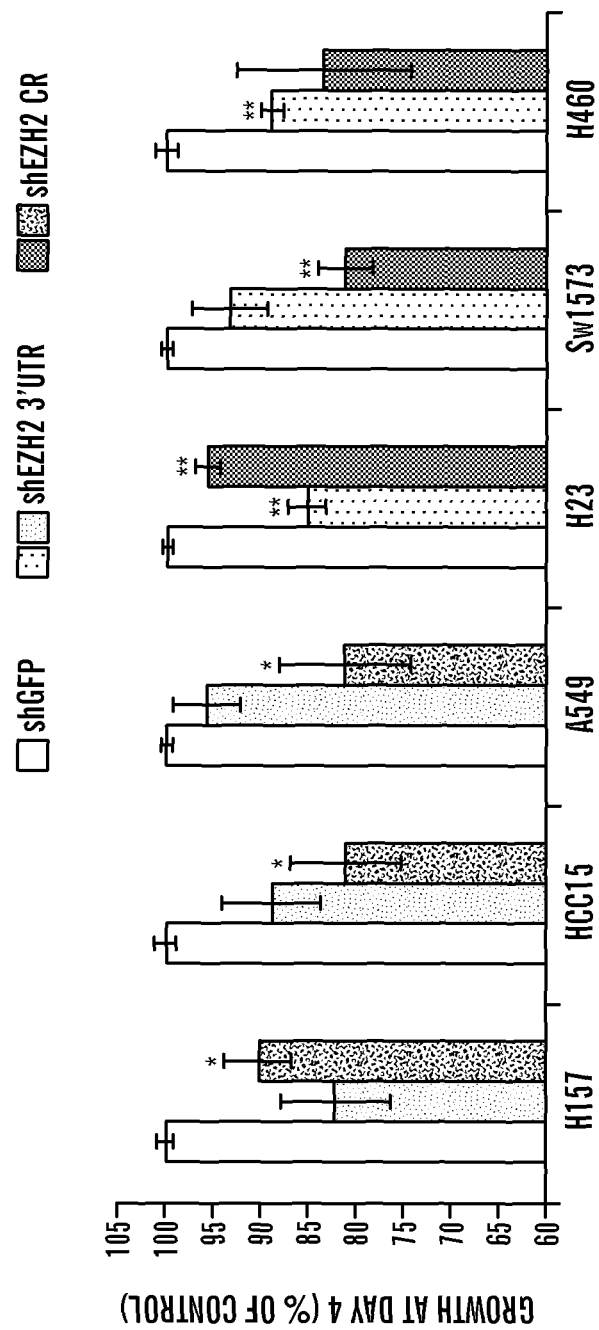

Next, in order to begin testing EZH2 inhibition as a therapy for NSCLC, 26 human NSCLC lines that vary in genotype, stage and subtype[44,45] were obtained (FIG. 29). It was confirmed that several of these lines express high levels of EZH2 compared to cells isolated from normal lung tissue, consistent with previous reports (FIG. 18B). To stably knock-down EZH2 expression, several lines were infected with one of two different small hairpin constructs targeting EZH2. By Western Blot, EZH2 protein and the PRC2 catalytic mark, H3K27me3, were decreased in every cell line transduced with these hairpins compared to matched shGFP transduced cells, though the knock-down and loss of H3K27me3 were both more complete with the coding region (CR) hairpin than the 3' UTR-targeting hairpin (FIGS. 18C and 24A). At the 4-day time-point, shEZH2 CR knock-down cell lines showed 5-20% reduction in growth compared to matched shGFP cultures (FIG. 24B).

Figure 18D:
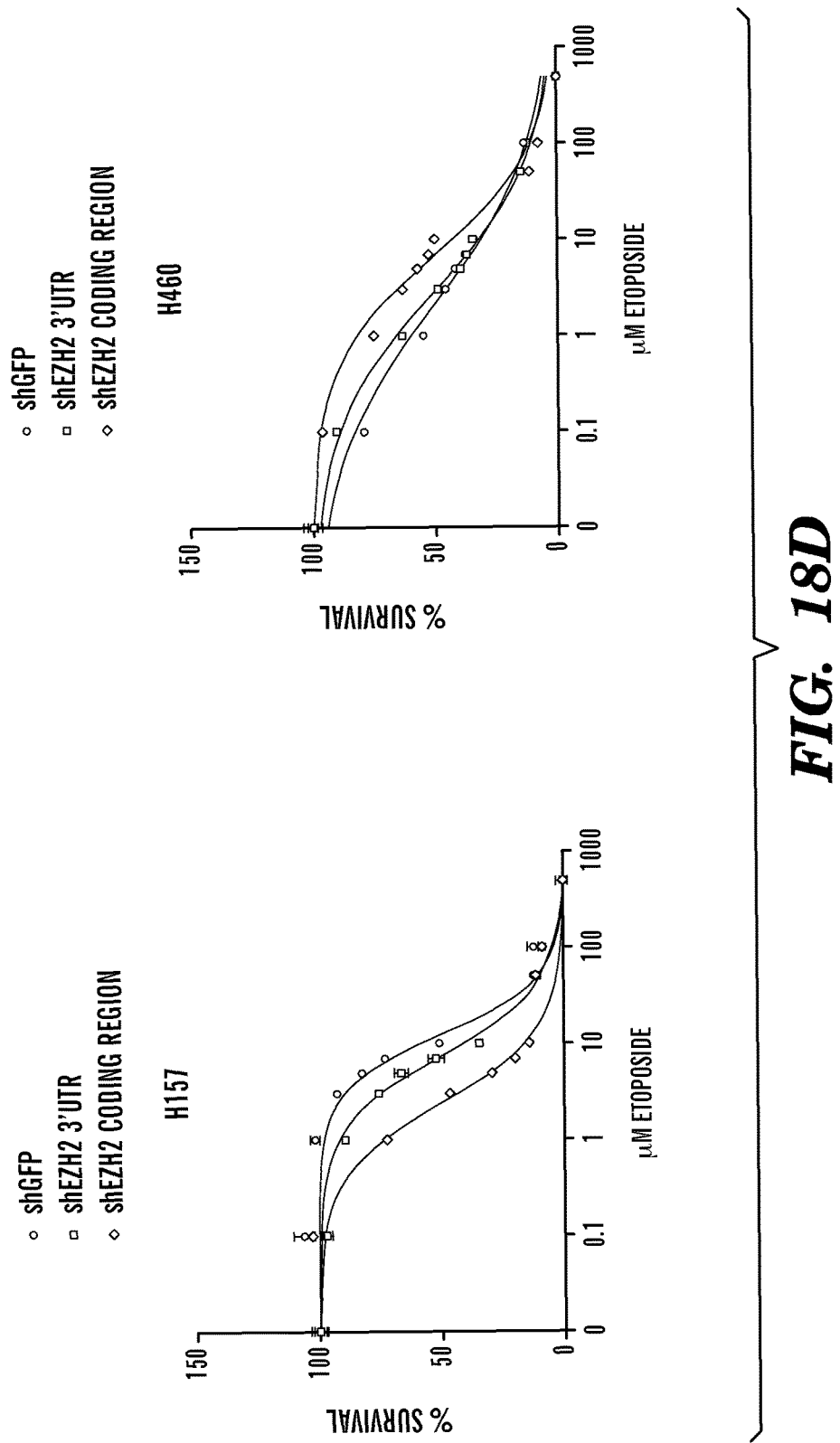
Figure 18F:
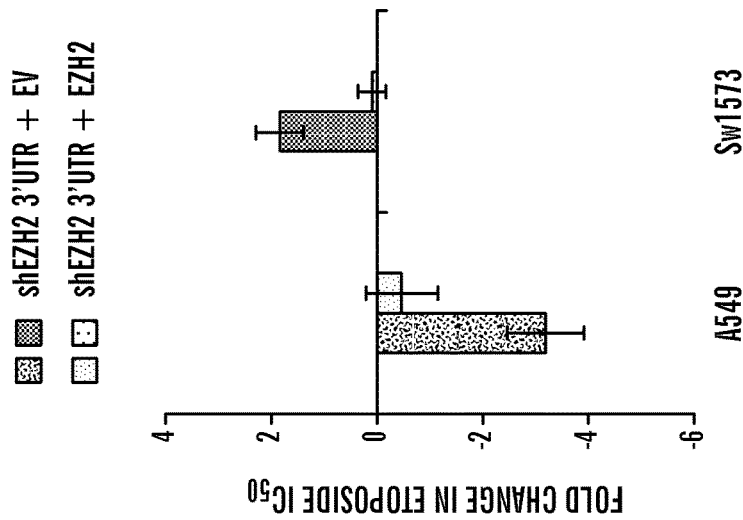
Figure 18E:
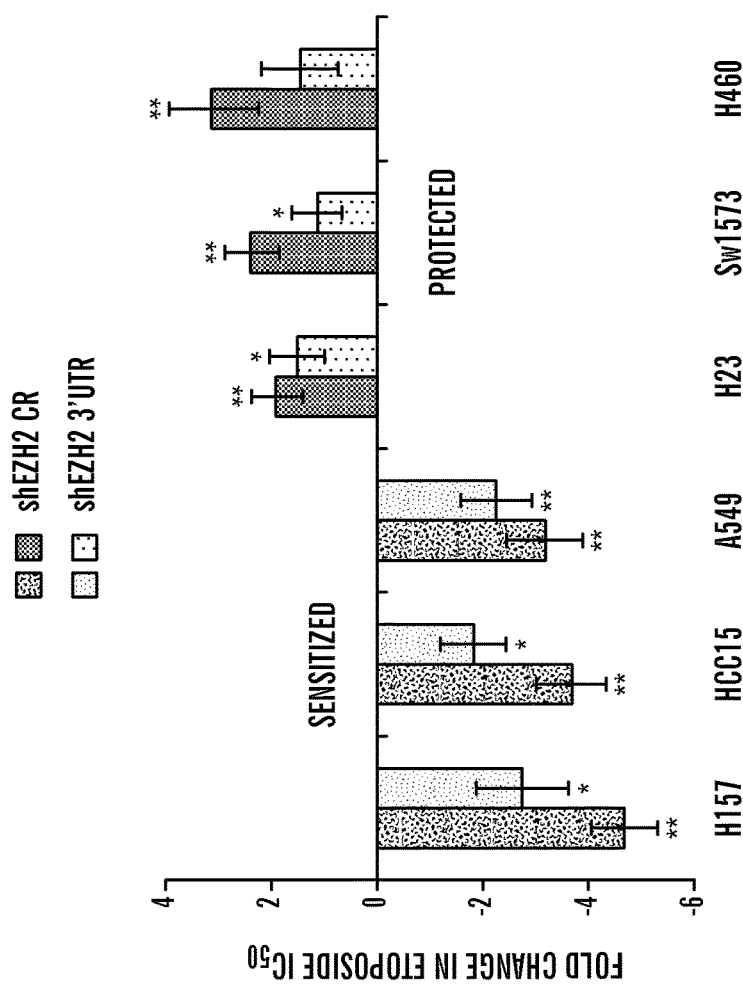
Figure 24C:
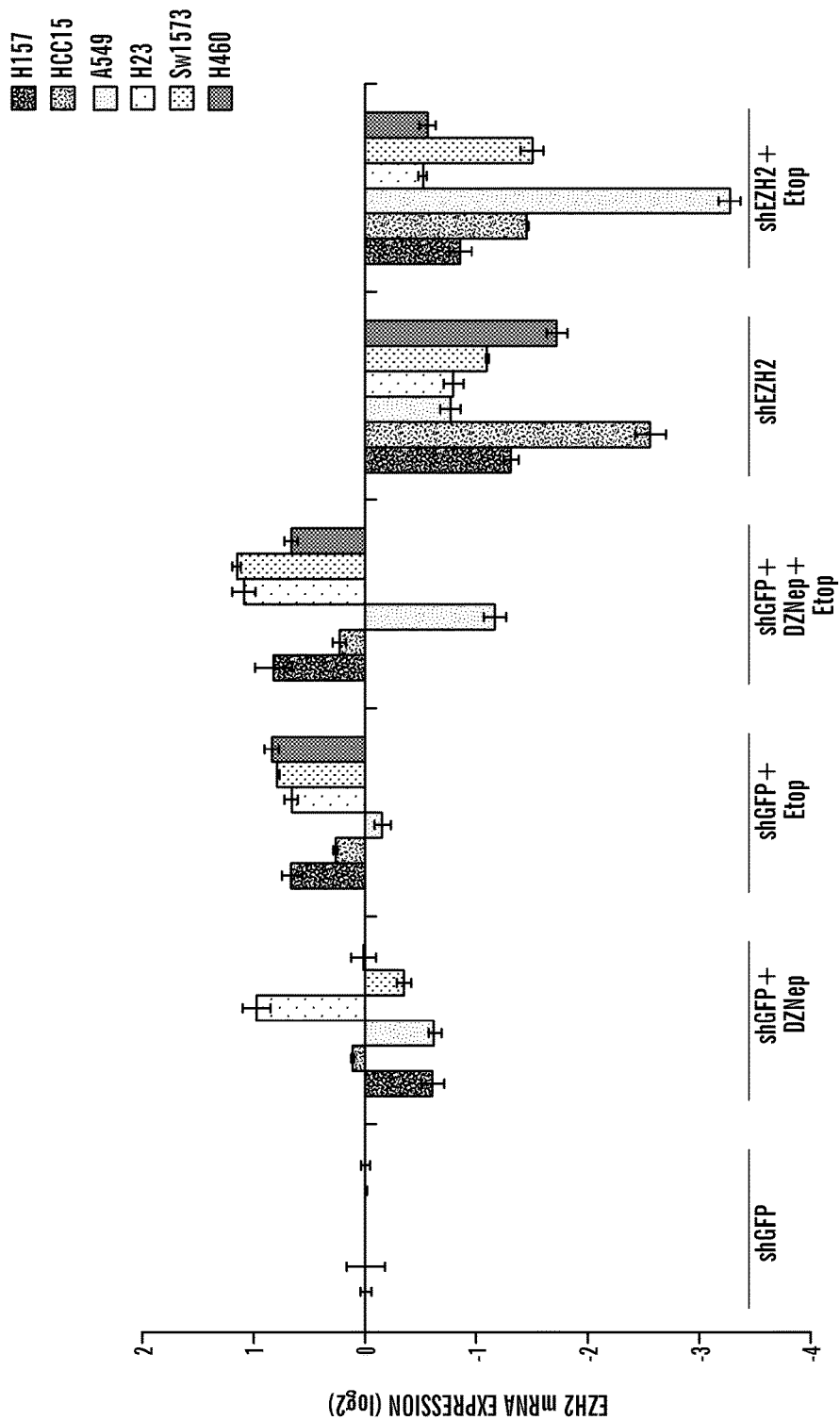

To test if EZH2 knock-down cells were more sensitive to standard chemotherapy, cell viability assays were performed with the commonly used chemotherapy etoposide. shGFP and shEZH2 cell lines were treated for 4 days with a range of doses of etoposide, and cell viability was measured. Dose response curves were performed in biological triplicates, and the etoposide $IC_{50}$s were extrapolated for each shGFP and shEZH2 pair of lines (FIG. 18D). The fold changes in etoposide $IC_{50}$ were graphed (FIG. 18E). Some cell lines, termed 'sensitized', were more sensitive to etoposide, with a lower etoposide $IC_{50}$, when EZH2 was knocked down, whereas other cell lines, termed 'protected' were more viable, with a higher etoposide $IC_{50}$, as shEZH2 lines. EZH2 mRNA levels were assessed after the 4 day etoposide treatment to ensure that the knock-down remained, and results demonstrate that the sensitized and protected phenotypes were not due to differential degree of EZH2 knockdown nor to significant differential expression of EZH2 in response to drug treatment (FIG. 24C).

To clearly demonstrate that EZH2 knock-down was the primary reason for differential etoposide response, virus was used to introduce ectopic EZH2 cDNA into both the A549 (sensitized) and Sw1573 (protected) shEZH2 3'UTR expressing lines. In these rescue experiments, cultures infected with the EZH2 cDNA construct and sorted for infection showed levels of EZH2 similar to those observed in the shGFP control cell lines (FIG. 24A). Etoposide dose response curves were performed with these cell lines, using sorted shGFP and empty vector-infected/sorted shEZH2 3'UTR cell lines as controls. Both the A549 and Sw1573 empty-vector expressing shEZH2 3'UTR cell lines showed the same fold changes in etoposide response relative to shGFP controls as non-infected cells from our previous experiments (compare FIG. 18F to 18E). Importantly, there was no statistical difference in etoposide response between shGFP and EZH2 cDNA-expressing shEZH2 3'UTR cells. These results indicated that EZH2 levels determine how NSCLC cell lines respond to etoposide.

Chemical EZH2 Inhibition Sensitizes BRG1 and EGFR Mutant Cells to TopoII Inhibitors.

Figure 19A:
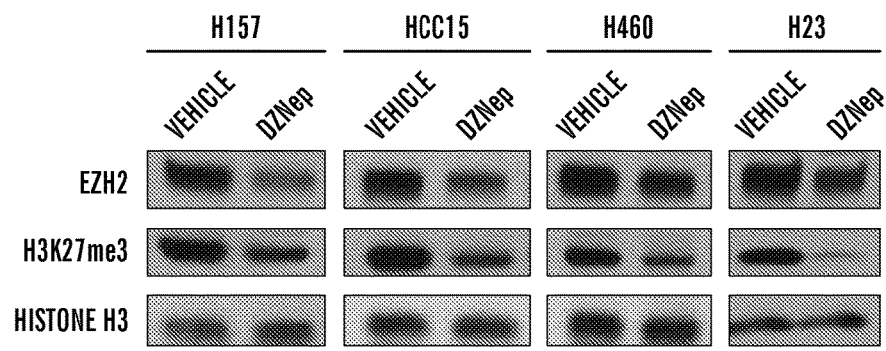
FIGS. 19A-19D demonstrate that chemical EZH2 inhibition sensitizes BRG1 or EGFR mutants to TopoII inhibitors.
Figure 19B:
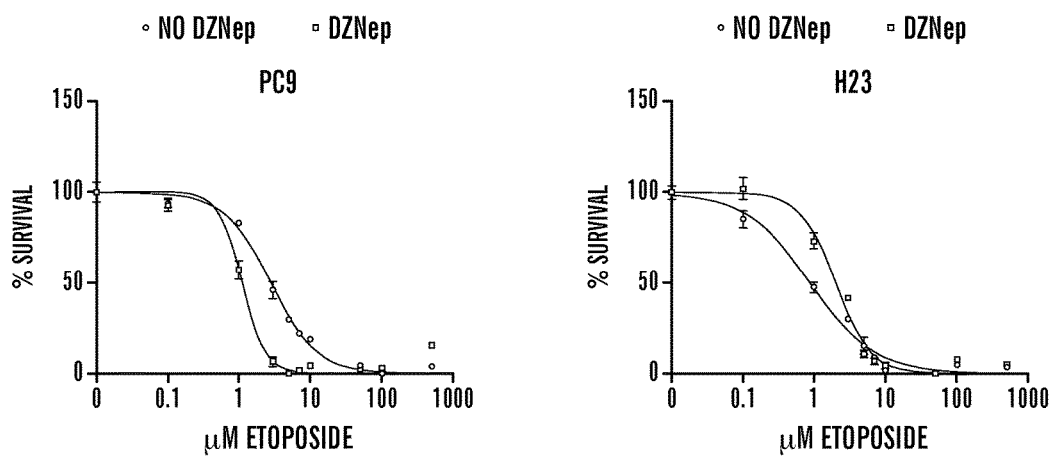
Figure 25A:
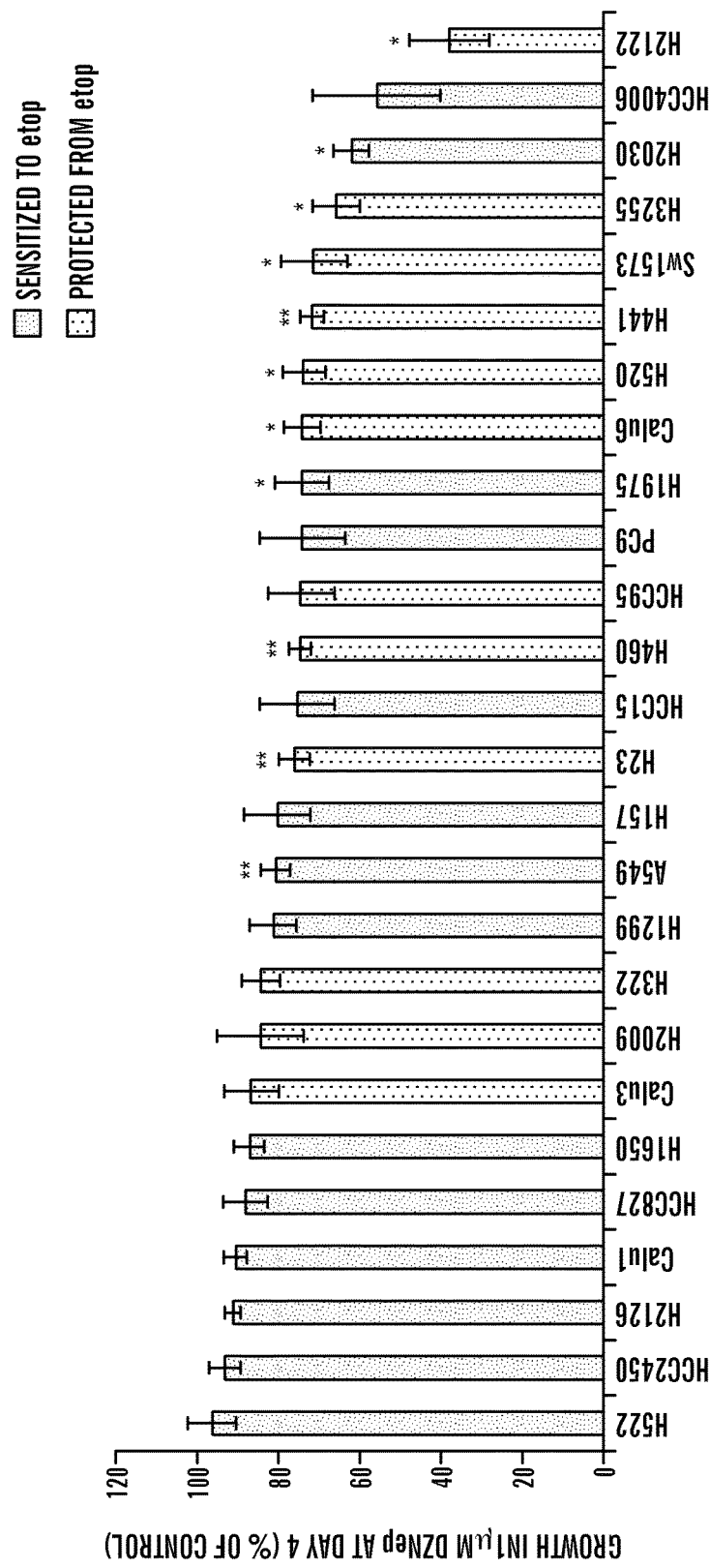

Next, to learn if etoposide sensitivities could be changed by another method of EZH2 inhibition, chemical reduction of EZH2 with the S-adenosylhomocystein hydrolase inhibitor DZNep was tested. DZNep reduces pools of methyl groups required for PRC2 function, and leads to proteosomal degradation of PRC2 components including EZH2[18,20]. Western Blot confirmed that 4 days of 1 μM DZNep effectively reduced EZH2 protein abundance and the H3K27me3 catalytic mark (FIG. 19A). 11 of 26 cell lines showed a significant reduction in growth at the 4-day time-point in response to 1 μM DZNep (FIG. 25A). Next, etoposide dose response curves were performed in the presence or absence of DZNep at the same 4-day time-point. 14 of the 26 cell lines, including H157, A549 and PC9 (p=0.001, 0.009 and <0.0001 respectively), were more sensitive to etoposide in the presence of DZNep, while the other lines, such as H23, H460 and H441 (p=0.0003, 0.001 and 0.0002 respectively), were less sensitive to the chemotherapy in the presence of DZNep (FIGS. 25B and 8C). The classification of a cell line as protected or sensitized was the same as was observed for shEZH2. There was no significant difference in the etoposide $IC_{50}$ values of the sensitized and protected cell lines in the absence of DZNep; the etoposide $IC_{50}$ difference between the groups was only evident in the presence of DZNep (p=0.43 for no DZNep, p=0.032 for DZNep, FIG. 25B). This indicates that sensitization was not unique to chemotherapy resistant cell lines as seen in previous studies[46,47].

Figure 19C:
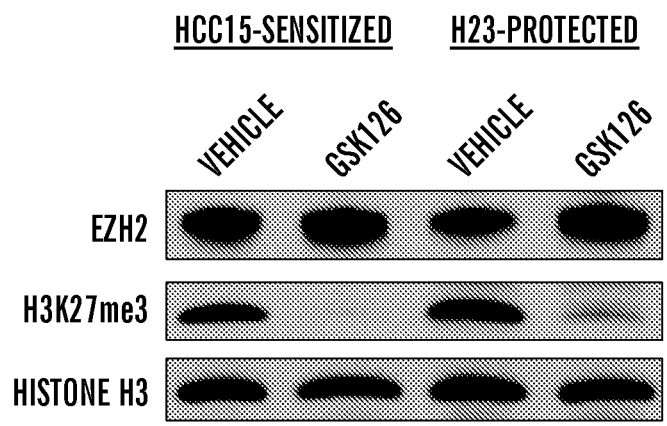
Figure 19D:
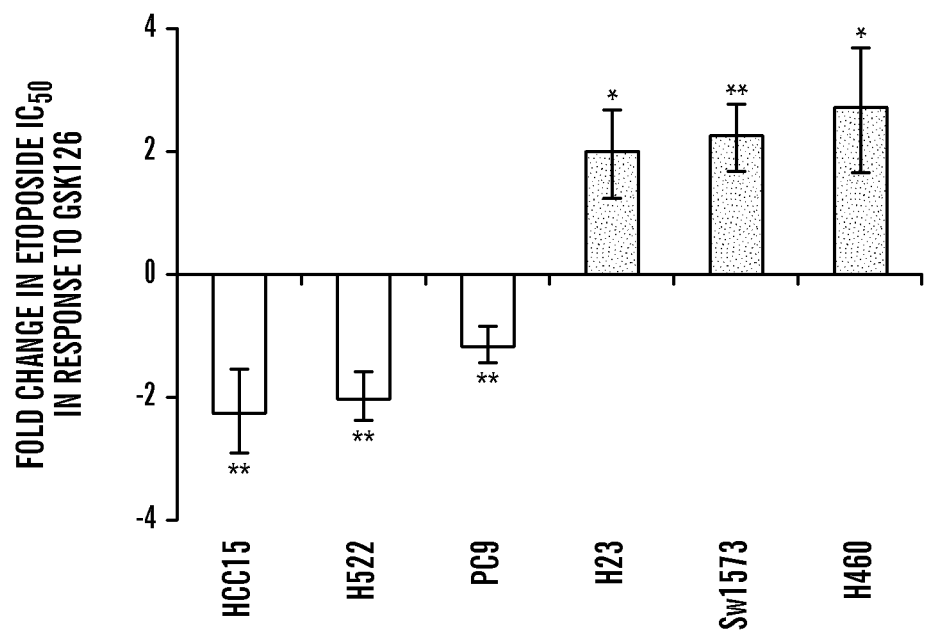

To learn if the changes in chemotherapy sensitivity that EZH2 inhibition caused were specific to TopoII-targeted chemotherapies, doxorubicin, which also targets the TopoII complex, was tested[9]. Cell lines segregated into the same protected and sensitized classes with doxorubicin combined with DZNep (FIG. 8C). Etoposide is almost always administered with cisplatin to NSCLC patients'. When cisplatin (5 μM, ~$IC_{30}$) was administered in combination with etoposide/DZNep treatment, the changes in etoposide $IC_{50}$ in response to DZNep were still evident, showing that the effect of DZNep on etoposide sensitivity is intact in this more clinically relevant situation (FIG. 25C). Furthermore, the pattern of sensitized and protected cells was not observed when cisplatin and DZNep were combined, suggesting that cisplatin response is not mechanistically linked to the EZH2/TopoII inhibition phenotype (FIG. 8D). Lastly, it was sought to validate our results using a novel compound that specifically targets EZH2 methyltransferase activity, GSK126. Cell lines were treated in culture for 7 days with 10 μM GSK126, and observed a marked decrease in H3K27me3 levels while EZH2 levels remained unchanged as expected (FIG. 19C). Etoposide dose response curves showed that GSK126 treated cell lines fell into the same TopoII inhibitor-sensitized and -protected classes as observed with DZNep or shEZH2 (FIG. 19D).

To uncover biomarkers that could potentially be used to identify the protected and sensitized phenotypes, the mutational annotation available for the NSCLC lines was examined. 12 of the 14 sensitized cell lines harbored inactivating mutations in BRG1 or activating mutations in EGFR, while 10 of the 12 protected cell lines were wild-type for the two genes (FIG. 29, Fisher's exact test p=0.001). H23 is a line protected from etoposide by DZNep, yet has a late coding region BRG1 mutation predicted to produce a protein with an intact ATPase domain[44], supporting the lack of sensitization in the EZH2/TopoII inhibitor assay. No correlation of TP53, KRAS, NRAS, LKB1 or PIK3CA mutations with the protected and sensitized phenotypes was observed (FIG. 29). However, for both KRAS and PIK3CA, results suggest that protected lines may be enriched for these mutations, though neither reached significance with the current cohort of cell lines (p=0.054 for KRAS, p=0.051 for PIK3CA, Fisher's Exact Test). Together these results indicate that EZH2 inhibition sensitizes some NSCLC cell lines to TopoII inhibition, while causing TopoII inhibitor resistance in others, and that these phenotypes correlated with mutations in BRG1 and EGFR.

In Vitro Sensitivities to DZNep/Etoposide Predict In Vivo Responses.

To determine if the protected and sensitized phenotypes could be observed in vivo, xenograft-bearing mice were treated with etoposide and DZNep. 12 days after cell injection, when small but visible tumors had developed (data not shown), mice were randomized into groups that received etoposide, DZNep, or both. For the cell line H157, which was sensitized to etoposide by DZNep in vitro, DZNep alone was weakly effective at reducing tumor size compared to vehicle treated tumors (FIG. 3A and data not shown, vehicle vs. DZNep p=0.08). However, dual etoposide and DZNep therapy prevented tumors from forming in 4/6 mice, proving more efficacious than etoposide or DZNep alone (etoposide vs. dual p=0.003, DZNep vs. dual p=0.03). Similarly, the protected phenotype of the H23 cell line was recapitulated in vivo in response to dual etoposide and DZNep therapy. H23 xenografts were sensitive to DZNep as a single therapy (FIG. 3B, data not shown, vehicle vs. DZNep p=0.001), but those that received dual therapy grew significantly larger than those treated with either DZNep or etoposide alone (dual vs. DZNep p=0.005, dual vs. etoposide p=0.0005). Together these data demonstrate that the sensitized and protected phenotypes can be observed in vivo.

Next, mouse models of lung cancer representing predicted sensitized (EGFR-T790M/L858R transgenic; EGFR hereafter[48]) and protected (Kras-G12D/p53-null; Kras/p53 hereafter[49]) tumor types were treated to test our ability to predict response to DZNep and etoposide. These models represent a predicted 'protected' cancer in the Kras/p53 model, which is wild-type for Brg1 and Egfr, and a predicted 'sensitized' cancer in the EGFR mutant model, which is wild-type for Brg1 (confirmed by unpublished RNA-seq). Mice with radiographically documented lung masses reflecting active lung cancer were used for each experimental and control condition at the start of treatment (week 0). Chemotherapy, EZH2 inhibitor, or combination therapy was then administered to cohorts of mice for 4 weeks. MRI was performed at 2 weeks and 4 weeks post treatment start date (data not shown). Marked tumor regression in the EGFR mouse model was observed in response to 4 weeks of dual etoposide/DZNep treatment, while mice in the other treatment arms showed continued tumor growth (data not shown and FIG. 20A, p=0.008 dual vs. DZNep, p=0.004 dual vs. etoposide). This is in striking contrast to the protected Kras/p53 model, in which tumors proceeded to grow during the 4 weeks despite dual treatment (FIG. 20B, p=0.4). Drug efficacy in both models was confirmed by histology and immuno-histochemistry for EZH2, which was dramatically reduced in both the EGFR and Kras/p53 tumors in response to dual therapy (data not shown). In addition pEGFR is greatly reduced by dual treatment, fitting with the mechanism we demonstrate in the next figures. These data indicate that tumors mutant for BRG1 (H157 xenografts) or relying upon activation of EGFR (EGFR mice), are sensitized to TopoII inhibition by DZNep in vivo, suggesting a new possible therapeutic avenue for these two genotypes of NSCLC.

Dual Etoposide/EZH2 Inhibition Differentially Affects Cell Cycle, Apoptosis and Anaphase Bridging.

Figure 21A:
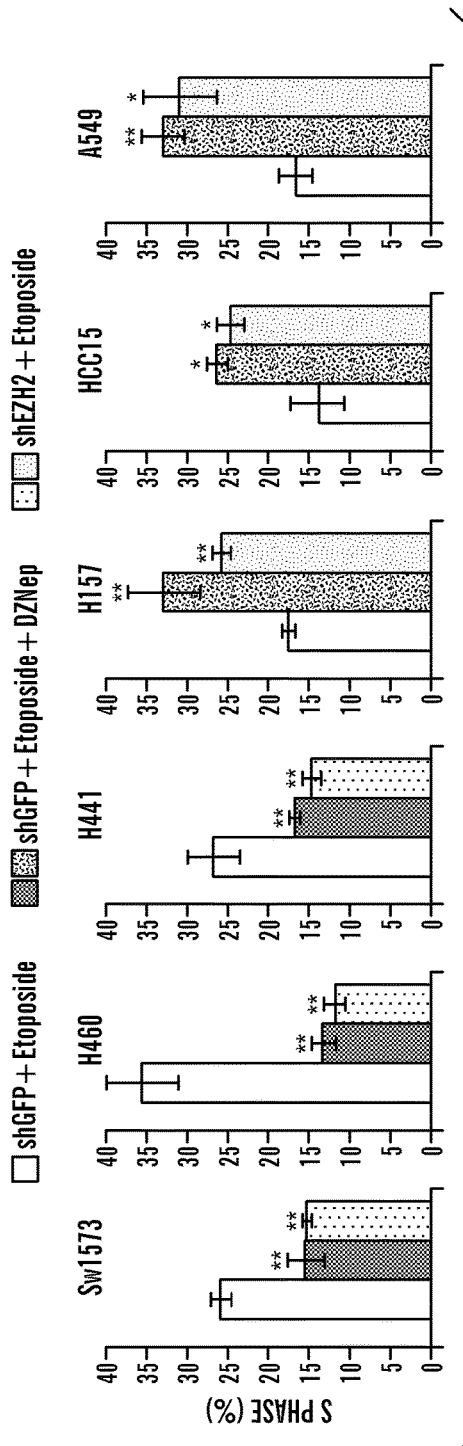
FIGS. 21A-21E demonstrate that dual etoposide/EZH2 inhibition differentially affects cell cycle, apoptosis and anaphase bridging.
Figure 21B:
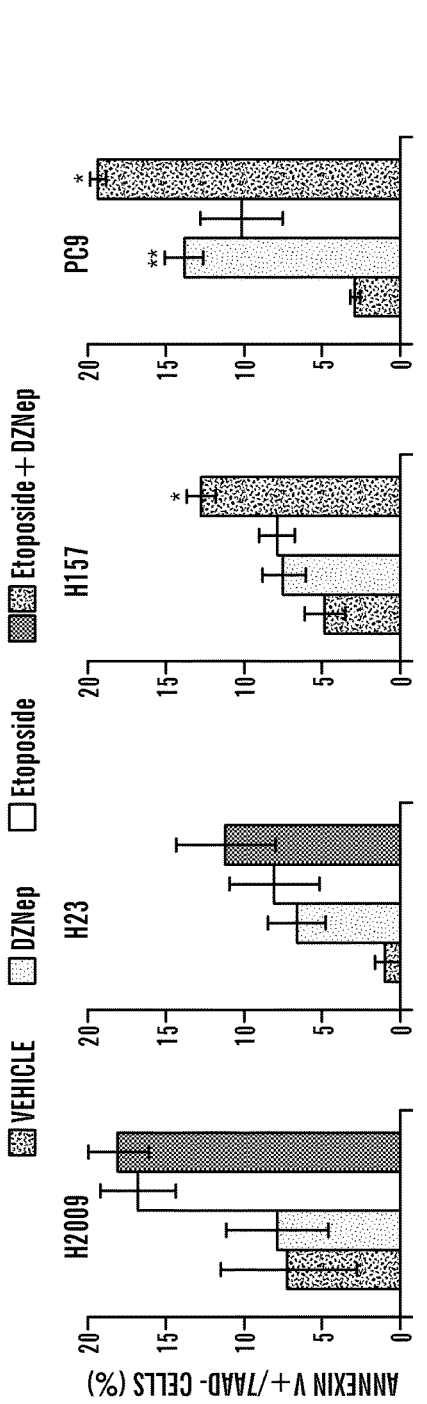
Figure 26A:
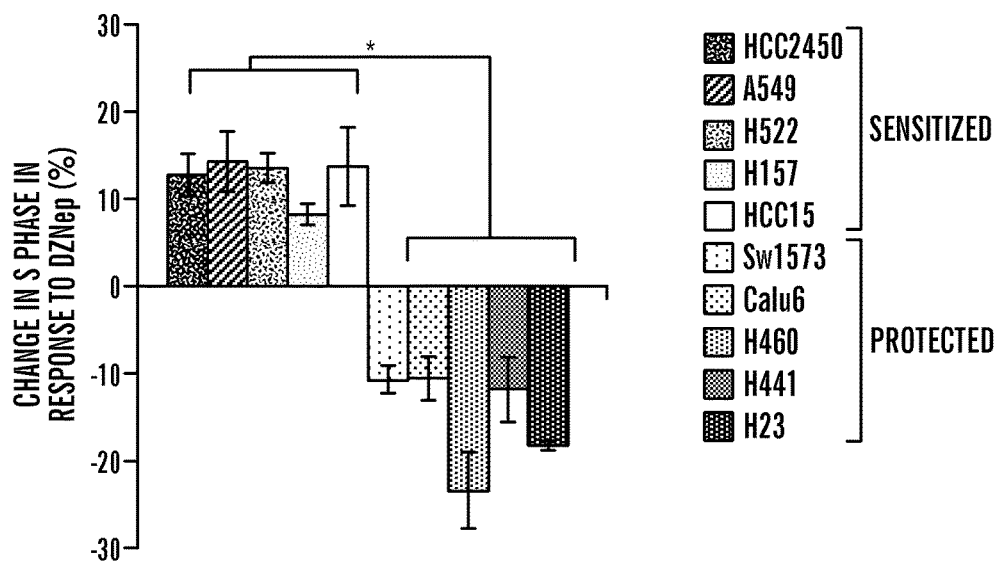
FIGS. 26A-26C demonstrate the effect of EZH2 on cell cycle.
Figure 26B:
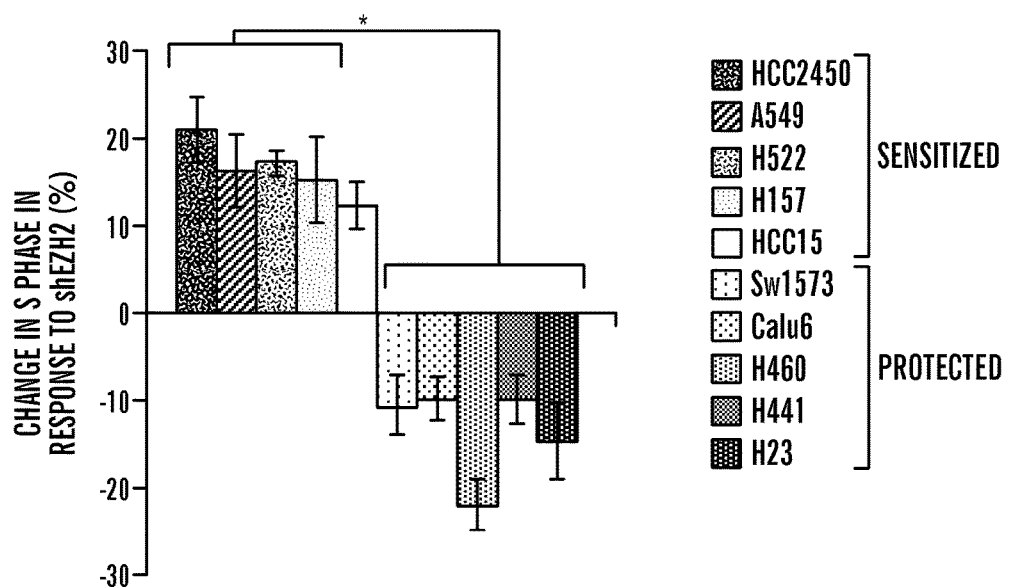
Figure 26C:
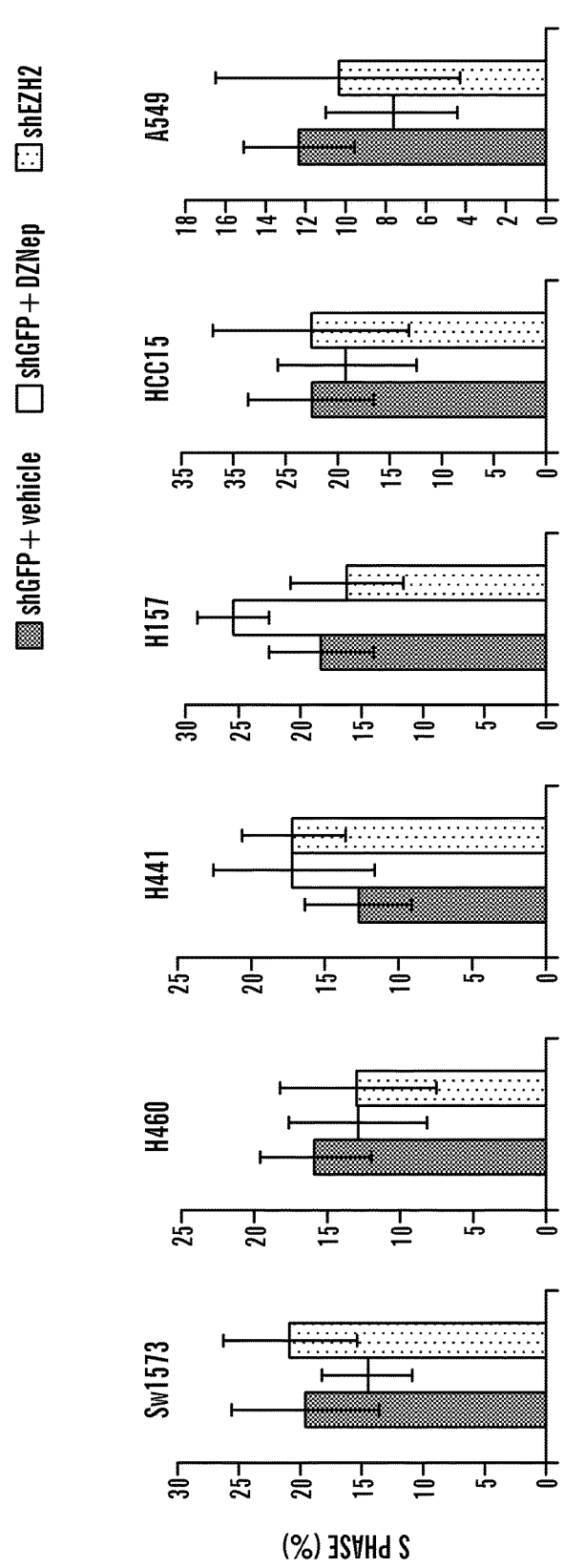

Next, the hypothesis that EZH2 inhibition caused changes in cell cycle status, rendering cells more or less sensitive to chemotherapy was tested. It was reasoned that protected lines may undergo a cell cycle arrest in response to EZH2 inhibition, thus sparing them from etoposide-induced DNA damage, while sensitized lines may be unable to arrest and instead continue to cycle in the presence of etoposide. shGFP, shEZH2, and shGFP cells treated with 1 µM DZNep were treated for 4 days with vehicle or 5 µM etoposide (~$IC_{50}$) and stained with 7AAD to assess cell cycle profiles by flow cytometry. Protected etoposide-treated lines had an average of 14% fewer cells in S phase when in response to DZNep or shEZH2 compared to treatment with etoposide alone; in contrast, sensitized etoposide-treated lines had an average of 14% more cells in S phase in response to DZNep or shEZH2 (FIGS. 21A, 26A, and 26B). Importantly, the S phase content of the sensitized and protected lines was not significantly changed in response to EZH2 inhibition alone, suggesting that cell cycle changes are specific to dual treatment (FIG. 26C). To test the hypothesis that the increase in S phase in sensitized etoposide-treated lines translated into higher levels of apoptosis, Annexin V/7AAD flow cytometry was performed. Cultures treated for 4 days with 1 µM DZNep, 5 µM etoposide, or both were collected and stained with Annexin V and 7AAD, and the percentage of apoptotic cells (Annexin V+/7AAD−) cells was assessed by flow cytometry (FIG. 21B). While the protected lines H2009 and H23 showed no difference in apoptotic levels in etoposide compared to dual treated cultures, the sensitized lines H157 and PC9 had significantly higher apoptotic fractions in dual treated cultures than in cultures treated with etoposide as a single agent (p=0.017 and p=0.026, respectively). Together these data indicate that sensitized cell lines respond to combined EZH2/TopoII inhibition with altered cell cycle responses that predispose cells to increased etoposide-induced apoptosis.

Figure 21C:
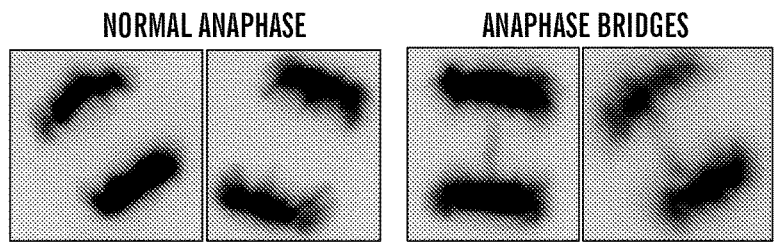
Figure 21D:
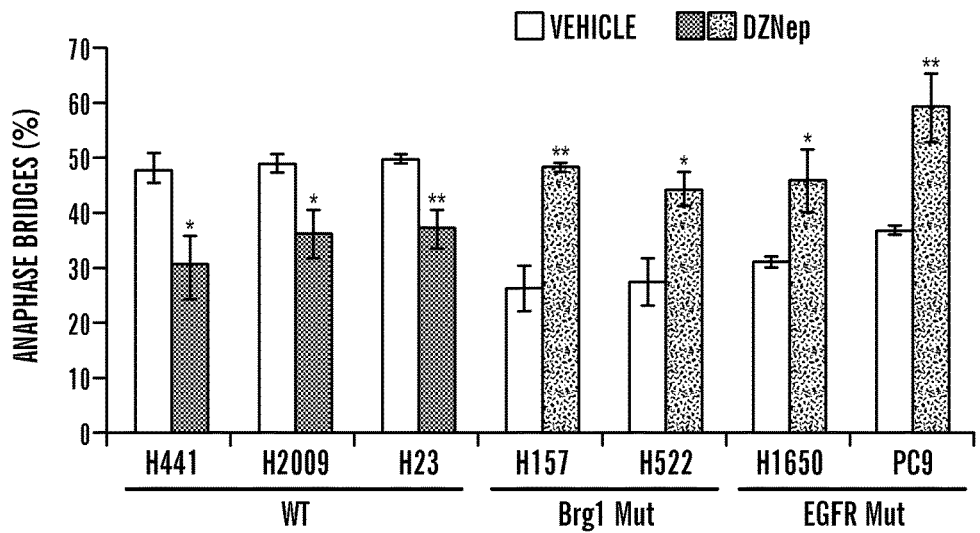
Figure 21E:
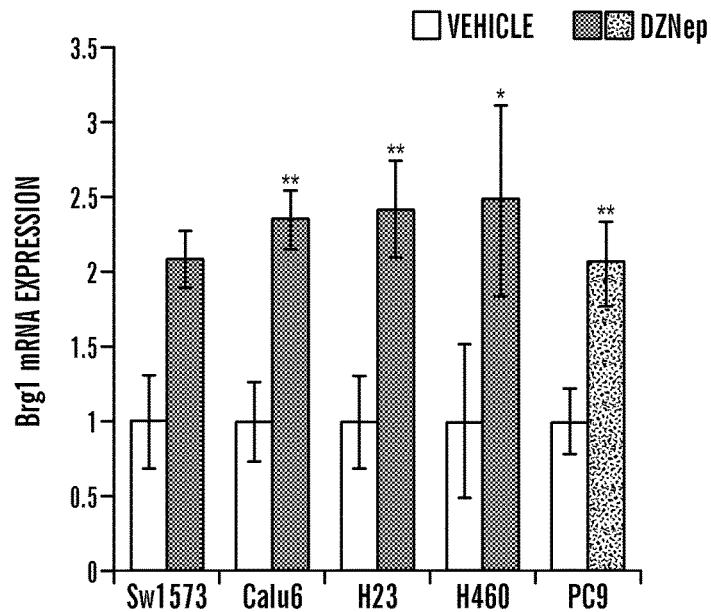

To further address the mechanism through which EZH2 inhibition changes sensitivity specifically to TopoII inhibitors, the recent report of a physical interaction between BRG1 and TopoII that allows for increased TopoII function[10] was considered. Given that BRG1 and EZH2 are known to be genetically antagonistic[50], it was hypothesized that protected cell lines had up-regulation of BRG1 in response to EZH2 inhibition and therefore had increased TopoII function. In order to test this hypothesis, anaphase structures in DZNep and vehicle-treated cultures were imaged, quantifying the numbers of anaphase bridges that are indicative of a failure of TopoII to decatenate DNA prior to mitosis (FIG. 21C). BRG1 mutant cell lines had lower baseline levels of anaphase bridging than Brg1 wild-type cell lines. However, when challenged with DZNep, BRG1 mutant cell lines showed increased anaphase bridging, while BRG1 wild-type lines showed a significant decrease (FIG. 21D). To learn if the decrease in anaphase bridging of the BRG1 wild-type cell lines corresponded to an increase in BRG1 levels, real time RT-PCR for BRG1 transcript was performed (FIG. 21E). In 5 different cell lines, 4 of which are wild-type for EGFR (Sw1573, Calu6, H23 and H460) and one of which is EGFR mutant (PC9), BRG1 transcript was reproducibly increased by DZNep treatment. Together these data indicate that increased BRG1 is an effect of EZH2 inhibition, which leads to a decrease in anaphase bridging and protection from TopoII inhibition. In contrast, the increased anaphase bridging after EZH2 inhibition in BRG1 mutants likely explains their increased sensitivity to TopoII inhibition and subsequent apoptosis.

BRG1 and EGFR are Genetically Antagonistic.

While the observed anaphase bridging of BRG1 mutants in response to EZH2 inhibition explained their increased sensitivity to TopoII inhibition, it was still unclear why EGFR mutants also fell into this chemo-sensitized category. In the panel of cell lines, 30% have a BRG1 mutation and 23% have an EGFR mutation. With these mutation frequencies, ~7% of cell lines are expected to have both BRG1 and EGFR mutations. However, no NSCLC cell line in this panel or elsewhere that harbored both mutations was observed (FIG. 29, Table 4, Fisher's exact test p=0.005). To examine the pattern of BRG1 and EGFR mutations in primary human lung cancers, lung adenocarcinoma whole exome sequencing from The Cancer Genome Atlas (TCGA) and a recent publication were queried[29]. Of the 412 adenocarcinoma samples, 56 (14%) had exon 19 deletion or missense mutation in EGFR, while 41 (10%) had missense, nonsense, deletion or insertion mutations in BRG1. With these allele frequencies, 1.4% of the tumor samples were expected to have both BRG1 and EGFR mutations, though only 2 (0.5%) were observed (Fisher's exact test, p=0.03), and both contain EGFR mutations that may be passenger/non-functional mutations (E574L, H1129Y). With compilation of the cell line and primary tumor data, the anti-correlation of EGFR mutations and BRG1 mutations was more significant (Fisher's exact test, p=0.002).

Figure 27A:
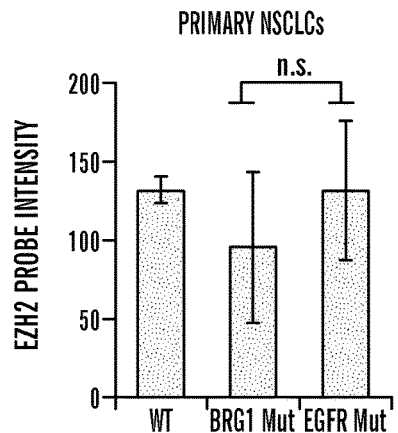
FIG. 27A depicts a graph of averaged EZH2 probe (203358_s_at) intensity within each NSCLC sample of the genotype indicated.
Figure 27B:
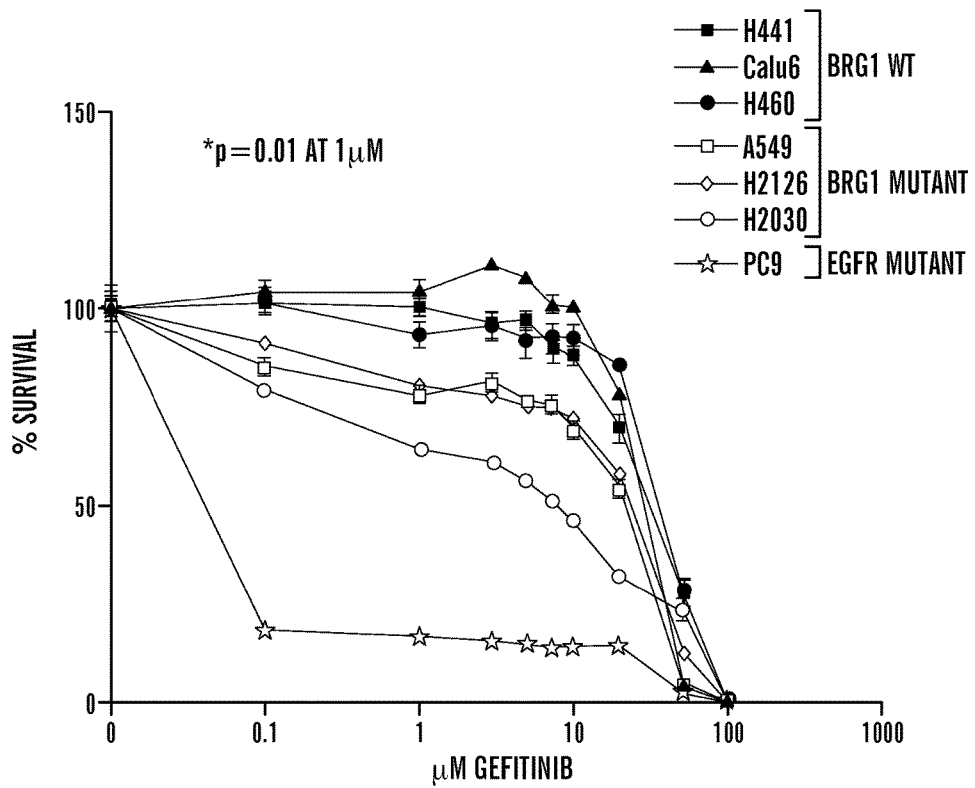
FIG. 27B depicts a graph of gefitinib dose response curves performed on the indicated cell lines after 4 days of treatment. At 1 μM gefitinib, the relative survival of the 3 BRG1 mutant cell lines was compared to that of the 3 BRG1 wild-type (WT) cell lines, p=0.01. The EGFR mutant cell line PC9 is shown for comparison.

The negative correlation of BRG1 and EGFR mutations suggests that these pathways interact genetically and that these mutations may be functionally redundant. Supporting this idea, in the Director's Challenge dataset of primary human lung adenocarcinomas[41], a strong negative correlation was found between EGFR and BRG1 expression, supporting the theory that loss of BRG1 may be permissive for high expression of EGFR (FIG. 5A, Spearman's correlation=−0.619, p=0.0002). Likewise in a primary NSCLC dataset[30], tumors with mutations in BRG1 had significantly higher expression of EGFR than EGFR/BRG1 wild-type tumors, while there was no difference in EZH2 levels among the genotypes (FIGS. 5B and 27A, p=0.002). To explore the relationship between these mutations in our cell lines, available gene array data was used to compare gene expression signatures in the various genotypes. Overlap between differentially expressed genes in EGFR mutant lines vs. EGFR/BRG1 wild-type lines, and BRG1 mutant lines vs. EGFR/BRG1 wild-type lines was queried (FIG. 11A). Interestingly, it was found that EGFR was the top shared up-regulated gene, over-expressed 3.1-fold in BRG1 mutant cell lines and 3.25-fold in EGFR mutant cell lines, both compared to EGFR/BRG1 wild-type lines (FIG. 5C, Table 5, p=0.014). Importantly, we also confirmed with these arrays that baseline EZH2 transcript levels do not differ among the various genotypes (FIG. 11B, p=0.5). Immuno-fluorescence for EGFR confirmed that BRG1 mutant cell lines have high expression of EGFR compared to BRG1 wild-type cell lines, which have very little detectable EGFR staining (data not shown). Although gefitinib, and other EGFR specific inhibitors, are thought to cause death preferentially of cells with activating mutations in EGFR[32], we assessed whether there was any detectable difference in gefitinib sensitivities of the BRG1-mutant/EGFR$^{high}$ cells vs. the BRG1-wild-type/EGF$^{low}$ cells. It was observed that the IC$_{50}$ for gefitinib among the cultures is identical, but the growth inhibition at sub-IC$_{50}$ concentrations of gefitinib was significantly different between BRG1-mutant and BRG1-wild-type cell lines (FIG. 27B).

Figure 11D:
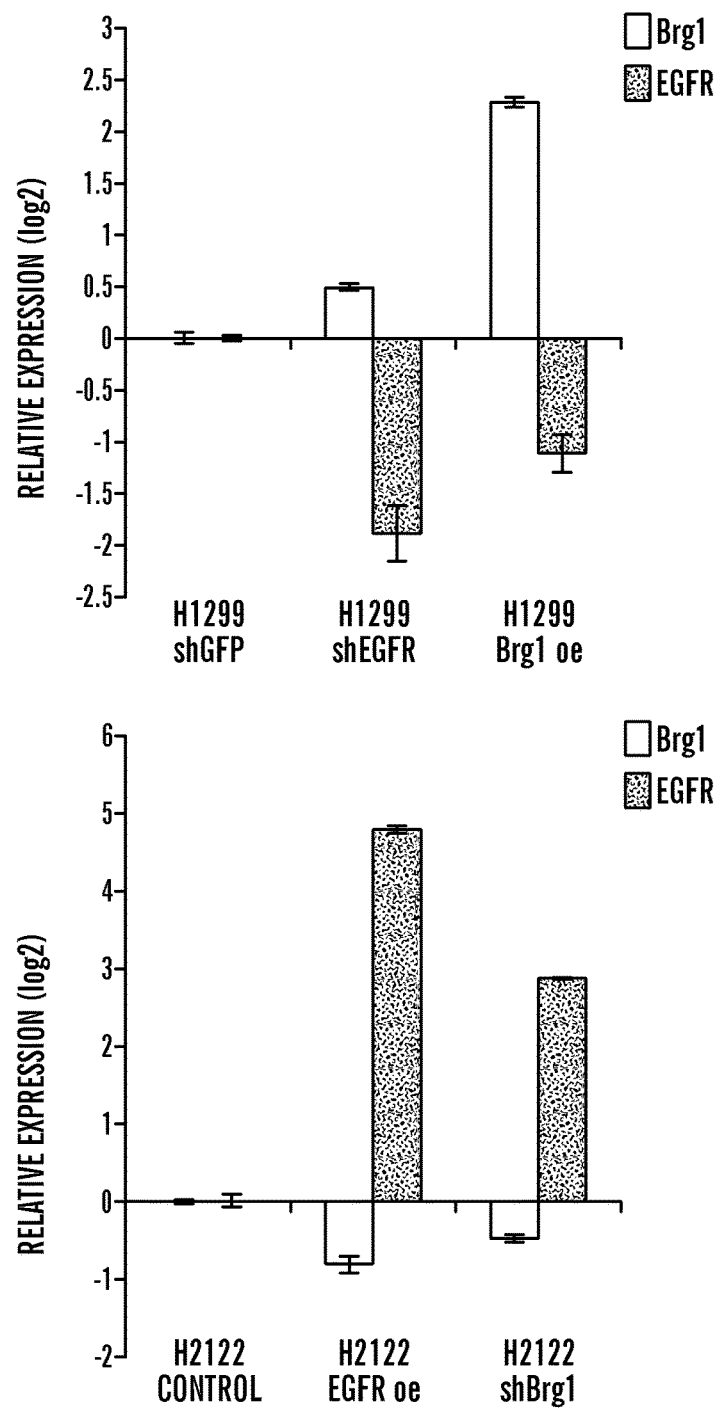
Figure 22:
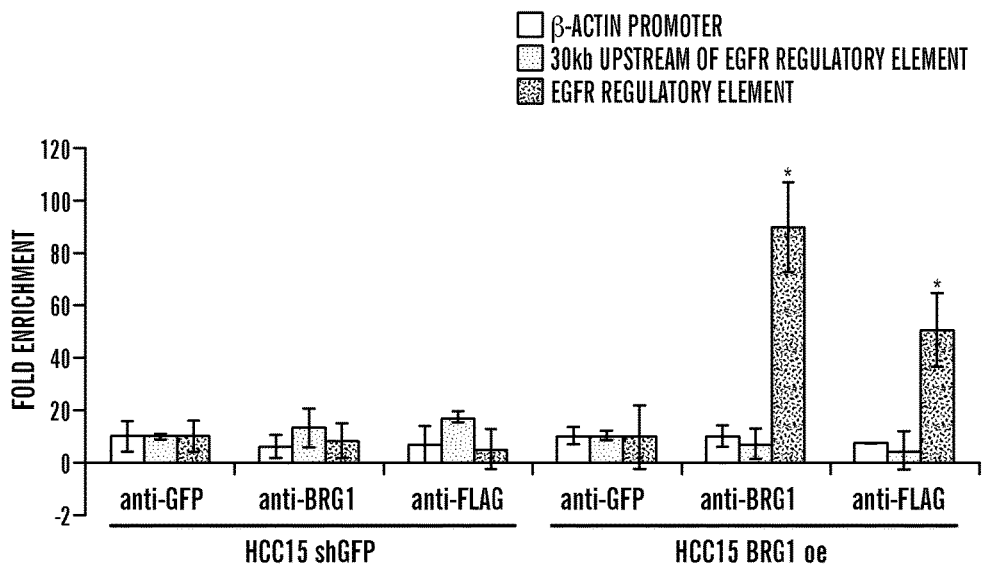
FIG. 22 demonstrates that BRG1 and EGFR are genetically antagonistic. Chromatin immuno-precipitation for GFP (control), BRG1 or the FLAG-tag on the over-expressed BRG1 in the HCC15 shGFP (control) and BRG1 over-expressing cell lines. Real time PCR was performed with primers for indicated genomic sites, n=3 biological replicates, * indicates p<0.03.

To further explore the genetic relationship between these two pathways, EGFR and BRG1 expression were manipulated via knock-down and over-expression in NSCLC cell lines. In the BRG1 mutant cell line HCC15, which expressed high levels of wild-type EGFR, re-introduction of BRG1 significantly decreased the amount of EGFR transcript, while EGFR knock-down led to an increase in the truncated mutant Brg1 mRNA (FIG. 18A, p=0.005). These changes were confirmed by immuno-fluorescence (data not shown). In contrast, in the H460 line, which is wild-type for BRG1 and has little detectable EGFR expression, knock-down of BRG1 led to up-regulation of EGFR (p=0.009) and over-expression of wild-type EGFR led to a decrease in BRG1 transcript (FIG. 18B, p=0.002). These results were observed in several cell lines (FIG. 11D). The ENCODE database[51] shows a chromatin immuno-precipitation (ChIP) peak for BRG1 in the regulatory element upstream of the EGFR transcriptional start site in HeLa-S3 cells. Therefore, it was hypothesized that the mechanism through which BRG1 over-expression was down-regulating EGFR was through direct binding of the SWI/SNF complex to the EGFR regulatory element. To validate this hypothesis, ChIP assays were performed in the HCC15 shGFP (control) and HCC15 BRG1 over-expressing cell lines (FIG. 22). It was found that BRG1, immuno-precipitated with an antibody recognizing the protein itself or the FLAG-tag, was significantly associated with the EGFR regulatory element (p=0.02 for both IPs). Together these data indicate that BRG1 loss-of-function mutations and EGER gain-of-function mutations are mutually exclusive in NSCLC, and that BRG1 and EGFR are genetically antagonistic due to binding of BRG1 to an EGFR regulatory element that leads to down-regulation of EGFR transcript.

Brg1 and EGFR Control the Sensitized Phenotype

Figure 28A:
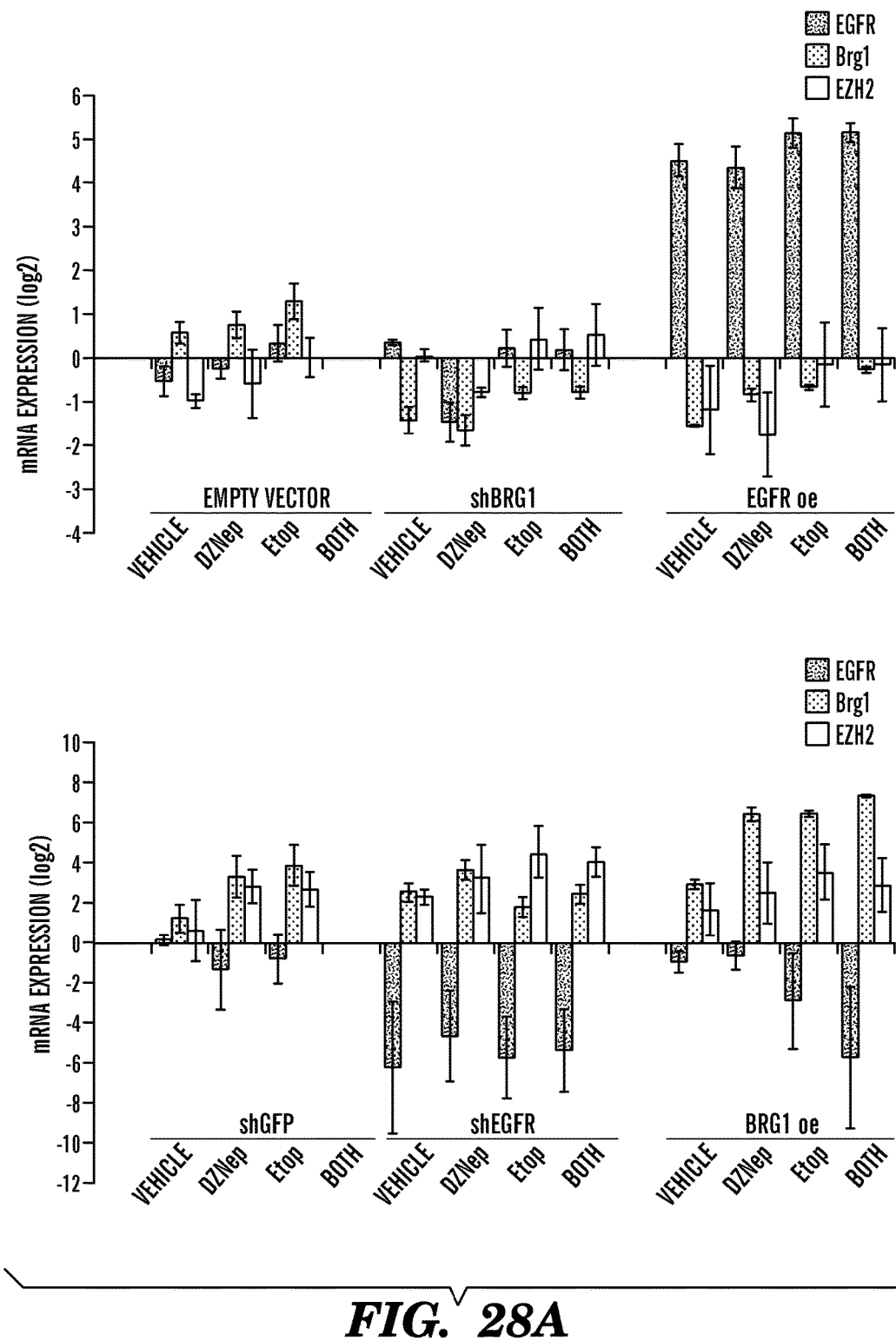

To learn what impact modulation of EGFR and BRG1 levels had on the protected and sensitized phenotypes, etoposide dose response curves were performed on the BRG1 and EGFR knock-down and over-expression cell lines. For the HCC15 control cell line, DZNep decreased the etoposide IC$_{50}$ 2-fold, consistent with its sensitized phenotype (p<0.0001). However, BRG1 over-expressing HCC15 lines showed an increase in etoposide IC$_{50}$, suggesting that the phenotype of the line was converted from sensitized to protected through re-introduction of BRG1 (FIG. 23A, p=0.037). In the HCC15 shEGFR line, the line was no longer sensitized to etoposide by DZNep, but was not protected either, consistent with the fact that this line still lacks functional BRG1 protein. For the protected cell line, DZNep raised the etoposide IC$_{50}$ 2-fold in the H460 control cells (p=0.028), yet had no effect on etoposide IC$_{50}$ when EGFR was over-expressed (p=0.35) or BRG1 was knocked-down (FIG. 6b, p=0.5). We confirmed that 4 days of etoposide, DZNep or dual treatment did not change the over-expression and knock-down of EGFR and BRG1 by RT-qPCR (FIG. 28B). These data demonstrate that the sensitized and protected phenotypes are partially reliant upon the levels of BRG1 and EGFR within the cells.

Figure 23C:
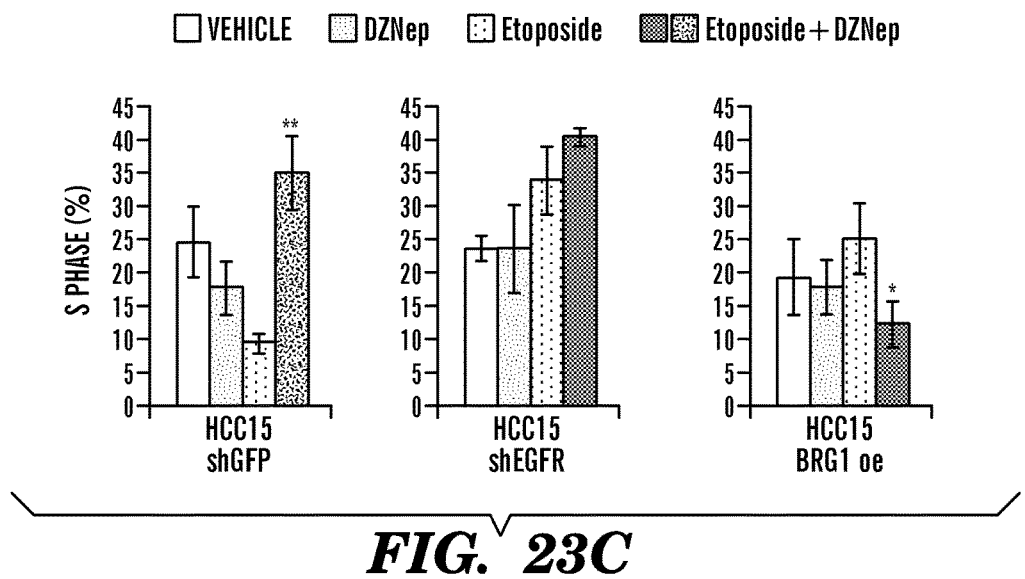
Figure 23D:
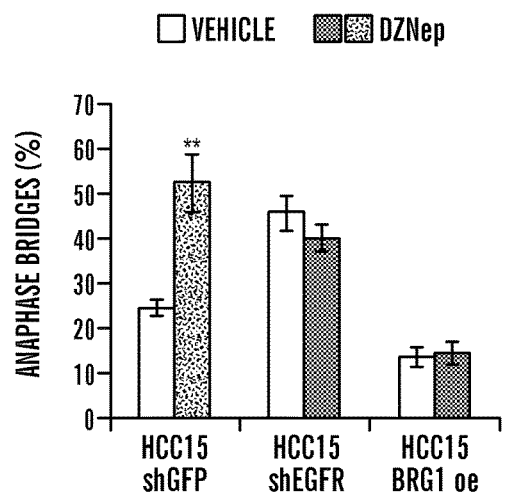
Figure 23E:
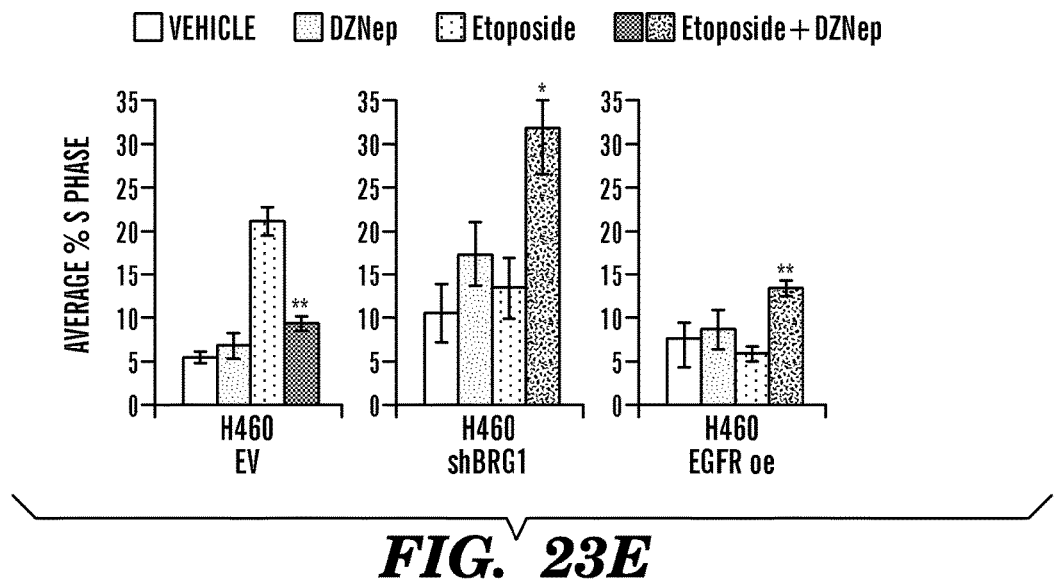
Figure 23F:
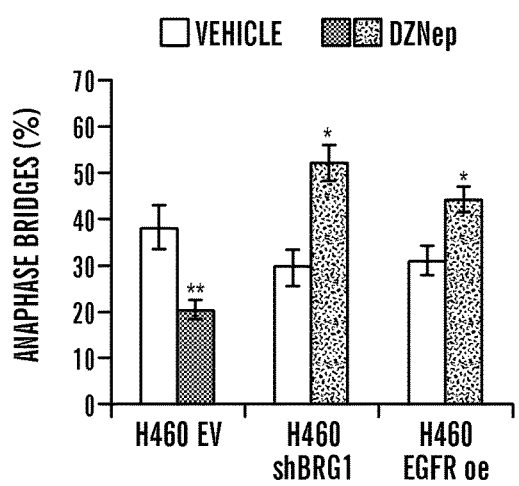
Figure 28C:
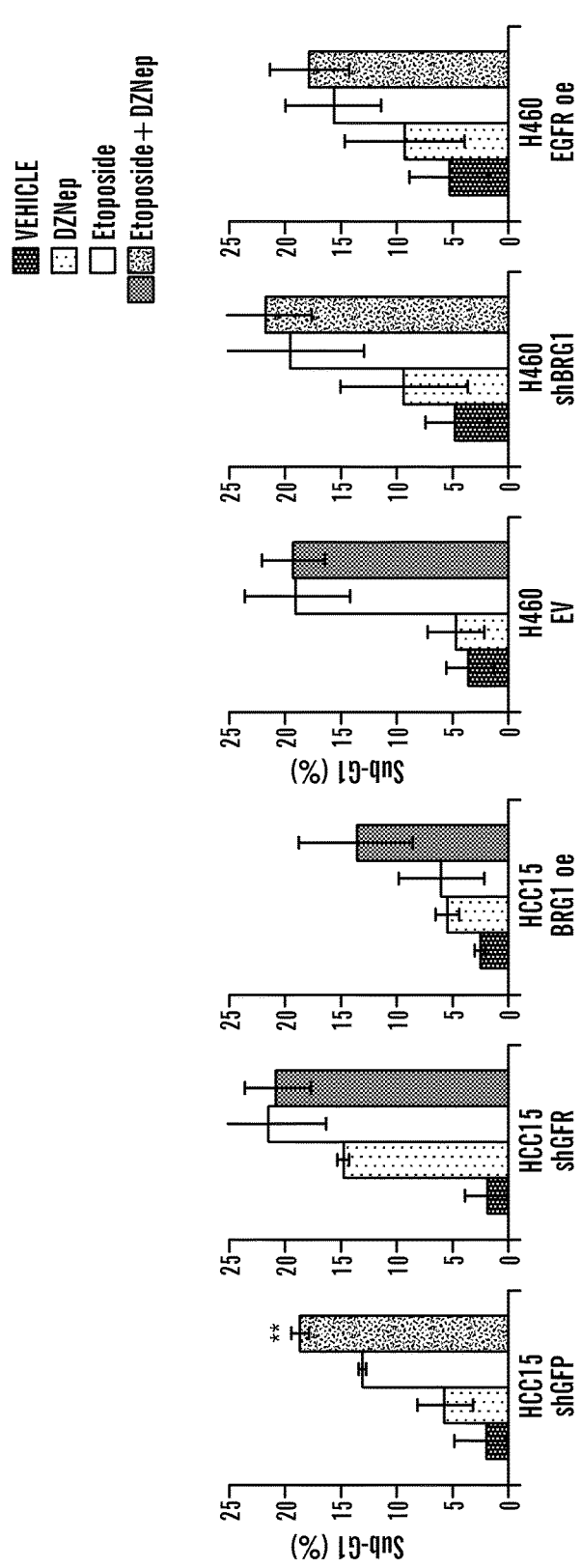

Finally, it examined whether changes in etoposide sensitivity of the BRG1- and EGFR-modulated DZNep-treated cell lines were attributable to cell cycle, apoptotic and anaphase bridge changes. While shBRG1 in the BRG1 wild-type line H460 led to decreased proliferation, BRG1 over-expression in the mutant line HCC15 led to increased proliferation (FIG. 28B). Despite their increased proliferation in the absence of etoposide, etoposide-treated HCC15 BRG1 over-expressing cell lines did not accumulate in S phase in response to DZNep as the control shGFP cells did (FIG. 23C, p=0.02). HCC15 shEGFR showed higher percent S phase in response to etoposide alone than do shGFP control cells, but have no additional increase in S phase in response to DZNep/etoposide dual treatment. Consistent with results from other sensitized lines, the HCC15 control cells showed an increase in sub-G1/apoptotic cells in response to dual therapy, but this change was not evident in either shEGFR or BRG1 over-expression cultures (FIG. 28C). Likewise, the anaphase bridging phenotype clearly demonstrated an increase in TopoII dysfunction in response to DZNep in the HCC15 control line, but not in the shEGFR or BRG1 over-expressing lines (FIG. 23D). The protected H460 control cell line showed a depletion of S phase in response to the dual therapy; however, the etoposide treated H460 shBRG1 and EGFR over-expressing cell lines were enriched for S phase (FIG. 23E, p=0.02 for shBrg1, p<0.001 for EGFR over-expression). While none of these cultures showed differences in sub-G1/apoptotic cells (FIG. 28C), the decrease in anaphase bridges normally observed in H460 cells was reversed by BRG1 knock-down or EGFR over-expression (FIG. 23F, p<0.04). Together these data demonstrate that EZH2/TopoII inhibition altered cell cycle dynamics, apoptosis and anaphase bridging, and that these effects were mediated by the levels of BRG1 and EGFR expression in the cells.

Discussion

Figure 23G:
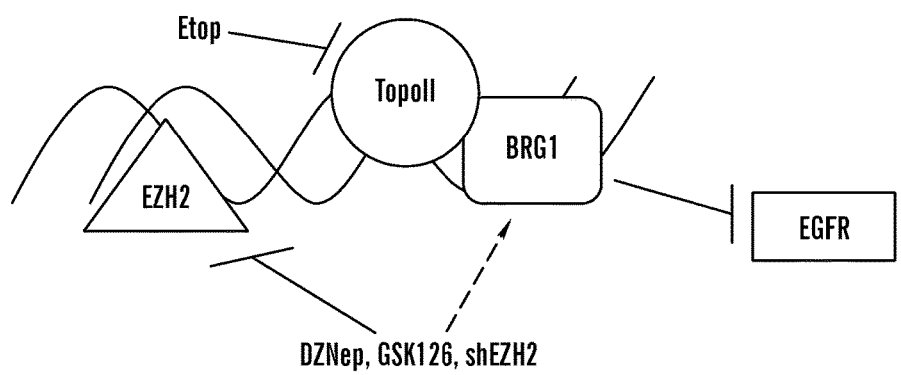

Targeting of epigenetic enzymes such as EZH2 could be a novel therapeutic approach for lung cancer patients; yet, clear demonstration of how EZH2 inhibitors interact with current therapies and specific genotypes of NSCLCs is lacking. It is demonstrated that susceptibility to combined TopoII and EZH2 inhibition is predictable by NSCLC genotype. BRG1 loss-of-function mutants represent on class of TopoII/EZH2-inhibitor 'sensitized' cells that cannot up-regulate Brg1 in response to EZH2 and therefore have impaired TopoII function that rendered them sensitive to etoposide. Another, unexpected class of sensitized tumors is EGFR mutants, which respond to EZH2 inhibition with BRG1 up-regulation and apoptosis, the later likely due to direct negative regulation of EGFR by BRG1[52] (FIG. 23G). Endogenous mouse lung cancer models were used to verify the link between tumor genotype and EZH2 inhibitor effects on chemotherapy response. The differential effects of EZH2 inhibition on chemotherapy in vitro allowed the prediction of responses to therapies in vivo, suggesting that dual EZH2/TopoII inhibitor therapy will be an option for patients with either EGFR or BRG1 mutant NSCLCs.

The data described herein indicate that patients with lung cancers bearing EGFR or BRG1 mutations will benefit from dual EZH2/TopoII inhibitor strategies. This work also indicates that this combination may be ineffective or even detrimental to patients with EGFR/BRG1 WT tumors due to the reduced efficacy of TopoII inhibitors such as etoposide. The mouse model that was used to validate the sensitized phenotype harbors lung tumors driven by EGFR T790M and L858R mutations[48]. The T790M mutation represents the canonical gefitinib/erlotinib "gatekeeper" resistance mutation, suggesting that dual EZH2/TopoII inhibition could be an option for patients that developed resistance to first line EGFR TKI strategies[34]. Because we showed BRG1 could bind at a site upstream of the EGFR start codon, it is possible that EZH2 inhibitors, through BRG1 up-regulation will negatively regulate both point mutant and exon 19 deletion forms of EGFR. Furthermore, BRG1 mutations have only recently been identified in lung cancers and there are currently no specific treatments available for this subset of lung cancer patients; EZH2/TopoII inhibitor combination could offer the first therapeutic intervention for BRG1 mutant lung cancers. No correlation of TP53, KRAS, NRAS, LKB1 or PIK3CA mutations with the protected and sensitized phenotypes was observed, yet it remains possible that other predominant NSCLC oncogenotypes will exhibit differential responses to EZH2/TopoII inhibitor combinations.

It was found that in NSCLC patient datasets, BRG1 inactivating mutations and EGFR activating mutations were significantly anti-correlated. This finding is in agreement with two recent publications showing that EGFR mutant tumors in Asian populations, where EGFR mutations occur at a much higher frequency than in US patients, also appear to preferentially lack BRG1 mutations[53,54]. It was found that BRG1 mutant tumors and cell lines had higher total EGFR levels, and it is not yet known if this translates into higher active EGFR (pEGFR) in BRG1 mutant tumors[53]. In support of the hypothesis that BRG1 mutants have more EGFR signaling, BRG1 mutant cell lines were slightly more sensitive to gefitinib than BRG1 wild-type cell lines (Fillmore and Kim data not shown). Some NSCLC patients with wild-type EGFR clinically benefit from gefitinib and erlotinib therapy by stabilizing disease and preventing further progression[55,56], and it will be interesting to observe whether these patients were BRG1 mutation carriers. It was also found that re-expression of BRG1 protein in a BRG1 mutant cell line led to down-regulation of EGFR, and that BRG1 was significantly associated with an upstream regulatory element of EGFR in these cells. One theory of how BRG1, which is often thought to activate genes through displacement of nucleosomes from key promoter elements[57], can elicit gene silencing is through blocking the binding of transcriptional co-activators such as p300[58]. Also, recent work suggests that on a genome-wide scale, BRG1 deletion causes derepression of more than 1,000 genes in MEFs, again supporting that the SWI/SNF complex participates in transcriptional silencing of target genes[59].

In agreement with previous work, it was found herein that expression of an EZH2-expression signature was highly correlated with poor prognosis in all stages and differentiation states of lung adenocarcinoma. On this list of EZH2 co-expressed genes was TOP2A and numerous genes involved in the decatenation checkpoint, suggesting at the minimum a genetic interaction between these pathways. It is demonstrated herein that in BRG1 and EGFR mutant cell lines, EZH2 inhibition caused sensitization to the TopoII inhibitors etoposide and doxorubicin. Unlike Brg1-deficient MEFs, BRG1 mutant cell lung cancer cell lines did not show dysfunction in TopoII function, as assessed by anaphase bridging, until EZH2 was inhibited. Recently, research has uncovered roles of EZH2 outside of histone methylation[13,14], and it is possible that genetic interaction with TopoII may be another non-histone mechanism for EZH2 action.

Therapeutic strategies targeting epigenetic factors have risen as promising new candidates for lung cancer and other difficult-to-treat cancers. Rationales for epigenetic therapy approaches include the possibility that targeting universally required chromatin enzymes will benefit a broader patient population than drugs targeting specific oncogenic changes.

Methods

Cell Lines and Small Hairpins.

Cell lines used are listed in FIG. 29. All cell lines were maintained in RPMI 1640 media with 10% fetal bovine serum, 4 mM L-glutamine and penicillin/streptomycin at 37° C., 5% $CO_2$. The pLK0.1 EZH2 shRNA construct clones TRCN0000040076 and TRCN0000040073 were purchased from SIGMA and the shGFP plasmid 12273 is available on Addgene. Both shBRG1 and the matched empty vector were provided by the Smale lab[60] and are available on Addgene, the Brg1 over-expression plasmid 19148 was purchased through Addgene, and the shEGFR and EGFR WT over-expression constructs were provided by the Jänne lab[61]. The EZH2 over-expression construct was derived by cloning human EZH2 cDNA into pLenti7.3/V5-DEST (Invitrogen). Lentivirus was packaged in 293T cells using established protocols[62], and retrovirus was packaged in PlatE cells again using established protocols[63]. Cell lines were infected with viral-containing supernatant containing 6 μg/mL polybrene (SIGMA) for a period of 10-18 hours. Infected cultures were selected with 1 μg/mL puromycin (all sh constructs and EGFR oe, SIMGA), 200 μg/mL hygromycin (BRG1 oe, Invitrogen), or by flow cytometry for GFP (EZH2 oe) 5 days post infection.

Small Hairpin Sequences:

GFP:
(SEQ ID NO: 15)
GCCC(GCAAGCTGACCCTGAAGTTCAT)TCAAGAG(ATGAACTTCAGGGT

CAGCTTGC)TTTT

-continued

EZH2 coding region:
(SEQ ID NO: 16)
CCGG(CGGAAATCTTAAACCAAGAAT)CTCGAG(ATTCTTGGTTTAAGAT

TTCCG)TTTTT

EZH2 3' UTR:
(SEQ ID NO: 32)
CCGG(TATTGCCTTCTCACCAGCTGC)CTCGAG(GCAGCTGGTGAGAAGG

CAATA)TTTTT

EGFR:
(SEQ ID NO: 17)
CCGG(GCTGAGAATGTGGAATACCTA)CTCGAG(TAGGTATTCCACATTC

TCAGC)TTTTT

BRG1:
(SEQ ID NO: 18)
TTTG(TGGATAAGCAGCACAAGATT)TCAAGAG(AATCTTCTGCTGCTTC

TCCA)TTTTT

Drugs.

Etoposide, cisplatin, and doxorubicin (SIGMA) were diluted to a stock of 100 mM in DMSO for all cell culture experiments. DZNep was diluted in DMSO to a stock of 10 mM. GSK126 was purchased from Xcess Bio as a 10 mM stock in DMSO. All stocks were diluted in DMSO to 1000× concentration prior to addition into media at 2× concentration and final dilution onto plated cells 1:1.

Cytotox Assays.

Cell lines were dissociated, counted and plated at 5000 cells per well in flat bottom opaque tissue culture treated 96 well plates (CytoOne). Edge wells were filled with PBS. The following day, 2× drug diluted in media was added to each well such that the well then contained 100 ul media with 1× drug concentration at the following doses: etoposide; 0, 0.1, 1, 3, 5, 7, 10, 50, 100, 500 µM, cisplatin; 0, 0.1, 1, 5, 10, 30, 70, 100, 500 µM, or doxorubicin; 0, 0.01, 0.1, 0.5, 1, 3, 5, 7, 10, 50 µM. After 4 days, CELLTITER-GLO™ (Promega) was added and luminescence was read on a BioTec plate reader to determine relative cell number in each well. Data were averaged for triplicate or quadruplicate technical replicates and normalized to the untreated wells. Results from three or four independent biological replicate experiments were input into GRAPHPAD PRISM™ software to extrapolate $IC_{50}$ and s.e.m. of $IC_{50}$ for a given cell line.

Flow Cytometry.

For 7AAD-cell cycle analysis, cell lines were plated at 1.5×10⁶ cells per 10 cm plate and treated with drug for 4 days. Cells were then dissociated, fixed with 100% ice cold Ethanol for at least 2 hours, incubated for 30 minutes with 1 mg/mL DNase-free RNase A (Thermo) and resuspended in 20 µg/mL 7-Aminoactinomycin D (7AAD; Invitrogen). 30,000 events were collected on the BD FORTESSA™ and analyzed with the MODFIT LT™ software. Results from three to four independent biological replicate experiments were averaged for each cell line.

For Annexin V/7AAD apoptosis analysis, cell lines were plated at 1×10⁵ cells per well of 6 well plate and treated with drug for 4 days. Supernatant was retained and added to trypsinized suspensions of adherent cells. Cells were stained with Annexin V-FITC (BD Biosciences) according to manufacturer's instructions, and resuspended with 1 µg/mL 7AAD prior to analysis on BD FORTESSA™.

Quantitative RT PCR

RNA from treated cell lines was extracted using Absolutely RNA™ kits (Agilent) and cDNA was made using the SuperScript III™ kit (Invitrogen). Relative gene expression was assayed with Sybr green on the StepOnePlus™ Real-Time PCR System (Applied Biosystems). Relative expression was calculated by Gene of Interest($Ct_{reference}$-$Ct_{experimental}$)-CYPA($Ct_{reference}$-$Ct_{eexperimental}$) and graphed on the log 2 scale. For all experiments, the reference sample was a matched untreated or control transduced cell line.

For normal human lung samples, tissue adjacent to lung tumors was provided and dissociated with Dispase (BD Biosciences) for 45 minutes at 37° C. then titurated through a 5 mL pipet. Tissue was then incubated in DMEM, 10% fetal bovine serum, 4 mM L-glutamine and penicillin/streptomycin at 37° C., 5% $CO_2$ on tissue culture treated plates overnight to allow adherence of fibroblasts. The following day, supernatant, which included visible alveolar and bronchiolar structures, was collected, pelleted, and RNA was isolated as described. 4 patient samples were assayed and averaged for FIG. 1b.

Primer Sequences:

```
CYPA:
F TCATCTGCACTGCCAAGACTG      (SEQ ID NO: 19)

R CATGCCTTCTTTCACTTTGCC      (SEQ ID NO: 20)

EZH2:
F AGGAGTTTGCTGCTGCTCTC       (SEQ ID NO: 21)

R CCGAGAATTTGCTTCAGAGG       (SEQ ID NO: 22)

BRG1:
F AGCGATGACGTCTCTGAGGT       (SEQ ID NO: 11)

R GTACAGGGACACCAGCCACT       (SEQ ID NO: 12)

EGFR:
F TAACAAGCTCACGCAGTTGG       (SEQ ID NO: 13)

R GTTGAGGGCAATGAGGACAT       (SEQ ID NO: 14)
```

Xenograft Experiments.

Cell lines were dissociated into single cells, counted and resuspended at 1×10⁶ cells per 250 µL of 1:1 media/matrigel (BD). 8- to 16-week-old Foxn1nu (nude) mice (Harlan) were injected subcutaneously with 1×10⁶ cells in 2-4 spots on flanks. Etoposide and DZNep were administered from day 12 to day 17 post injections; etoposide: 20 mg/kg/day i.p. in corn oil once per day for 5 consecutive days, and DZNep 2 mg/kg/day i.p. in corn oil twice per week for 1 week, or 1 mg/kg/day i.p. in corn oil twice per week for 2 weeks. Tumor growth was measured every other day by caliper. All mouse experiments were approved by the CHB Animal Care and Use Committee and by the Dana-Farber Cancer Institute Institutional Animal Care and Use Committee, both accredited by AAALAC, and were performed in accordance with relevant institutional and national guidelines and regulations.

Generation of the EZH2 Co-Expressed Gene Signature.

ONCOMINE™[35] was used to query the top 20 genes co-expressed with EZH2 in all datasets containing human non-small cell lung cancer samples and co-expression data[36-43]. 20 was the number of probes chosen to examine from each study in order to yield a list between 100-200 genes, which allowed for robust hierarchal clustering of samples similar to that in previous studies[36]. Of the 180 probes, 64 were redundant, leading to a list of 116 genes highly co-expressed with EZH2 (Table 2). Because data sets on Oncomine were from various microarray platforms, the gene list was then used to generate a probe list for the 116 genes corresponding to probes on the U133A Affymetrix array using the batch query function on the NetAffx™ website (available on the World Wide Web at http://www.affymetrix.com/analysis/index.affx).

Kaplan-Meier Analysis

Raw gene expression data from human lung adenocarcinoma samples were obtained. Probe intensities from the Affymetrix U133A™ platform used in these studies were normalized and modeled using dChip™ software (available on the World Wide Web at http://biosun1.harvard.edu/complab/dchip). Kaplan-Meier survival analyses were implemented after the samples were hierarchically clustered using centroid linkage into two risk groups using the EZH2 co-expressed gene signature. Differences of the survival risk between the two risk groups were assessed using the Mantel-Haenszel log rank test. The large area between the two risk groups and its associated small p value from the Mantel-Haenszel log rank test implicate a robust survival classification model.

Cell Line Micro-Array

All array data is publically available on Gene Expression Omnibus (available on the World Wide Web at http://www.ncbi.nlm.nih.gov/geo/). Array quality was assessed using the R/Bioconductor™ package (available on the World Wide Web at http://www.bioconductor.org/). Raw CEL files from U133A Affymetrix arrays were processed using the robust multiarray average (RMA) algorithm[64]. To identify genes correlating with the phenotypic groups, we used limma[65] to fit a statistical linear model to the data and then tested for differential gene expression in the three groups, WT: H460, H441, H2122, H2009, Calu6, HCC95, EGFR mutant: H1650, HCC827, HCC4006, H1975, H3255, PC9, Brg1 mutant: A549, H1299, H157, H2126, H522, HCC15. Results were adjusted for multiple testing using the Benjamini and Hochberg (BH) method[66], and significance was determined using a False-Discovery-Rate cutoff of less than 5%.

Statistical Analysis.

Except where indicated, a 2-tailed Student's t-test with equal variance was used to compare measurements between 2 conditions. Unless noted otherwise, pooled data is represented by the mean and standard error. Except where indicated p-values less than 0.05 were considered significant.

Western Blot

Whole cell extracts were made in RIPA buffer (0.5% Deoxycholate, 1% IGEPAL-CA630, 0.1% sodium dodecyl sulfate, 150 mM NaCL, 50 mM Tris-8.1), lysates were cleared by centrifugation, and protein concentrations were quantified with the Pierce BCA Protein Assay Kit (Thermo). For Western blotting, 25 μg of protein extract per sample was denatured with heat and reducing agents, separated on a 4-12% acrylimide gel (BioRad) and transferred to nitrocellulose (GE Healthcare). Antibodies used for Western blotting were: EZH2 (clone D2C9; Cell Signaling; 1:200), Histone H3 (polyclonal; AbCAM ab1791; 1:2000) and H3K27me3 (polyclonal; Millipore 07-449; 1:1000) all incubated overnight at 4° C. Secondary antibody, anti-rabbit-HRP (Santa Cruz sc-2313; 1:5,000), was incubated for 1 hour at room temperature. After washing, chemi-luminescence was visualized with Western Lightning Plus-ECL (PerkinElmer) and exposure onto KODAK BioMax XAR™ film.

Anaphase Bridge Analysis.

To quantify anaphase bridges, cells were grown on 4-well cultures slides (Lab Tek II). Adherent cells were fixed with 4% paraformaldehyde for 20 min, washed and stained with Vectashield™ with 4',6-diamidino-2-phenylindole (DAPI; Vector Labs). Images were taken of each anaphase structure, and the number of anaphases with bridges over the total number of anaphases (between 11 and 34 total anaphases per well of a 4-well chamber slide) was recorded for each of three or more independent biological replicate experiments. Imaging was performed with a Nikon 90i™ camera and NIS-Elements™ software and processed with NIS-Elements and Adobe Photoshop™.

Immuno-Fluorescence

Cells were Fixed in 4% Paraformaldehyde and Permeabilized with 10% Normal Donkey Scrum (NDS; Jackson ImmunoResearch), 0.25% Triton-X (SIGMA), both in PBS.

Primary antibodies, Brg1 (clone G-7, Santa Cruz), EGFR (polyclonal; Cell Signaling 2232), were incubated overnight at 1:100 dilution in PBS, 10% NDS. Slides were washed 3× and secondary antibodies, anti-mouse-AlexaFluor594 and anti-rabbit-AlexaFluor488 (Invitrogen) were incubated at 1:500 for 1 hour. After washing, cover slips were mounted with Vectashield™ with 4',6-diamidino-2-phenylindole (DAPI; Vector Labs). Imaging was performed with a Nikon 90i™ camera and NIS-Elements™ software and processed with NIS-Elements™ and Adobe Photoshop™.

Treatment and MRI of Endogenous Mouse Models

Doxycycline inducible EGFR-TL (L858R/T790M) transgenic mice[48], and Lox-Stop-Lox-Kras$^{G12D}$;p53$^{fl/fl}$ (Kras/p53) mice[49,67] were housed in a pathogen-free environment at the Harvard School of Public Health and were handled in strict accordance with Good Animal Practice as defined by the Office of Laboratory Animal Welfare. All animal work was done with Dana-Farber Cancer Institute IACUC approval. Cohorts of EGFR TL/CCSP-rtTA were put on a doxycycline diet at 6 weeks of age to induce the expression of mutant EGFR, while Kras/p53 mice received intranasal adeno-Cre between 6 and 8 weeks of age. Mice were evaluated by Magnetic resonance imaging (MRI) 12 to 16 weeks after doxycycline diet or adeno-Cre infection to document and quantify the lung cancer burden before being assigned to various treatment study cohorts. Treated mice in all cohorts have the similar initial tumor burden. Tumor bearing mice were treated either with vehicle (corn oil), etoposide 10 mg/kg i.p. 3× per week for 4 weeks; DZNep 4 mg/kg i.p. 2× per week for 4 weeks, or both etoposide and DZNep. The mice were imaged by MRI biweekly to determine the reduction in tumor volume during the respective treatments as described previously[34]. The tumor burden volume and quantification were reconstructed on 3D slicer software (http://www.slicer.org). Immunohistochemistry was performed as described with anti-EZH2 (clone D2C9; Cell Signaling) or anti-pEGFR (Y1068; clone D7A5; Cell Signaling) and developed using Vectastain Elite ABC Kit™ (Vector Labs). Imaging was performed with a Nikon 90i™ camera and NIS-Elements™ software and processed with NIS-Elements™ and Adobe Photoshop™.

Chromatin Immunoprecipitation (ChIP)

5×10$^6$ Cells were Fixed in 1% Formaldehyde for 10 minutes prior to addition of glycine to a concentration of 1 mM. Cells were pelleted, washed and resuspended in ChIP sonication buffer (1% Triton X-100, 0.1% Deoxycholate, 50 mM Tris 8.1, 150 mM NaCl, 5 mM EDTA) containing protease and phosphastase inhibitors (Roche). Samples were sonicated for a total of 3 minutes in 30 second cycles with 1 minute breaks. Sonicated samples were centrifuged for 15 minutes to clear the lysates, and resulting whole cell extracts were used for pull-downs. Antibodies directed against GFP (Ab-1; Neomarkers), Brg1 (G-7; Santa Cruz) and Flag (M2; SIGMA) were incubated with equal proportions of whole cell extracts at 1:30 dilution overnight, rotating at 4° C. 1:1

Protein A and Protein G agarose beads (GE Healthcare) were added and incubated for 2 hours at 4° C. Beads were then pelleted and washed with high salt wash buffer (1% Triton X-100, 0.1% Deoxycholate, 50 mM Tris-8.1, 500 mM NaCl, 5 mM EDTA), followed by LiCl immune complex buffer (250 mM LiCl, 0.5% IGEPAL-CA630, 0.5% Deoxycholate, 10 mM Tris-8.1, 1 mM EDTA), and TE (10 mM Tris-8.1, 1 mM EDTA) prior to suspension in Elution buffer (1% SDS, 0.1 M NaHCO2, 0.01 mg/ml salmon sperm DNA (GE Healthcare)). Crosslinks were reversed at 65° C. overnight, beads were pelleted, and resulting supernatant was incubated with 0.4 mg/mL Proteinase K (SIGMA) for 2 hours at 37° C. DNA from each sample was purified using Qiagen PCR purification columns following the manufacturer's instructions. Samples were resuspended in 100 µL 10 mM Tris-8.1 and 2 µl were used for each Sybr Green™ PCR reaction (Applied Biosystems). Enrichment was calculated by $2\hat{\,}$average($Ct_{reference}-Ct_{experimental}$) for each genomic region of interest. Reference samples were the GFP, both Brg 1 and FLAG samples were experimental. Statistical analyses were performed on log 2 transformed data for 3 independent biological replicates.

Primer Sequences:

```
β-Actin:
F  TCGAGCCATAAAAGGCAACT     (SEQ ID NO: 33)

R  TCTCCCTCCTCCTCTTCCTC     (SEQ ID NO: 34)

EGFR regulatory element:
F  CCTTGTAGATTGGGGCTGAG     (SEQ ID NO: 35)

R  AGTTTGGGGGTGGAAGAAAG     (SEQ ID NO: 36)

30 kb upstream of regulatory element:
F  GGCTGAGACAGAGGGAACAC     (SEQ ID NO: 37)

R  CCATCTCAGCCTCCCAAGTA     (SEQ ID NO: 38)
```

References

1. Jemal, A. et al. Global cancer statistics. *C A: A Cancer Journal for Clinicians* 61, 69-90 (2011).
2. Siegel, R., Naishadham, D. & Jemal, A. Cancer statistics, 2013. *C A: A Cancer Journal for Clinicians* 63, 11-30 (2013).
3. Langer, C. J. et al. Patterns of care survey (PCS) in lung cancer: how well does current U. S. practice with chemotherapy in the non-metastatic setting follow the literature? *Lung Cancer* 48, 93-102 (2005).
4. Zornosa, C. et al. First-Line Systemic Therapy Practice Patterns and Concordance With NCCN Guidelines for Patients Diagnosed With Metastatic NSCLC Treated at NCCN Institutions. *Journal of the National Comprehensive Cancer Network* 10, 847-856 (2012).
5. Movsas, B. et al. Randomized Phase II Trial of Cisplatin, Etoposide, and Radiation Followed by Gemcitabine Alone or by Combined Gemcitabine and Docetaxel in Stage III A/B Unresectable Non-small Cell Lung Cancer. *Journal of Thoracic Oncology* 5, 673-679 10.1097/JTO.0b013e3181d60e8f (2010).
6. Jalal, S. I. et al. Updated survival and outcomes for older adults with inoperable stage III non-small-cell lung cancer treated with cisplatin, etoposide, and concurrent chest radiation with or without consolidation docetaxel: analysis of a phase III trial from the Hoosier Oncology Group (HOG) and U S Oncology. *Annals of Oncology* 23, 1730-1738 (2013).
7. Wang, L. et al. Randomized phase I I study of concurrent cisplatin/etoposide or paclitaxel/carboplatin and thoracic radiotherapy in patients with stage III non-small cell lung cancer. *Lung Cancer* 77, 89-96 (2012).
8. Siddik, Z. H. Cisplatin: mode of cytotoxic action and molecular basis of resistance. *Oncogene* 22, 7265-7279 (2003).
9. Deweese, J. E. & Osheroff, N. The DNA cleavage reaction of topoisomerase II: wolf in sheep's clothing. *Nucleic Acids Research* 37, 738-748 (2009).
10. Dykhuizen, E. C. et al. BAF complexes facilitate decatenation of DNA by topoisomerase II. *Nature* advance online publication(2013).
11. Baylin, S. B. & Jones, P. A. A decade of exploring the cancer epigenome—biological and translational implications. *Nat Rev Cancer* 11, 726-734 (2011).
12. Simon, J. A. & Lange, C. A. Roles of the EZH2 histone methyltransferase in cancer epigenetics. *Mutation Research/Fundamental and Molecular Mechanisms of Mutagenesis* 647, 21-29 (2008).
13. Kim, E. et al. Phosphorylation of EZH2 Activates STAT3 Signaling via STAT3 Methylation and Promotes Tumorigenicity of Glioblastoma Stem-like Cells. *Cancer Cell* 23, 839-852 (2013).
14. He, A. et al. PRC2 directly methylates GATA4 and represses its transcriptional activity. *Genes & Development* 26, 37-42 (2012).
15. Xu, K. et al. EZH2 Oncogenic Activity in Castration-Resistant Prostate Cancer Cells Is Polycomb-Independent. *Science* 338, 1465-1469 (2012).
16. Chou, D. M. et al. A chromatin localization screen reveals poly (ADP ribose)-regulated recruitment of the repressive polycomb and NuRD complexes to sites of DNA damage. *Proceedings of the National Academy of Sciences* 107, 18475-18480 (2010).
17. Sauvageau, M. & Sauvageau, G. Polycomb Group Proteins: Multi-Faceted Regulators of Somatic Stem Cells and Cancer. *Cell Stem Cell* 7, 299-313 (2010).
18. Tan, J. et al. Pharmacologic disruption of Polycomb-repressive complex 2-mediated gene repression selectively induces apoptosis in cancer cells. *Genes & Development* 21, 1050-1063 (2007).
19. Avan, A. et al. Molecular Mechanisms Involved in the Synergistic Interaction of the EZH2 Inhibitor 3-Deazaneplanocin A with Gemcitabine in Pancreatic Cancer Cells. *Molecular Cancer Therapeutics* 11, 1735-1746 (2012).
20. Choudhury, S. R. et al. (–)-Epigallocatechin-3-gallate and DZNep reduce polycomb protein level via a proteasome-dependent mechanism in skin cancer cells. *Carcinogenesis* 32, 1525-1532 (2011).
21. Crea, F. et al. Pharmacologic disruption of Polycomb Repressive Complex 2 inhibits tumorigenicity and tumor progression in prostate cancer. *Molecular Cancer* 10, 40 (2011).
22. Puppe, J. et al. BRCA1-deficient mammary tumor cells are dependent on EZH2 expression and sensitive to Polycomb Repressive Complex 2-inhibitor 3-deazaneplanocin A. *Breast Cancer Research* 11, R63 (2009).
23. Kikuchi, J. et al. Epigenetic therapy with 3-deazaneplanocin A, an inhibitor of the histone methyltransferase EZH2, inhibits growth of non-small cell lung cancer cells. *Lung Cancer* 78, 138-143 (2012).
24. Miranda, T. B. et al. DZNep is a global histone methylation inhibitor that reactivates developmental genes not silenced by DNA methylation. *Molecular Cancer Therapeutics* 8, 1579-1588 (2009).

25. Qi, W. et al. Selective inhibition of Ezh2 by a small molecule inhibitor blocks tumor cells proliferation. *Proceedings of the National Academy of Sciences* 109, 21360-21365 (2012).
26. Knutson, S. K. et al. Durable tumor regression in genetically altered malignant rhabdoid tumors by inhibition of methyltransferase EZH2. *Proceedings of the National Academy of Sciences* 110, 7922-7927 (2012).
27. McCabe, M. T. et al. EZH2 inhibition as a therapeutic strategy for lymphoma with EZH2-activating mutations. *Nature* 492, 108-112 (2012).
28. Herbst, R. S., Heymach, J. V. & Lippman, S. M. Lung Cancer. *New England Journal of Medicine* 359, 1367-1380 (2008).
29. Imielinski, M. et al. Mapping the Hallmarks of Lung Adenocarcinoma with Massively Parallel Sequencing. *Cell* 150, 1107-1120 (2012).
30. TCGA. Comprehensive genomic characterization of squamous cell lung cancers. *Nature* 489, 519-525 (2012).
31. Rodriguez-Nieto, S. et al. Massive parallel DNA pyrosequencing analysis of the tumor suppressor BRG1/SMARCA4 in lung primary tumors. *Human Mutation* 32, E1999-E2017 (2011).
32. Lynch, T. J. et al. Activating Mutations in the Epidermal Growth Factor Receptor Underlying Responsiveness of Non-Small-Cell Lung Cancer to Gefitinib. *New England Journal of Medicine* 350, 2129-2139 (2004).
33. Paez, J. G. et al. EGFR Mutations in Lung Cancer: Correlation with Clinical Response to Gefitinib Therapy. *Science* 304, 1497-1500 (2004).
34. Ji, H. et al. The impact of human EGFR kinase domain mutations on lung tumorigenesis and in vivo sensitivity to EGFR-targeted therapies. *Cancer Cell* 9, 485-495 (2006).
35. Rhodes, D. R. et al. Oncomine 3.0: genes, pathways, and networks in a collection of 18,000 cancer gene expression profiles. *Neoplasia* 9(2007).
36. Beer, D. G. et al. Gene-expression profiles predict survival of patients with lung adenocarcinoma. *Nat Med* 8, 816-824 (2002).
37. Garber, M. E. et al. Diversity of gene expression in adenocarcinoma of the lung. *Proceedings of the National Academy of Sciences* 98, 13784-13789 (2001).
38. Gordon, G. J. et al. Translation of Microarray Data into Clinically Relevant Cancer Diagnostic Tests Using Gene Expression Ratios in Lung Cancer and Mesothelioma. *Cancer Research* 62, 4963-4967 (2002).
39. Landi, M. T. et al. Gene Expression Signature of Cigarette Smoking and Its Role in Lung Adenocarcinoma Development and Survival. *PLoS ONE* 3, e1651 (2008).
40. Rohrbeck, A. et al. Gene expression profiling for molecular distinction and characterization of laser captured primary lung cancers. *Journal of Translational Medicine* 6, 69 (2008).
41. Shedden, K. et al. Gene expression-based survival prediction in lung adenocarcinoma: a multi-site, blinded validation study. *Nat Med* 14, 822-827 (2008).
42. Su, A. I. et al. Molecular Classification of Human Carcinomas by Use of Gene Expression Signatures. *Cancer Research* 61, 7388-7393 (2001).
43. Yu, K. et al. A Precisely Regulated Gene Expression Cassette Potently Modulates Metastasis and Survival in Multiple Solid Cancers. *PLoS Genet* 4, e1000129 (2008).
44. Medina, P. P. et al. Frequent BRG1/SMARCA4-inactivating mutations in human lung cancer cell lines. *Human Mutation* 29, 617-622 (2008).
45. Yamamoto, H. et al. PIK3CA Mutations and Copy Number Gains in Human Lung Cancers. *Cancer Research* 68, 6913-6921 (2008).
46. Ougolkov, A. V., Bilim, V. N. & Billadeau, D. D. Regulation of Pancreatic Tumor Cell Proliferation and Chemoresistance by the Histone Methyltransferase Enhancer of Zeste Homologue 2. *Clinical Cancer Research* 14, 6790-6796 (2008).
47. Lv, Y. et al. The expression and significance of the enhancer of zest homolog 2 in lung adenocarcinoma. *Oncology Reports* 28, 147-154 (2013).
48. Li, D. et al. Bronchial and Peripheral Murine Lung Carcinomas Induced by T790M-L858R Mutant EGFR Respond to HKI-272 and Rapamycin Combination Therapy. *Cancer Cell* 12, 81-93 (2007).
49. Jackson, E. L. et al. The Differential Effects of Mutant p53 Alleles on Advanced Murine Lung Cancer. *Cancer Research* 65, 10280-10288 (2005).
50. Wilson, B. G. et al. Epigenetic Antagonism between Polycomb and SWI/SNF Complexes during Oncogenic Transformation. *Cancer Cell* 18, 316-328 (2010).
51. ENCODE. An integrated encyclopedia of DNA elements in the human genome. *Nature* 489, 57-74 (2013).
52. Rothenberg, S. M. et al. Modeling oncogene addiction using RNA interference. *Proceedings of the National Academy of Sciences* 105, 12480-12484 (2008).
53. Matsubara, D. et al. Lung cancer with loss of BRG1/BRM, shows epithelial mesenchymal transition phenotype and distinct histologic and genetic features. *Cancer Science* 104, 266-273 (2013).
54. Oike, T. et al. A Synthetic Lethality-Based Strategy to Treat Cancers Harboring a Genetic Deficiency in the Chromatin Remodeling Factor BRG1. *Cancer Research* 73, 5508-5518 (2013).
55. Engelman, J. A. & Jänne, P. A. Factors Predicting Response to EGFR Tyrosine Kinase Inhibitors. *Semin Respir Crit Care Med* 26, 314-322 (2005).
56. Giaccone, G. Epidermal Growth Factor Receptor Inhibitors in the Treatment of Non-Small-Cell Lung Cancer. *Journal of Clinical Oncology* 23, 3235-3242 (2005).
57. Simon, J. A. & Kingston, R. E. Mechanisms of Polycomb gene silencing: knowns and unknowns. *Nat Rev Mol Cell Biol* 10, 697-708 (2009).
58. Dai, Y., Ngo, D., Jacob, J., Forman, L. W. & Faller, D. V. Prohibitin and the SWI/SNF ATPase subunit BRG1 are required for effective androgen antagonist-mediated transcriptional repression of androgen receptor-regulated genes. *Carcinogenesis* 29, 1725-1733 (2008).
59. Tolstorukov, M. Y. et al. Swi/Snf chromatin remodeling/tumor suppressor complex establishes nucleosome occupancy at target promoters. *Proceedings of the National Academy of Sciences* 110, 10165-10170 (2013).
60. Ramirez-Carrozzi, V. R. et al. Selective and antagonistic functions of SWI/SNF and Mi-2 nucleosome remodeling complexes during an inflammatory response. *Genes & Development* 20, 282-296 (2006).
61. Engelman, J. A. et al. Allelic dilution obscures detection of a biologically significant resistance mutation in EGFR-amplified lung cancer. *The Journal of Clinical Investigation* 116, 2695-2706 (2006).
62. Fillmore, C. M. et al. Estrogen expands breast cancer stem-like cells through paracrine FGF/Tbx3 signaling. *Proceedings of the National Academy of Sciences* 107, 21737-21742 (2010).
63. Zacharek, S. J. et al. Lung Stem Cell Self-Renewal Relies on BMI1-Dependent Control of Expression at Imprinted Loci. *Cell Stem Cell* 9, 272-281 (2010).

64. Irizarry, R. A. et al. Exploration, normalization, and summaries of high density oligonucleotide array probe level data. *Biostatistics* 4, 249-264 (2003).
65. Smyth, G. K., Michaud, J. I. & Scott, H. S. Use of within-array replicate spots for assessing differential expression in microarray experiments. *Bioinformatics* 21, 2067-2075 (2005).
66. Hochberg, Y. & Benjamini, Y. More powerful procedures for multiple hypothesis testing. *Statistical Medicine,* 811-818 (1990).
67, Curtis, S. J. et al. Primary Tumor Genotype Is an Important Determinant in Identification of Lung Cancer Propagating Cells. *Cell Stem Cell* 7, 127-133 (2010).

What is claimed herein is:

1. A method of treating cancer, the method comprising: determining a subject to have a sensitizing mutation of BRG1, EGFR, or B-RAF in a cancer cell; and administering or prescribing an EZH2 inhibitor and a topoisomerase II inhibitor to the subject.

2. The method of claim 1, wherein the EZH2 inhibitor is selected from the group consisting of:
an inhibitory nucleic acid; 3-Deazaneplanocin A (DZNep); and S-adenosyl-L-homocysteine.

3. The method of claim 1, wherein the second chemotherapeutic agent is a topoisomerase II inhibitor selected from the group consisting of:
doxorubicin; etoposide; amsacrine; teniposide; ICRF-193; genistein; daunorubicin;
mitoxantrone; ellipticines; aurintricarboxylic acid; and HU-331.

4. The method of claim 1, wherein the sensitizing mutation of BRG1 comprises a mutation selected from the group consisting of:
a mutation which inactivates the ATPase activity of BRG1; a mutation which decreases the expression of BRG1; P270*; Q729*; W764R; T58*; and M272*;
wherein the * denotes truncation.

5. The method of claim 1, wherein the sensitizing mutation of EGFR comprises a mutation selected from the group consisting of:
a mutation which increased the expression level of EGFR; E746_A750del; E746_A749del; T790M; and L858R.

6. The method of claim 1, wherein the sensitizing mutation of B-RAF comprises a mutation selected from the group consisting of:
G496A and L597V.

7. The method of claim 1, wherein the presence of the mutation is determined using an assay selected from the group consisting of:
hybridization; sequencing; exome capture; polymerase chain reaction (PCR); and high-throughput sequencing.

8. The method of claim 1, wherein the mutation is present in the genomic DNA of the cancer cell.

9. The method of claim 1, wherein the mutation is present in the mRNA transcripts of the cancer cell.

10. The method of claim 1, wherein the cancer is selected from the group consisting of:
lung cancer; non-small cell lung cancer; ovarian cancer; EGFR-expressing ovarian cancer;
B-Raf V600E melanomas; breast cancer; colon cancer; EGFR-mutated cancers; EGFR-mutated breast cancers; and EGFR-mutated colon cancers.

11. The method of claim 1, further comprising the step of generating a report based on the detection of a sensitizing mutation in BRG1, EGFR, or B-RAF by a non-human machine.

12. A method of treating cancer in a subject in need thereof, the method comprising:
selecting a subject having a sensitizing mutation of BRG1, EGFR, or B-RAF in a cancer cell; and administering or prescribing an EZH2 inhibitor and a topoisomerase II inhibitor to the subject.

* * * * *

SEQUENCE LISTING

```
<160> NUMBER OF SEQ ID NOS: 38

<210> SEQ ID NO 1
<211> LENGTH: 751
<212> TYPE: PRT
<213> ORGANISM: Homo sapiens

<400> SEQUENCE: 1

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Gly Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Arg Lys Cys Asn Tyr Ser Phe
    290                 295                 300

His Ala Thr Pro Asn Thr Tyr Lys Arg Lys Asn Thr Glu Thr Ala Leu
305                 310                 315                 320
```

```
Asp Asn Lys Pro Cys Gly Pro Gln Cys Tyr Gln His Leu Glu Gly Ala
            325                 330                 335
Lys Glu Phe Ala Ala Ala Leu Thr Ala Glu Arg Ile Lys Thr Pro Pro
        340                 345                 350
Lys Arg Pro Gly Gly Arg Arg Gly Arg Leu Pro Asn Asn Ser Ser
        355                 360                 365
Arg Pro Ser Thr Pro Thr Ile Asn Val Leu Glu Ser Lys Asp Thr Asp
    370                 375                 380
Ser Asp Arg Glu Ala Gly Thr Glu Thr Gly Gly Glu Asn Asn Asp Lys
385                 390                 395                 400
Glu Glu Glu Glu Lys Lys Asp Glu Thr Ser Ser Ser Glu Ala Asn
                405                 410                 415
Ser Arg Cys Gln Thr Pro Ile Lys Met Lys Pro Asn Ile Glu Pro Pro
        420                 425                 430
Glu Asn Val Glu Trp Ser Gly Ala Glu Ala Ser Met Phe Arg Val Leu
            435                 440                 445
Ile Gly Thr Tyr Tyr Asp Asn Phe Cys Ala Ile Ala Arg Leu Ile Gly
    450                 455                 460
Thr Lys Thr Cys Arg Gln Val Tyr Glu Phe Arg Val Lys Glu Ser Ser
465                 470                 475                 480
Ile Ile Ala Pro Ala Pro Ala Glu Asp Val Asp Thr Pro Pro Arg Lys
                485                 490                 495
Lys Lys Arg Lys His Arg Leu Trp Ala Ala His Cys Arg Lys Ile Gln
            500                 505                 510
Leu Lys Lys Asp Gly Ser Ser Asn His Val Tyr Asn Tyr Gln Pro Cys
        515                 520                 525
Asp His Pro Arg Gln Pro Cys Asp Ser Ser Cys Pro Cys Val Ile Ala
    530                 535                 540
Gln Asn Phe Cys Glu Lys Phe Cys Gln Cys Ser Ser Glu Cys Gln Asn
545                 550                 555                 560
Arg Phe Pro Gly Cys Arg Cys Lys Ala Gln Cys Asn Thr Lys Gln Cys
                565                 570                 575
Pro Cys Tyr Leu Ala Val Arg Glu Cys Asp Pro Asp Leu Cys Leu Thr
            580                 585                 590
Cys Gly Ala Ala Asp His Trp Asp Ser Lys Asn Val Ser Cys Lys Asn
        595                 600                 605
Cys Ser Ile Gln Arg Gly Ser Lys Lys His Leu Leu Leu Ala Pro Ser
    610                 615                 620
Asp Val Ala Gly Trp Gly Ile Phe Ile Lys Asp Pro Val Gln Lys Asn
625                 630                 635                 640
Glu Phe Ile Ser Glu Tyr Cys Gly Glu Ile Ile Ser Gln Asp Glu Ala
                645                 650                 655
Asp Arg Arg Gly Lys Val Tyr Asp Lys Tyr Met Cys Ser Phe Leu Phe
            660                 665                 670
Asn Leu Asn Asn Asp Phe Val Val Asp Ala Thr Arg Lys Gly Asn Lys
        675                 680                 685
Ile Arg Phe Ala Asn His Ser Val Asn Pro Asn Cys Tyr Ala Lys Val
    690                 695                 700
Met Met Val Asn Gly Asp His Arg Ile Gly Ile Phe Ala Lys Arg Ala
705                 710                 715                 720
Ile Gln Thr Gly Glu Glu Leu Phe Phe Asp Tyr Arg Tyr Ser Gln Ala
                725                 730                 735
Asp Ala Leu Lys Tyr Val Gly Ile Glu Arg Glu Met Glu Ile Pro
```

<210> SEQ ID NO 2
<211> LENGTH: 2723
<212> TYPE: DNA
<213> ORGANISM: Homo sapiens

<400> SEQUENCE: 2

```
ggcggcgctt gattgggctg gggggggccaa ataaaagcga tggcgattgg gctgccgcgt    60
ttggcgctcg gtccggtcgc gtccgacacc cggtgggact cagaaggcag tggagccccg   120
gcggcggcgg cggcggcgcg cggggggcgac gcgcgggaac aacgcgagtc ggcgcgcggg   180
acgaagaata atcatgggcc agactgggaa gaaatctgag aagggaccag tttgttggcg   240
gaagcgtgta aaatcagagt acatgcgact gagacagctc aagaggttca gacgagctga   300
tgaagtaaag agtatgttta gttccaatcg tcagaaaatt ttggaaagaa cggaaatctt   360
aaaccaagaa tggaaacagc gaaggataca gcctgtgcac atcctgactt ctgtgagctc   420
attgcgcggg actaggggagt gttcggtgac cagtgacttg gattttccaa cacaagtcat   480
cccattaaag actctgaatg cagttgcttc agtacccata atgtattctt ggtctcccct   540
acagcagaat tttatggtgg aagatgaaac tgttttacat aacattcctt atatgggaga   600
tgaagtttta gatcaggatg gtactttcat tgaagaacta ataaaaaatt atgatgggaa   660
agtacacggg gatagagaat gtgggtttat aaatgatgaa attttttgtgg agttggtgaa   720
tgcccttggt caatataatg atgatgacga tgatgatgat ggagacgatc ctgaagaaag   780
agaagaaaag cagaaagatc tggaggatca ccgagatgat aaagaaagcc gcccacctcg   840
gaaatttcct tctgataaaa tttttgaagc catttcctca atgtttccag ataagggcac   900
agcagaagaa ctaaaggaaa aatataaaga actcaccgaa cagcagctcc caggcgcact   960
tcctcctgaa tgtaccccca acatagatgg accaaatgct aaatctgttc agagagagca  1020
aagcttacac tcctttcata cgcttttctg taggcgatgt tttaaatatg actgcttcct  1080
acatcgtaag tgcaattatt cttttcatgc aacacccaac acttataagc ggaagaacac  1140
agaaacagct ctagacaaca aaccttgtgg accacagtgt taccagcatt tggagggagc  1200
aaaggagttt gctgctgctc tcaccgctga gcggataaag accccaccaa aacgtccagg  1260
aggccgcaga gaggacggc ttcccaataa cagtagcagg cccagcaccc ccaccattaa  1320
tgtgctggaa tcaaaggata cagacagtga tagggaagca gggactgaaa cgggggaga  1380
gaacaatgat aaagaagaag aagagaagaa agatgaaact tcgagctcct ctgaagcaaa  1440
ttctcggtgt caaacaccaa taaagatgaa gccaaatatt gaacctcctg agaatgtgga  1500
gtggagtggt gctgaagcct caatgtttag agtcctcatt ggcacttact atgacaattt  1560
ctgtgccatt gctaggttaa ttgggaccaa acatgtagaa caggtgtatg agtttagagt  1620
caaagaatct agcatcatag ctccagctcc cgctgaggat gtggatactc ctccaaggaa  1680
aaagaagagg aaacaccggt tgtgggctgc acactgcaga aagatacagc tgaaaaagga  1740
cggctcctct aaccatgttt acaactatca accctgtgat catccacggc agccttgtga  1800
cagttcgtgc cctttgtgtg atagcacaaa tttttgtgaa aagttttgtc aatgtagttc  1860
agagtgtcaa aaccgctttc ggggatgccg ctgcaaagca cagtgcaaca ccaagcagtg  1920
cccgtgctac ctggctgtcc gagagtgtga ccctgacctc tgtcttactt gtggagccgc  1980
tgaccattgg gacagtaaaa atgtgtcctg caagaactgc agtattcagc ggggctccaa  2040
aaagcatcta ttgctggcac catctgacgt ggcaggctgg gggattttta tcaaagatcc  2100
```

```
tgtgcagaaa aatgaattca tctcagaata ctgtggagag attatttctc aagatgaagc   2160
tgacagaaga gggaaagtgt atgataaata catgtgcagc tttctgttca acttgaacaa   2220
tgattttgtg gtggatgcaa cccgcaaggg taacaaaatt cgttttgcaa atcattcggt   2280
aaatccaaac tgctatgcaa aagttatgat ggttaacggt gatcacagga taggtatttt   2340
tgccaagaga gccatccaga ctggcgaaga gctgtttttt gattacagat acagccaggc   2400
tgatgccctg aagtatgtcg gcatcgaaag agaaatggaa atcccttgac atctgctacc   2460 tcctccccccc tcctctgaaa cagctgcctt agcttcagga acctcgagta ctgtgggcaa   2520
tttagaaaaa gaacatgcag tttgaaattc tgaatttgca aagtactgta agaataattt   2580
atagtaatga gtttaaaaat caactttta ttgccttctc accagctgca aagtgttttg   2640
taccagtgaa ttttttgcaat aatgcagtat ggtacatttt tcaactttga ataaagaata   2700
cttgaacttg tccttgttga atc                                           2723
```

<210> SEQ ID NO 3
<211> LENGTH: 1647
<212> TYPE: PRT
<213> ORGANISM: Homo sapiens

<400> SEQUENCE: 3

```
Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205

Pro Met Pro Gly Met Gln Gln Gln Met Pro Thr Leu Pro Pro Pro Ser
    210                 215                 220

Val Ser Ala Thr Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255
```

```
Gly Pro Asn Met Pro Pro Pro Gly Pro Ser Gly Val Pro Pro Gly Met
            260                 265                 270

Pro Gly Gln Pro Pro Gly Gly Pro Pro Lys Pro Trp Pro Glu Gly Pro
        275                 280                 285

Met Ala Asn Ala Ala Ala Pro Thr Ser Thr Pro Gln Lys Leu Ile Pro
        290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
                325                 330                 335

Ala Gln Pro Ala Pro Met Val Pro Leu His Gln Lys Gln Ser Arg Ile
        340                 345                 350

Thr Pro Ile Gln Lys Pro Arg Gly Leu Asp Pro Val Glu Ile Leu Gln
        355                 360                 365

Glu Arg Glu Tyr Arg Leu Gln Ala Arg Ile Ala His Arg Ile Gln Glu
        370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
                405                 410                 415

Arg Gln Glu Val Val Val Cys Met Arg Arg Asp Thr Ala Leu Glu Thr
                420                 425                 430

Ala Leu Asn Ala Lys Ala Tyr Lys Arg Ser Lys Arg Gln Ser Leu Arg
        435                 440                 445

Glu Ala Arg Ile Thr Glu Lys Leu Glu Lys Gln Gln Lys Ile Glu Gln
450                 455                 460

Glu Arg Lys Arg Arg Gln Lys His Gln Glu Tyr Leu Asn Ser Ile Leu
465                 470                 475                 480

Gln His Ala Lys Asp Phe Lys Glu Tyr His Arg Ser Val Thr Gly Lys
                485                 490                 495

Ile Gln Lys Leu Thr Lys Ala Val Ala Thr Tyr His Ala Asn Thr Glu
        500                 505                 510

Arg Glu Gln Lys Lys Glu Asn Glu Arg Ile Glu Lys Glu Arg Met Arg
        515                 520                 525

Arg Leu Met Ala Glu Asp Glu Glu Gly Tyr Arg Lys Leu Ile Asp Gln
        530                 535                 540

Lys Lys Asp Lys Arg Leu Ala Tyr Leu Leu Gln Gln Thr Asp Glu Tyr
545                 550                 555                 560

Val Ala Asn Leu Thr Glu Leu Val Arg Gln His Lys Ala Ala Gln Val
                565                 570                 575

Ala Lys Glu Lys Lys Lys Lys Lys Lys Lys Lys Ala Glu Asn Ala
        580                 585                 590

Glu Gly Gln Thr Pro Ala Ile Gly Pro Asp Gly Glu Pro Leu Asp Glu
        595                 600                 605

Thr Ser Gln Met Ser Asp Leu Pro Val Lys Val Ile His Val Glu Ser
        610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
                645                 650                 655

Ser Glu Glu Ser Gly Ser Glu Glu Glu Glu Glu Glu Glu Glu Glu Glu
                660                 665                 670

Gln Pro Gln Ala Ala Gln Pro Pro Thr Leu Pro Val Glu Glu Lys Lys
```

-continued

```
            675                 680                 685
Lys Ile Pro Asp Pro Asp Ser Asp Val Ser Glu Val Asp Ala Arg
        690                 695                 700
His Ile Ile Glu Asn Ala Lys Gln Asp Val Asp Glu Tyr Gly Val
705                 710                 715                 720
Ser Gln Ala Leu Ala Arg Gly Leu Gln Ser Tyr Tyr Ala Val Ala His
                725                 730                 735
Ala Val Thr Glu Arg Val Asp Lys Gln Ser Ala Leu Met Val Asn Gly
            740                 745                 750
Val Leu Lys Gln Tyr Gln Ile Lys Gly Leu Glu Trp Leu Val Ser Leu
            755                 760                 765
Tyr Asn Asn Asn Leu Asn Gly Ile Leu Ala Asp Glu Met Gly Leu Gly
            770                 775                 780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
                805                 810                 815
Asn Trp Ala Tyr Glu Phe Asp Lys Trp Ala Pro Ser Val Val Lys Val
                820                 825                 830
Ser Tyr Lys Gly Ser Pro Ala Ala Arg Arg Ala Phe Val Pro Gln Leu
            835                 840                 845
Arg Ser Gly Lys Phe Asn Val Leu Leu Thr Thr Tyr Glu Tyr Ile Ile
            850                 855                 860
Lys Asp Lys His Ile Leu Ala Lys Ile Arg Trp Lys Tyr Met Ile Val
865                 870                 875                 880
Asp Glu Gly His Arg Met Lys Asn His His Cys Lys Leu Thr Gln Val
                885                 890                 895
Leu Asn Thr His Tyr Val Ala Pro Arg Arg Leu Leu Leu Thr Gly Thr
                900                 905                 910
Pro Leu Gln Asn Lys Leu Pro Glu Leu Trp Ala Leu Leu Asn Phe Leu
            915                 920                 925
Leu Pro Thr Ile Phe Lys Ser Cys Ser Thr Phe Glu Gln Trp Phe Asn
            930                 935                 940
Ala Pro Phe Ala Met Thr Gly Glu Lys Val Asp Leu Asn Glu Glu Glu
945                 950                 955                 960
Thr Ile Leu Ile Ile Arg Arg Leu His Lys Val Leu Arg Pro Phe Leu
                965                 970                 975
Leu Arg Arg Leu Lys Lys Glu Val Glu Ala Gln Leu Pro Glu Lys Val
            980                 985                 990
Glu Tyr Val Ile Lys Cys Asp Met Ser Ala Leu Gln Arg Val Leu Tyr
        995                 1000                1005
Arg His Met Gln Ala Lys Gly Val Leu Leu Thr Asp Gly Ser Glu
        1010                1015                1020
Lys Asp Lys Lys Gly Lys Gly Thr Lys Thr Leu Met Asn Thr
        1025                1030                1035
Ile Met Gln Leu Arg Lys Ile Cys Asn His Pro Tyr Met Phe Gln
        1040                1045                1050
His Ile Glu Glu Ser Phe Ser Glu His Leu Gly Phe Thr Gly Gly
        1055                1060                1065
Ile Val Gln Gly Leu Asp Leu Tyr Arg Ala Ser Gly Lys Phe Glu
        1070                1075                1080
Leu Leu Asp Arg Ile Leu Pro Lys Leu Arg Ala Thr Asn His Lys
        1085                1090                1095
```

```
Val Leu Leu Phe Cys Gln Met Thr Ser Leu Met Thr Ile Met Glu
1100             1105             1110

Asp Tyr Phe Ala Tyr Arg Gly Phe Lys Tyr Leu Arg Leu Asp Gly
1115             1120             1125

Thr Thr Lys Ala Glu Asp Arg Gly Met Leu Leu Lys Thr Phe Asn
1130             1135             1140

Glu Pro Gly Ser Glu Tyr Phe Ile Phe Leu Leu Ser Thr Arg Ala
1145             1150             1155

Gly Gly Leu Gly Leu Asn Leu Gln Ser Ala Asp Thr Val Ile Ile
1160             1165             1170

Phe Asp Ser Asp Trp Asn Pro His Gln Asp Leu Gln Ala Gln Asp
1175             1180             1185

Arg Ala His Arg Ile Gly Gln Gln Asn Glu Val Arg Val Leu Arg
1190             1195             1200

Leu Cys Thr Val Asn Ser Val Glu Glu Lys Ile Leu Ala Ala Ala
1205             1210             1215

Lys Tyr Lys Leu Asn Val Asp Gln Lys Val Ile Gln Ala Gly Met
1220             1225             1230

Phe Asp Gln Lys Ser Ser His Glu Arg Arg Ala Phe Leu Gln
1235             1240             1245

Ala Ile Leu Glu His Glu Glu Gln Asp Glu Ser Arg His Cys Ser
1250             1255             1260

Thr Gly Ser Gly Ser Ala Ser Phe Ala His Thr Ala Pro Pro Pro
1265             1270             1275

Ala Gly Val Asn Pro Asp Leu Glu Glu Pro Pro Leu Lys Glu Glu
1280             1285             1290

Asp Glu Val Pro Asp Glu Thr Val Asn Gln Met Ile Ala Arg
1295             1300             1305

His Glu Glu Glu Phe Asp Leu Phe Met Arg Met Asp Leu Asp Arg
1310             1315             1320

Arg Arg Glu Glu Ala Arg Asn Pro Lys Arg Lys Pro Arg Leu Met
1325             1330             1335

Glu Glu Asp Glu Leu Pro Ser Trp Ile Ile Lys Asp Asp Ala Glu
1340             1345             1350

Val Glu Arg Leu Thr Cys Glu Glu Glu Glu Lys Met Phe Gly
1355             1360             1365

Arg Gly Ser Arg His Arg Lys Glu Val Asp Tyr Ser Asp Ser Leu
1370             1375             1380

Thr Glu Lys Gln Trp Leu Lys Ala Ile Glu Glu Gly Thr Leu Glu
1385             1390             1395

Glu Ile Glu Glu Glu Val Arg Gln Lys Lys Ser Ser Arg Lys Arg
1400             1405             1410

Lys Arg Asp Ser Asp Ala Gly Ser Ser Thr Pro Thr Thr Ser Thr
1415             1420             1425

Arg Ser Arg Asp Lys Asp Asp Glu Ser Lys Lys Gln Lys Lys Arg
1430             1435             1440

Gly Arg Pro Pro Ala Glu Lys Leu Ser Pro Asn Pro Pro Asn Leu
1445             1450             1455

Thr Lys Lys Met Lys Lys Ile Val Asp Ala Val Ile Lys Tyr Lys
1460             1465             1470

Asp Ser Ser Ser Gly Arg Gln Leu Ser Glu Val Phe Ile Gln Leu
1475             1480             1485
```

```
Pro Ser Arg Lys Glu Leu Pro Glu Tyr Tyr Glu Leu Ile Arg Lys
    1490                1495                1500

Pro Val Asp Phe Lys Lys Ile Lys Glu Arg Ile Arg Asn His Lys
    1505                1510                1515

Tyr Arg Ser Leu Asn Asp Leu Glu Lys Asp Val Met Leu Leu Cys
    1520                1525                1530

Gln Asn Ala Gln Thr Phe Asn Leu Glu Gly Ser Leu Ile Tyr Glu
    1535                1540                1545

Asp Ser Ile Val Leu Gln Ser Val Phe Thr Ser Val Arg Gln Lys
    1550                1555                1560

Ile Glu Lys Glu Asp Asp Ser Glu Gly Glu Glu Ser Glu Glu Glu
    1565                1570                1575

Glu Glu Gly Glu Glu Glu Gly Ser Glu Ser Glu Ser Arg Ser Val
    1580                1585                1590

Lys Val Lys Ile Lys Leu Gly Arg Lys Glu Lys Ala Gln Asp Arg
    1595                1600                1605

Leu Lys Gly Gly Arg Arg Arg Pro Ser Arg Gly Ser Arg Ala Lys
    1610                1615                1620

Pro Val Val Ser Asp Asp Asp Ser Glu Glu Glu Gln Glu Glu Asp
    1625                1630                1635

Arg Ser Gly Ser Gly Ser Glu Glu Asp
    1640                1645

<210> SEQ ID NO 4
<211> LENGTH: 5779
<212> TYPE: DNA
<213> ORGANISM: Homo sapiens

<400> SEQUENCE: 4
ggagaggccg ccgcggtgct gagggggagg ggagccggcg agcgcgcgcg cagcggggc      60 gcgggtggcg cgcgtgtgtg tgaagggggg gcggtggccg aggcgggcgg gcgcgcgcgc    120
gaggcttccc ctcgtttggc ggcggcggcg gcttctttgt ttcgtgaaga aagcgagac    180 gcccattctg cccccggccc cgcgcggagg ggcgggggag gcgccgggaa gtcgacggcg    240
ccggcggctc ctgcgtctcg ccctttttgcc caggctagag tgcagtggtg cggtcatggt    300
tcactgcagc ctcaacctcc tggactcagc aggaggccac tgtctgcagc tcccgtgaag    360
atgtccactc cagacccacc cctgggcgga actcctcggc caggtccttc cccgggccct    420
ggcccttccc ctggagccat gctgggccct agcccgggtc cctcgccggg ctccgcccac    480
agcatgatgg ggcccagccc agggccgccc tcagcaggac accccatccc cacccagggg    540
cctggagggt accctcagga caacatgcac cagatgcaca agcccatgga gtccatgcat    600
gagaagggca tgtcggacga cccgcgctac aaccagatga aggaatggga gatgcggtca    660
ggggcccatg ctgggatggg gccccgccc agccccatgg accagcactc ccaaggttac    720
ccctcgcccc tgggtggctc tgagcatgcc tctagtccag ttccagccag tggcccgtct    780
tcggggcccc agatgtcttc cgggccagga ggtgccccgc tggatggtgc tgacccccag    840 gccttgggc agcagaaccg gggcccaacc ccatttaacc agaaccagct gcaccagctc    900
agagctcaga tcatggccta caagatgctg gccaggggg agccccctccc cgaccacctg    960 cagatggcgg tgcagggcaa gcggccgatg cccgggatgc agcagcagat gccaacgcta   1020
cctccaccct cggtgtccgc aacaggaccc ggccctggcc ctggccctgg ccccggcccg   1080
ggtcccggcc cggcacctcc aaattacagc aggcctcatg gtatgggagg gcccaacatg   1140
```

```
cctcccccag gaccctcggg cgtgccccc  gggatgccag gccagcctcc tggagggcct   1200
cccaagccct ggcctgaagg acccatggcg aatgctgctg ccccacgag  cacccctcag   1260 aagctgattc ccccgcagcc aacgggccgc ccttccccg  cgccccctgc cgtcccaccc   1320
gccgcctcgc ccgtgatgcc accgcagacc cagtccccg  ggcagccggc ccagcccgcg   1380
cccatggtgc cactgcacca gaagcagagc cgcatcaccc ccatccagaa gccgcgggc    1440 ctcgaccctg tggagatcct gcaggagcgc gagtacaggc tgcaggctcg catcgcacac   1500
cgaattcagg aacttgaaaa ccttcccggg tccctggccg gggatttgcg aaccaaagcg   1560
accattgagc tcaaggccct caggctgctg aacttccaga ggcagctgcg ccaggaggtg   1620
gtggtgtgca tgcggaggga cacagcgctg agacagccc  tcaatgctaa ggcctacaag   1680
cgcagcaagc gccagtccct gcgcgaggcc cgcatcactg agaagctgga gaagcagcag   1740
aagatcgagc aggagcgcaa gcgccggcag aagcaccagg aatacctcaa tagcattctc   1800
cagcatgcca aggatttcaa ggaatatcac agatccgtca caggcaaaat ccagaagctg   1860
accaaggcag tggccacgta ccatgccaac acggagcggg agcagaagaa agagaacgag   1920
cggatcgaga aggagcgcat gcggaggctc atggctgaag atgaggaggg gtaccgcaag   1980
ctcatcgacc agaagaagga caagcgcctg gcctacctct tgcagcagac agacgagtac   2040
gtggctaacc tcacggagct ggtgcggcag cacaaggctg cccaggtcgc caaggagaaa   2100
aagaagaaaa agaaaaagaa gaaggcagaa atgcagaag  acagacgcc  tgccattggg   2160 ccggatggcg agcctctgga cgagaccagc cagatgagcg acctcccggt gaaggtgatc   2220
cacgtggaga gtgggaagat cctcacaggc acagatgccc ccaaagccgg gcagctggag   2280
gcctggctcg agatgaaccc ggggtatgaa gtagctccga ggtctgatag tgaagaaagt   2340
ggctcagaag aagaggaaga ggaggaggag gaagagcagc cgcaggcagc acagcctccc   2400
accctgcccg tggaggagaa gaagaagatt ccagatccag acagcgatga cgtctctgag   2460
gtggacgcgc ggcacatcat tgagaatgcc aagcaagatg tcgatgatga atatggcgtg   2520
tcccaggccc ttgcacgtgg cctgcagtcc tactatgccg tggcccatgc tgtcactgag   2580
agagtggaca agcagtcagc gcttatggtc aatggtgtcc tcaaacagta ccagatcaaa   2640
ggtttggagt ggctggtgtc cctgtacaac aacaacctga  cggcatcct  ggccgacgag   2700 atgggcctgg ggaagaccat ccagaccatc gcgctcatca cgtacctcat ggagcacaaa   2760
cgcatcaatg ggcccttcct catcatcgtg cctctctcaa cgctgtccaa ctgggcgtac   2820
gagtttgaca gtgggccccc ctccgtggtg aaggtgtctt acaagggatc cccagcagca   2880
agacgggcct ttgtccccca gctccggagt gggaagttca acgtcttgct gacgacgtac   2940
gagtacatca tcaaagacaa gcacatcctc gccaagatcc gttggaagta catgattgtg   3000
gacgaaggtc accgcatgaa gaaccaccac tgcaagctga cgcaggtgct caacacgcac   3060
tatgtggcac cccgccgcct gctgctgacg ggcacaccgc tgcagaacaa gcttcccgag   3120
ctctgggcgc tgctcaactt cctgctgccc accatcttca gagctgcag  caccttcgag   3180 cagtggttta acgcaccctt tgccatgacc ggggaaaagg tggacctgaa tgaggaggaa   3240
accattctca tcatccggcg tctccacaaa gtgctgcggc ccttcttgct ccgacgactc   3300
aagaaggaag tcgaggccca gttgcccgaa aaggtggagt acgtcatcaa gtgcgacatg   3360
tctgcgctgc agcgagtgct ctaccgccca atgcaggcca agggcgtgct gctgactgat   3420
ggctccgaga aggacaagaa gggcaaaggc ggcaccaaga ccctgatgaa caccatcatg   3480
cagctgcgga agatctgcaa ccaccccctac atgttccagc acatcgagga gtccttttcc   3540
```

```
gagcacttgg ggttcactgg cggcattgtc caagggctgg acctgtaccg agcctcgggt    3600
aaatttgagc ttcttgatag aattcttccc aaactccgag caaccaacca caaagtgctg    3660
ctgttctgcc aaatgacctc cctcatgacc atcatggaag attactttgc gtatcgcggc    3720
tttaaatacc tcaggcttga tggaaccacg aaggcggagg accggggcat gctgctgaaa    3780
accttcaacg agcccggctc tgagtacttc atcttcctgc tcagcacccg ggctgggggg    3840
ctcggcctga acctccagtc ggcagacact gtgatcattt tgacagcga ctggaatcct    3900 caccaggacc tgcaagcgca ggaccgagcc caccgcatcg ggcagcagaa cgaggtgcgt    3960
gtgctccgcc tctgcaccgt caacagcgtg gaggagaaga tcctagctgc agccaagtac    4020
aagctcaacg tggaccagaa ggtgatccag gccggcatgt tcgaccagaa gtcctccagc    4080
catgagcggc gcgccttcct gcaggccatc ctggagcacg aggagcagga tgagagcaga    4140
cactgcagca cgggcagcgg cagtgccagc ttcgcccaca ctgcccctcc gccagcgggc    4200
gtcaaccccg acttggagga gccacctcta aaggaggaag acgaggtgcc cgacgacgag    4260
accgtcaacc agatgatcgc ccggcacgag gaggagtttg atctgttcat gcgcatggac    4320
ctggaccgca ggcgcgagga ggcccgcaac cccaagcgga agccgcgcct catggaggag    4380
gacgagctcc cctcgtggat catcaaggac gacgcggagg tggagcggct gacctgtgag    4440
gaggaggagg agaagatgtt cggccgtggc tcccgccacc gcaaggaggt ggactacagc    4500
gactcactga cggagaagca gtggctcaag gccatcgagg agggcacgct ggaggagatc    4560
gaagaggagg tccggcagaa gaaatcatca cggaagcgca agcgagacag cgacgccggc    4620
tcctccaccc cgaccaccag cacccgcagc cgcgacaagg acgacgagag caagaagcag    4680
aagaagcgcg gcggccgcc tgccgagaaa ctctcccca acccacccaa cctcaccaag    4740
aagatgaaga agattgtgga tgccgtgatc aagtacaagg acagcagcag tggacgtcag    4800
ctcagcgagg tcttcatcca gctgcccctcg cgaaaggagc tgcccgagta ctacgagctc    4860
atccgcaagc ccgtggactt caagaagata aaggagcgca ttcgcaacca caagtaccgc    4920
agcctcaacg acctagagaa ggacgtcatg ctcctgtgcc agaacgcaca gaccttcaac    4980
ctggagggct ccctgatcta tgaagactcc atcgtcttgc agtcggtctt caccagcgtg    5040
cggcagaaaa tcgagaagga ggatgacagt gaaggcgagg agagtgagga ggaggaagag    5100
ggcgaggagg aaggctccga atccgaatct cggtccgtca agtgaagat caagcttggc    5160 cggaaggaga aggcacagga ccggctgaag ggcggccggc ggcggccgag ccgagggtcc    5220
cgagccaagc cggtcgtgag tgacgatgac agtgaggagg aacaagagga ggaccgctca    5280
ggaagtggca gcgaagaaga ctgagccccg acattccagt ctcgaccccg agcccctcgt    5340
tccagagctg agatggcata ggccttagca gtaacgggta gcagcagatg tagtttcaga    5400
cttggagtaa aactgtataa acaaaagaat cttccatatt tatacagcag agaagctgta    5460
ggactgtttg tgactggccc tgtcctggca tcagtagcat ctgtaacagc attaactgtc    5520
ttaaagagag agagagagaa ttccgaattg gggaacacac gatacctgtt tttcttttcc    5580
gttgctggca gtactgttgc gccgcagttt ggagtcactg tagttaagtg tggatgcatg    5640
tgcgtcaccg tccactcctc ctactgtatt ttattggaca ggtcagactc gccggggcc    5700 cggcgagggt atgtcagtgt cactggatgt caaacagtaa taaattaaac caacaacaaa    5760
acgcacagcc aaaaaaaaa                                                 5779
```

<210> SEQ ID NO 5

```
<211> LENGTH: 1210
<212> TYPE: PRT
<213> ORGANISM: Homo sapiens

<400> SEQUENCE: 5

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
```

-continued

```
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                    485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
                515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
                595                 600                 605

Lys Tyr Ala Asp Ala Gly His Val Cys His Leu Cys His Pro Asn Cys
                    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
                675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
                770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                    805                 810                 815
```

```
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
            835                 840                 845
Gln His Val Lys Ile Thr Asp Phe Gly Leu Ala Lys Leu Leu Gly Ala
            850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
            915                 920                 925
Lys Gly Glu Arg Leu Pro Gln Pro Pro Ile Cys Thr Ile Asp Val Tyr
            930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
            995                 1000                1005
Asp Val Val Asp Ala Asp Glu Tyr Leu Ile Pro Gln Gln Gly Phe
            1010                1015                1020
Phe Ser Ser Pro Ser Thr Ser Arg Thr Pro Leu Leu Ser Ser Leu
            1025                1030                1035
Ser Ala Thr Ser Asn Asn Ser Thr Val Ala Cys Ile Asp Arg Asn
            1040                1045                1050
Gly Leu Gln Ser Cys Pro Ile Lys Glu Asp Ser Phe Leu Gln Arg
            1055                1060                1065
Tyr Ser Ser Asp Pro Thr Gly Ala Leu Thr Glu Asp Ser Ile Asp
            1070                1075                1080
Asp Thr Phe Leu Pro Val Pro Glu Tyr Ile Asn Gln Ser Val Pro
            1085                1090                1095
Lys Arg Pro Ala Gly Ser Val Gln Asn Pro Val Tyr His Asn Gln
            1100                1105                1110
Pro Leu Asn Pro Ala Pro Ser Arg Asp Pro His Tyr Gln Asp Pro
            1115                1120                1125
His Ser Thr Ala Val Gly Asn Pro Glu Tyr Leu Asn Thr Val Gln
            1130                1135                1140
Pro Thr Cys Val Asn Ser Thr Phe Asp Ser Pro Ala His Trp Ala
            1145                1150                1155
Gln Lys Gly Ser His Gln Ile Ser Leu Asp Asn Pro Asp Tyr Gln
            1160                1165                1170
Gln Asp Phe Phe Pro Lys Glu Ala Lys Pro Asn Gly Ile Phe Lys
            1175                1180                1185
Gly Ser Thr Ala Glu Asn Ala Glu Tyr Leu Arg Val Ala Pro Gln
            1190                1195                1200
Ser Ser Glu Phe Ile Gly Ala
            1205                1210
```

<210> SEQ ID NO 6
<211> LENGTH: 5616
<212> TYPE: DNA
<213> ORGANISM: Homo sapiens

<400> SEQUENCE: 6

| | | | | | |
|---|---|---|---|---|---|
| ccccggcgca | gcgcggccgc | agcagcctcc | gcccccgca | cggtgtgagc | gcccgacgcg | 60 |
| gccgaggcgg | ccggagtccc | gagctagccc | cggcggccgc | cgccgcccag | accggacgac | 120 |
| aggccacctc | gtcggcgtcc | gcccgagtcc | ccgcctcgcc | gccaacgcca | caaccaccgc | 180 |
| gcacggcccc | ctgactccgt | ccagtattga | tcgggagagc | cggagcgagc | tcttcgggga | 240 |
| gcagcgatgc | gaccctccgg | gacggccggg | gcagcgctcc | tggcgctgct | ggctgcgctc | 300 |
| tgcccggcga | gtcgggctct | ggaggaaaag | aaagtttgcc | aaggcacgag | taacaagctc | 360 |
| acgcagttgg | gcacttttga | agatcatttt | ctcagcctcc | agaggatgtt | caataactgt | 420 |
| gaggtggtcc | ttgggaattt | ggaaattacc | tatgtgcaga | ggaattatga | tctttccttc | 480 |
| ttaaagacca | tccaggaggt | ggctggttat | gtcctcattg | ccctcaacac | agtggagcga | 540 |
| attcctttgg | aaaacctgca | gatcatcaga | ggaaatatgt | actacgaaaa | ttcctatgcc | 600 |
| ttagcagtct | tatctaacta | tgatgcaaat | aaaaccggac | tgaaggagct | gcccatgaga | 660 |
| aatttacagg | aaatcctgca | tggcgccgtg | cggttcagca | caaccctgc | cctgtgcaac | 720 |
| gtggagagca | tccagtggcg | ggacatagtc | agcagtgact | ttctcagcaa | catgtcgatg | 780 |
| gacttccaga | accacctggg | cagctgccaa | aagtgtgatc | caagctgtcc | caatgggagc | 840 |
| tgctggggtg | caggagagga | gaactgccag | aaactgacca | aaatcatctg | tgcccagcag | 900 |
| tgctccgggc | gctgccgtgg | caagtccccc | agtgactgct | gccacaacca | gtgtgctgca | 960 |
| ggctgcacag | gcccccggga | gagcgactgc | ctggtctgcc | gcaaattccg | agacgaagcc | 1020 |
| acgtgcaagg | acacctgccc | cccactcatg | ctctacaacc | ccaccacgta | ccagatggat | 1080 |
| gtgaaccccg | agggcaaata | cagctttggt | gccacctgcg | tgaagaagtg | tccccgtaat | 1140 |
| tatgtggtga | cagatcacgg | ctcgtgcgtc | cgagcctgtg | gggccgacag | ctatgagatg | 1200 |
| gaggaagacg | gcgtccgcaa | gtgtaagaag | tgcgaagggc | cttgccgcaa | agtgtgtaac | 1260 |
| ggaataggta | ttggtgaatt | taaagactca | ctctccataa | atgctacgaa | tattaaacac | 1320 |
| ttcaaaaact | gcacctccat | cagtggcgat | ctccacatcc | tgccggtggc | atttaggggt | 1380 |
| gactccttca | cacatactcc | tcctctggat | ccacaggaac | tggatattct | gaaaaccgta | 1440 |
| aaggaaatca | cagggttttt | gctgattcag | gcttggcctg | aaaacaggac | ggacctccat | 1500 |
| gcctttgaga | acctagaaat | catacgcggc | aggaccaagc | aacatggtca | gttttctctt | 1560 |
| gcagtcgtca | gcctgaacat | aacatccttg | ggattacgct | ccctcaagga | gataagtgat | 1620 |
| ggagatgtga | taatttcagg | aaacaaaaat | ttgtgctatg | caaatacaat | aaactggaaa | 1680 |
| aaactgtttg | ggacctccgg | tcagaaaacc | aaaattataa | gcaacagagg | tgaaaacagc | 1740 |
| tgcaaggcca | caggccaggt | ctgccatgcc | ttgtgctccc | ccgagggctg | ctggggcccg | 1800 |
| gagcccaggg | actgcgtctc | ttgccggaat | gtcagccgag | caggaatg | cgtggacaag | 1860 |
| tgcaaccttc | tggagggtga | gccaagggag | tttgtggaga | ctctgagtg | catacagtgc | 1920 |
| cacccagagt | gcctgcctca | ggccatgaac | atcacctgca | caggacgggg | accagacaac | 1980 |
| tgtatccagt | gtgcccacta | cattgacggc | ccccactgcg | tcaagacctg | cccggcagga | 2040 |
| gtcatgggag | aaaacaacac | cctggtctgg | aagtacgcag | acgccggcca | tgtgtgccac | 2100 |
| ctgtgccatc | caaactgcac | ctacggatgc | actgggccag | gtcttgaagg | ctgtccaacg | 2160 |

```
aatgggccta agatcccgtc catcgccact gggatggtgg gggccctcct cttgctgctg    2220
gtggtggccc tggggatcgg cctcttcatg cgaaggcgcc acatcgttcg gaagcgcacg    2280
ctgcggaggc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc ccacgtgtg ccgcctgctg     2580
ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caaagggcat gaactacttg gaggaccgtc gcttggtgca ccgcgacctg    2760
gcagccagga acgtactggt gaaaacaccg cagcatgtca agatcacaga ttttgggctg    2820
gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggt gtaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc agggggatga agaatgcat ttgccaagtc ctacagactc caacttctac     3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agccaaatgg catctttaag ggctccacag ctgaaaatgc agaataccta    3840
agggtcgcgc cacaaagcag tgaatttatt ggagcatgac cacggaggat agtatgagcc    3900
ctaaaaatcc agactctttc gatacccagg accagccac agcaggtcct ccatcccaac     3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt ccctttgagc agaaattat     4140
ctttcaaaga ggtatatttg aaaaaaaaaa aaagtatatg tgaggatttt tattgattgg    4200
ggatcttgga gtttttcatt gtcgctattg atttttactt caatgggctc ttccaacaag    4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
```

-continued

```
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgttttga aactcagtat gctgcccctg tcttgctgtc atgaaatcag   4680
caagagagga tgacacatca aataataact cggattccag cccacattgg attcatcagc   4740
atttggacca atagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920
accccccaaa attagtttgt gttacttatg gaagatagtt ttctcctttt acttcacttc   4980
aaaagctttt tactcaaaga gtatatgttc cctccaggtc agctgccccc aaaccccctc   5040
cttacgcttt gtcacacaaa aagtgtctct gccttgagtc atctattcaa gcacttacag   5100
ctctggccac aacagggcat tttacaggtg cgaatgacag tagcattatg agtagtgtgg   5160
aattcaggta gtaaatatga aactagggtt tgaaattgat aatgctttca caacatttgc   5220
agatgtttta gaaggaaaaa agttccttcc taaaataatt tctctacaat tggaagattg   5280
gaagattcag ctagttagga gcccacctttt tttcctaatc tgtgtgtgcc ctgtaacctg   5340
actggttaac agcagtcctt tgtaaacagt gtttttaaact ctcctagtca atatccaccc   5400
catccaattt atcaaggaag aaatggttca gaaaatatttt tcagcctaca gttatgttca   5460
gtcacacaca catacaaaat gttccttttg cttttaaagt aattttttgac tcccagatca   5520
gtcagagccc ctacagcatt gttaagaaag tatttgattt ttgtctcaat gaaaataaaa   5580
ctatattcat ttccactcta aaaaaaaaaa aaaaaa                              5616
```

<210> SEQ ID NO 7
<211> LENGTH: 766
<212> TYPE: PRT
<213> ORGANISM: Homo sapiens

<400> SEQUENCE: 7

```
Met Ala Ala Leu Ser Gly Gly Gly Gly Gly Ala Glu Pro Gly Gln
 1               5                  10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175
```

```
Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
                275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
                355                 360                 365

Val His Ile Asn Thr Ile Glu Pro Val Asn Ile Asp Asp Leu Ile Arg
    370                 375                 380

Asp Gln Gly Phe Arg Gly Asp Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
    515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585                 590

Gly Asp Phe Gly Leu Ala Thr Val Lys Ser Arg Trp Ser Gly Ser His
```

|     | 595 |     |     | 600 |     |     | 605 |     |     |     |     |
| --- | --- | --- | --- | --- | --- | --- | --- | --- | --- | --- | --- |
| Gln | Phe | Glu | Gln | Leu | Ser | Gly | Ser | Ile | Leu | Trp | Met | Ala | Pro | Glu | Val |
|     |     | 610 |     |     |     |     | 615 |     |     |     |     | 620 |

Ile Arg Met Gln Asp Lys Asn Pro Tyr Ser Phe Gln Ser Asp Val Tyr
625                     630                     635                     640

Ala Phe Gly Ile Val Leu Tyr Glu Leu Met Thr Gly Gln Leu Pro Tyr
                        645                     650                     655

Ser Asn Ile Asn Asn Arg Asp Gln Ile Ile Phe Met Val Gly Arg Gly
                        660                     665                     670

Tyr Leu Ser Pro Asp Leu Ser Lys Val Arg Ser Asn Cys Pro Lys Ala
                    675                     680                     685

Met Lys Arg Leu Met Ala Glu Cys Leu Lys Lys Lys Arg Asp Glu Arg
                690                     695                     700

Pro Leu Phe Pro Gln Ile Leu Ala Ser Ile Glu Leu Leu Ala Arg Ser
705                     710                     715                     720

Leu Pro Lys Ile His Arg Ser Ala Ser Glu Pro Ser Leu Asn Arg Ala
                        725                     730                     735

Gly Phe Gln Thr Glu Asp Phe Ser Leu Tyr Ala Cys Ala Ser Pro Lys
                    740                     745                     750

Thr Pro Ile Gln Ala Gly Gly Tyr Gly Ala Phe Pro Val His
                755                     760                     765

<210> SEQ ID NO 8
<211> LENGTH: 2949
<212> TYPE: DNA
<213> ORGANISM: Homo sapiens

<400> SEQUENCE: 8

```
cgcctcccctt cccctcccc gcccgacagc ggccgctcgg gccccggctc tcggttataa      60
gatggcggcg ctgagcggtg cggtggtgg cggcgcggag ccgggccagg ctctgttcaa     120
cggggacatg gagcccgagg ccggcgccgg cgccggcgcc gcggcctctt cggctgcgga     180
ccctgccatt ccggaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgattttc tgtttctagc tctgcatcaa tggataccgt     420
tacatcttct tcctcttcta gcctttcagt gctaccttca tctctttcag ttttttcaaaa    480
tcccacagat gtggcacgga gcaaccccaa gtcaccacaa aaacctatcg ttagagtctt     540
cctgcccaac aaacagagga cagtggtacc tgcaaggtgt ggagttacag tccgagacag     600
tctaaagaaa gcactgatga tgagaggtct aatcccagag tgctgtgctg tttacagaat     660
tcaggatgga gagaagaaac caattggttg ggacactgat atttcctggc ttactggaga     720
agaattgcat gtggaagtgt tggagaatgt tccacttaca acacacaact ttgtacgaaa     780
aacgtttttc accttagcat tttgtgactt ttgtcgaaag ctgcttttcc agggtttccg     840
ctgtcaaaca tgtggttata aatttcacca gcgttgtagt acagaagttc cactgatgtg     900
tgttaattat gaccaacttg atttgctgtt tgtctccaag ttctttgaac cacccaat      960
accacaggaa gaggcgtcct tagcagagac tgccctaaca tctggatcat ccccttccgc    1020
acccgcctcg gactctattg gccccaaat tctcaccagt ccgtctcctt caaaatccat    1080
tccaattcca cagcccttcc gaccagcaga tgaagatcat cgaaatcaat tgggcaacg     1140
agaccgatcc tcatcagctc ccaatgtgca tataaacaca atagaacctg tcaatattga    1200
```

```
tgacttgatt agagaccaag gatttcgtgg tgatggagga tcaaccacag gtttgtctgc    1260 tacccccct gcctcattac ctggctcact aactaacgtg aaagccttac agaaatctcc    1320
aggacctcag cgagaaagga agtcatcttc atcctcagaa gacaggaatc gaatgaaaac    1380
acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca tttgtggat    1920 ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctaccatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttctttta    2880 taacaatttg gaaaatgtgg atgtcttta tttccttgaa gcaataaact aagtttcttt    2940
ttataaaaa                                                           2949

<210> SEQ ID NO 9
<211> LENGTH: 2708
<212> TYPE: DNA
<213> ORGANISM: Homo sapiens

<400> SEQUENCE: 9
ggcggcgctt gattgggctg gggggccaa ataaaagcga tggcgattgg gctgccgcgt       60
ttggcgctcg gtccggtcgc gtccgacacc cggtgggact cagaaggcag tggagccccg     120
gcggcggcgg cggcggcgcg cggggcgac gcgcgggaac aacgcgagtc ggcgcgcggg      180
acgaagaata atcatgggcc agactgggaa gaaatctgag aagggaccag tttgttggcg     240
gaagcgtgta aaatcagagt acatgcgact gagacagctc aagaggttca gacgagctga    300
```

```
tgaagtaaag agtatgttta gttccaatcg tcagaaaatt ttggaaagaa cggaaatctt      360
aaaccaagaa tggaaacagc gaaggataca gcctgtgcac atcctgactt ctgtgagctc      420
attgcgcggg actagggagt gttcggtgac cagtgacttg gattttccaa cacaagtcat      480
cccattaaag actctgaatg cagttgcttc agtacccata atgtattctt ggtctcccct      540
acagcagaat tttatggtgg aagatgaaac tgttttacat aacattcctt atatgggaga      600
tgaagtttta gatcaggatg gtactttcat tgaagaacta ataaaaaatt atgatgggaa      660
agtacacggg gatagagaat gtgggtttat aaatgatgaa attttgtgg agttggtgaa       720 tgcccttggt caatataatg atgatgacga tgatgatgat ggagacgatc ctgaagaaag      780
agaagaaaag cagaaagatc tggaggatca ccgagatgat aaagaaagcc gcccacctcg      840
gaaatttcct tctgataaaa ttttgaagc catttcctca atgtttccag ataagggcac       900
agcagaagaa ctaaaggaaa aatataaaga actcaccgaa cagcagctcc caggcgcact      960
tcctcctgaa tgtacccccA acatagatgg accaaatgct aaatctgttc agagagagca     1020
aagcttacac tcctttcata cgcttttctg taggcgatgt tttaaatatg actgcttcct     1080
acatcctttt catgcaacac ccaacactta taagcggaag aacacagaaa cagctctaga     1140
caacaaacct tgtggaccac agtgttacca gcatttggag ggagcaaagg agtttgctgc     1200
tgctctcacc gctgagcgga taaagacccc accaaaacgt ccaggaggcc gcagaagagg     1260
acggcttccc aataacagta gcaggcccag cacccccacc attaatgtgc tggaatcaaa     1320
ggatacagac agtgataggg aagcagggac tgaaacgggg ggagagaaca atgataaaga     1380
agaagaagag aagaaagatg aaacttcgag ctcctctgaa gcaaattctc ggtgtcaaac     1440
accaataaag atgaagccaa atattgaacc tcctgagaat gtggagtgga gtggtgctga     1500
agcctcaatg tttagagtcc tcattggcac ttactatgac aatttctgtg ccattgctag     1560
gttaattggg accaaaacat gtagacaggt gtatgagttt agagtcaaag aatctagcat     1620
catagctcca gctcccgctg aggatgtgga tactcctcca aggaaaaaga agaggaaaca     1680
ccggttgtgg gctgcacact gcagaaagat acagctgaaa aaggacggct cctctaacca     1740
tgtttacaac tatcaaccct gtgatcatcc acggcagcct tgtgacagtt cgtgcccttg     1800
tgtgatagca caaaatttt gtgaaaagtt ttgtcaatgt agttcagagt gtcaaaaccg      1860
ctttccggga tgccgctgca aagcacagtc aacaccaag cagtgcccgt gctacctggc      1920
tgtccgagag tgtgaccctg acctctgtct tacttgtgga gccgctgacc attgggacag     1980
taaaaatgtg tcctgcaaga actgcagtat tcagcgggc tccaaaaagc atctattgct      2040
ggcaccatct gacgtggcag gctggggat ttttatcaaa gatcctgtgc agaaaaatga      2100
attcatctca gaatactgtg gagagattat ttctcaagat gaagctgaca gaagagggaa     2160
agtgtatgat aaatacatgt gcagctttct gttcaacttg aacaatgatt ttgtggtgga     2220
tgcaacccgc aagggtaaca aaattcgttt tgcaaatcat tcggtaaatc caaactgcta     2280
tgcaaaagtt atgatggtta acggtgatca caggataggt attttggcca agagagccat     2340
ccagactggc gaagagctgt tttttgatta cagatacagc caggctgatg ccctgaagta     2400
tgtcggcatc gaaagagaaa tggaaatccc ttgacatctg ctacctcctc cccctcctc      2460 tgaaacagct gccttagctt caggaacctc gagtactgtg ggcaatttag aaaaagaaca     2520
tgcagtttga aattctgaat ttgcaaagta ctgtaagaat aatttatagt aatgagttta     2580
aaaatcaact ttttattgcc ttctcaccag ctgcaaagtt ttttgtacca gtgaatttt      2640 gcaataatgc agtatggtac attttcaac tttgaataaa gaatacttga acttgtcctt      2700
``` gttgaatc 2708

<210> SEQ ID NO 10
<211> LENGTH: 746
<212> TYPE: PRT
<213> ORGANISM: Homo sapiens

<400> SEQUENCE: 10

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

```
Thr Ile Asn Val Leu Glu Ser Lys Asp Thr Asp Ser Asp Arg Glu Ala
    370                 375                 380
Gly Thr Glu Thr Gly Gly Glu Asn Asn Asp Lys Glu Glu Glu Glu Lys
385                 390                 395                 400
Lys Asp Glu Thr Ser Ser Ser Glu Ala Asn Ser Arg Cys Gln Thr
                405                 410                 415
Pro Ile Lys Met Lys Pro Asn Ile Glu Pro Pro Glu Asn Val Glu Trp
            420                 425                 430
Ser Gly Ala Glu Ala Ser Met Phe Arg Val Leu Ile Gly Thr Tyr Tyr
                435                 440                 445
Asp Asn Phe Cys Ala Ile Ala Arg Leu Ile Gly Thr Lys Thr Cys Arg
    450                 455                 460
Gln Val Tyr Glu Phe Arg Val Lys Glu Ser Ser Ile Ile Ala Pro Ala
465                 470                 475                 480
Pro Ala Glu Asp Val Asp Thr Pro Pro Arg Lys Lys Arg Lys His
                485                 490                 495
Arg Leu Trp Ala Ala His Cys Arg Lys Ile Gln Leu Lys Lys Asp Gly
            500                 505                 510
Ser Ser Asn His Val Tyr Asn Tyr Gln Pro Cys Asp His Pro Arg Gln
        515                 520                 525
Pro Cys Asp Ser Ser Cys Pro Cys Val Ile Ala Gln Asn Phe Cys Glu
    530                 535                 540
Lys Phe Cys Gln Cys Ser Ser Glu Cys Gln Asn Arg Phe Pro Gly Cys
545                 550                 555                 560
Arg Cys Lys Ala Gln Cys Asn Thr Lys Gln Cys Pro Cys Tyr Leu Ala
                565                 570                 575
Val Arg Glu Cys Asp Pro Asp Leu Cys Leu Thr Cys Gly Ala Ala Asp
            580                 585                 590
His Trp Asp Ser Lys Asn Val Ser Cys Lys Asn Cys Ser Ile Gln Arg
        595                 600                 605
Gly Ser Lys Lys His Leu Leu Leu Ala Pro Ser Asp Val Ala Gly Trp
    610                 615                 620
Gly Ile Phe Ile Lys Asp Pro Val Gln Lys Asn Glu Phe Ile Ser Glu
625                 630                 635                 640
Tyr Cys Gly Glu Ile Ile Ser Gln Asp Glu Ala Asp Arg Arg Gly Lys
                645                 650                 655
Val Tyr Asp Lys Tyr Met Cys Ser Phe Leu Phe Asn Leu Asn Asn Asp
            660                 665                 670
Phe Val Val Asp Ala Thr Arg Lys Gly Asn Lys Ile Arg Phe Ala Asn
        675                 680                 685
His Ser Val Asn Pro Asn Cys Tyr Ala Lys Val Met Met Val Asn Gly
    690                 695                 700
Asp His Arg Ile Gly Ile Phe Ala Lys Arg Ala Ile Gln Thr Gly Glu
705                 710                 715                 720
Glu Leu Phe Phe Asp Tyr Arg Tyr Ser Gln Ala Asp Ala Leu Lys Tyr
                725                 730                 735
Val Gly Ile Glu Arg Glu Met Glu Ile Pro
            740                 745

<210> SEQ ID NO 11
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 11
agcgatgacg tctctgaggt                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtacagggac accagccact                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taacaagctc acgcagttgg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttgagggca atgaggacat                                              20

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcccgcaagc tgaccctgaa gttcattcaa gagatgaact tcagggtcag cttgctttt    59

<210> SEQ ID NO 16
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccggcggaaa tcttaaacca agaatctcga gattcttggt ttaagatttc cgtttt       57

<210> SEQ ID NO 17
<211> LENGTH: 57
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 17
ccgggctgag aatgtggaat acctactcga gtaggtattc cacattctca gcttttt      57

<210> SEQ ID NO 18
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tttgtggata agcagcacaa gatttcaaga gaatcttctg ctgcttctcc attttt       56

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcatctgcac tgccaagact g                                             21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
catgccttct ttcactttgc c                                             21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aggagtttgc tgctgctctc                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccgagaattt gcttcagagg                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tacggctcct attgccaaac                                        20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcttcagtt tgttgccttg                                        20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggcctctgat ctccgatttc                                        20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgggctctaa attggctcac                                        20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgaaattca cccctttcc                                         20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccctaggctg tgctcacttc                                        20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 29
ccggctaact ctgaggacac                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgagctgttt acgtttgacg                                              20

<210> SEQ ID NO 31
<211> LENGTH: 4
<212> TYPE: PRT
<213> ORGANISM: Unknown
<220> FEATURE:
<223> OTHER INFORMATION: Description of Unknown: "DEAD" box motif
      peptide

<400> SEQUENCE: 31

Asp Glu Ala Asp
1

<210> SEQ ID NO 32
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccggtattgc cttctcacca gctgcctcga ggcagctggt gagaaggcaa tattttt     57

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcgagccata aaaggcaact                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tctccctcct cctcttcctc                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 35
ccttgtagat tggggctgag                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agtttggggg tggaagaaag                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggctgagaca gagggaacac                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccatctcagc ctcccaagta                                               20
```